United States Patent
Parlati et al.

(10) Patent No.: US 10,441,587 B2
(45) Date of Patent: Oct. 15, 2019

(54) TREATMENT OF LUNG CANCER WITH INHIBITORS OF GLUTAMINASE

(71) Applicant: Calithera Biosciences, Inc., South San Francisco, CA (US)

(72) Inventors: Francesco Parlati, San Francisco, CA (US); Melissa G. Works, Menlo Park, CA (US); Mirna L. M. Rodriguez, San Jose, CA (US); Dong Zhang, San Jose, CA (US)

(73) Assignee: Calithera Biosciences, Inc., South San Francisco, CA (US)

( * ) Notice: Subject to any disclaimer, the term of this patent is extended or adjusted under 35 U.S.C. 154(b) by 16 days.

(21) Appl. No.: 15/091,816

(22) Filed: Apr. 6, 2016

(65) Prior Publication Data
US 2016/0287585 A1  Oct. 6, 2016

Related U.S. Application Data

(60) Provisional application No. 62/149,489, filed on Apr. 17, 2015, provisional application No. 62/143,494, filed on Apr. 6, 2015.

(51) Int. Cl.
*A61K 31/433* (2006.01)
*A61K 31/501* (2006.01)
*A61K 31/4184* (2006.01)
*C12Q 1/6886* (2018.01)

(52) U.S. Cl.
CPC ........ *A61K 31/501* (2013.01); *A61K 31/4184* (2013.01); *C12Q 1/6886* (2013.01); *C12Q 2600/106* (2013.01); *C12Q 2600/156* (2013.01); *C12Q 2600/158* (2013.01)

(58) Field of Classification Search
CPC .......................... A61K 31/433; A61K 31/501
See application file for complete search history.

(56) References Cited

U.S. PATENT DOCUMENTS

| | | |
|---|---|---|
| 6,451,828 B1 | 9/2002 | Newcomb et al. |
| 8,604,016 B2 | 12/2013 | Li et al. |
| 8,865,718 B2 | 10/2014 | Li et al. |
| 9,687,485 B2 | 6/2017 | Steggerda et al. |
| 9,938,267 B2 | 4/2018 | Li et al. |
| 1,019,519 A1 | 2/2019 | Bennett et al. |
| 2004/0198716 A1 | 10/2004 | Arad et al. |
| 2005/0260697 A1 | 11/2005 | Wang et al. |
| 2010/0330197 A1 | 12/2010 | Higashiguchi et al. |
| 2012/0302605 A1 | 11/2012 | DeWitt |
| 2013/0109643 A1 | 5/2013 | Riggins et al. |
| 2013/0157998 A1 | 6/2013 | Li et al. |
| 2014/0050699 A1 | 2/2014 | Li et al. |
| 2014/0142081 A1 | 5/2014 | Lemieux et al. |
| 2014/0142146 A1 | 5/2014 | Lemieux et al. |
| 2014/0194421 A1 | 7/2014 | Li et al. |
| 2014/0369961 A1 | 12/2014 | Li et al. |
| 2015/0004134 A1 | 1/2015 | Bennett et al. |
| 2015/0258082 A1 | 9/2015 | Parlati et al. |
| 2016/0010158 A1 | 1/2016 | Wang et al. |
| 2016/0022674 A1 | 1/2016 | Steggerda et al. |
| 2016/0287564 A1* | 10/2016 | Gross .................. A61K 31/519 |
| 2017/0333430 A1 | 11/2017 | Steggerda et al. |
| 2018/0055825 A1 | 3/2018 | Liang et al. |
| 2018/0055842 A1 | 3/2018 | Bennett et al. |
| 2018/0055843 A1 | 3/2018 | Parlati et al. |

FOREIGN PATENT DOCUMENTS

| | | |
|---|---|---|
| WO | WO-2011143160 A2 | 11/2011 |
| WO | WO-2012006506 A1 | 1/2012 |
| WO | WO-2013/044596 A1 | 4/2013 |
| WO | WO-2013078123 A1 | 5/2013 |
| WO | WO-2013/177426 A2 | 11/2013 |
| WO | WO-2014039960 A1 | 3/2014 |
| WO | WO-2014043633 A1 | 3/2014 |
| WO | WO-2014/078645 A1 | 5/2014 |
| WO | WO-2014/079136 A1 | 5/2014 |
| WO | WO-2014/081925 A1 | 5/2014 |
| WO | WO-2014089048 A1 | 6/2014 |
| WO | WO-2015061432 A1 | 4/2015 |
| WO | WO-2015/138902 A1 | 9/2015 |
| WO | WO-2015/192014 A1 | 12/2015 |
| WO | WO-2016/004418 A1 | 1/2016 |
| WO | WO-2016/014890 A1 | 1/2016 |
| WO | WO-2016/022969 A1 | 2/2016 |
| WO | WO-2016/054388 A1 | 4/2016 |
| WO | WO-2016/077632 A2 | 5/2016 |
| WO | WO-2016/160980 A1 | 10/2016 |

OTHER PUBLICATIONS

Liu et al. Int. J. Clin. Exp.Pathol., 2013, vol. 6, No. 9, pp. 1880-1889.*
Kaufman et al. JAMA, 2017, vol. 317, Issue 18, pp. 1835-1837.*
Lee et al., Korean J. Pathol., 2014, vol. 48, No. 2, pp. 100-107.*
Borodovsky et al., "5-azacytidine reduces methylation, promotes differentiation and induces tumor regression in a patient-derived IDH1 mutant glioma xenograft," Oncotarget, 4(10): 1737-1737 (Sep. 16, 2013).
Costello et al., "Evidence for changes in RREB-1, ZIP3, and zinc in the early development of pancreatic adenocarcinoma," J Gastrointest Cancer, 43:570-8 (2012).
Dai et al., "Studies on the novel a-glucosidase inhibitory activity and structure-activity relationships for andrographolide analogues," Bioorg Med Chem Lett, 16:2710-13 (2006).
Hensley et al., "Glutamine and cancer: Cell biology, physiology, and clinical opportunities," J Clin Investig, 123(9):3678-84 (2013).

(Continued)

Primary Examiner — Samira J Jean-Louis

(74) Attorney, Agent, or Firm — David P. Halstead; Foley Hoag LLP

(57) ABSTRACT

The invention relates to methods of treating lung cancer using glutaminase inhibitors. In particular, results demonstrate that lung cancers characterized by an EGFR or KRAS mutation are treated by glutaminase inhibitors.

12 Claims, 3 Drawing Sheets

(56) References Cited

OTHER PUBLICATIONS

Figure 1:
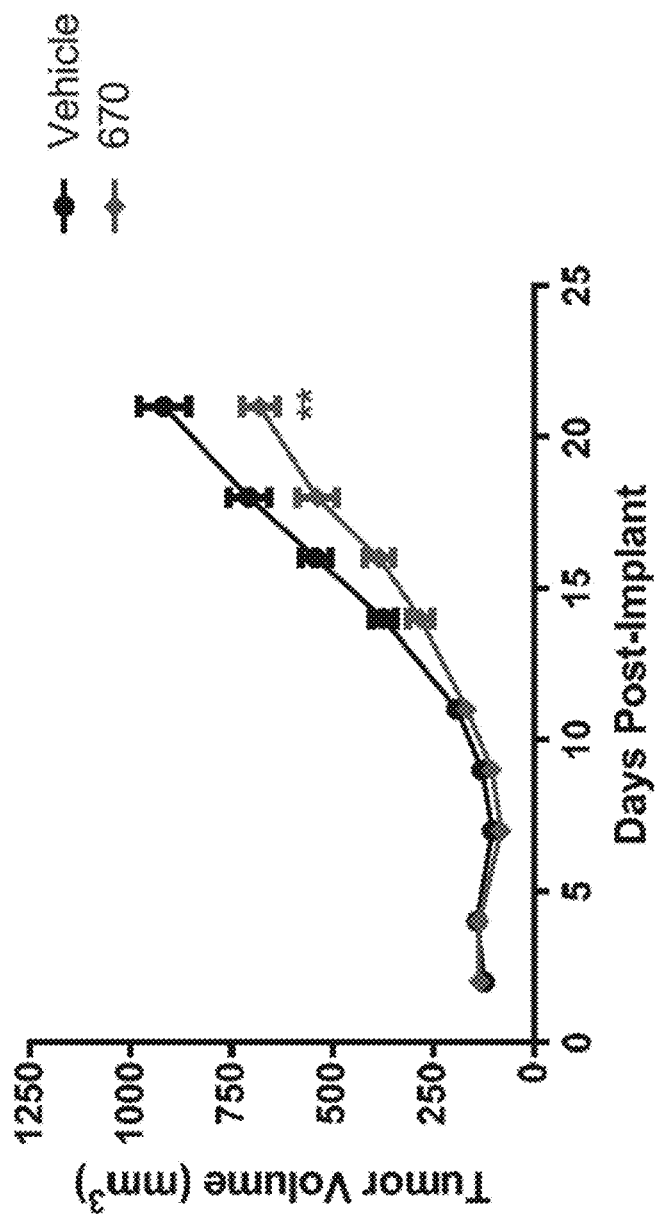

Holliday et al., "Choosing the right cell line for breast cancer research," Breast Cancer Res, 13:215 (2011).
International Search Report for Application No. PCT/US2016/026127, dated Jul. 27, 2016.
Johnson et al., "Relationships between drug activity and NCI preclinical in vitro and in vivo models and early clinical trials," Brit J Cancer, 84(10):1424-31 (2001).
Kim, A., "Clinical impact of gene expression profiling on oncology diagnosis, prognosis, and treatment," Combinatorial Chem & High Throughput Screening, 7:183-206 (2004).
Martin et al., "Do structurally similar molecules have similar biological activity?" J Med Chem, 45:4350-8 (2002).
McCleland, et al., "Lactate dehydrogenase B is required for the growth of KRAS-Dependent lung adenocarcinomas," Clin Cancer Res, 19(4): 773-784 (2013).
Medina, M., "Glutamine and cancer," J Nutr, 131(9 Suppl):2539S-42S (2001).
Osol, A. [Editor]. "Chapter 27: Structure-activity relationship and drug design," Remington's Pharmaceutical Sciences (Sixteenth Edition). 1980. pp. 420-435.
Sporn et al., "Chemoprevention of cancer," Carcinogenesis, 21(3):525-30 (2000).
Thoppil et al., "Terpenoids as potential chemopreventive and therapeutic agents in liver cancer," World J Hepatol, 3(9):228-249 (2011).
Voskoglou-Nomikos et al., "Clinical predictive value of the in vitro cell line, human xenograft, and mouse allograft preclinical cancer models," Clin Cancer Res, 9:4227-39 (2003).
Written Opinion of the International Searching Authority for Application No. PCT/US2016/026127, dated Jul. 27, 2016.
CAS RN 1400068-83-8 STN Entry Date Oct. 8, 2012; N,N1-(5,51-(pentane-1,5-diyl)]bis(1,3,4-thiadiazole-5,2-diyl))bis(2-methoxybenzamide).
CAS RN 331234-76-5, STN Entry Date Apr. 13, 2001; N,N1-[thiobis(2,1-ethanediyl-1,3,4-thiadiazole-5,2-diyl)]bis-1H-1,2,4-triazole-3-carboxmide.
Chemical Abstract Registry No. 296888-91-0, indexed in the Registry File on STN CAS Online Oct. 18, 2000.
Chemical Abstract Registry No. 666208-63-5, indexed in the Registry File on STN CAS Online Mar. 22, 2004.
DeLabarre B. a et al., "Full-Length Human Glutaminase in Complex with an Allosteric Inhibitor", Biochemistry, vol. 50, pp. 10764-10770 (2011).
Gehlen H. et al., "Uber die Einwirkung von Isocyanaten auf substituierte 2-Amino-1,3,4-oxdiazole", Justus Leibigs Annalen der Chemie, vol. 692, pp. 151-165 (1966).
Gehlen H., et al. "Uber die Acylierung der 2-Amino-5-(alkyl, aryl)-1.3.4-oxdiazole," Liebigs Ann. Chem. 703, 131-135 (1967).
Gross et al., "Antitumor Activity of the Glutaminase Inhibitor CB-839 in Triple-Negative Breast Cancer", Mol. Cancer Ther., 13(4):890-901 (2014).
Horig et al., "From bench to clinic and back: Perspective on the 1st IQPC Translational Research conference", Journal of Translational Medicine, vol. 2, p. 44 (2004).
Ito et al., "A medium-term rat liver bioassay for rapid in vivo detection of carcinogenic potential of chemicals," Cancer Science, 94(1):3-8 (2003).
Pajic et al., "Cell cycle activation by c-myc in a Burkitt's lymphoma model cell ine", International Journal of Cancer, vol. 87, pp. 787-793 (2000).
Parlati et al., "Antitumor Activity of the Glutaminase Inhibitor CB-839 in Hematological Malignances", 55th ASH Annual Meeting and Exposition, Dec. 9, 2013, New Orleans, LA, abstract No. 4226.
Rajagopalan K.N. et al., "Role of Glutamine in Cancer: Therapeutic and Imaging Implications", Journal of Nuclear Medicine, vol. 52, pp. 1005-1008 (2011).
Robinson et al., "Novel mechanism of inhibition of rat kidney-type glutaminase by bis-2-(-5 phenylacetamido-1,2,4-thiadiazol-2-yl)ethyl sulfide (BPTES)", Biochem. J., vol. 406, pp. 407-414 (2007).
Schäfer et al., "Failure is an option: learning from unsuccessful proof-of-concept trials", Drug Discovery Today, vol. 13, pp. 913-916 (2008).
Seltzer et al., "Inhibition of glutaminase preferentially slows growth of glioma cells with mutant IDH1", Cancer Research, vol. 70, pp. 8981-8987 (2010).
Shimano Y. et al., "Synthesis of Poly(diacylthiosemicarbazide)s from Diacylisothiocyanates and Dihydrazides, and Their Thermal Cyclodehydration"Kobunshi Ronbunshu, vol. 37, No. 2, pp. 131-137 (1980).
Shukla, K., et al, "Design, Synthesis and Pharmacological Evaluation of Bis-2-(5-phenylacetamido-1-2, 4-thiadiazol-2-yl)ethyl 1 sulphide 3 (BPTES) Analogs as Glutaminase Inhibitors", Journal of Medicinal Chemistry, vol. 55, No. 23, pp. 10551-10563 (2012).
Thangavelu, K. et al., "Structural basis for the allosteric inhibitory mechanism of human kidney-type glutaminase (KGA) and its regulation by Raf-Mek-Erk signaling in cancer cell metabolism, Proceedings of the National Acedemy of Sciences of the United States of America", vol. 109, No. 20, pp. 7705-7710 (2012).
Wang et al., "Targeting mitochondrial glutaminase activity inhibits oncogenic transformation", Cancer Cells, vol. 18, pp. 207-219 (2010).
Bromley-Dulfano, et al., "Antitumor activity of the glutaminase inhibitor CB-839 in hematological malignances," Blood, 122(21): 4226 (2013).
Jacque, et al., "Targeting glutaminolysis has antileukemic activity in acute myeloid leukemia and synergizes with BCL-2 inhibition," Blood, 126(11): 1346-1356 (2015).
Zimmerman, et al., "Allosteric glutaminase inhibitors based on a 1,4-Di(5-amino-1,3,4-thiadiazol-2-yl)butane scaffold," ACS Med Chem Lett, 7(5): 520-524 (2016).
Tseng, et al., "The synthesis of daidzein derivatives," J Natural Taiwan Normal University, 30: 537-545 (1985).
International Search Report and Written Opinion for Application No. PCT/US2016/055316 dated Jan. 12, 2017.
Simpson et al., "Modifying metabolically sensitive histone marks by inhibiting glutamine metabolism affects gene expression and alters cancer cell phenotype," Epigenetics, 7(12):1413-20 (2012).
Wang et al., "Targeting mitochondrial glutaminase activity inhibits oncogenic transformation," Cancer Cell, 18(3):207-19 (2010).
Prat et al., "Phenotypic and molecular characterization of the claudin-low intrinsic subtype of breast cancer," Breast Cancer Res, 12(5):R68 (2010).
Kung et al., "Glutamine synthetase is a genetic determinant of cell type-specific glutamine independence in breast epithelia," PLOS Genetics, 7(8):e1002229 (2011).
Extended European Search Report from European Application No. 15761424.9 dated Jul. 31, 2017.
Lacy et al., "Pomalidomide (CC4047) plus low dose dexamethasone (Pom/dex) is active and well tolerated in lenalidomide refractory multiple myeloma (MM)," Leukemia, 24(11): 1934-1939 (2010).
Lopez-Girona et al., "Cereblon is a direct protein target for immunomodulatory and antiproliferative activities of lenalidomide and pomalidomide," Leukemia, 26(11):2326-2335 (2012).
Nars et al., "Immunomodulatory effects of low dose chemotherapy and perspectives of its combination with immunotherapy," Int J Cancer, 132(11):2471-2478 (2013).
Parlati et al., "Glutaminase inhibitor CB-839 synergizes with pomalidomide in preclinical multiple myeloma models," American Society of Hematology Annual Meeting—Dec. 6-9, 2014.
Altman et al., "From Krebs to Clinic: Glutamine Metabolism to Cancer Therapy," Nat Rev Cancer, 6(10):619-634 (2016).
CAS Registry No. 714283-67-7 STN Entry Date Jul. 22, 2004.
Chen et al., "Targeting glutamine induces apoptosis: a cancer therapy approach," Int J Mol Sci, 16(9):22830-22855 (2015).
Chen et al., "Targeting the epidermal growth factor receptor in non-small cell lung cancer cells: the effect of combining RNA interference with tyrosine kinase inhibitors or cetuximab," BMC medicine, 10:28 (2012).

(56) References Cited

OTHER PUBLICATIONS

Clinical Trials, "Study of the Glutaminase Inhibitor CB-839 in Solid Tumors," ClinicalTrials.gov (2016).
Dholaria et al., "Emerging Therapeutic Agents for Lung Cancer," Journal of Hematology & Oncology, 9(138) (2016).
Extended European Search Report issued by the European Patent Office in corresponding Application No. 15830024.4, dated Nov. 24, 2017.
Extended European Search Report issued by the European Patent Office in corresponding Application No. EP 15805792.7, dated Jan. 2, 2018.
Extended European Search Report for EP Patent Application EP16774100, dated Jan. 9th, 2019.
Extended European Search Report for EP Patent Application No. EP16777159, dated Nov. 27th, 2018.
Filipp et al., "Glutamine-fueled mitochondrial metabolism is decoupled from glycolysis in melanoma," Pigment Cell Melanoma Res, 25:732-739 (2012).
Gameiro et al., "In Vivo HIF-Mediated Reductive Carboxylation Is Regulated by Citrate Levels and Sensitizes VHL-Deficient Cells to Glutamine Deprivation," Cell Metabolism, 17:372 (2013).
Gao et al., "c-Myc suppression of miR-23a/b enhances mitochondrial glutaminase expression and glutamine metabolism," Nature, 458(7239):762-5 (2009).
Haynes et al., "Occurrence of Pharmaceutically Acceptable Anions and Cations in the Cambridge Structural Database," J Pharm Sci, 94: 2111-2120 (2005).
International Preliminary Report on Patentability for International Application No. PCT/US2017/048581 dated Mar. 7, 2019.
International Search Report and Written Opinion for International Application No. PCT/US2017/048398 dated Nov. 12, 2017.
International Search Report and Written Opinion for International Application No. PCT/US2017/048400 dated Nov. 28, 2017.
International Search Report and Written Opinion for International Application No. PCT/US2018/021689 dated Jul. 19, 2018.
Jacque et al., "Targeting Glutaminolysis has Antileukemic Activity in Acute Myeloid Leukemia and Synergizes with BCL-2 Inhibition," Blood, 126(11):1345-1356 (2015).
Janmaat et al., "Enhanced cytotoxicity induced by gefitinib and specific inhibitors of the Ras or phosphatidyl inositol-3 kinase pathways in non-small cell lung cancer cells," International journal of cancer, 118(1):209-214 (2006).
Janne et al., "Factors underlying sensitivity of cancers to small-molecule kinase inhibitors," Nat Rev Drug Discov, 8:709-723 (2009).
Momcilovic et al., "Targeted inhibition of EGFR and glutaminase induces metabolic crisis in EGFR mutant lung cancer," Cell reports, 18(3):601-610 (2017).
Pomerantz et al., "The 8q24 cancer risk variant rs6983267 shows long-range interaction with MYC in colorectal cancer," Nat Genet, 41(8):882-884 (2009).
Schiller et al., "Efficacy and safety of axitinib in patients with advanced non-small-cell lung cancer: results from a phase II study," J Clin Oncol, 27(23): 3836-3841 (2009).
Shimamura et al., "Epidermal growth factor receptors harboring kinase domain mutations associate with the heat shock protein 90 chaperone and are destabilized following exposure to geldanamycins," Cancer research, 65(14):6401-6408 (2005).
Son et al., "Glutamine supports pancreatic cancer growth through a KRAS-regulated metabolic pathway," Nature, 496:101-105 (2013).
Tan et al., "Bcl-2/Bcl-xL inhibition increases the efficacy of MEK inhibition alone and in combination with PI3 kinase inhibition in lung and pancreatic tumor models," Molecular cancer therapeutics, 12(6):853-864 (2013).
Tanizaki et al., "MET tyrosine kinase inhibitor crizotinib (PF-02341066) shows differential antitumor effects in non-small cell lung cancer according to MET alterations," J Thorac Oncol, 6(10):1624-1631 (2011).
Toppmeyer et al., "Safety and efficacy of the multidrug resistance inhibitor Incel (biricodar; VX-710) in combination with paclitaxel for advanced breast cancer refractory to paclitaxel," Clin Cancer Res, 8(3):670-678 (2002).
Tuupanen et al., "The common colorectal cancer predisposition SNP rs6983267 at chromosome 8q24 confers potential to enhanced Wnt signaling," Nat Genet, 41(8):885-890 (2009).
Vaishampayan, "Cabozantinib as a Novel Therapy for Renal Cell Carcinoma," Curr. Oncol. Rep. 15:76-82 (2013).
Van den Heuvel et al., "Analysis of glutamine dependency in non-small cell lung cancer: GLS1 splice variant GAC is essential for cancer cell growth," Cancer Biol Ther, 13(12):1185-94 (2012).
Xiang et al., "Targeted inhibition of tumor-specific glutaminase diminishes cell-autonomous tumorigenesis," J Clin Invest, 125(6):2293-2306 (2015).
Xie et al., "Inhibition of Mitochondrial Glutaminase Activity Reverses Acquired Erlotinib Resistance in Non-small Cell Lung Cancer," Oncotarget, 7(1):610-621 (2015).
Zhao et al., "Targeting Cellular Metabolism to Improve Cancer Therapeutics," Cell Death & Disease 4(3):e532 (2013).

\* cited by examiner

TREATMENT OF LUNG CANCER WITH INHIBITORS OF GLUTAMINASE

RELATED APPLICATIONS

This application claims the benefit of priority to U.S. Provisional Patent Application No. 62/143,494, filed Apr. 6, 2015 and U.S. Provisional Patent Application No. 62/149,489, filed Apr. 17, 2015, which applications are hereby incorporated by reference in their entirety.

BACKGROUND

Glutamine supports cell survival, growth and proliferation through metabolic and non-metabolic mechanisms. In actively proliferating cells, the metabolism of glutamine to lactate, also referred to as "glutaminolysis" is a major source of energy in the form of NADPH. The first step in glutaminolysis is the deamination of glutamine to form glutamate and ammonia, which is catalyzed by the glutaminase enzyme (GLS). Thus, deamination via glutaminase is a control point for glutamine metabolism.

Ever since Warburg's observation that ascites tumor cells exhibited high rates of glucose consumption and lactate secretion in the presence of oxygen (Warburg, 1956), researchers have been exploring how cancer cells utilize metabolic pathways to be able to continue actively proliferating. Several reports have demonstrated how glutamine metabolism supports macromolecular synthesis necessary for cells to replicate (Curthoys, 1995; DeBardinis, 2008).

Thus, glutaminase has been theorized to be a potential therapeutic target for the treatment of diseases characterized by actively proliferating cells, such as cancer. The lack of suitable glutaminase inhibitors has made validation of this target impossible until the recent creation of compounds that are specific and capable of being formulated for in vivo use (U.S. Pat. No. 8,604,016). As glutaminase inhibitors enter the clinical arena, methods are needed to identify patients that would best benefit from treatment with these compounds.

SUMMARY OF INVENTION

The present invention provides a method for treating lung cancer in a patient, comprising determining whether the lung cancer is characterized by a KRAS mutation or EGFR mutation, and if the lung cancer is characterized by a KRAS mutation or EGFR mutation, then administering to the patient an effective amount of a glutaminase inhibitor. In some embodiments, the KRAS mutation or EGFR mutation results in a different amino acid sequence of the KRAS or EGFR (e.g., relative to a wild-type (predominant) form). In other embodiments, the KRAS mutation or EGFR mutation results in a different level of expression or activity of the KRAS or EGFR (e.g., relative to a wild-type cell of a similar type).

In some embodiments, the glutaminase inhibitor is a compound of formula I,

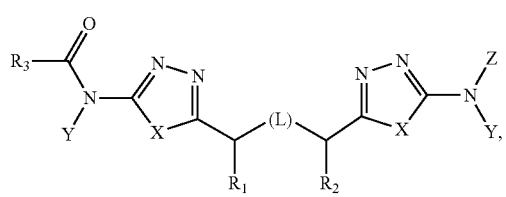

(I)

or a pharmaceutically acceptable salt thereof, wherein:

L represents $CH_2SCH_2$, $CH_2CH_2$, $CH_2CH_2CH_2$, $CH_2$, $CH_2S$, $SCH_2$, $CH_2NHCH_2$, $CH=CH$, or

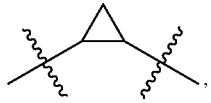 [SMILES: *C1CC1*]

preferably $CH_2CH_2$, wherein any hydrogen atom of a CH or $CH_2$ unit may be replaced by alkyl or alkoxy, any hydrogen of an NH unit may be replaced by alkyl, and any hydrogen atom of a $CH_2$ unit of $CH_2CH_2$, $CH_2CH_2CH_2$ or $CH_2$ may be replaced by hydroxy;

X, independently for each occurrence, represents S, O or $CH=CH$, preferably S or $CH=CH$, wherein any hydrogen atom of a CH unit may be replaced by alkyl;

Y, independently for each occurrence, represents H or $CH_2O(CO)R_7$;

$R_7$, independently for each occurrence, represents H or substituted or unsubstituted alkyl, alkoxy, aminoalkyl, alkylaminoalkyl, heterocyclylalkyl, arylalkyl, or heterocyclylalkoxy;

Z represents H or $R_3(CO)$;

$R_1$ and $R_2$ each independently represent H, alkyl, alkoxy or hydroxy;

$R_3$, independently for each occurrence, represents substituted or unsubstituted alkyl, hydroxyalkyl, aminoalkyl, acylaminoalkyl, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, heteroaryloxyalkyl or $C(R_8)(R_9)(R_{10})$, $N(R_4)(R_5)$ or $OR_6$, wherein any free hydroxyl group may be acylated to form $C(O)R_7$;

$R_4$ and $R_5$ each independently represent H or substituted or unsubstituted alkyl, hydroxyalkyl, acyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form $C(O)R_7$;

$R_6$, independently for each occurrence, represents substituted or unsubstituted alkyl, hydroxyalkyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form $C(O)R_7$; and $R_8$, $R_9$ and $R_{10}$ each independently represent H or substituted or unsubstituted alkyl, hydroxy, hydroxyalkyl, amino, acylamino, aminoalkyl, acylaminoalkyl, alkoxycarbonyl, alkoxycarbonylamino, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, or $R_8$ and $R_9$ together with the carbon to which they are attached, form a carbocyclic or heterocyclic ring system, wherein any free hydroxyl group may be acylated to form $C(O)R_7$, and wherein at least two of $R_8$, $R_9$ and $R_{10}$ are not H.

In further embodiments, the invention relates to methods of identifying a lung cancer patient that may benefit from treatment with a glutaminase inhibitor, comprising determining whether a lung cancer cell of the patient has a mutation in KRAS or EGFR, wherein a mutation in KRAS or EGFR in the lung cancer cell of the patient indicates that the patient may benefit from treatment with a glutaminase inhibitor.

DETAILED DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows that oral administration of compound 670 to mice results in reduced tumor size in a H2122 lung adenocarcinoma xenograft model.

Figure 2:
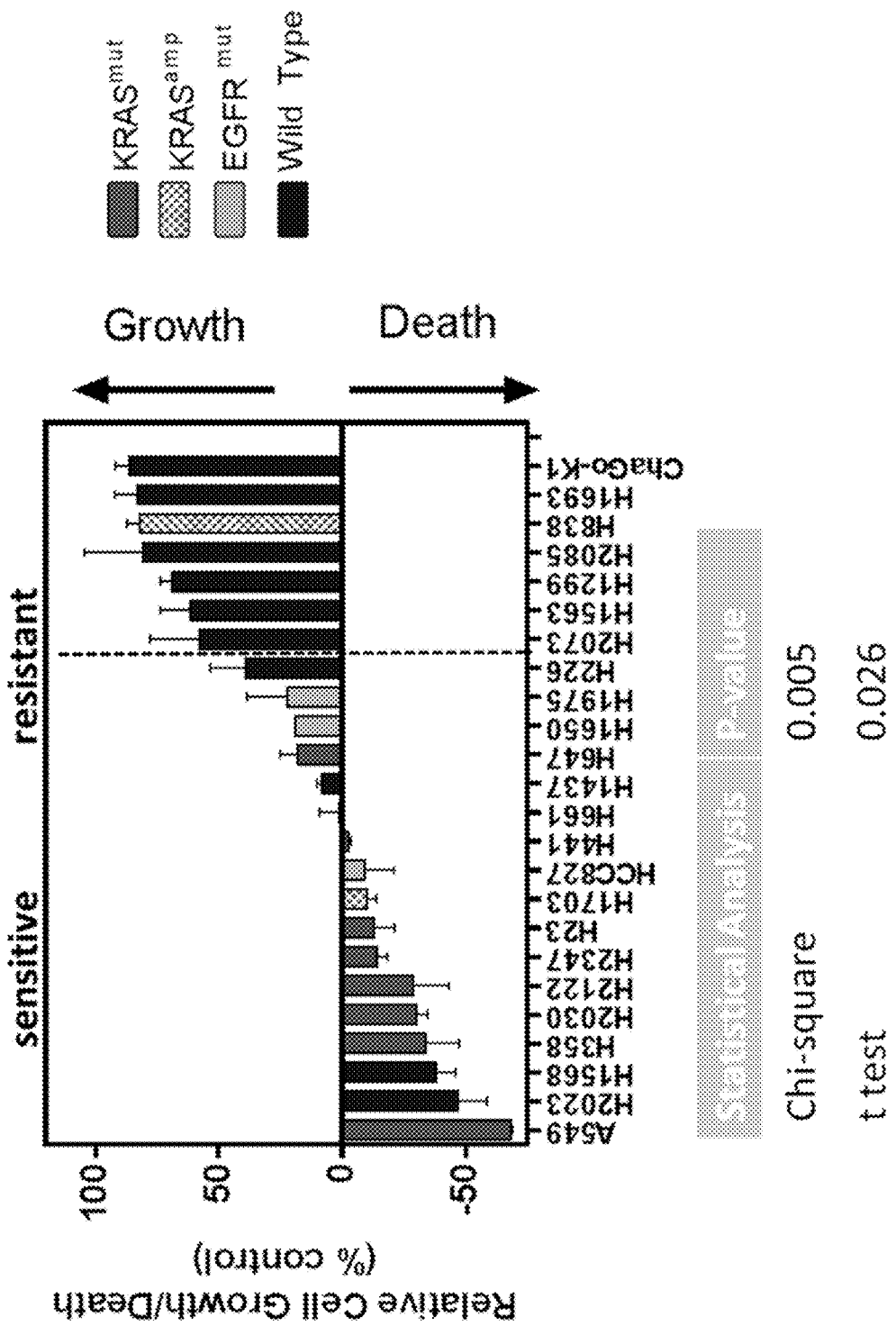

FIG. 2 contains a bar graph depicting a correlation between EGFR or KRAS mutation in various non-small cell lung cancer cell lines and sensitivity to compound 670.

Figure 3:
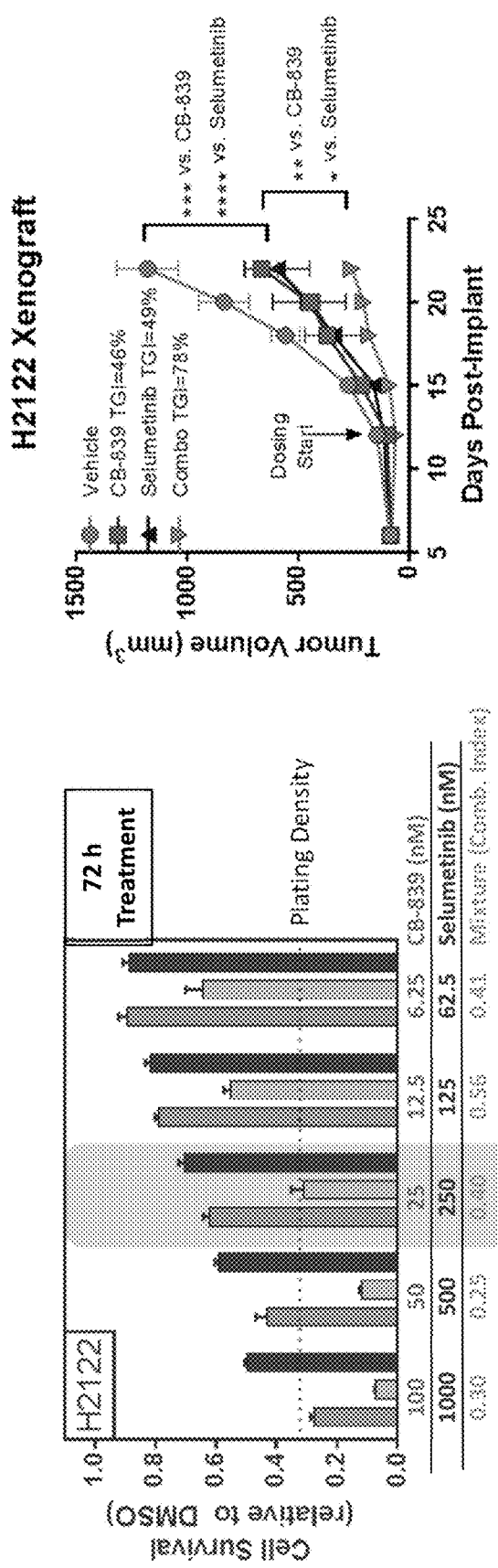

FIG. 3 contains a bar graph that demonstrates the therapeutic efficacy of compound CB-839, selumetinib, and the combination of CB-839 and selumetinib in lung cancer cells having a KRAS mutation (H2122 cell line). The combination therapy yields synergistic anti-proliferative activity in these cancer cells. FIG. 3 also provides a graph showing the results of an in vivo xenograft study of the combination of CB-839 and selumetinib in lung cancer tumors having a KRAS mutation.

DETAILED DESCRIPTION OF THE INVENTION

The present invention is based on the discovery of a biomarker in non-small cell lung cancer (nscic) cell lines that indicates sensitivity of the nscic cells to treatment with a glutaminase inhibitor. As shown in data presented herein, not all nscic cell lines exhibit the same sensitivity to treatment with a glutaminase inhibitor. Further, this effect is not observed in certain other types of cancer cell lines (data not shown).

The present invention provides a method for treating lung cancer in a patient, comprising determining whether the lung cancer is characterized by a KRAS mutation or EGFR mutation, and if the lung cancer is characterized by a KRAS mutation or EGFR mutation, then administering to the patient an effective amount of a glutaminase inhibitor.

In further embodiments, the invention relates to methods of identifying a lung cancer patient that may benefit from treatment with a glutaminase inhibitor, comprising determining whether a lung cancer cell of the patient has a KRAS mutation or EGFR mutation, wherein a KRAS mutation or EGFR mutation in the lung cancer cell of the patient indicates that the patient may benefit from treatment with a glutaminase inhibitor.

In some embodiments, the KRAS mutation or EGFR mutation results in a different amino acid sequence of the KRAS or EGFR (e.g., relative to a wild-type (predominant) form). In other embodiments, the KRAS mutation or EGFR mutation results in a different level of expression or activity of the KRAS or EGFR (e.g., relative to a wild-type cell of a similar type).

Determining whether a lung cancer cell of the patient has a KRAS mutation or EGFR mutation can be done by directly performing an assay and/or observing the results of an assay, by reviewing a report of the assay results (e.g., in medical records), by consulting with a person who knows the results of the assay, or by any other means of ascertaining, directly or indirectly, the phenotype of the patient's lung cancer cells.

I. Compounds

In certain embodiments, the invention relates to methods of treating lung cancer characterized by a biomarker using a glutaminase inhibitor.

In certain embodiments, the glutaminase inhibitor is a compound of formula I,

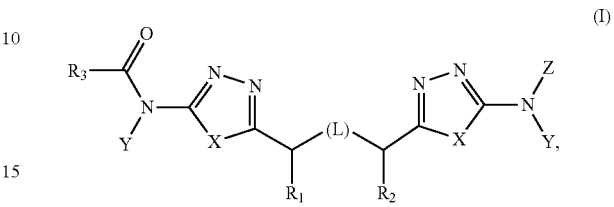

or a pharmaceutically acceptable salt thereof, wherein:

L represents $CH_2SCH_2$, $CH_2CH_2$, $CH_2CH_2CH_2$, $CH_2$, $CH_2S$, $SCH_2$, $CH_2NHCH_2$, $CH=CH$, or

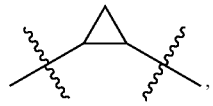 [SMILES: *C1CC1*]

preferably $CH_2CH_2$, wherein any hydrogen atom of a CH or $CH_2$ unit may be replaced by alkyl or alkoxy, any hydrogen of an NH unit may be replaced by alkyl, and any hydrogen atom of a $CH_2$ unit of $CH_2CH_2$, $CH_2CH_2CH_2$ or $CH_2$ may be replaced by hydroxy;

X, independently for each occurrence, represents S, O or $CH=CH$, preferably S or $CH=CH$, wherein any hydrogen atom of a CH unit may be replaced by alkyl;

Y, independently for each occurrence, represents H or $CH_2O(CO)R_7$;

$R_7$, independently for each occurrence, represents H or substituted or unsubstituted alkyl, alkoxy, aminoalkyl, alkylaminoalkyl, heterocyclylalkyl, arylalkyl, or heterocyclylalkoxy;

Z represents H or $R_3(CO)$;

$R_1$ and $R_2$ each independently represent H, alkyl, alkoxy or hydroxy;

$R_3$, independently for each occurrence, represents substituted or unsubstituted alkyl, hydroxyalkyl, aminoalkyl, acylaminoalkyl, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, heteroaryloxyalkyl or $C(R_8)(R_9)(R_{10})$, $N(R_4)(R_5)$ or $OR_6$, wherein any free hydroxyl group may be acylated to form $C(O)R_7$;

$R_4$ and $R_5$ each independently represent H or substituted or unsubstituted alkyl, hydroxyalkyl, acyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form $C(O)R_7$;

$R_6$, independently for each occurrence, represents substituted or unsubstituted alkyl, hydroxyalkyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form $C(O)R_7$; and $R_8$, $R_9$ and $R_{10}$ each independently represent H or substituted or unsubstituted alkyl, hydroxy, hydroxyalkyl, amino, acylamino, aminoalkyl, acylaminoalkyl, alkoxycarbonyl, alkoxycarbonylamino, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, or $R_8$ and $R_9$ together with the carbon to which they are attached, form a carbocyclic or heterocyclic ring system, wherein any free hydroxyl group may be acylated to form $C(O)R_7$, and wherein at least two of $R_8$, $R_9$ and $R_{10}$ are not H.

In certain embodiments wherein alkyl, hydroxyalkyl, amino, acylamino, aminoalkyl, acylaminoalkyl, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl are substituted, they are substituted with one or more substituents selected from substituted or unsubstituted alkyl, such as perfluoroalkyl (e.g., trifluoromethyl), alkenyl, alkoxy, alkoxyalkyl, aryl, aralkyl, arylalkoxy, aryloxy, aryloxyalkyl, hydroxyl, halo, alkoxy, such as perfluoroalkoxy (e.g., trifluoromethoxy), alkoxyalkoxy, hydroxyalkyl, hydroxyalkylamino, hydroxyalkoxy, amino, aminoalkyl, alkylamino, aminoalkylalkoxy, aminoalkoxy, acylamino, acylaminoalkyl, such as perfluoro acylaminoalkyl (e.g., trifluoromethylacylaminoalkyl), acyloxy, cycloalkyl, cycloalkylalkyl, cycloalkylalkoxy, heterocyclyl, heterocyclylalkyl, heterocyclyloxy, heterocyclylalkoxy, heteroaryl, heteroarylalkyl, heteroarylalkoxy, heteroaryloxy, heteroaryloxyalkyl, heterocyclylaminoalkyl, heterocyclylaminoalkoxy, amido, amidoalkyl, amidine, imine, oxo, carbonyl (such as carboxyl, alkoxycarbonyl, formyl, or acyl, including perfluoroacyl (e.g., $C(O)CF_3$)), carbonylalkyl (such as carboxyalkyl, alkoxycarbonylalkyl, formylalkyl, or acylalkyl, including perfluoroacylalkyl (e.g., -alkylC(O)CF$_3$)), carbamate, carbamatealkyl, urea, ureaalkyl, sulfate, sulfonate, sulfamoyl, sulfone, sulfonamide, sulfonamidealkyl, cyano, nitro, azido, sulfhydryl, alkylthio, thiocarbonyl (such as thioester, thioacetate, or thioformate), phosphoryl, phosphate, phosphonate or phosphinate.

In certain embodiments, L represents $CH_2SCH_2$, $CH_2CH_2$, $CH_2CH_2CH_2$, $CH_2$, $CH_2S$, $SCH_2$, or $CH_2NHCH_2$, wherein any hydrogen atom of a $CH_2$ unit may be replaced by alkyl or alkoxy, and any hydrogen atom of a $CH_2$ unit of $CH_2CH_2$, $CH_2CH_2CH_2$ or $CH_2$ may be replaced by hydroxyl. In certain embodiments, L represents $CH_2SCH_2$, $CH_2CH_2$, $CH_2S$ or $SCH_2$. In certain embodiments, L represents $CH_2CH_2$. In certain embodiments, L is not $CH_2SCH_2$.

In certain embodiments, Y represents H.

In certain embodiments, X represents S or CH=CH. In certain embodiments, one or both X represents CH=CH. In certain embodiments, each X represents S. In certain embodiments, one X represents S and the other X represents CH=CH.

In certain embodiments, Z represents $R_3(CO)$. In certain embodiments wherein Z is $R_3(CO)$, each occurrence of $R_3$ is not identical (e.g., the compound of formula I is not symmetrical).

In certain embodiments, $R_1$ and $R_2$ each represent H.

In certain embodiments, $R_3$ represents arylalkyl, heteroarylalkyl, cycloalkyl or heterocycloalkyl. In certain embodiments, $R_3$ represents $C(R_8)(R_9)(R_{10})$, wherein $R_8$ represents aryl, arylalkyl, heteroaryl or heteroaralkyl, such as aryl, arylalkyl or heteroaryl, $R_9$ represents H, and $R_{10}$ represents hydroxy, hydroxyalkyl, alkoxy or alkoxyalkyl, such as hydroxy, hydroxyalkyl or alkoxy.

In certain embodiments, L represents $CH_2SCH_2$, $CH_2CH_2$, $CH_2S$ or $SCH_2$, such as $CH_2CH_2$, $CH_2S$ or $SCH_2$, Y represents H, X represents S, Z represents $R_3(CO)$, $R_1$ and $R_2$ each represent H, and each $R_3$ represents arylalkyl, heteroarylalkyl, cycloalkyl or heterocycloalkyl. In certain such embodiments, each occurrence of $R_3$ is identical.

In certain embodiments, L represents $CH_2SCH_2$, $CH_2CH_2$, $CH_2S$ or $SCH_2$, Y represents H, X represents S, Z represents $R_3(CO)$, $R_1$ and $R_2$ each represent H, and each $R_3$ represents $C(R_8)(R_9)(R_{10})$, wherein $R_8$ represents aryl, arylalkyl, heteroaryl or heteroaralkyl, such as aryl, arylalkyl or heteroaryl, $R_9$ represents H, and $R_{10}$ represents hydroxy, hydroxyalkyl, alkoxy or alkoxyalkyl, such as hydroxy, hydroxyalkyl or alkoxy. In certain such embodiments, each occurrence of $R_3$ is identical.

In certain embodiments, L represents $CH_2CH_2$, Y represents H, X represents S or CH=CH, Z represents $R_3(CO)$, $R_1$ and $R_2$ each represent H, and each $R_3$ represents substituted or unsubstituted arylalkyl, heteroarylalkyl, cycloalkyl or heterocycloalkyl. In certain such embodiments, each X represents S. In other embodiments, one or both occurrences of X represents CH=CH, such as one occurrence of X represents S and the other occurrence of X represents CH=CH. In certain embodiments of the foregoing, each occurrence of $R_3$ is identical. In other embodiments of the foregoing wherein one occurrence of X represents S and the other occurrence of X represents CH=CH, the two occurrences of $R_3$ are not identical.

In certain embodiments, L represents $CH_2CH_2$, Y represents H, X represents S, Z represents $R_3(CO)$, $R_1$ and $R_2$ each represent H, and each $R_3$ represents $C(R_8)(R_9)(R_{10})$, wherein $R_8$ represents aryl, arylalkyl or heteroaryl, $R_9$ represents H, and $R_{10}$ represents hydroxy, hydroxyalkyl or alkoxy. In certain such embodiments, $R_8$ represents aryl and $R_{10}$ represents hydroxyalkyl. In certain such embodiments, each occurrence of $R_3$ is identical.

In certain embodiments wherein L represents $CH_2$, $CH_2CH_2CH_2$ or $CH_2CH_2$, X represents O, and Z represents $R_3(CO)$, both $R_3$ groups are not alkyl, such as methyl, or $C(R_8)(R_9)(R_{10})$, wherein $R_8$, $R_9$ and $R_{10}$ are each independently hydrogen or alkyl.

In certain embodiments wherein L represents $CH_2CH_2$, X represents S, and Z represents $R_3(CO)$, both $R_3$ groups are not phenyl or heteroaryl, such as 2-furyl.

In certain embodiments wherein L represents $CH_2CH_2$, X represents O, and Z represents $R_3(CO)$, both $R_3$ groups are not $N(R_4)(R_5)$ wherein $R_4$ is aryl, such as phenyl, and $R_5$ is H.

In certain embodiments wherein L represents $CH_2SCH_2$, X represents S, and Z represents $R_3(CO)$, both $R_3$ groups are not aryl, such as optionally substituted phenyl, aralkyl, such as benzyl, heteroaryl, such as 2-furyl, 2-thienyl or 1,2,4-trizole, substituted or unsubstituted alkyl, such as methyl, chloromethyl, dichloromethyl, n-propyl, n-butyl, t-butyl or hexyl, heterocyclyl, such as pyrimidine-2,4(1H,3H)-dione, or alkoxy, such as methoxy, pentyloxy or ethoxy.

In certain embodiments wherein L represents $CH_2SCH_2$, X represents S, and Z represents $R_3(CO)$, both $R_3$ groups are not $N(R_4)(R_5)$ wherein $R_4$ is aryl, such as substituted or unsubstituted phenyl (e.g., phenyl, 3-tolyl, 4-tolyl, 4-bromophenyl or 4-nitrophenyl), and $R_5$ is H.

In certain embodiments wherein L represents $CH_2CH_2CH_2$, X represents S, and Z represents $R_3(CO)$, both $R_3$ groups are not alkyl, such as methyl, ethyl, or propyl, cycloalkyl, such as cyclohexyl, or $C(R_8)(R_9)(R_{10})$, wherein any of $R_8$, $R_9$ and $R_{10}$ together with the C to which they are attached, form any of the foregoing.

In certain embodiments, the compound is not one of the following:
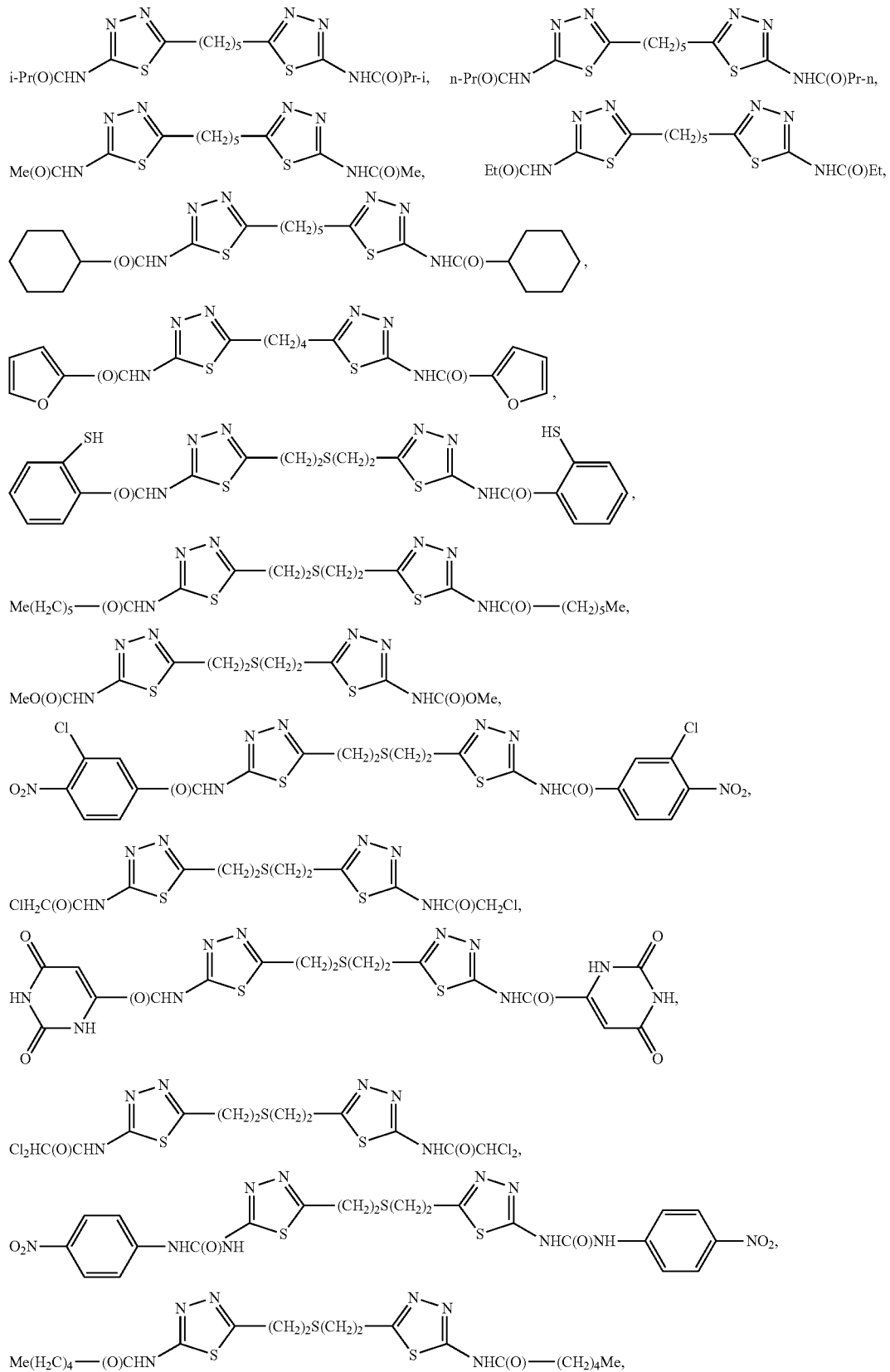

-continued
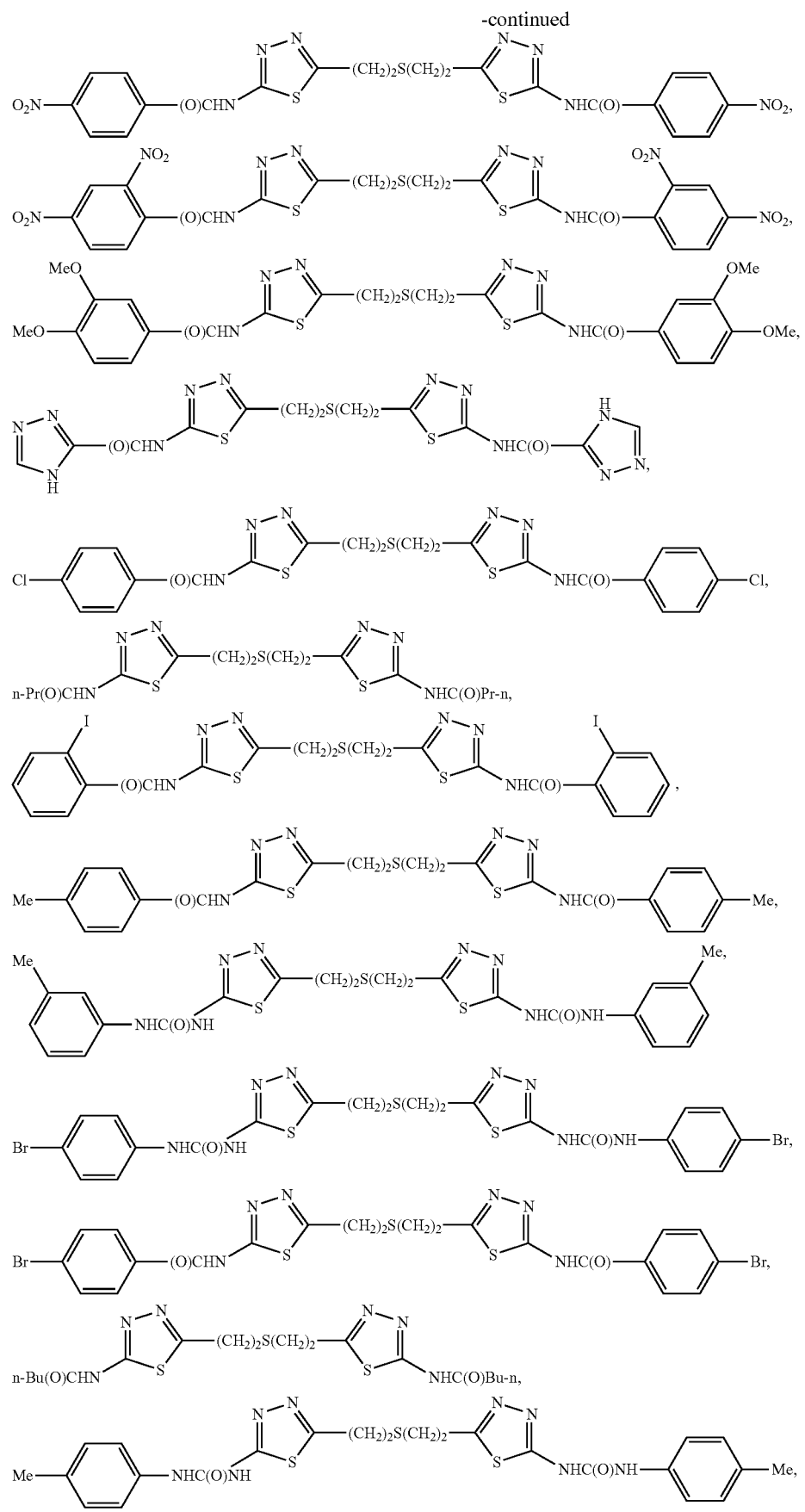

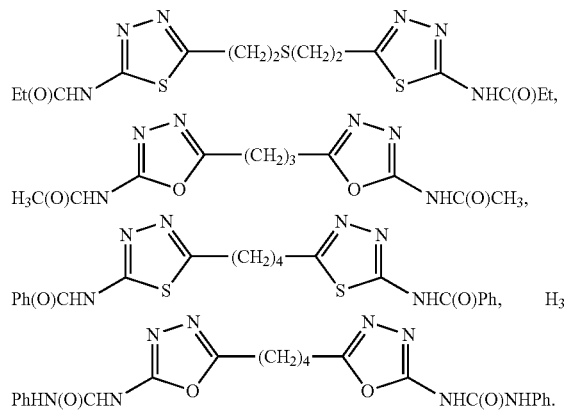
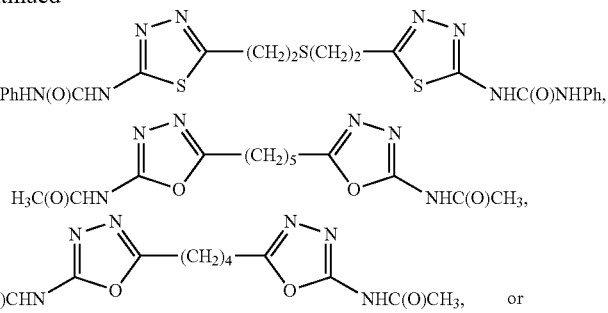
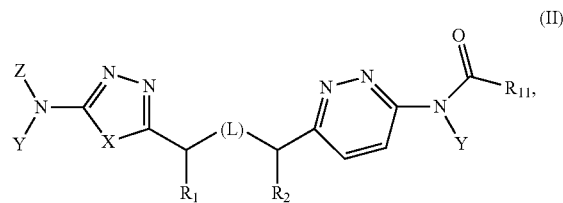

In further embodiments of the methods of the invention, the glutaminase inhibitor is a compound of formula II,

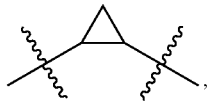
(II)

or a pharmaceutically acceptable salt thereof, wherein:

L represents $CH_2SCH_2$, $CH_2CH_2$, $CH_2CH_2CH_2$, $CH_2$, $CH_2S$, $SCH_2$, $CH_2NHCH_2$, $CH=CH$, or preferably $CH_2CH_2$, wherein any hydrogen atom of a CH or $CH_2$ unit may be replaced by alkyl or alkoxy, any hydrogen of an NH unit may be replaced by alkyl, and any hydrogen atom of a $CH_2$ unit of $CH_2CH_2$, $CH_2CH_2CH_2$ or $CH_2$ may be replaced by hydroxy;

X represents S, O or $CH=CH$, preferably S or $CH=CH$, wherein any hydrogen atom of a CH unit may be replaced by alkyl;

Y, independently for each occurrence, represents H or $CH_2O(CO)R_7$ $R_7$, independently for each occurrence, represents H or substituted or unsubstituted alkyl, alkoxy, aminoalkyl, alkylaminoalkyl, heterocyclylalkyl, arylalkyl, or heterocyclylalkoxy;

Z represents H or $R_3(CO)$;

$R_1$ and $R_2$ each independently represent H, alkyl, alkoxy or hydroxy, preferably H;

$R_3$ represents substituted or unsubstituted alkyl, hydroxyalkyl, aminoalkyl, acylaminoalkyl, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, heteroaryloxyalkyl or $C(R_8)(R_9)(R_{10})$, $N(R_4)(R_5)$ or $OR_6$, wherein any free hydroxyl group may be acylated to form $C(O)R_7$;

$R_4$ and $R_5$ each independently represent H or substituted or unsubstituted alkyl, hydroxyalkyl, acyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form $C(O)R_7$;

$R_6$, independently for each occurrence, represents substituted or unsubstituted alkyl, hydroxyalkyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form $C(O)R_7$; and $R_8$, $R_9$ and $R_{10}$ each independently represent H or substituted or unsubstituted alkyl, hydroxy, hydroxyalkyl, amino, acylamino, aminoalkyl, acylaminoalkyl, alkoxycarbonyl, alkoxycarbonylamino, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, or $R_8$ and $R_9$ together with the carbon to which they are attached, form a carbocyclic or heterocyclic ring system, wherein any free hydroxyl group may be acylated to form $C(O)R_7$, and wherein at least two of $R_8$, $R_9$ and $R_{10}$ are not H;

$R_{11}$ represents substituted or unsubstituted aryl, arylalkyl, aryloxy, aryloxyalkyl, heteroaryl, heteroarylalkyl, heteroaryloxy, or heteroaryloxyalkyl, or $C(R_{12})(R_{13})(R_{14})$, $N(R_4)(R_{14})$ or $OR_{14}$, wherein any free hydroxyl group may be acylated to form $C(O)R_7$;

$R_{12}$ and $R_{13}$ each independently respresent H or substituted or unsubstituted alkyl, hydroxy, hydroxyalkyl, amino, acylamino, aminoalkyl, acylaminoalkyl, alkoxycarbonyl, alkoxycarbonylamino, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form $C(O)R_7$, and wherein both of $R_{12}$ and $R_{13}$ are not H; and $R_{14}$ represents substituted or unsubstituted aryl, arylalkyl, aryloxy, aryloxyalkyl, heteroaryl, heteroarylalkyl, heteroaryloxy, or heteroaryloxyalkyl.

In certain embodiments wherein alkyl, hydroxyalkyl, amino, acylamino, aminoalkyl, acylaminoalkyl, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl are substituted, they are substituted with one or more substituents selected from substituted or unsubstituted alkyl, such as perfluoroalkyl (e.g., trifluoromethyl), alkenyl, alkoxy, alkoxyalkyl, aryl, aralkyl, arylalkoxy, aryloxy, aryloxyalkyl, hydroxyl, halo, alkoxy, such as perfluoroalkoxy (e.g., trifluoromethylalkoxy), alkoxyalkoxy, hydroxyalkyl, hydroxyalkylamino, hydroxyalkoxy, amino, aminoalkyl, alkylamino, aminoalkylalkoxy, aminoalkoxy, acylamino, acylaminoalkyl, such as perfluoro acylaminoalkyl (e.g., trifluoromethylacylaminoalkyl), acyloxy, cycloalkyl, cycloalkylalkyl, cycloalkylalkoxy, heterocyclyl, heterocyclylalkyl, heterocyclyloxy, heterocyclylalkoxy, heteroaryl, heteroarylalkyl, heteroarylalkoxy, heteroaryloxy, heteroaryloxyalkyl, heterocyclylaminoalkyl, heterocyclylaminoalkoxy, amido, amidoalkyl, amidine, imine, oxo, carbonyl (such as carboxyl, alkoxycarbonyl, formyl, or acyl, including perfluoroacyl (e.g., $C(O)CF_3$)), carbonylalkyl (such as carboxyalkyl, alkoxycarbonylalkyl, formylalkyl, or acylalkyl, including perfluoroacylalkyl (e.g., -alkyl$C(O)CF_3$)), carbamate, carbamatealkyl, urea, ureaalkyl, sulfate, sulfonate, sulfamoyl, sulfone, sulfonamide, sulfonamidealkyl, cyano, nitro, azido, sulfhydryl, alkylthio, thiocarbonyl (such as thioester, thioacetate, or thioformate), phosphoryl, phosphate, phosphonate or phosphinate.

In certain embodiments, $R_{11}$ represents substituted or unsubstituted arylalkyl, such as substituted or unsubstituted benzyl.

In certain embodiments, L represents $CH_2SCH_2$, $CH_2CH_2$, $CH_2CH_2CH_2$, $CH_2$, $CH_2S$, $SCH_2$, or $CH_2NHCH_2$, wherein any hydrogen atom of a $CH_2$ unit may be replaced by alkyl or alkoxy, and any hydrogen atom of a $CH_2$ unit of $CH_2CH_2$, $CH_2CH_2CH_2$ or $CH_2$ may be replaced by hydroxyl. In certain embodiments, L represents $CH_2SCH_2$, $CH_2CH_2$, $CH_2S$ or $SCH_2$, preferably $CH_2CH_2$. In certain embodiments, L is not $CH_2SCH_2$.

In certain embodiments, each Y represents H. In other embodiments, at least one Y is $CH_2O(CO)R_7$.

In certain embodiments, X represents S or CH=CH. In certain embodiments, X represents S.

In certain embodiments, $R_1$ and $R_2$ each represent H.

In certain embodiments, Z represents $R_3(CO)$. In certain embodiments wherein Z is $R_3(CO)$, $R_3$ and $R_{11}$ are not identical (e.g., the compound of formula I is not symmetrical).

In certain embodiments, Z represents $R_3(CO)$ and $R_3$ represents arylalkyl, heteroarylalkyl, cycloalkyl or heterocycloalkyl. In certain embodiments, Z represents $R_3(CO)$ and $R_3$ represents $C(R_8)(R_9)(R_{10})$, wherein $R_8$ represents aryl, arylalkyl, heteroaryl or heteroaralkyl, such as aryl, arylalkyl or heteroaryl, $R_9$ represents H, and $R_{10}$ represents hydroxy, hydroxyalkyl, alkoxy or alkoxyalkyl, such as hydroxy, hydroxyalkyl or alkoxy. In certain embodiments, Z represents $R_3(CO)$ and $R_3$ represents heteroarylalkyl.

In certain embodiments, L represents $CH_2SCH_2$, $CH_2CH_2$, $CH_2S$ or $SCH_2$, such as $CH_2CH_2$, Y represents H, X represents S, Z represents $R_3(CO)$, $R_1$ and $R_2$ each represent H, $R_3$ represents arylalkyl, heteroarylalkyl, cycloalkyl or heterocycloalkyl, and $R_{11}$ represents arylalkyl. In certain such embodiments, $R_3$ represents heteroarylalkyl.

In certain embodiments, L represents $CH_2SCH_2$, $CH_2CH_2$, $CH_2S$ or $SCH_2$, such as $CH_2CH_2$, Y represents H, X represents S, Z represents $R_3(CO)$, $R_1$ and $R_2$ each represent H, and $R_3$ represents $C(R_8)(R_9)(R_{10})$, wherein $R_8$ represents aryl, arylalkyl, heteroaryl or heteroaralkyl, such as aryl, arylalkyl or heteroaryl, $R_9$ represents H, and $R_{10}$ represents hydroxy, hydroxyalkyl, alkoxy or alkoxyalkyl, such as hydroxy, hydroxyalkyl or alkoxy, and $R_{11}$ represents arylalkyl. In certain such embodiments, $R_8$ represents heteroaryl.

In certain embodiments, L represents $CH_2CH_2$, Y represents H, X represents S or CH=CH, such as S, Z represents $R_3(CO)$, $R_1$ and $R_2$ each represent H, $R_3$ represents substituted or unsubstituted arylalkyl, heteroarylalkyl, cycloalkyl or heterocycloalkyl, and $R_{11}$ represents arylalkyl. In certain such embodiments, $R_3$ represents heteroarylalkyl.

In certain embodiments, L represents $CH_2CH_2$, Y represents H, X represents S, Z represents $R_3(CO)$, $R_1$ and $R_2$ each represent H, $R_3$ represents $C(R_8)(R_9)(R_{10})$, wherein $R_8$ represents aryl, arylalkyl or heteroaryl, $R_9$ represents H, and $R_{10}$ represents hydroxy, hydroxyalkyl or alkoxy, and $R_{11}$ represents arylalkyl. In certain such embodiments, $R_8$ represents aryl and $R_{10}$ represents hydroxyalkyl. In certain other embodiments, $R_8$ represents heteroaryl.

In certain embodiments, the compound is selected from any one of the compounds described in U.S. Pat. No. 8,604,016 or U.S. Patent Application Publication No. 2014/0194421, the contents of both of which are incorporated herein by reference.

In certain embodiments of the methods described herein, the glutaminase inhibitor is a compound having the structure of Formula (III):

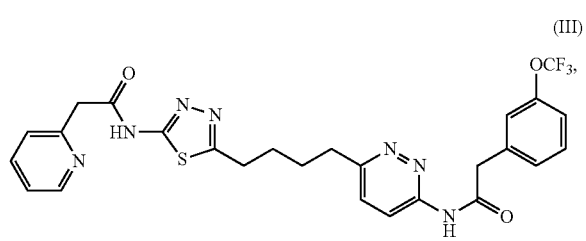 [SMILES: O=C(Cc1cccc(OC(F)(F)F)c1)Nc1ccc(CCCCc2nnc(NC(=O)Cc3ccccn3)s2)nn1]

or a pharmaceutically acceptable salt thereof. The compound of formula (III) is alternatively referred to herein as CB-839 or Compound 670.

In certain embodiments of the methods of treating lung cancer described herein, the glutaminase inhibitor is a compound selected from any of the compounds disclosed in Table 1.

TABLE 1

Selected Compounds of Formula I

| Compound ID | Structure |
|---|---|
| 1 | 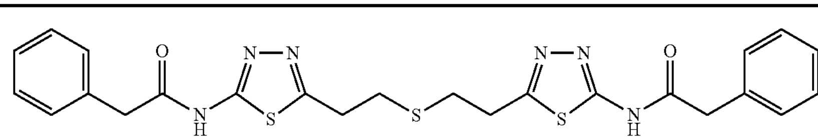 |

TABLE 1-continued

Selected Compounds of Formula I

| Compound ID | Structure |
|---|---|
| 2 | 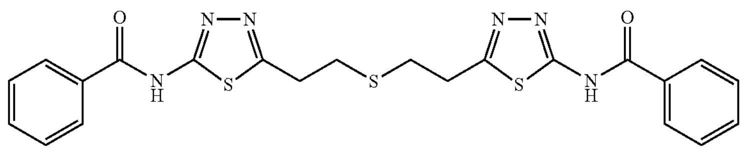 [SMILES: O=C(Nc1nnc(CCSCCc2nnc(NC(=O)c3ccccc3)s2)s1)c1ccccc1] |
| 3 | 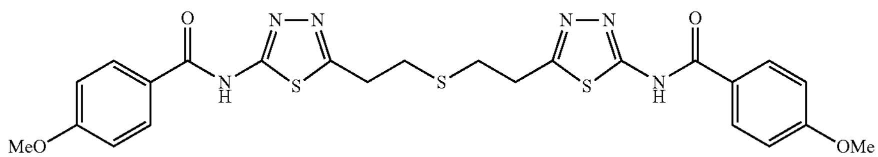 [SMILES: COc1ccc(C(=O)Nc2nnc(CCSCCc3nnc(NC(=O)c4ccc(OC)cc4)s3)s2)cc1] |
| 4 | 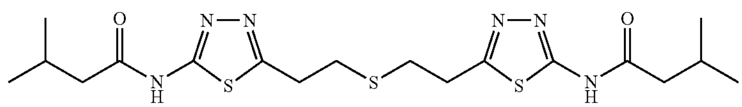 [SMILES: CC(C)CC(=O)Nc1nnc(CCSCCc2nnc(NC(=O)CC(C)C)s2)s1] |
| 5 | 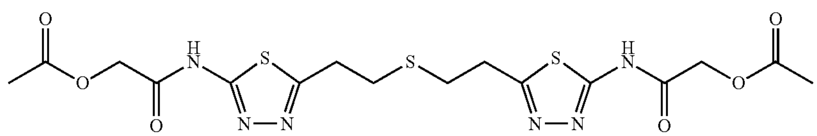 [SMILES: CC(=O)OCC(=O)Nc1nnc(CCSCCc2nnc(NC(=O)COC(C)=O)s2)s1] |
| 6 | 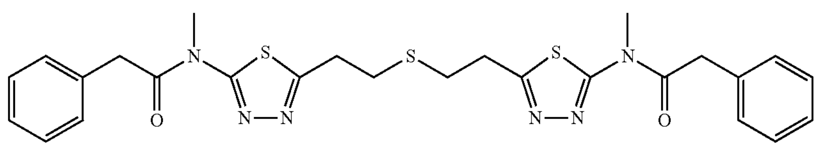 [SMILES: CN(C(=O)Cc1ccccc1)c1nnc(CCSCCc2nnc(N(C)C(=O)Cc3ccccc3)s2)s1] |
| 7 | 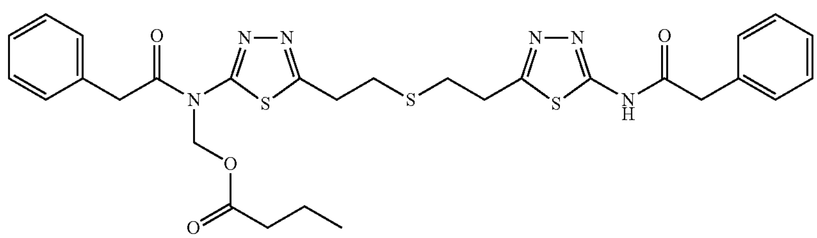 [SMILES: CCCC(=O)OCN(C(=O)Cc1ccccc1)c1nnc(CCSCCc2nnc(NC(=O)Cc3ccccc3)s2)s1] |
| 8 | 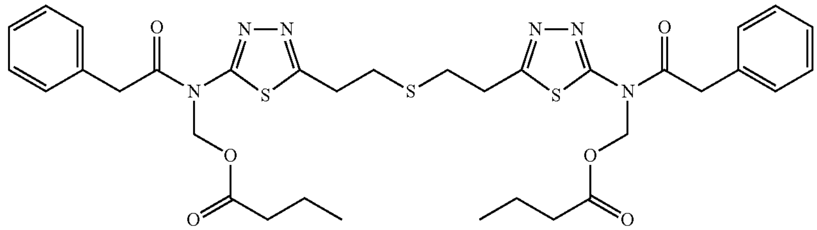 [SMILES: CCCC(=O)OCN(C(=O)Cc1ccccc1)c1nnc(CCSCCc2nnc(N(COC(=O)CCC)C(=O)Cc3ccccc3)s2)s1] |

TABLE 1-continued

Selected Compounds of Formula I

| Compound ID | Structure |
|---|---|
| 9 | 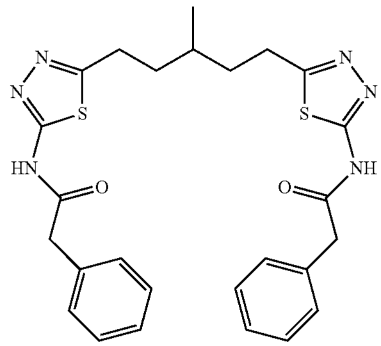 [SMILES: CC(CCc1nnc(NC(=O)Cc2ccccc2)s1)CCc1nnc(NC(=O)Cc2ccccc2)s1] |
| 10 | 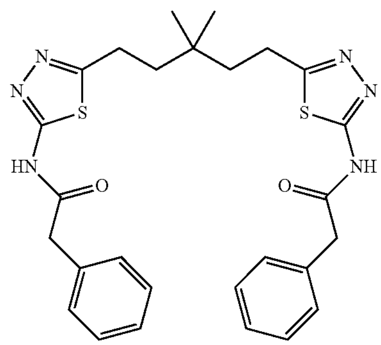 [SMILES: CC(C)(CCc1nnc(NC(=O)Cc2ccccc2)s1)CCc1nnc(NC(=O)Cc2ccccc2)s1] |
| 11 | 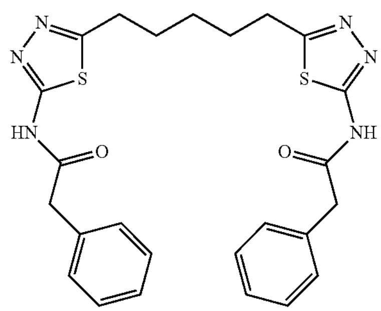 [SMILES: O=C(Cc1ccccc1)Nc1nnc(CCCCCc2nnc(NC(=O)Cc3ccccc3)s2)s1] |
| 12 | 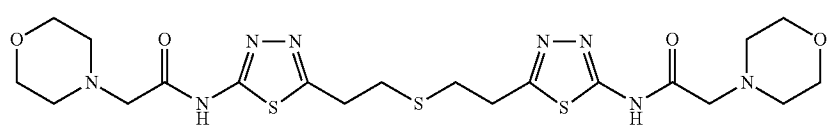 [SMILES: O=C(CN1CCOCC1)Nc1nnc(CCSCCc2nnc(NC(=O)CN3CCOCC3)s2)s1] |
| 13 | 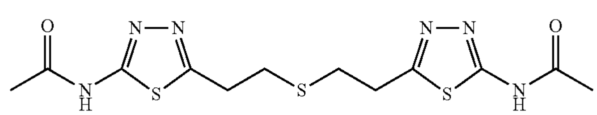 [SMILES: CC(=O)Nc1nnc(CCSCCc2nnc(NC(C)=O)s2)s1] |

TABLE 1-continued
Selected Compounds of Formula I
| Compound ID | Structure |
|---|---|
| 14 | 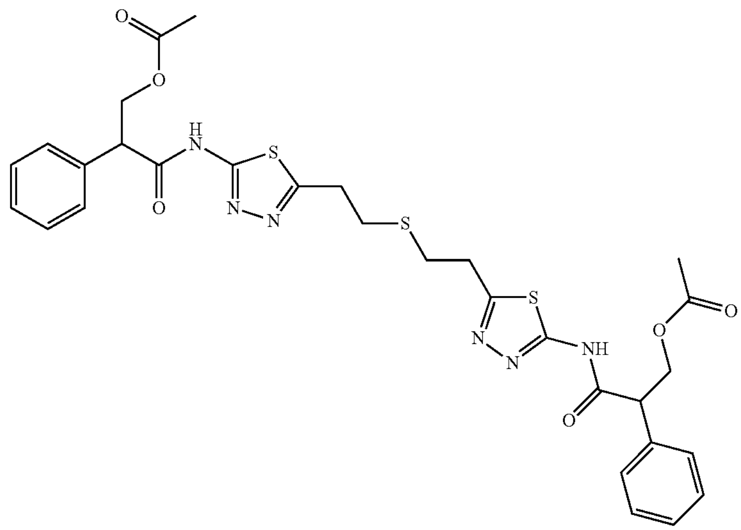 [SMILES: CC(=O)OCC(C(=O)Nc1nnc(CCSCCc2nnc(NC(=O)C(COC(C)=O)c3ccccc3)s2)s1)c1ccccc1] |
| 15 | 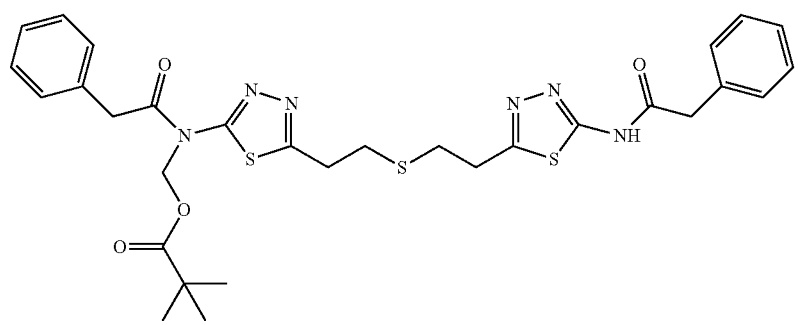 [SMILES: CC(C)(C)C(=O)OCN(C(=O)Cc1ccccc1)c1nnc(CCSCCc2nnc(NC(=O)Cc3ccccc3)s2)s1] |
| 16 | 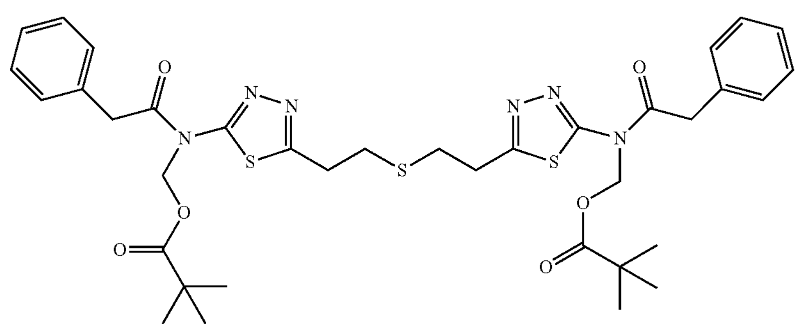 [SMILES: CC(C)(C)C(=O)OCN(C(=O)Cc1ccccc1)c1nnc(CCSCCc2nnc(N(COC(=O)C(C)(C)C)C(=O)Cc3ccccc3)s2)s1] |
| 17 | 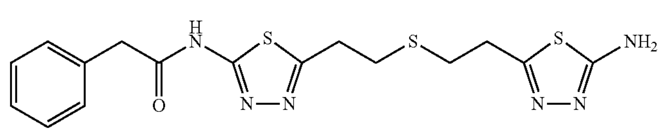 [SMILES: Nc1nnc(CCSCCc2nnc(NC(=O)Cc3ccccc3)s2)s1] |
| 18 | 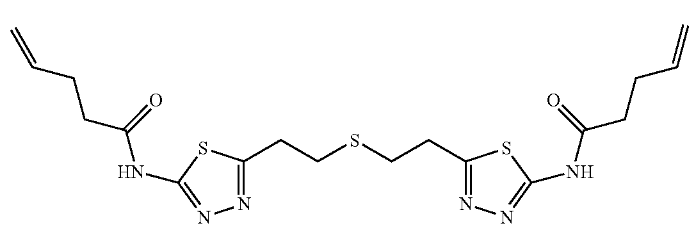 [SMILES: C=CCCC(=O)Nc1nnc(CCSCCc2nnc(NC(=O)CCC=C)s2)s1] |

TABLE 1-continued

Selected Compounds of Formula I

| Compound ID | Structure |
|---|---|
| 19 | 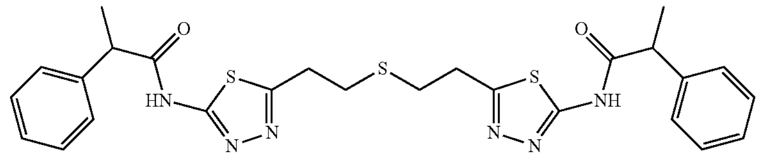 [SMILES: CC(C(=O)Nc1nnc(CCSCCc2nnc(NC(=O)C(C)c3ccccc3)s2)s1)c1ccccc1] |
| 20 | 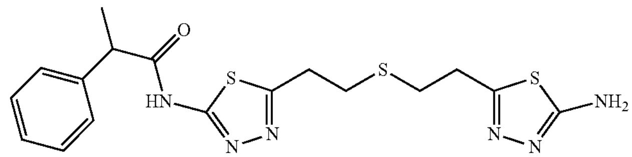 [SMILES: CC(C(=O)Nc1nnc(CCSCCc2nnc(N)s2)s1)c1ccccc1] |
| 21 | 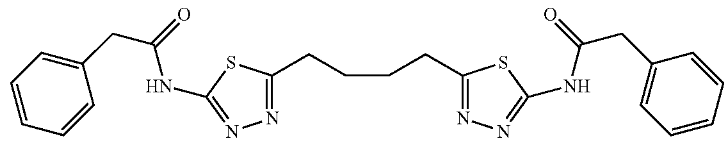 [SMILES: O=C(Cc1ccccc1)Nc1nnc(CCCCc2nnc(NC(=O)Cc3ccccc3)s2)s1] |
| 22 | 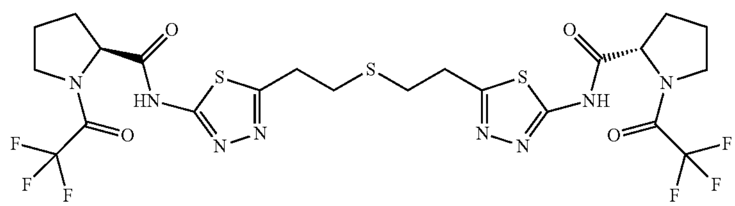 [SMILES: O=C(Nc1nnc(CCSCCc2nnc(NC(=O)[C@@H]3CCCN3C(=O)C(F)(F)F)s2)s1)[C@@H]1CCCN1C(=O)C(F)(F)F] |
| 23 | 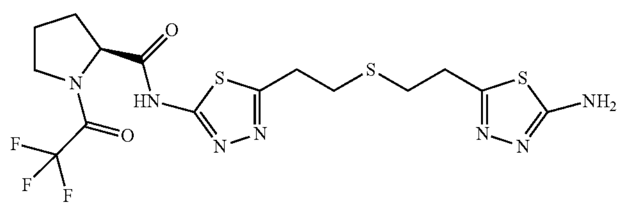 [SMILES: Nc1nnc(CCSCCc2nnc(NC(=O)[C@@H]3CCCN3C(=O)C(F)(F)F)s2)s1] |
| 24 | 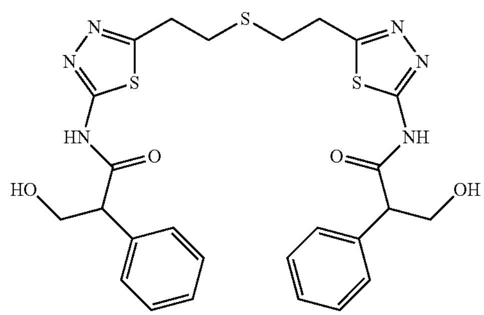 [SMILES: O=C(Nc1nnc(CCSCCc2nnc(NC(=O)C(CO)c3ccccc3)s2)s1)C(CO)c1ccccc1] |
| 25 | 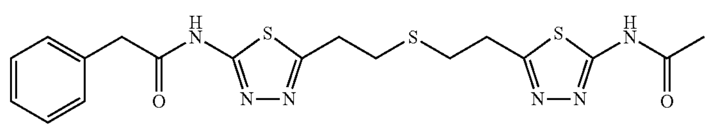 [SMILES: CC(=O)Nc1nnc(CCSCCc2nnc(NC(=O)Cc3ccccc3)s2)s1] |
| 26 | 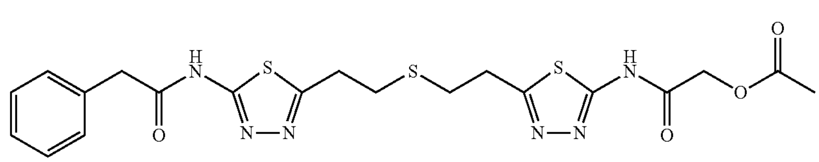 [SMILES: CC(=O)OCC(=O)Nc1nnc(CCSCCc2nnc(NC(=O)Cc3ccccc3)s2)s1] |

TABLE 1-continued

Selected Compounds of Formula I

| Compound ID | Structure |
| --- | --- |
| 27 | 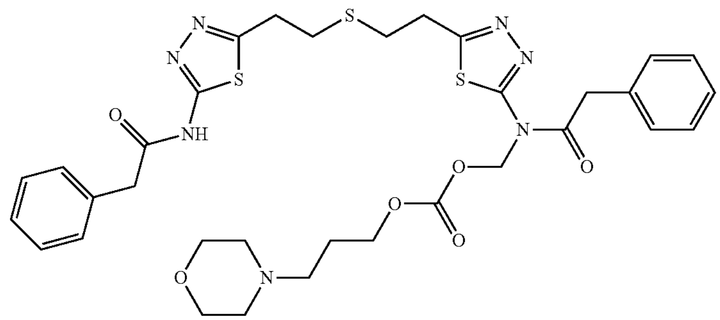 [SMILES: O=C(Cc1ccccc1)Nc1nnc(CCSCCc2nnc(N(COC(=O)OCCCN3CCOCC3)C(=O)Cc3ccccc3)s2)s1] |
| 28 | 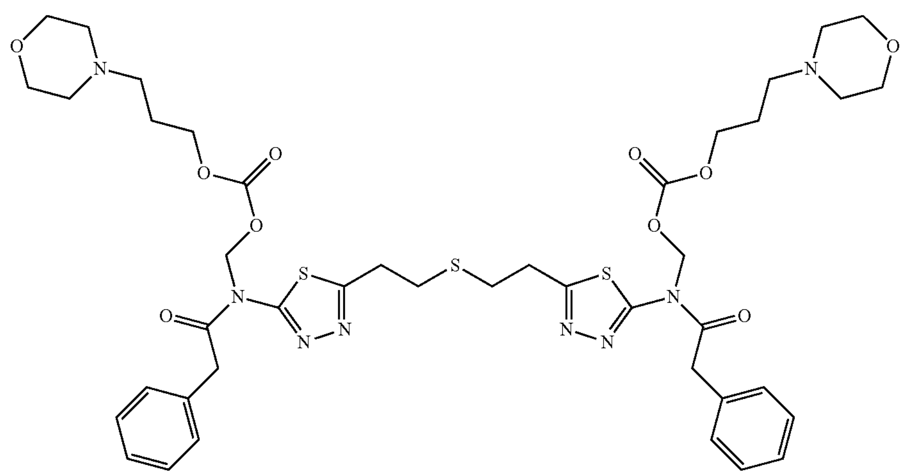 [SMILES: O=C(OCCCN1CCOCC1)OCN(C(=O)Cc1ccccc1)c1nnc(CCSCCc2nnc(N(COC(=O)OCCCN3CCOCC3)C(=O)Cc3ccccc3)s2)s1] |
| 29 | 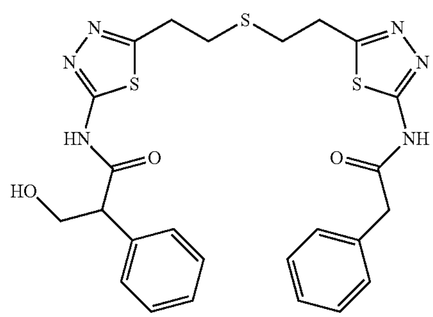 [SMILES: O=C(Cc1ccccc1)Nc1nnc(CCSCCc2nnc(NC(=O)C(CO)c3ccccc3)s2)s1] |
| 30 | 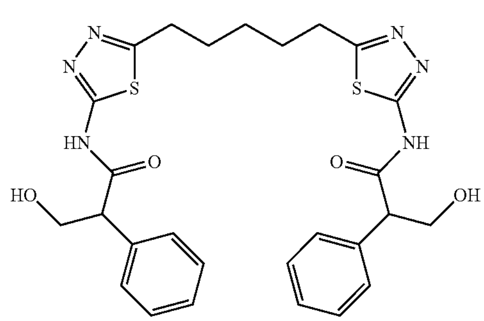 [SMILES: O=C(Nc1nnc(CCCCCc2nnc(NC(=O)C(CO)c3ccccc3)s2)s1)C(CO)c1ccccc1] |

TABLE 1-continued

Selected Compounds of Formula I

| Compound ID | Structure |
|---|---|
| 31 | 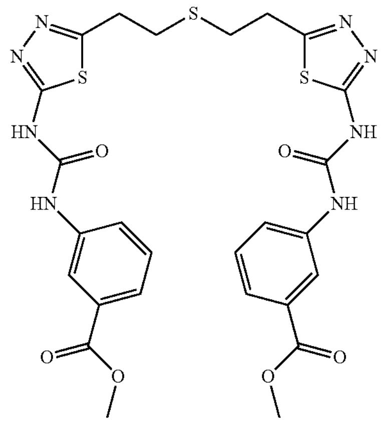 [SMILES: COC(=O)c1cccc(NC(=O)Nc2nnc(CCSCCc3nnc(NC(=O)Nc4cccc(C(=O)OC)c4)s3)s2)c1] |
| 32 | TFA |
| 33 | 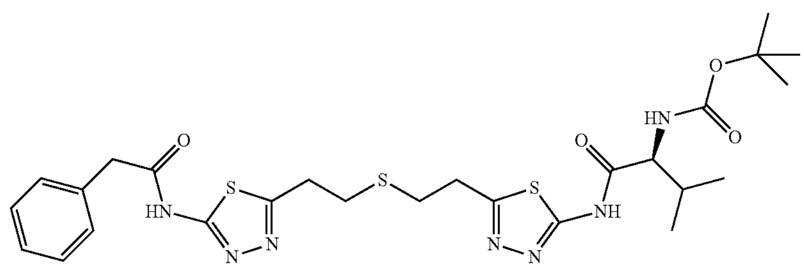 [SMILES: CC(C)[C@H](NC(=O)OC(C)(C)C)C(=O)Nc1nnc(CCSCCc2nnc(NC(=O)Cc3ccccc3)s2)s1] |
| 34 | 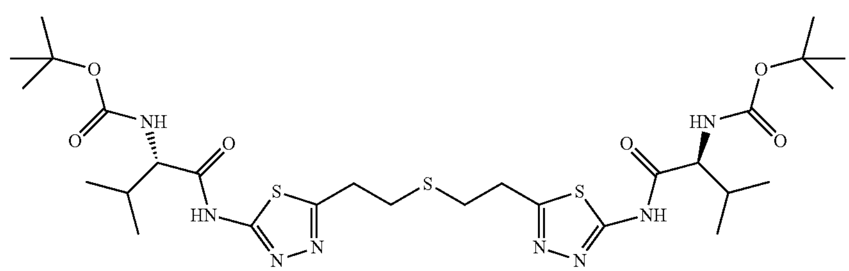 [SMILES: CC(C)[C@H](NC(=O)OC(C)(C)C)C(=O)Nc1nnc(CCSCCc2nnc(NC(=O)[C@@H](NC(=O)OC(C)(C)C)C(C)C)s2)s1] |
| 35 | 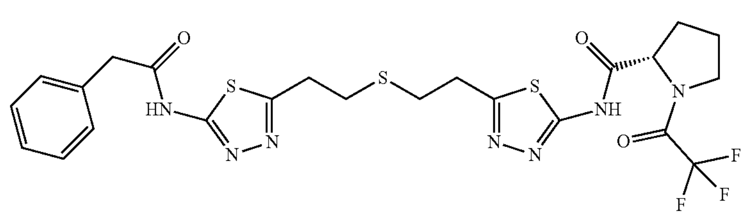 [SMILES: O=C(Cc1ccccc1)Nc1nnc(CCSCCc2nnc(NC(=O)[C@@H]3CCCN3C(=O)C(F)(F)F)s2)s1] |

TABLE 1-continued

Selected Compounds of Formula I

| Compound ID | Structure |
| --- | --- |
| 36 | 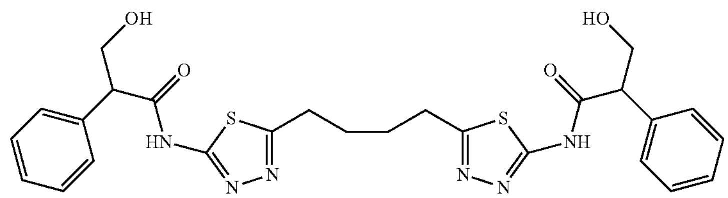 [SMILES: O=C(Nc1nnc(CCCCc2nnc(NC(=O)C(CO)c3ccccc3)s2)s1)C(CO)c1ccccc1] |
| 37 | 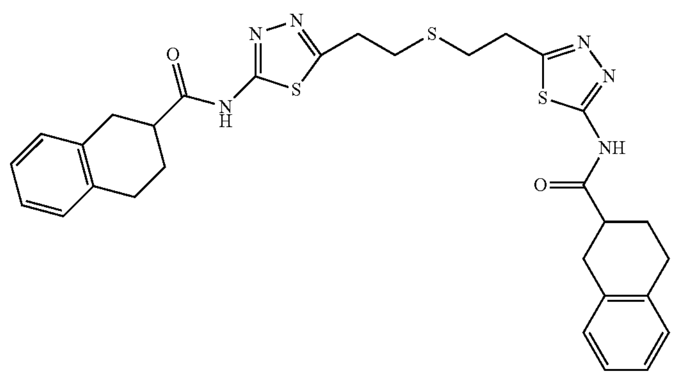 [SMILES: O=C(Nc1nnc(CCSCCc2nnc(NC(=O)C3CCc4ccccc4C3)s2)s1)C1CCc2ccccc2C1] |
| 38 | 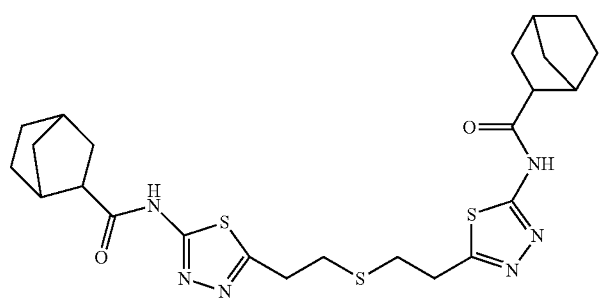 [SMILES: O=C(Nc1nnc(CCSCCc2nnc(NC(=O)C3CC4CCC3C4)s2)s1)C1CC2CCC1C2] |
| 39 | 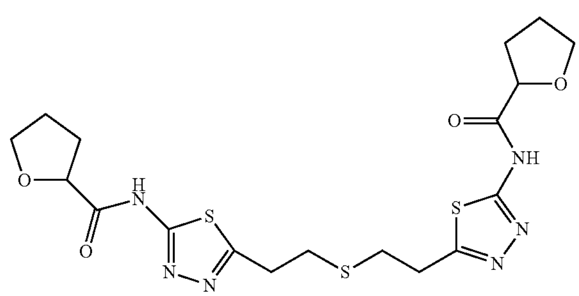 [SMILES: O=C(Nc1nnc(CCSCCc2nnc(NC(=O)C3CCCO3)s2)s1)C1CCCO1] |
| 40 | 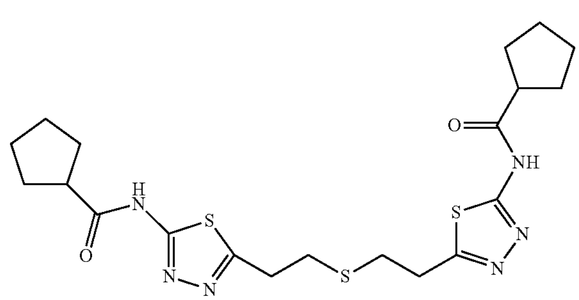 |

TABLE 1-continued

Selected Compounds of Formula I

| Compound ID | Structure |
|---|---|
| 41 | 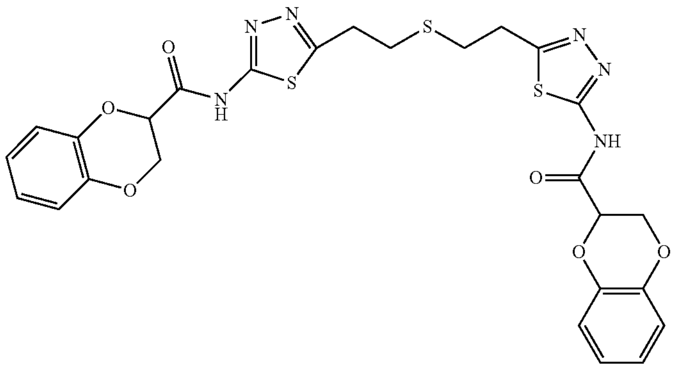 [SMILES: O=C(Nc1nnc(CCSCCc2nnc(NC(=O)C3COc4ccccc4O3)s2)s1)C1COc2ccccc2O1] |
| 42 | 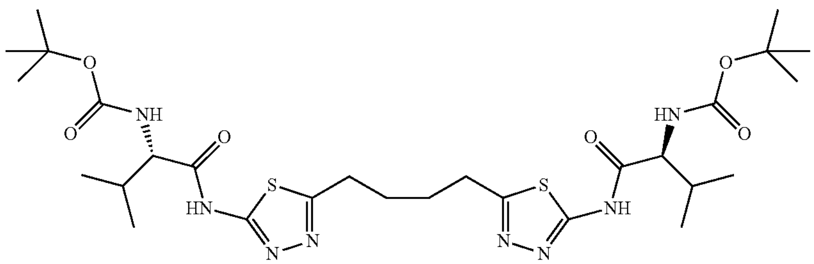 [SMILES: CC(C)[C@H](NC(=O)OC(C)(C)C)C(=O)Nc1nnc(CCCCc2nnc(NC(=O)[C@@H](NC(=O)OC(C)(C)C)C(C)C)s2)s1] |
| 43 | 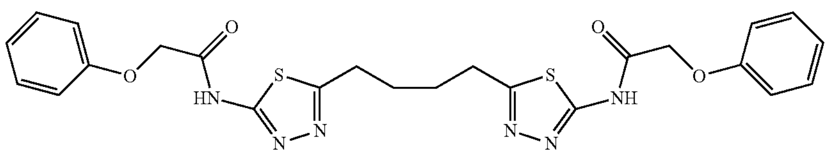 [SMILES: O=C(COc1ccccc1)Nc1nnc(CCCCc2nnc(NC(=O)COc3ccccc3)s2)s1] |
| 44 | 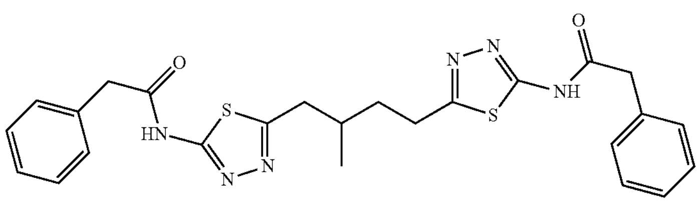 [SMILES: CC(CCc1nnc(NC(=O)Cc2ccccc2)s1)Cc1nnc(NC(=O)Cc2ccccc2)s1] |
| 45 | 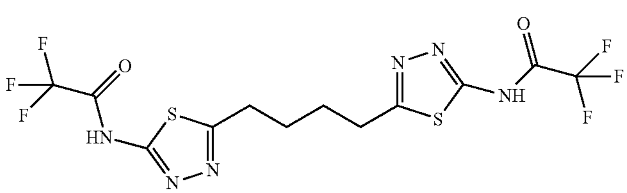 [SMILES: O=C(Nc1nnc(CCCCc2nnc(NC(=O)C(F)(F)F)s2)s1)C(F)(F)F] |
| 46 | 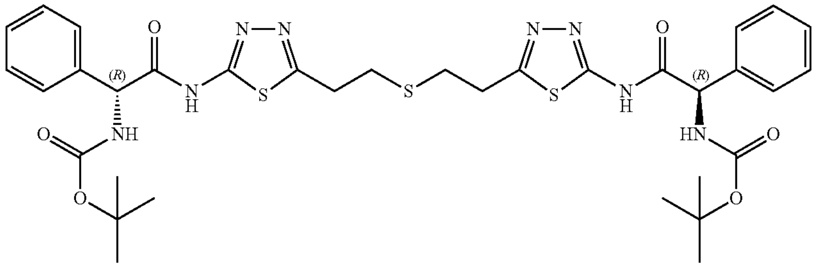 |

TABLE 1-continued

Selected Compounds of Formula I

| Compound ID | Structure |
|---|---|
| 47 | 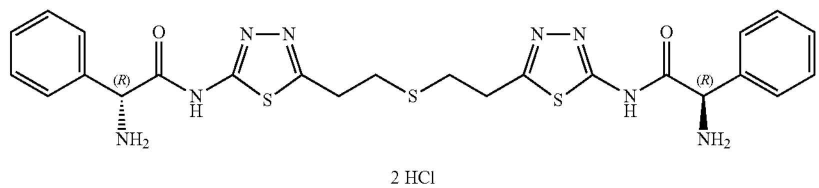 |
| 48 | 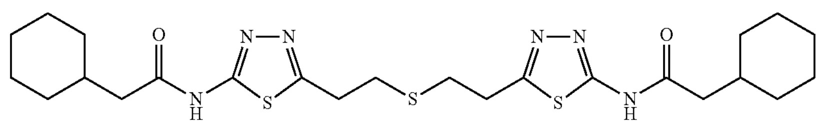 [SMILES: O=C(CC1CCCCC1)Nc1nnc(CCSCCc2nnc(NC(=O)CC3CCCCC3)s2)s1] |
| 49 | 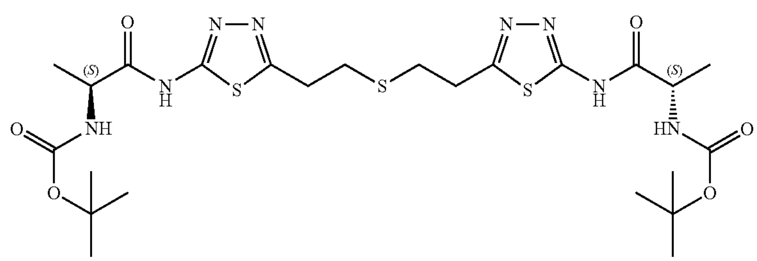 |
| 50 | 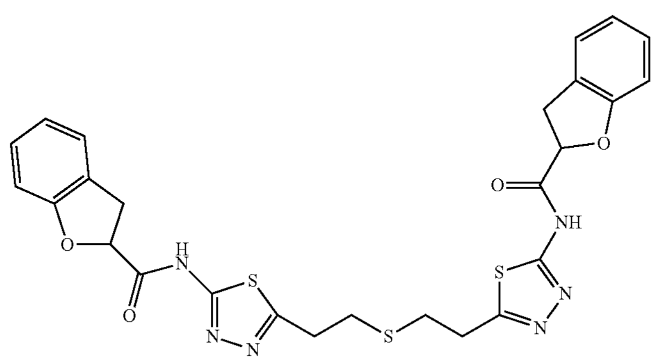 [SMILES: O=C(Nc1nnc(CCSCCc2nnc(NC(=O)C3Cc4ccccc4O3)s2)s1)C1Cc2ccccc2O1] |
| 51 | 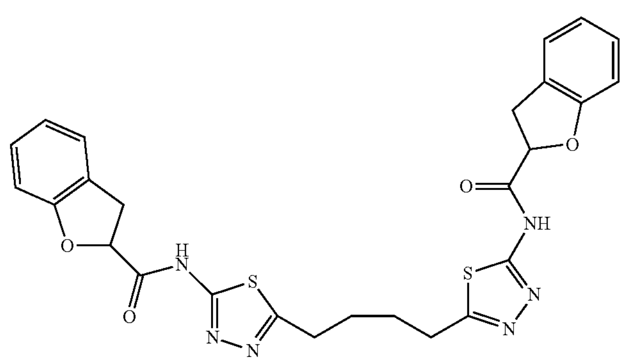 [SMILES: O=C(Nc1nnc(CCCCc2nnc(NC(=O)C3Cc4ccccc4O3)s2)s1)C1Cc2ccccc2O1] |

TABLE 1-continued

Selected Compounds of Formula I

| Compound ID | Structure |
|---|---|
| 52 | 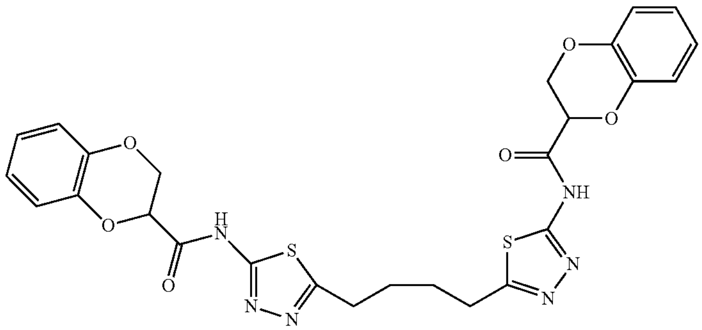 [SMILES: O=C(Nc1nnc(CCCCc2nnc(NC(=O)C3COc4ccccc4O3)s2)s1)C1COc2ccccc2O1] |
| 53 | 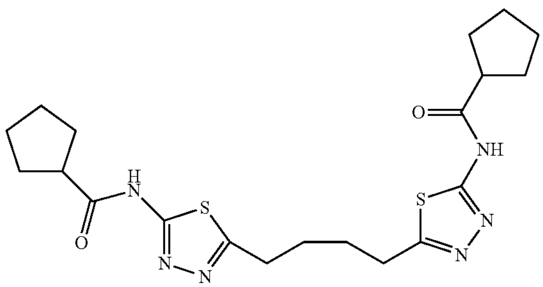 [SMILES: O=C(Nc1nnc(CCCCc2nnc(NC(=O)C3CCCC3)s2)s1)C1CCCC1] |
| 54 | 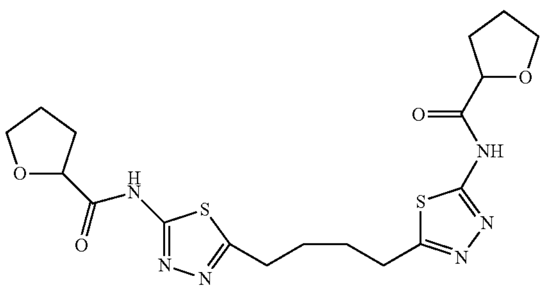 [SMILES: O=C(Nc1nnc(CCCCc2nnc(NC(=O)C3CCCO3)s2)s1)C1CCCO1] |
| 55 | 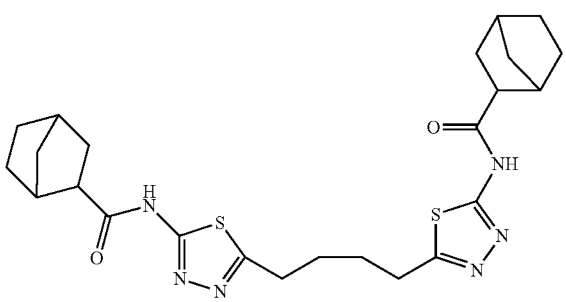 [SMILES: O=C(Nc1nnc(CCCCc2nnc(NC(=O)C3CC4CCC3C4)s2)s1)C1CC2CCC1C2] |
| 56 | 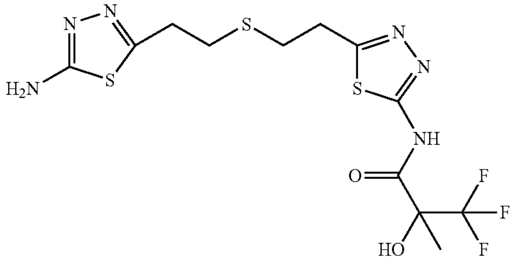 [SMILES: CC(O)(C(=O)Nc1nnc(CCSCCc2nnc(N)s2)s1)C(F)(F)F] |

TABLE 1-continued
Selected Compounds of Formula I
| Compound ID | Structure |
|---|---|
| 57 | 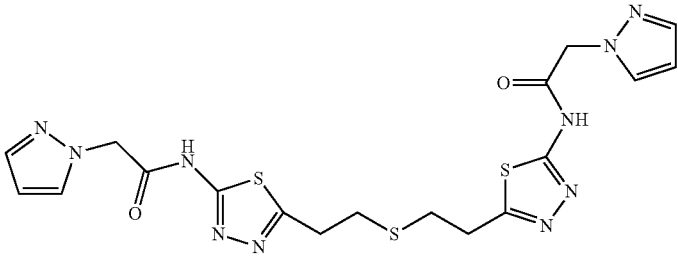 [SMILES: O=C(Cn1cccn1)Nc1nnc(CCSCCc2nnc(NC(=O)Cn3cccn3)s2)s1] |
| 58 | 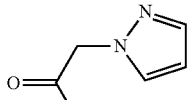 |
| 59 | 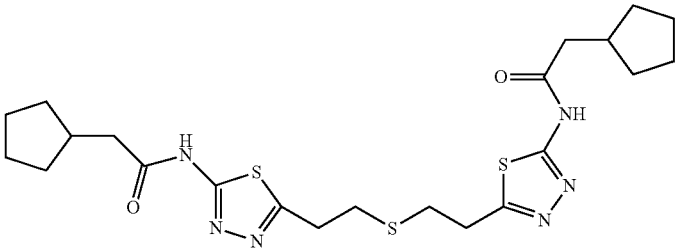 [SMILES: O=C(CC1CCCC1)Nc1nnc(CCSCCc2nnc(NC(=O)CC3CCCC3)s2)s1] |
| 60 | 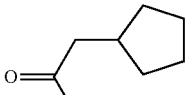 |
| 61 | 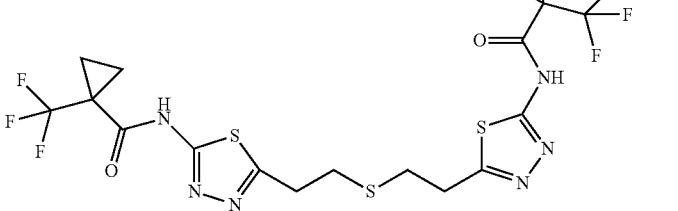 |

TABLE 1-continued

Selected Compounds of Formula I

| Compound ID | Structure |
|---|---|
| 62 | 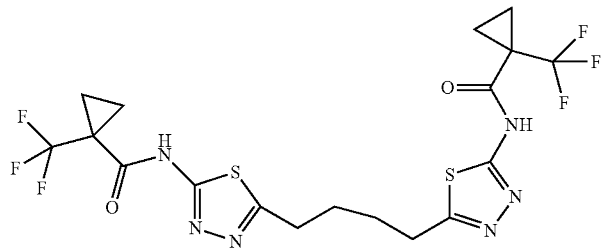 [SMILES: O=C(Nc1nnc(CCCCc2nnc(NC(=O)C3(C(F)(F)F)CC3)s2)s1)C1(C(F)(F)F)CC1] |
| 63 | 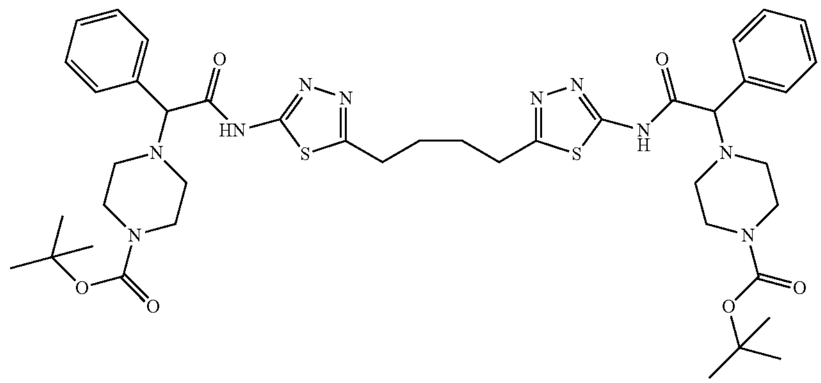 [SMILES: CC(C)(C)OC(=O)N1CCN(C(C(=O)Nc2nnc(CCCCc3nnc(NC(=O)C(c4ccccc4)N4CCN(C(=O)OC(C)(C)C)CC4)s3)s2)c2ccccc2)CC1] |
| 64 | 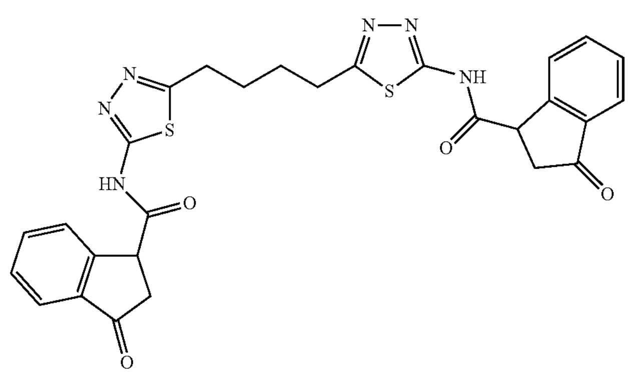 [SMILES: O=C1CC(C(=O)Nc2nnc(CCCCc3nnc(NC(=O)C4CC(=O)c5ccccc54)s3)s2)c2ccccc21] |
| 65 | 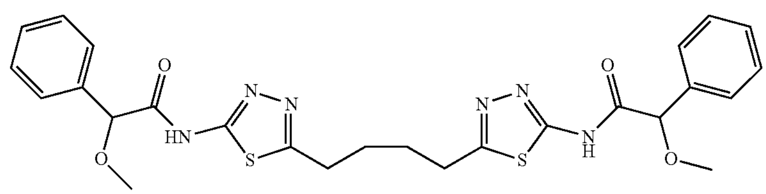 [SMILES: COC(C(=O)Nc1nnc(CCCCc2nnc(NC(=O)C(OC)c3ccccc3)s2)s1)c1ccccc1] |
| 66 | 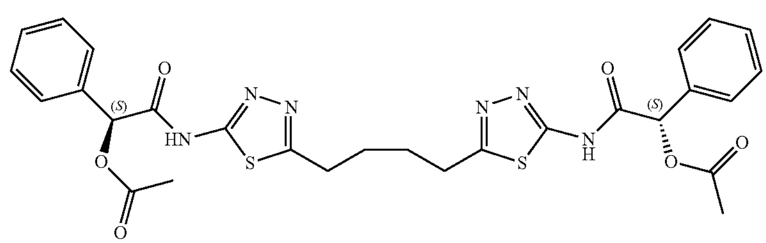 |

TABLE 1-continued

Selected Compounds of Formula I

| Compound ID | Structure |
|---|---|
| 67 | 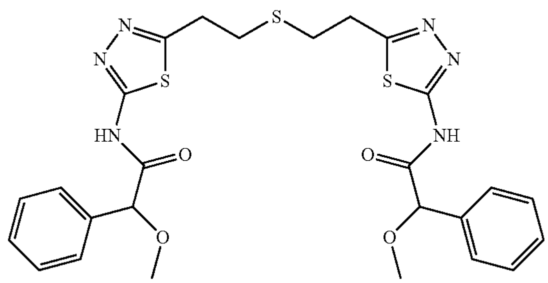 [SMILES: COC(C(=O)Nc1nnc(CCSCCc2nnc(NC(=O)C(OC)c3ccccc3)s2)s1)c1ccccc1] |
| 68 | 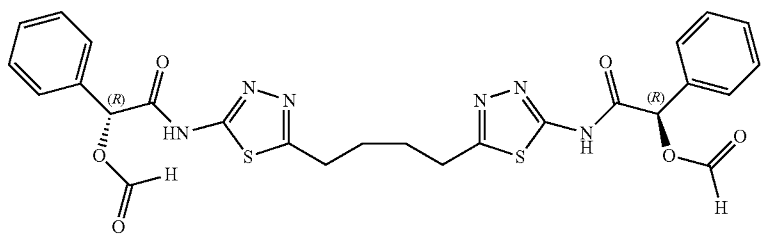 |
| 69 | 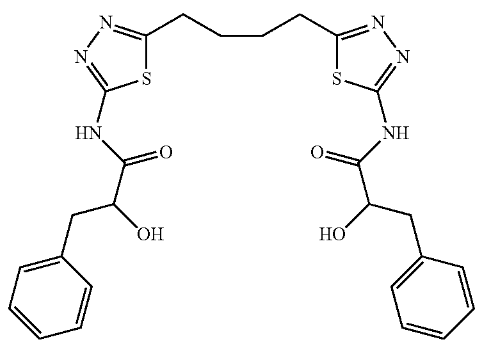 [SMILES: O=C(Nc1nnc(CCCCc2nnc(NC(=O)C(O)Cc3ccccc3)s2)s1)C(O)Cc1ccccc1] |
| 70 | 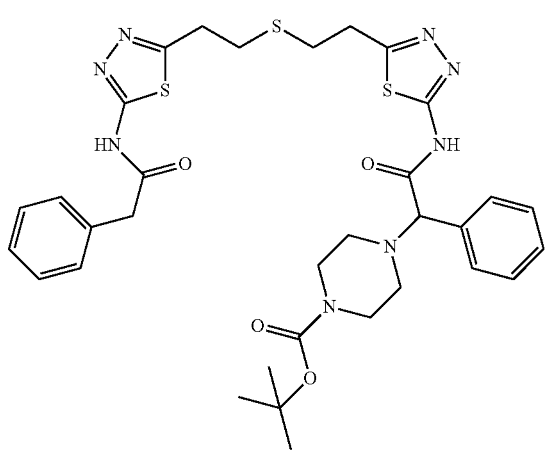 [SMILES: CC(C)(C)OC(=O)N1CCN(C(C(=O)Nc2nnc(CCSCCc3nnc(NC(=O)Cc4ccccc4)s3)s2)c2ccccc2)CC1] |

TABLE 1-continued

Selected Compounds of Formula I

| Compound ID | Structure |
|---|---|
| 71 | 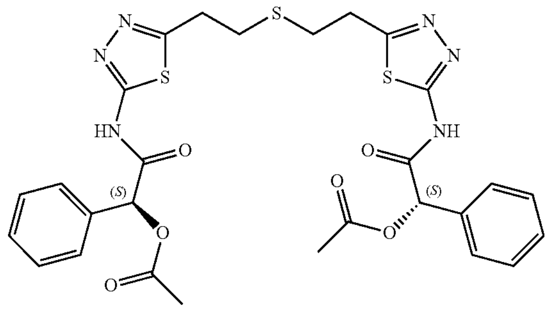 |
| 72 | 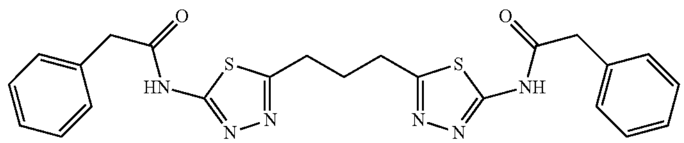 [SMILES: O=C(Cc1ccccc1)Nc1nnc(CCCc2nnc(NC(=O)Cc3ccccc3)s2)s1] |
| 73 | 2 TFA |
| 74 | 2 HCl |
| 75 | 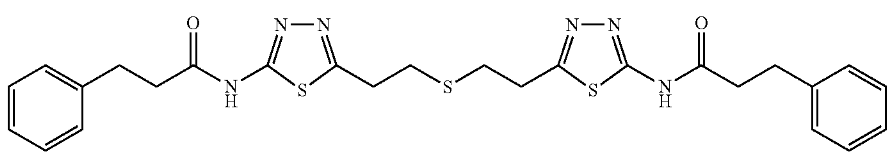 [SMILES: O=C(CCc1ccccc1)Nc1nnc(CCSCCc2nnc(NC(=O)CCc3ccccc3)s2)s1] |
| 76 | 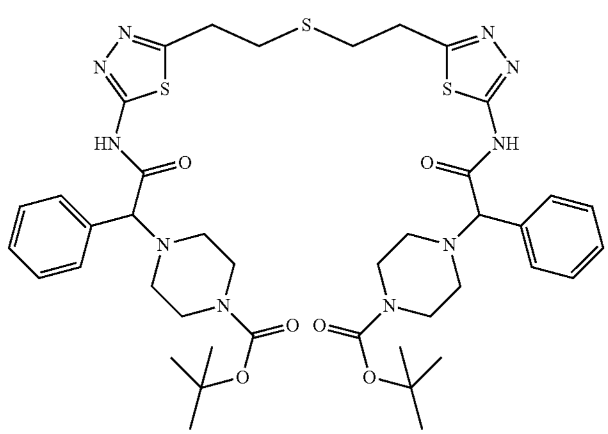 [SMILES: CC(C)(C)OC(=O)N1CCN(C(C(=O)Nc2nnc(CCSCCc3nnc(NC(=O)C(c4ccccc4)N4CCN(C(=O)OC(C)(C)C)CC4)s3)s2)c2ccccc2)CC1] |

TABLE 1-continued
Selected Compounds of Formula I
| Compound ID | Structure |
|---|---|
| 77 | 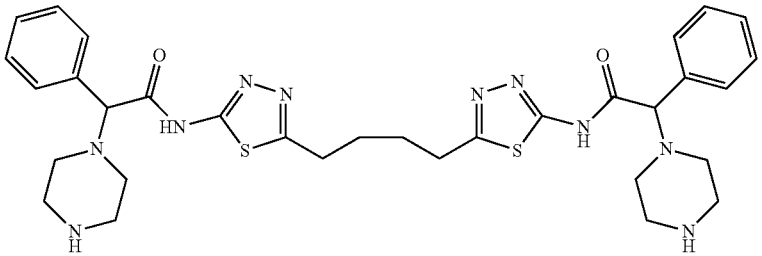 2 HCl |
| 78 | 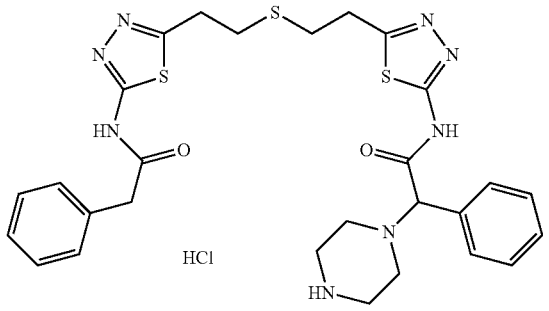 [SMILES: O=C(Cc1ccccc1)Nc1nnc(CCSCCc2nnc(NC(=O)C(c3ccccc3)N3CCNCC3)s2)s1 ; Cl] HCl |
| 79 | 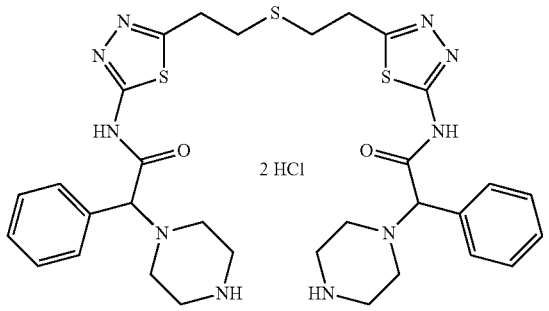 [SMILES: O=C(Nc1nnc(CCSCCc2nnc(NC(=O)C(c3ccccc3)N3CCNCC3)s2)s1)C(c1ccccc1)N1CCNCC1] 2 HCl |
| 80 | 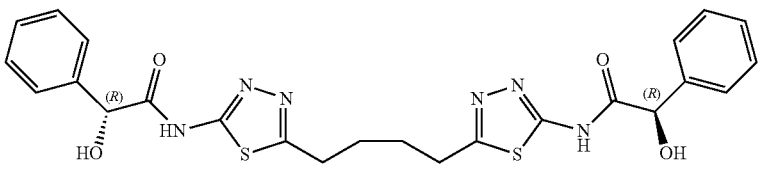 |
| 81 | 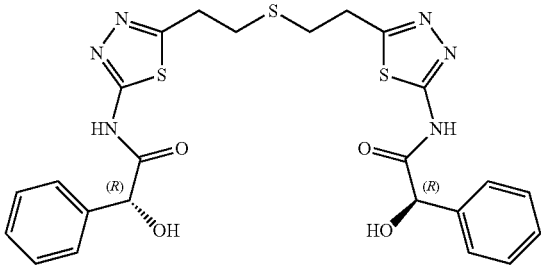 |

TABLE 1-continued

Selected Compounds of Formula I

| Compound ID | Structure |
|---|---|
| 82 | 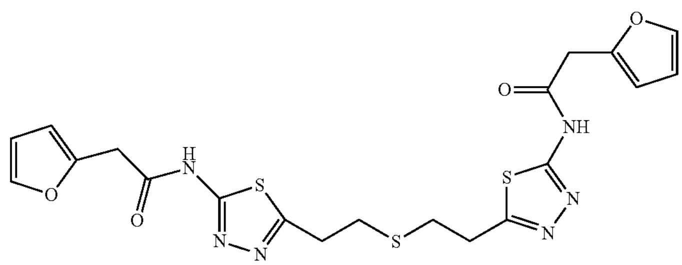 [SMILES: O=C(Cc1ccco1)Nc1nnc(CCSCCc2nnc(NC(=O)Cc3ccco3)s2)s1] |
| 83 | 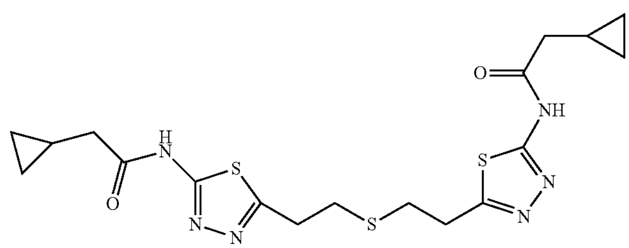 [SMILES: O=C(CC1CC1)Nc1nnc(CCSCCc2nnc(NC(=O)CC3CC3)s2)s1] |
| 84 | 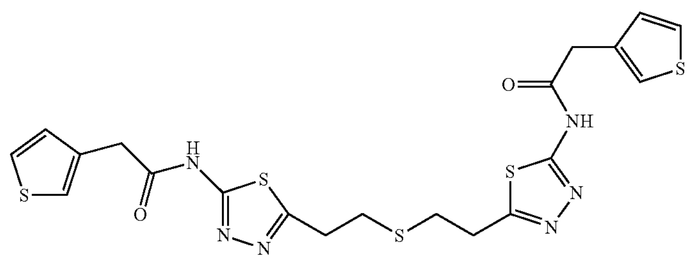 [SMILES: O=C(Cc1ccsc1)Nc1nnc(CCSCCc2nnc(NC(=O)Cc3ccsc3)s2)s1] |
| 85 | 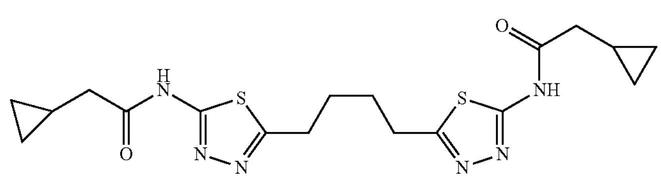 [SMILES: O=C(CC1CC1)Nc1nnc(CCCCc2nnc(NC(=O)CC3CC3)s2)s1] |
| 86 | 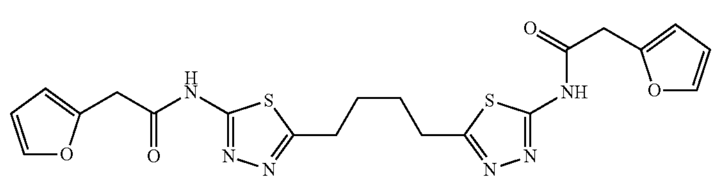 [SMILES: O=C(Cc1ccco1)Nc1nnc(CCCCc2nnc(NC(=O)Cc3ccco3)s2)s1] |
| 87 | 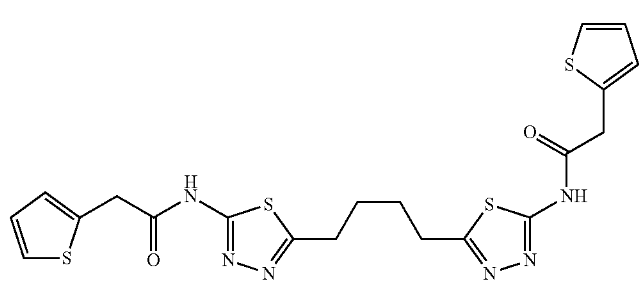 [SMILES: O=C(Cc1cccs1)Nc1nnc(CCCCc2nnc(NC(=O)Cc3cccs3)s2)s1] |

TABLE 1-continued

Selected Compounds of Formula I

| Compound ID | Structure |
|---|---|
| 88 | 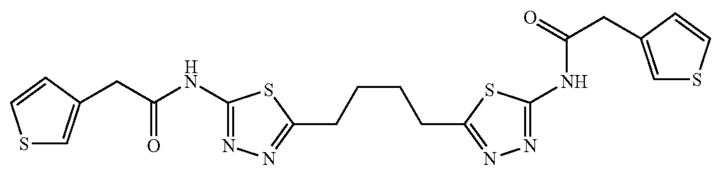 [SMILES: O=C(Cc1ccsc1)Nc1nnc(CCCCc2nnc(NC(=O)Cc3ccsc3)s2)s1] |
| 89 | 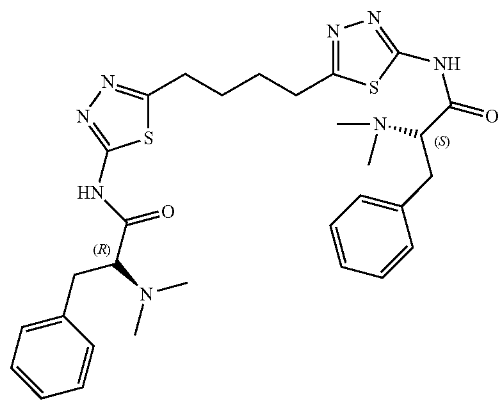 |
| 90 | 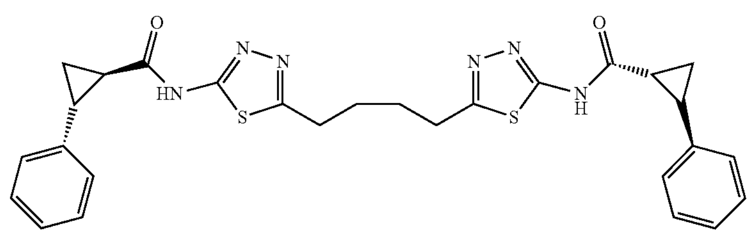 |
| 91 | 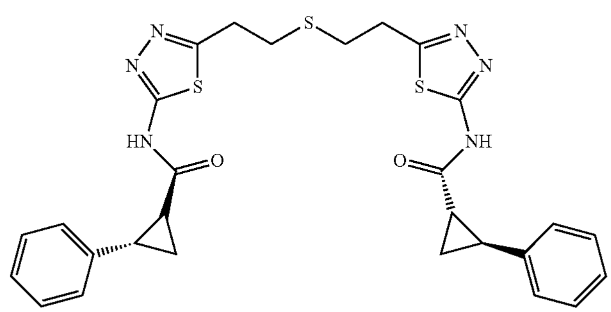 |
| 92 | 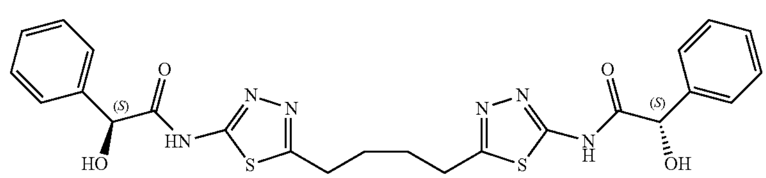 |

TABLE 1-continued

Selected Compounds of Formula I

| Compound ID | Structure |
|---|---|
| 93 | 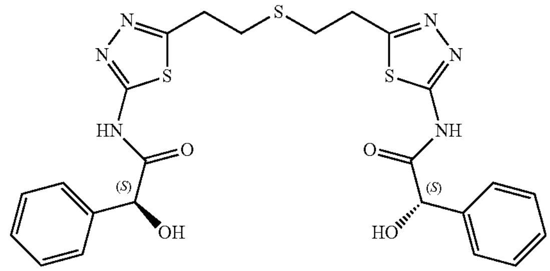 |
| 94 | 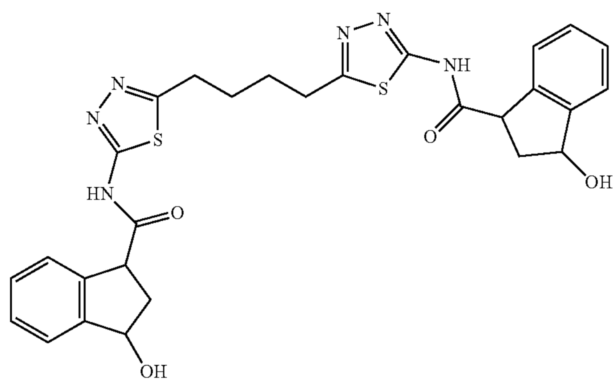 [SMILES: O=C(Nc1nnc(CCCCc2nnc(NC(=O)C3CC(O)c4ccccc43)s2)s1)C1CC(O)c2ccccc21] |
| 95 | 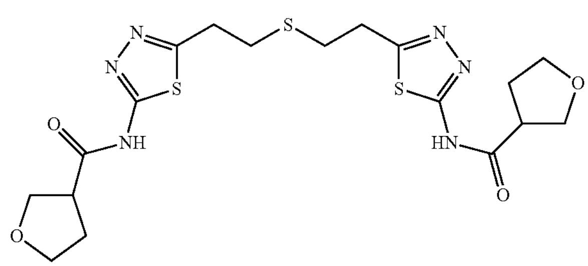 [SMILES: O=C(Nc1nnc(CCSCCc2nnc(NC(=O)C3CCOC3)s2)s1)C1CCOC1] |
| 96 | 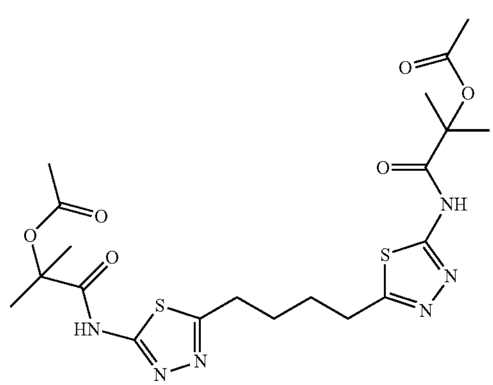 [SMILES: CC(=O)OC(C)(C)C(=O)Nc1nnc(CCCCc2nnc(NC(=O)C(C)(C)OC(C)=O)s2)s1] |

TABLE 1-continued

Selected Compounds of Formula I

| Compound ID | Structure |
|---|---|
| 97 | 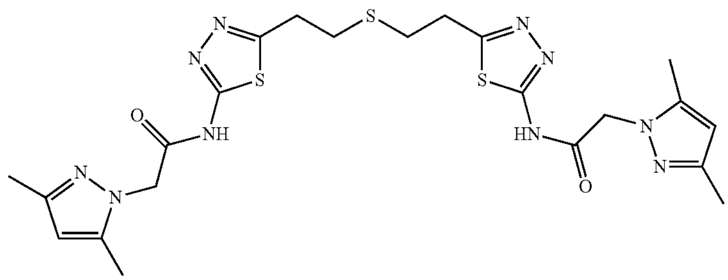 |
| 98 | 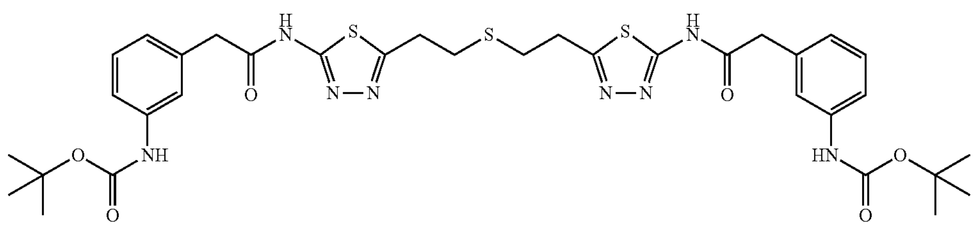 [SMILES: CC(C)(C)OC(=O)Nc1cccc(CC(=O)Nc2nnc(CCSCCc3nnc(NC(=O)Cc4cccc(NC(=O)OC(C)(C)C)c4)s3)s2)c1] |
| 99 | (2 HCl) |
| 100 | 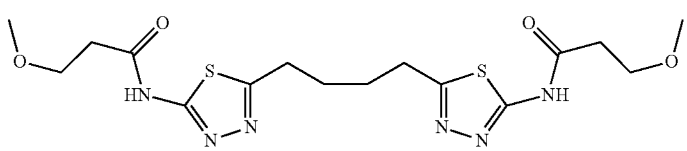 |
| 101 | 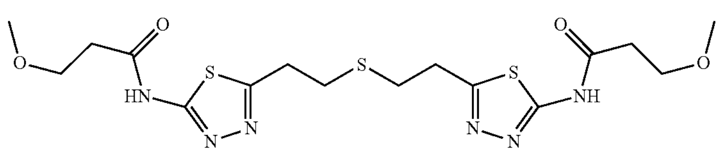 |
| 102 | 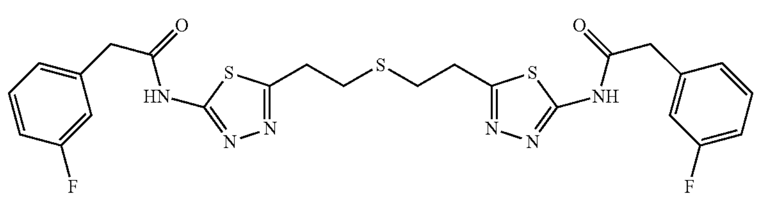 [SMILES: O=C(Cc1cccc(F)c1)Nc1nnc(CCSCCc2nnc(NC(=O)Cc3cccc(F)c3)s2)s1] |
| 103 | 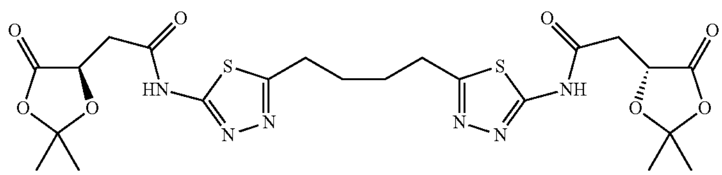 [SMILES: CC1(C)OC(=O)[C@@H](CC(=O)Nc2nnc(CCCCc3nnc(NC(=O)C[C@H]4OC(C)(C)OC4=O)s3)s2)O1] |

TABLE 1-continued

Selected Compounds of Formula I

| Compound ID | Structure |
|---|---|
| 104 | 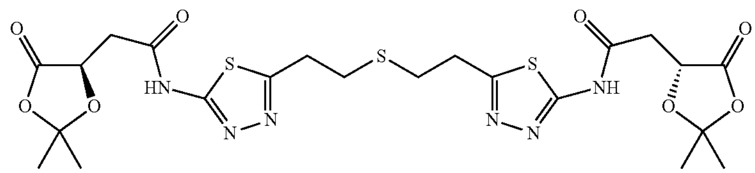 [SMILES: CC1(C)OC(=O)[C@@H](CC(=O)Nc2nnc(CCSCCc3nnc(NC(=O)C[C@H]4OC(C)(C)OC4=O)s3)s2)O1] |
| 105 | 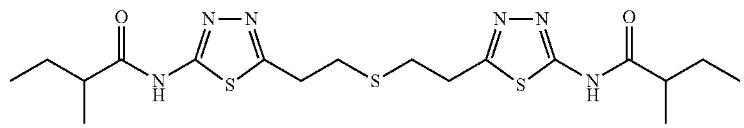 [SMILES: CCC(C)C(=O)Nc1nnc(CCSCCc2nnc(NC(=O)C(C)CC)s2)s1] |
| 106 | 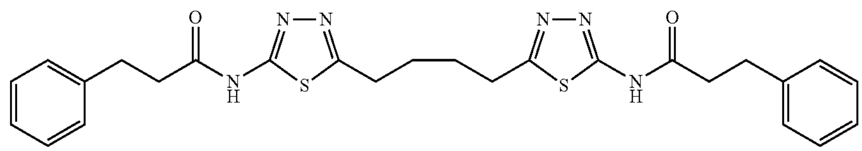 [SMILES: O=C(CCc1ccccc1)Nc1nnc(CCCCc2nnc(NC(=O)CCc3ccccc3)s2)s1] |
| 107 | 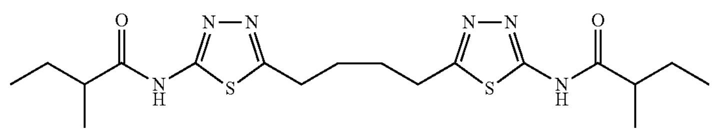 [SMILES: CCC(C)C(=O)Nc1nnc(CCCCc2nnc(NC(=O)C(C)CC)s2)s1] |
| 108 | 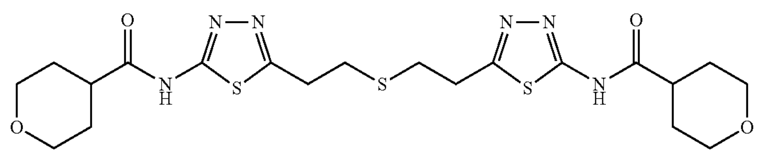 [SMILES: O=C(Nc1nnc(CCSCCc2nnc(NC(=O)C3CCOCC3)s2)s1)C1CCOCC1] |
| 109 | 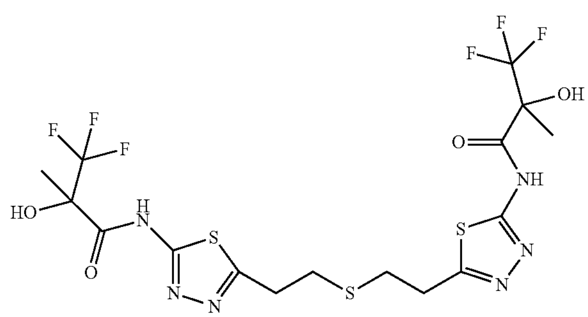 [SMILES: CC(O)(C(=O)Nc1nnc(CCSCCc2nnc(NC(=O)C(C)(O)C(F)(F)F)s2)s1)C(F)(F)F] |
| 110 | 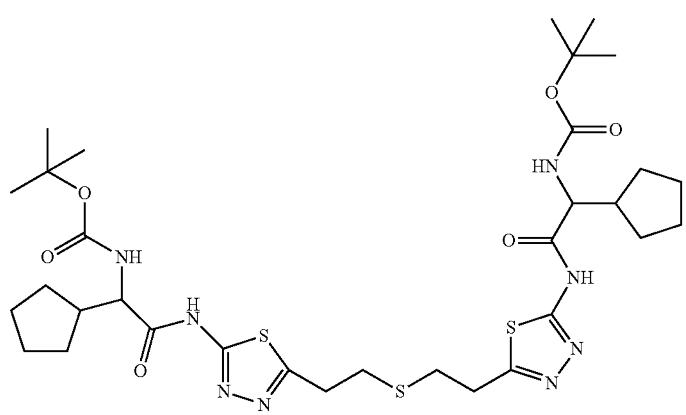 [SMILES: CC(C)(C)OC(=O)NC(C(=O)Nc1nnc(CCSCCc2nnc(NC(=O)C(NC(=O)OC(C)(C)C)C3CCCC3)s2)s1)C1CCCC1] |

TABLE 1-continued
Selected Compounds of Formula I
| Compound ID | Structure |
|---|---|
| 111 | 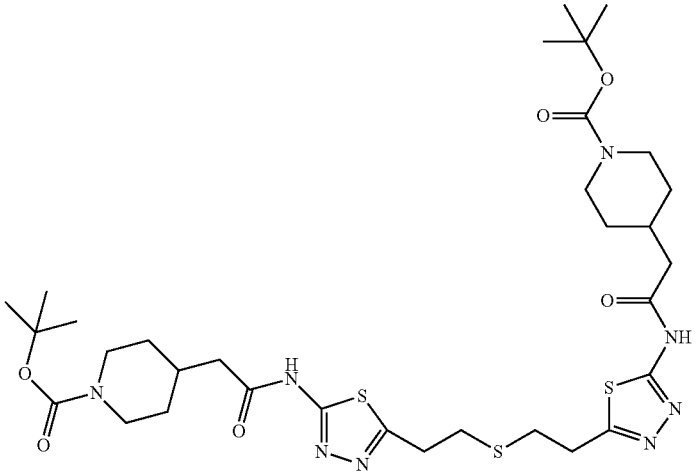 [SMILES: CC(C)(C)OC(=O)N1CCC(CC(=O)Nc2nnc(CCSCCc3nnc(NC(=O)CC4CCN(C(=O)OC(C)(C)C)CC4)s3)s2)CC1] |
| 112 | 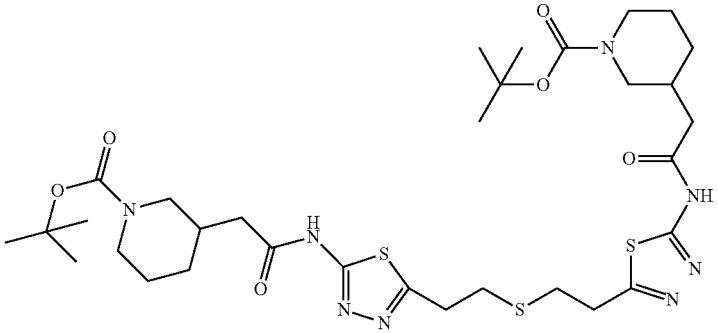 [SMILES: CC(C)(C)OC(=O)N1CCCC(CC(=O)NC(=N)SC(=N)CCSCCc2nnc(NC(=O)CC3CCCN(C(=O)OC(C)(C)C)C3)s2)C1] |
| 113 | 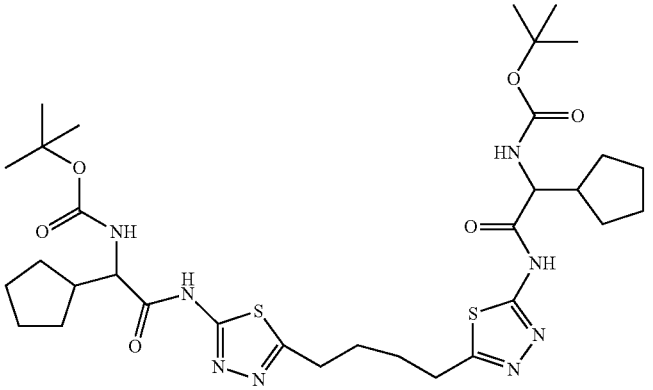 [SMILES: CC(C)(C)OC(=O)NC(C(=O)Nc1nnc(CCCCc2nnc(NC(=O)C(NC(=O)OC(C)(C)C)C3CCCC3)s2)s1)C1CCCC1] |

TABLE 1-continued
Selected Compounds of Formula I
| Compound ID | Structure |
|---|---|
| 114 | 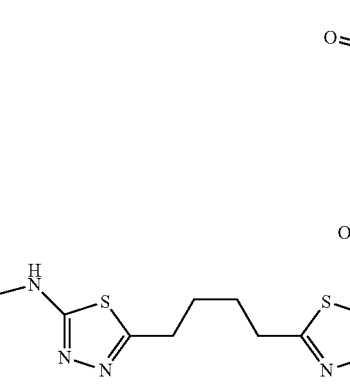 |
| 115 | 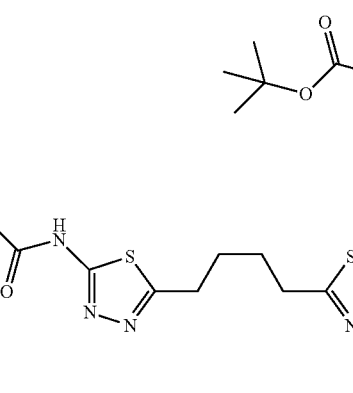 |
| 116 | 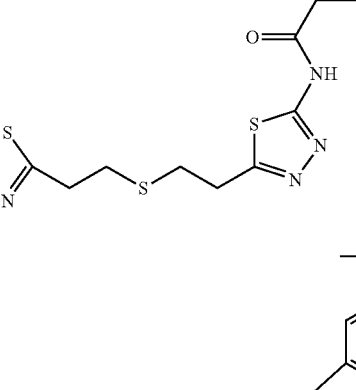 |
| 117 | 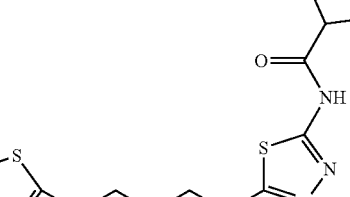 |

TABLE 1-continued
Selected Compounds of Formula I
| Compound ID | Structure |
|---|---|
| 118 | 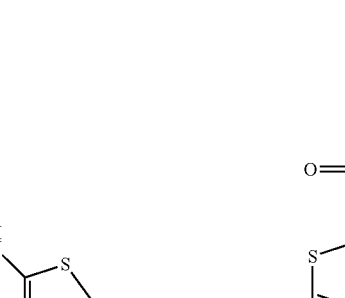 |
| 119 | 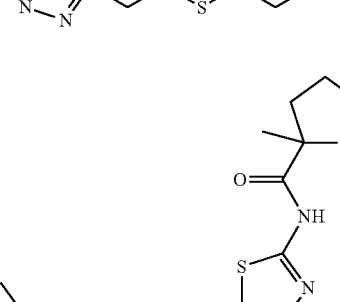 |
| 120 | 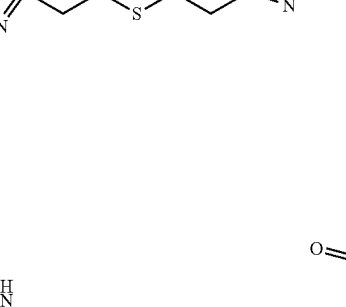 |
| 121 | 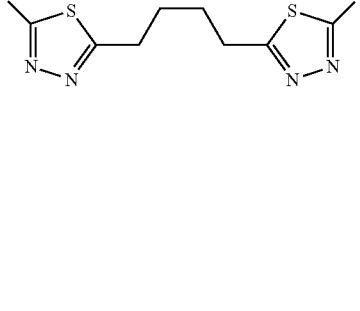 |

TABLE 1-continued

Selected Compounds of Formula I

| Compound ID | Structure |
|---|---|
| 122 | 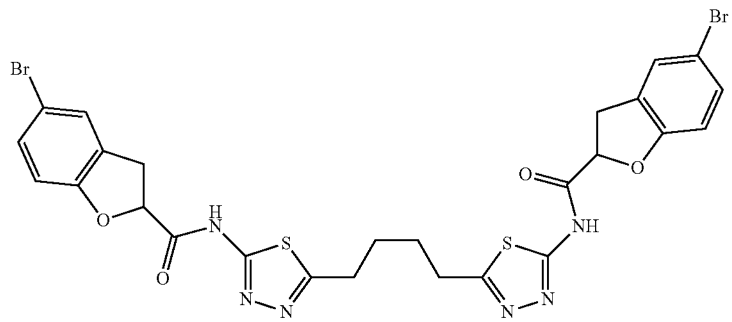 [SMILES: O=C(Nc1nnc(CCCCc2nnc(NC(=O)C3Cc4cc(Br)ccc4O3)s2)s1)C1Cc2cc(Br)ccc2O1] |
| 123 | 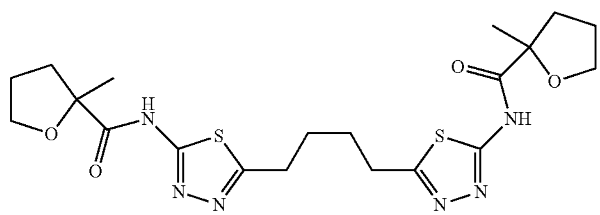 [SMILES: CC1(C(=O)Nc2nnc(CCCCc3nnc(NC(=O)C4(C)CCCO4)s3)s2)CCCO1] |
| 124 | 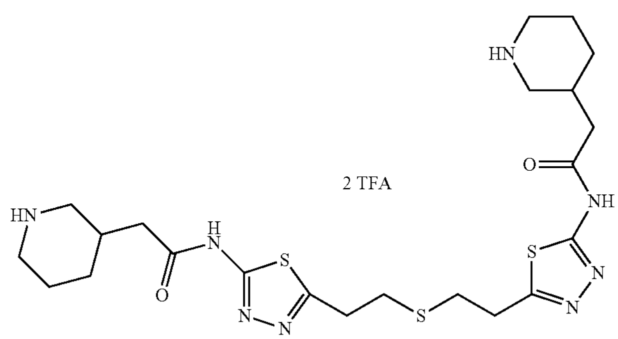 [SMILES: O=C(CC1CCCNC1)Nc1nnc(CCSCCc2nnc(NC(=O)CC3CCCNC3)s2)s1] |
| 125 | 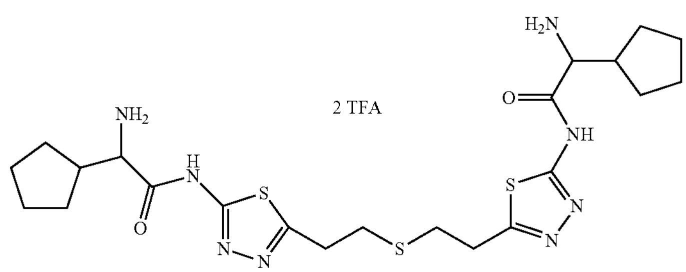 [SMILES: NC(C(=O)Nc1nnc(CCSCCc2nnc(NC(=O)C(N)C3CCCC3)s2)s1)C1CCCC1] |
| 126 | 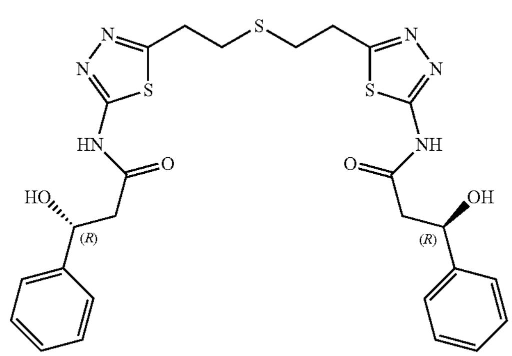 |

TABLE 1-continued
Selected Compounds of Formula I
| Compound ID | Structure |
| --- | --- |
| 127 | 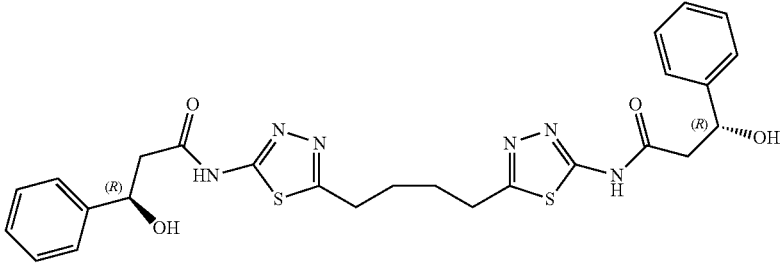 |
| 128 | 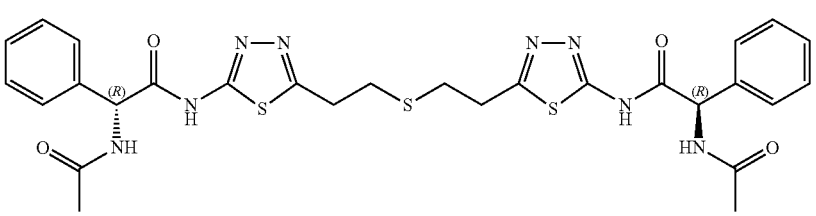 |
| 129 | 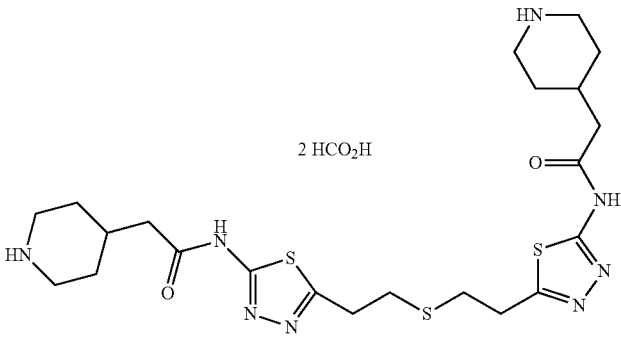 [SMILES: O=C(CC1CCNCC1)Nc1nnc(CCSCCc2nnc(NC(=O)CC3CCNCC3)s2)s1] |
| 130 | 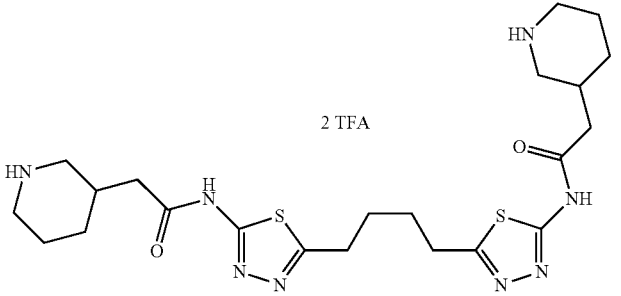 [SMILES: O=C(CC1CCCNC1)Nc1nnc(CCCCc2nnc(NC(=O)CC3CCCNC3)s2)s1] |
| 131 | 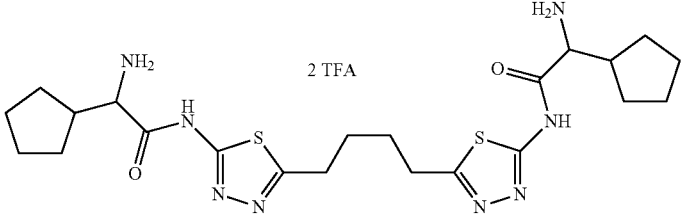 [SMILES: NC(C(=O)Nc1nnc(CCCCc2nnc(NC(=O)C(N)C3CCCC3)s2)s1)C1CCCC1] |

TABLE 1-continued

Selected Compounds of Formula I

| Compound ID | Structure |
|---|---|
| 132 | (structure: 2 HCl salt; bis-piperidinylmethyl-C(O)NH-thiadiazole linked by butylene chain) |
| 133 | (structure: bis-(2,3-dihydrobenzofuran-3-yl)-C(O)NH-thiadiazole linked by -CH₂CH₂-S-CH₂CH₂-) |
| 134 | (structure: bis-(benzo[1,3]dioxol-2-yl)-C(O)NH-thiadiazole linked by -CH₂CH₂-S-CH₂CH₂-) |
| 135 | (structure: bis-(2,3-dihydrobenzofuran-3-yl)-C(O)NH-thiadiazole linked by butylene chain) |

TABLE 1-continued

Selected Compounds of Formula I

| Compound ID | Structure |
|---|---|
| 136 | 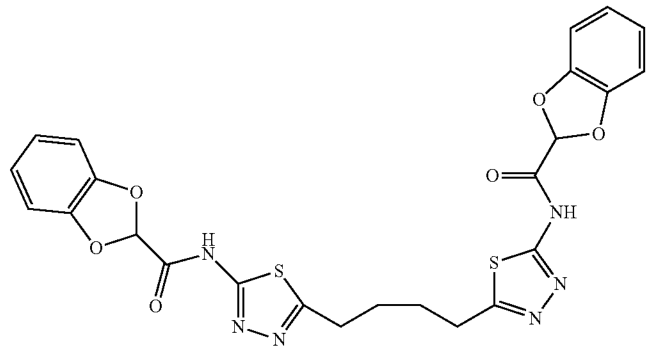 [SMILES: O=C(Nc1nnc(CCCCc2nnc(NC(=O)C3Oc4ccccc4O3)s2)s1)C1Oc2ccccc2O1] |
| 137 | 2 HCl |
| 138 | 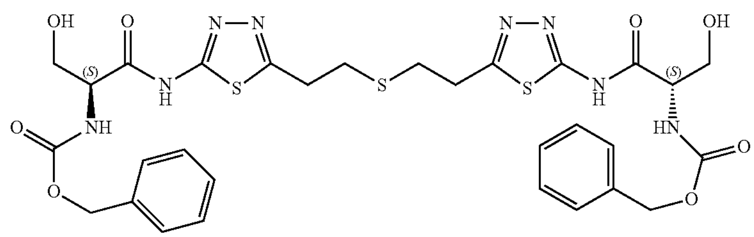 |
| 139 | 2 HCl |
| 140 | 2 HCl |
| 141 | 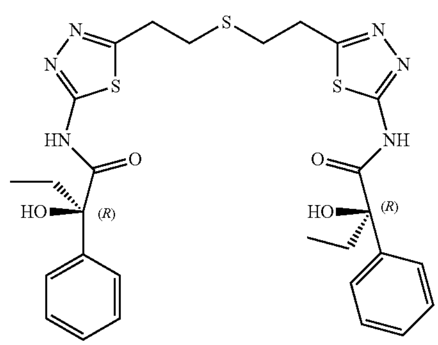 |

TABLE 1-continued

Selected Compounds of Formula I

| Compound ID | Structure |
|---|---|
| 142 | 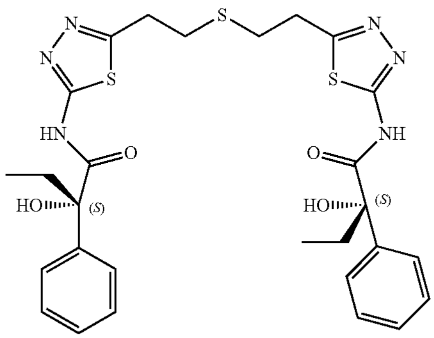 |
| 143 | 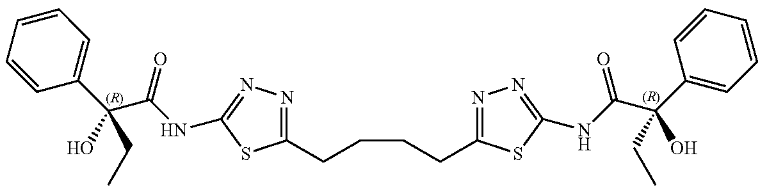 |
| 144 | 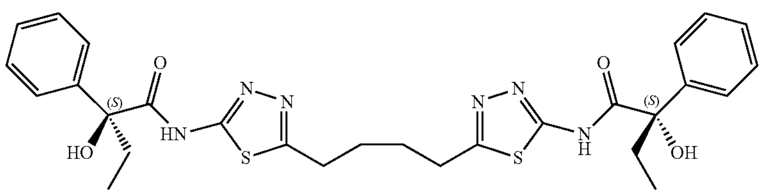 |
| 145 | 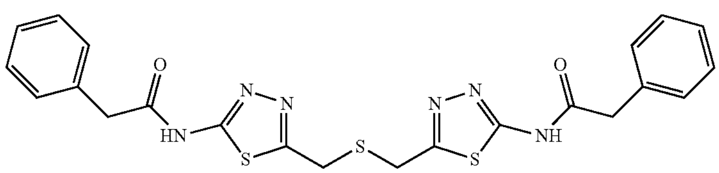 [SMILES: O=C(Cc1ccccc1)Nc1nnc(CSCc2nnc(NC(=O)Cc3ccccc3)s2)s1] |
| 146 | 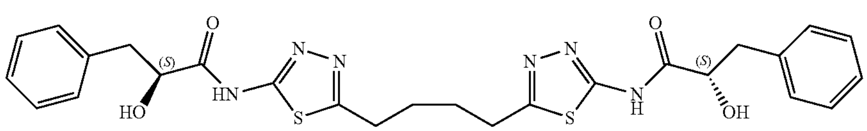 |
| 147 | 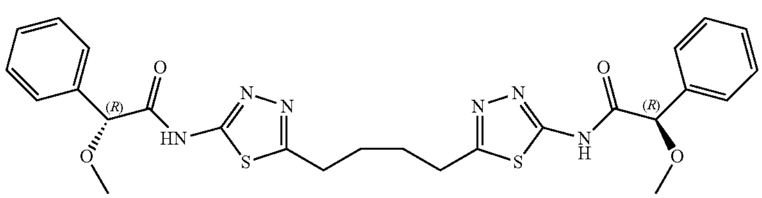 |
| 148 | 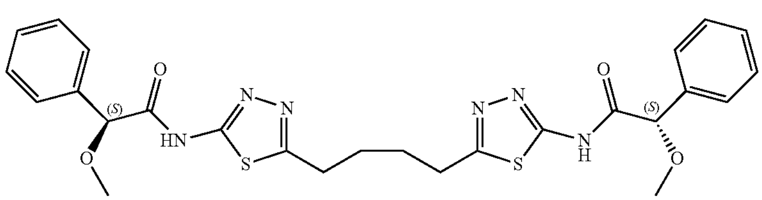 |

TABLE 1-continued
Selected Compounds of Formula I
| Compound ID | Structure |
|---|---|
| 149 | 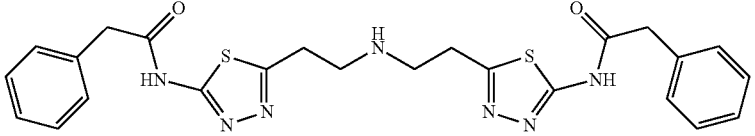 TFA |
| 150 | 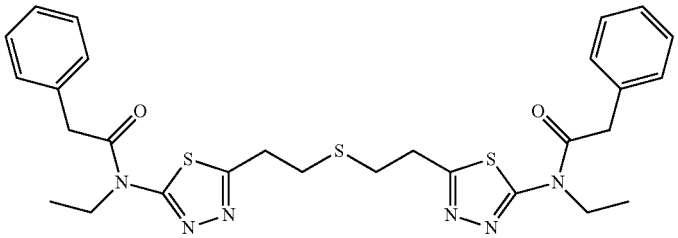 |
| 151 | 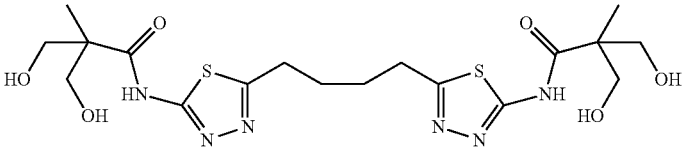 |
| 152 | 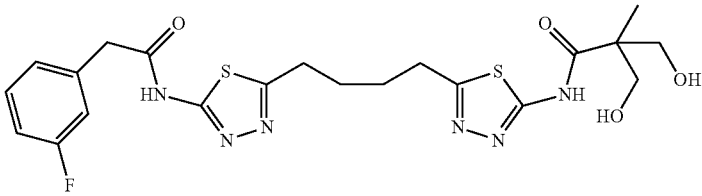 |
| 153 | 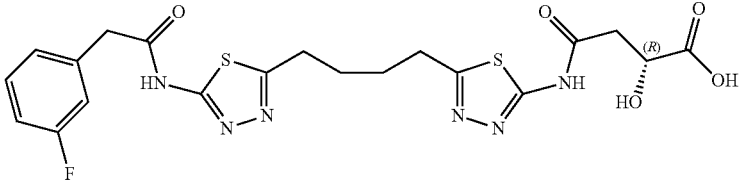 |
| 154 | 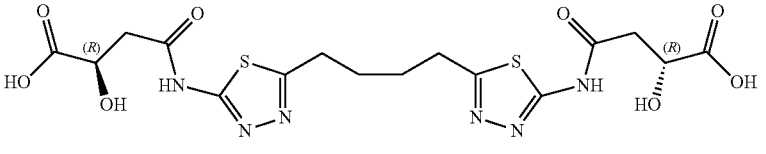 |
| 155 | 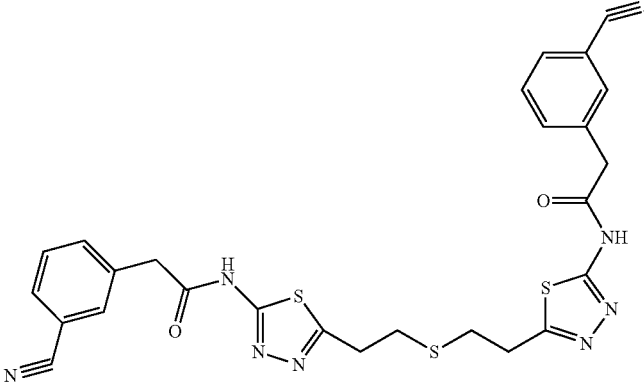 |

TABLE 1-continued

Selected Compounds of Formula I

| Compound ID | Structure |
|---|---|
| 156 | 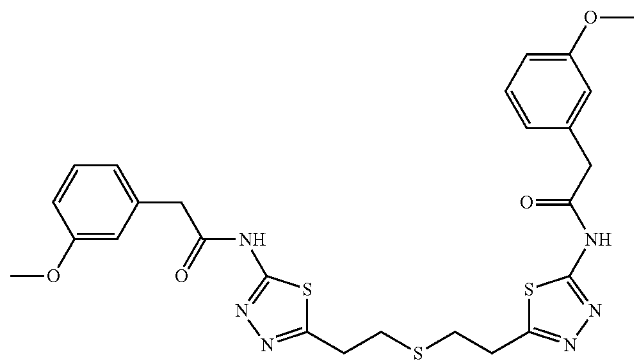 |
| 157 | 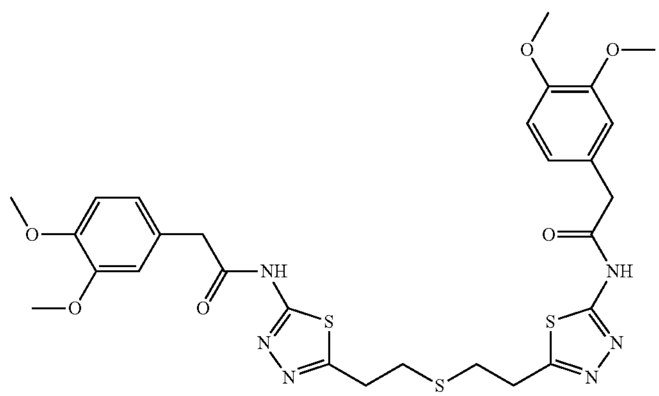 |
| 158 | 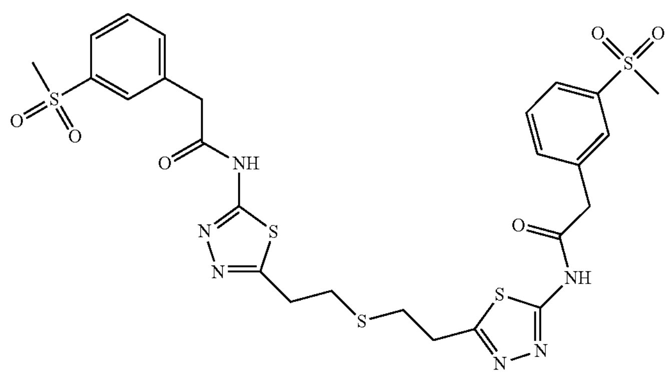 [SMILES: CS(=O)(=O)c1cccc(CC(=O)Nc2nnc(CCSCCc3nnc(NC(=O)Cc4cccc(S(C)(=O)=O)c4)s3)s2)c1] |
| 159 | 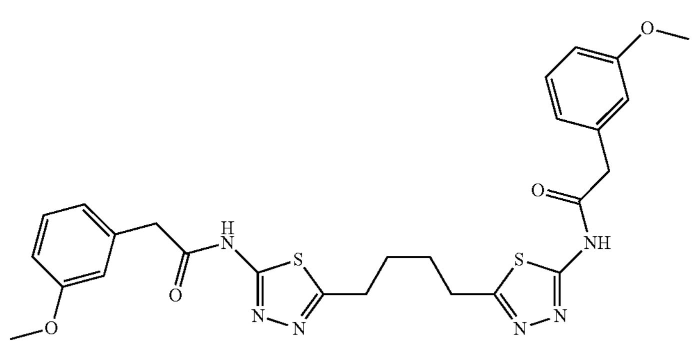 |

TABLE 1-continued

Selected Compounds of Formula I

| Compound ID | Structure |
|---|---|
| 160 | 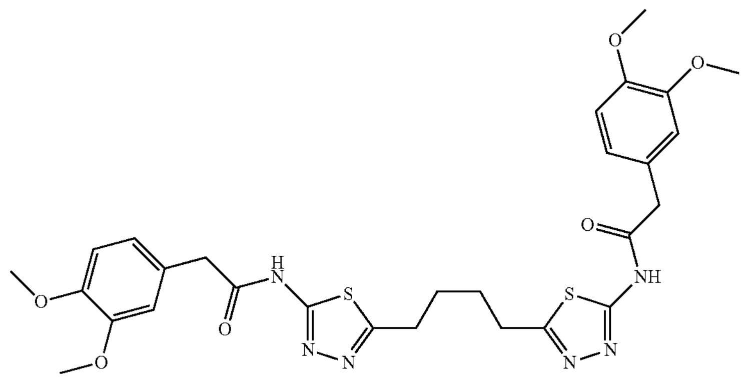 |
| 161 | 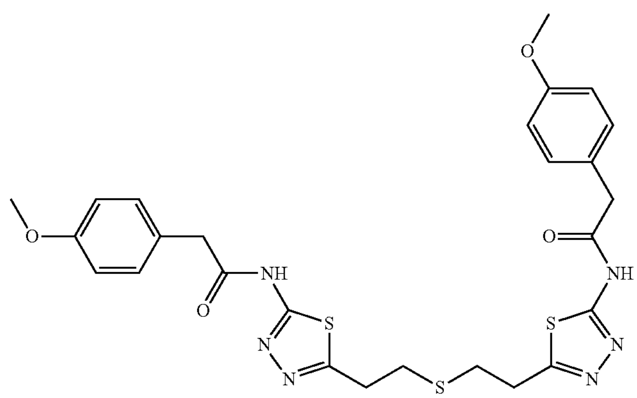 [SMILES: COc1ccc(CC(=O)Nc2nnc(CCSCCc3nnc(NC(=O)Cc4ccc(OC)cc4)s3)s2)cc1] |
| 162 | 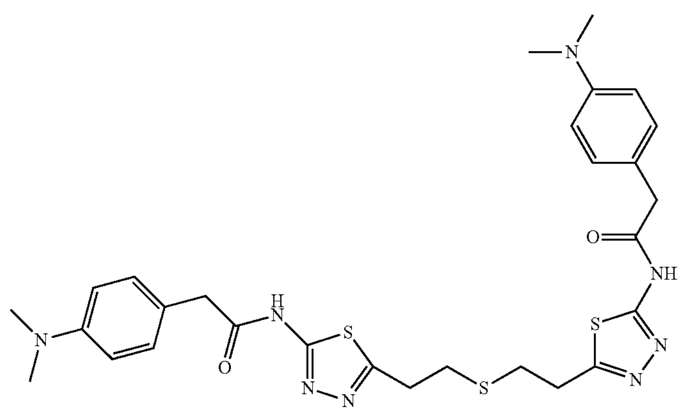 [SMILES: CN(C)c1ccc(CC(=O)Nc2nnc(CCSCCc3nnc(NC(=O)Cc4ccc(N(C)C)cc4)s3)s2)cc1] |
| 163 | 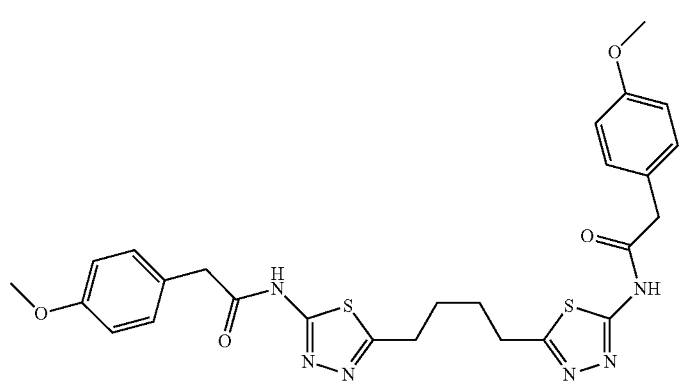 [SMILES: COc1ccc(CC(=O)Nc2nnc(CCCCc3nnc(NC(=O)Cc4ccc(OC)cc4)s3)s2)cc1] |

TABLE 1-continued

Selected Compounds of Formula I

| Compound ID | Structure |
|---|---|
| 164 | 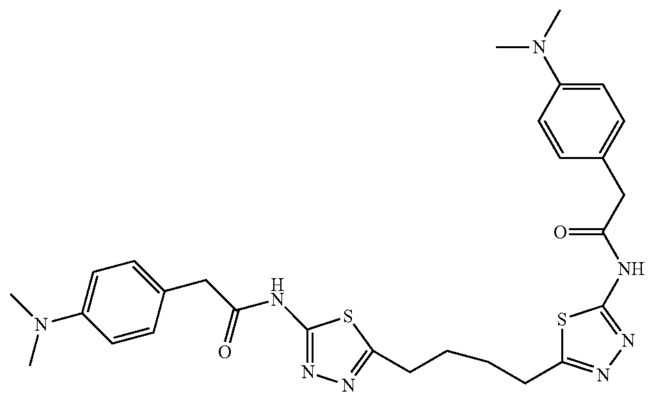 [SMILES: CN(C)c1ccc(CC(=O)Nc2nnc(CCCCc3nnc(NC(=O)Cc4ccc(N(C)C)cc4)s3)s2)cc1] |
| 165 | 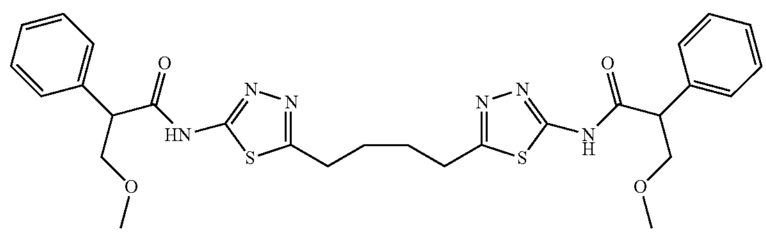 [SMILES: COCC(C(=O)Nc1nnc(CCCCc2nnc(NC(=O)C(COC)c3ccccc3)s2)s1)c1ccccc1] |
| 166 | 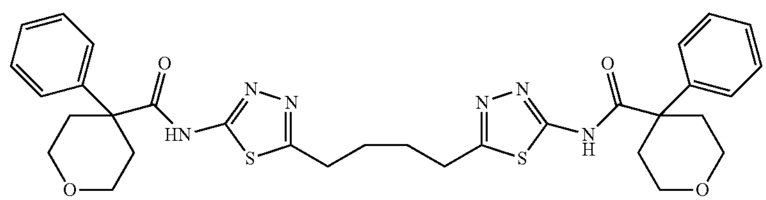 [SMILES: O=C(Nc1nnc(CCCCc2nnc(NC(=O)C3(c4ccccc4)CCOCC3)s2)s1)C1(c2ccccc2)CCOCC1] |
| 167 | 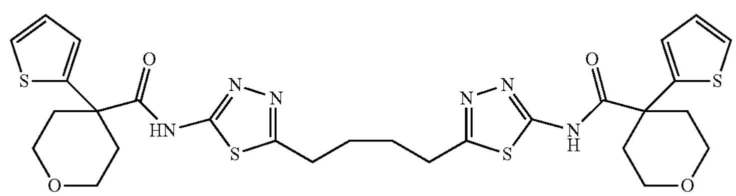 [SMILES: O=C(Nc1nnc(CCCCc2nnc(NC(=O)C3(c4cccs4)CCOCC3)s2)s1)C1(c2cccs2)CCOCC1] |
| 168 | 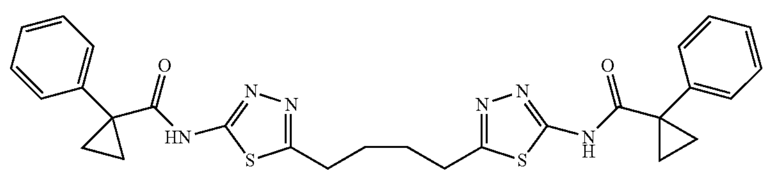 [SMILES: O=C(Nc1nnc(CCCCc2nnc(NC(=O)C3(c4ccccc4)CC3)s2)s1)C1(c2ccccc2)CC1] |
| 169 | 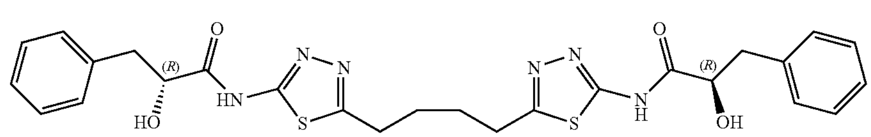 |
| 170 | 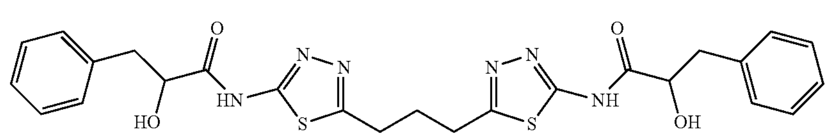 [SMILES: O=C(Nc1nnc(CCCc2nnc(NC(=O)C(O)Cc3ccccc3)s2)s1)C(O)Cc1ccccc1] |

TABLE 1-continued

Selected Compounds of Formula I

| Compound ID | Structure |
|---|---|
| 171 | 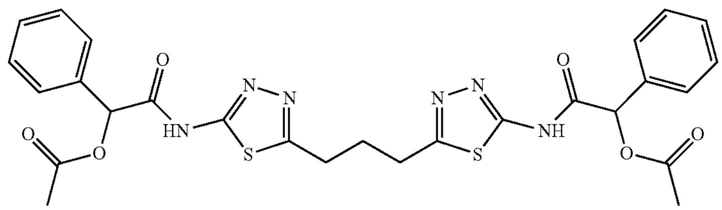 [SMILES: CC(=O)OC(C(=O)Nc1nnc(CCCc2nnc(NC(=O)C(OC(C)=O)c3ccccc3)s2)s1)c1ccccc1] |
| 172 | 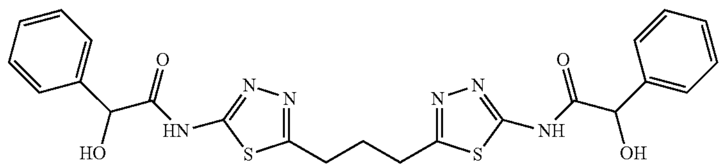 [SMILES: O=C(Nc1nnc(CCCc2nnc(NC(=O)C(O)c3ccccc3)s2)s1)C(O)c1ccccc1] |
| 173 | 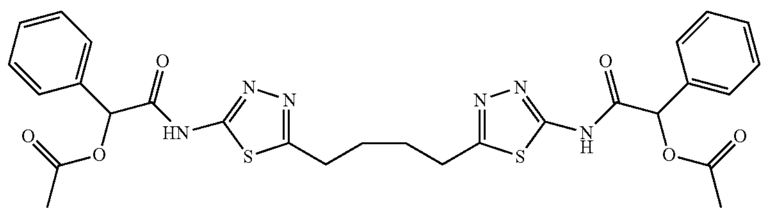 [SMILES: CC(=O)OC(C(=O)Nc1nnc(CCCCc2nnc(NC(=O)C(OC(C)=O)c3ccccc3)s2)s1)c1ccccc1] |
| 174 | 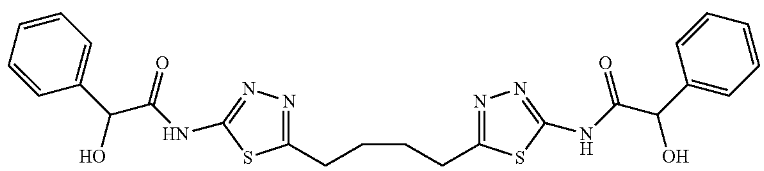 [SMILES: O=C(Nc1nnc(CCCCc2nnc(NC(=O)C(O)c3ccccc3)s2)s1)C(O)c1ccccc1] |
| 175 | 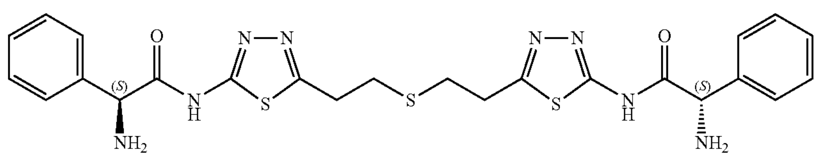 |
| 176 | 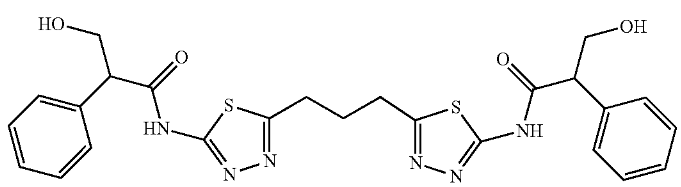 [SMILES: O=C(Nc1nnc(CCCc2nnc(NC(=O)C(CO)c3ccccc3)s2)s1)C(CO)c1ccccc1] |
| 177 | 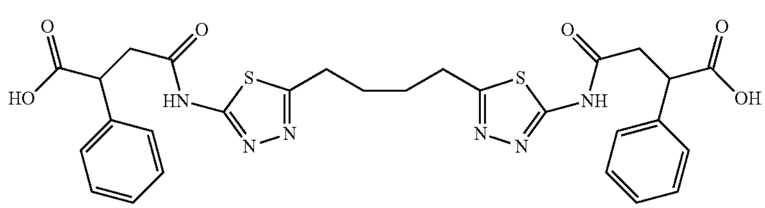 [SMILES: O=C(CC(C(=O)O)c1ccccc1)Nc1nnc(CCCCc2nnc(NC(=O)CC(C(=O)O)c3ccccc3)s2)s1] |
| 178 | 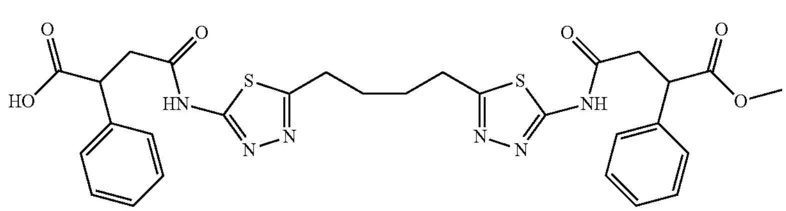 [SMILES: COC(=O)C(CC(=O)Nc1nnc(CCCCc2nnc(NC(=O)CC(C(=O)O)c3ccccc3)s2)s1)c1ccccc1] |

TABLE 1-continued
Selected Compounds of Formula I
| Compound ID | Structure |
|---|---|
| 179 | 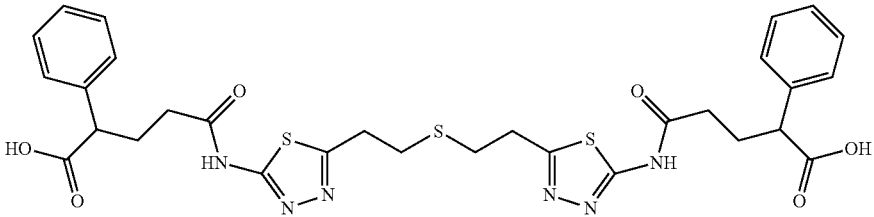 [SMILES: O=C(CCC(C(=O)O)c1ccccc1)Nc1nnc(CCSCCc2nnc(NC(=O)CCC(C(=O)O)c3ccccc3)s2)s1] |
| 180 | 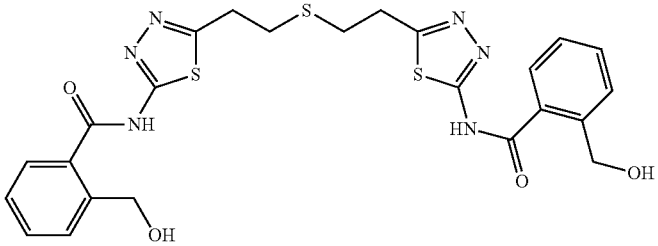 [SMILES: O=C(Nc1nnc(CCSCCc2nnc(NC(=O)c3ccccc3CO)s2)s1)c1ccccc1CO] |
| 181 | 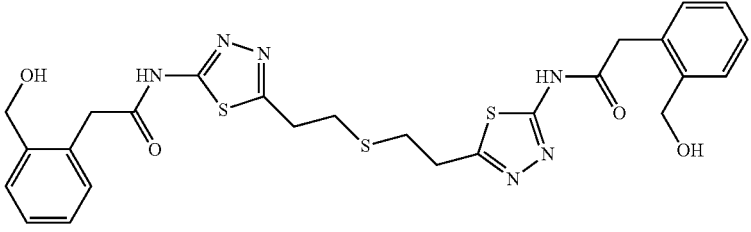 [SMILES: O=C(Cc1ccccc1CO)Nc1nnc(CCSCCc2nnc(NC(=O)Cc3ccccc3CO)s2)s1] |
| 182 | 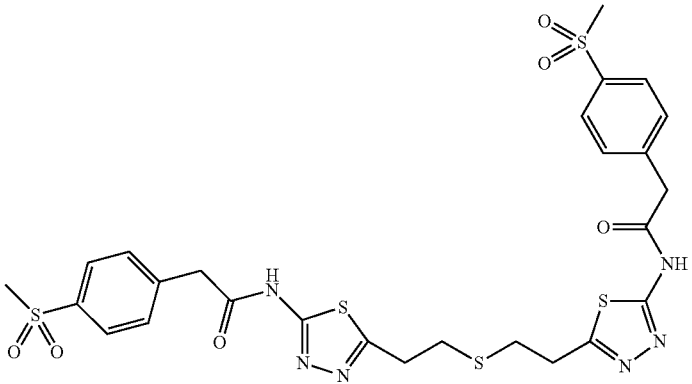 [SMILES: CS(=O)(=O)c1ccc(CC(=O)Nc2nnc(CCSCCc3nnc(NC(=O)Cc4ccc(S(C)(=O)=O)cc4)s3)s2)cc1] |
| 183 | 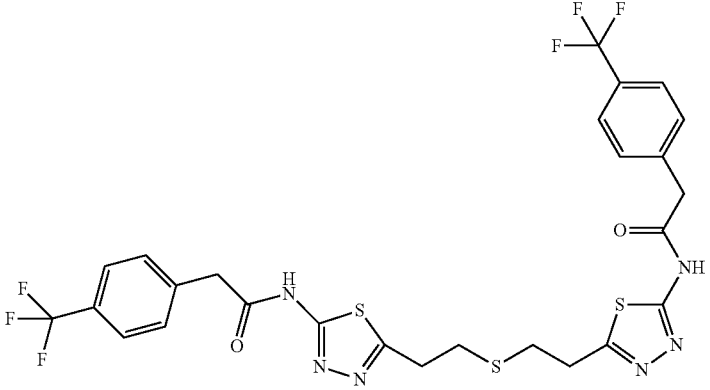 [SMILES: O=C(Cc1ccc(C(F)(F)F)cc1)Nc1nnc(CCSCCc2nnc(NC(=O)Cc3ccc(C(F)(F)F)cc3)s2)s1] |

TABLE 1-continued

Selected Compounds of Formula I

| Compound ID | Structure |
|---|---|
| 184 | 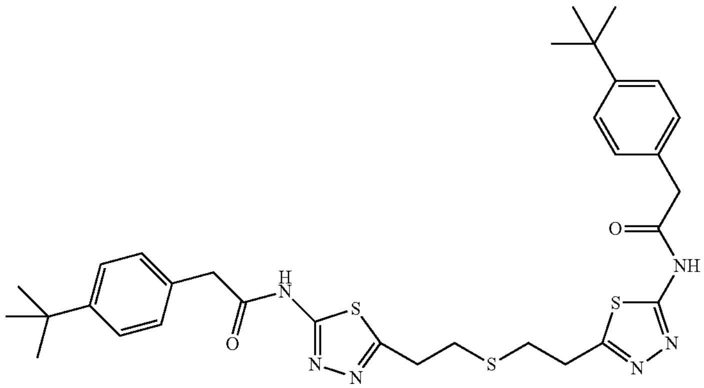 [SMILES: CC(C)(C)c1ccc(CC(=O)Nc2nnc(CCSCCc3nnc(NC(=O)Cc4ccc(C(C)(C)C)cc4)s3)s2)cc1] |
| 185 | 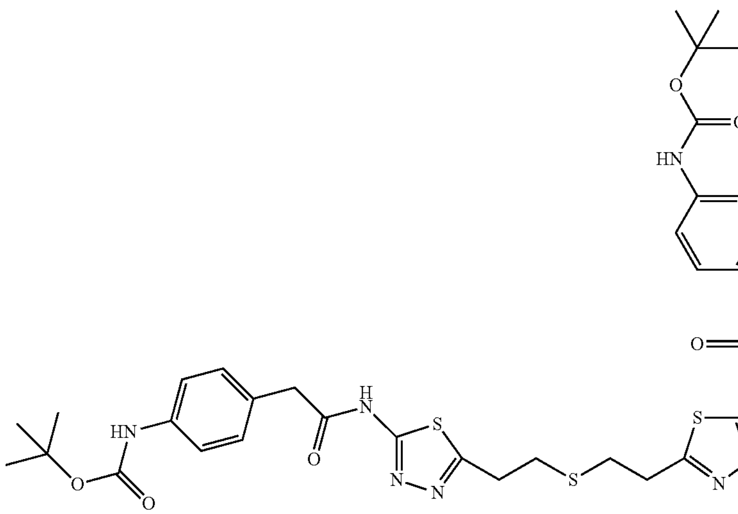 |
| 186 | (2 HCl) |
| 187 | (2 HCl) |

TABLE 1-continued

Selected Compounds of Formula I

| Compound ID | Structure |
|---|---|
| 188 | 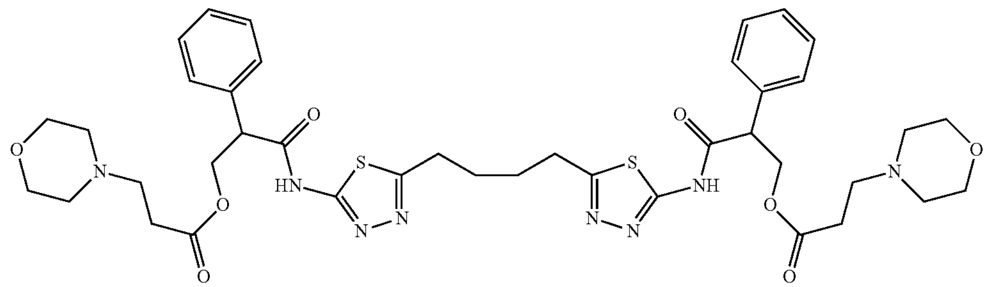 [SMILES: O=C(CCN1CCOCC1)OCC(C(=O)Nc1nnc(CCCCc2nnc(NC(=O)C(COC(=O)CCN3CCOCC3)c3ccccc3)s2)s1)c1ccccc1] |
| 189 | 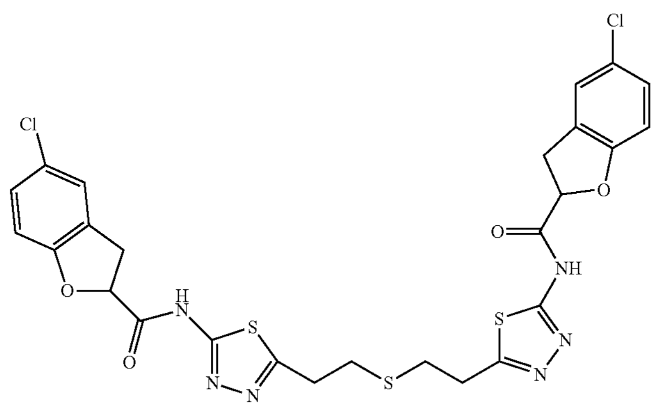 [SMILES: O=C(Nc1nnc(CCSCCc2nnc(NC(=O)C3Cc4cc(Cl)ccc4O3)s2)s1)C1Cc2cc(Cl)ccc2O1] |
| 190 | 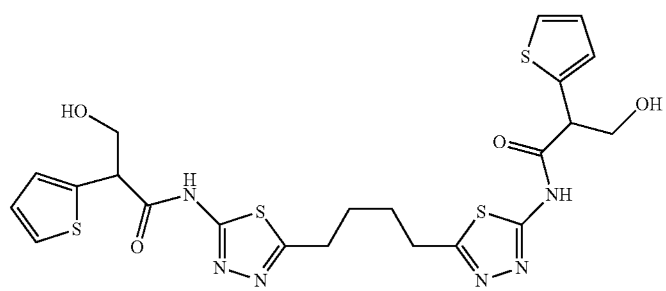 [SMILES: O=C(Nc1nnc(CCCCc2nnc(NC(=O)C(CO)c3cccs3)s2)s1)C(CO)c1cccs1] |
| 191 | 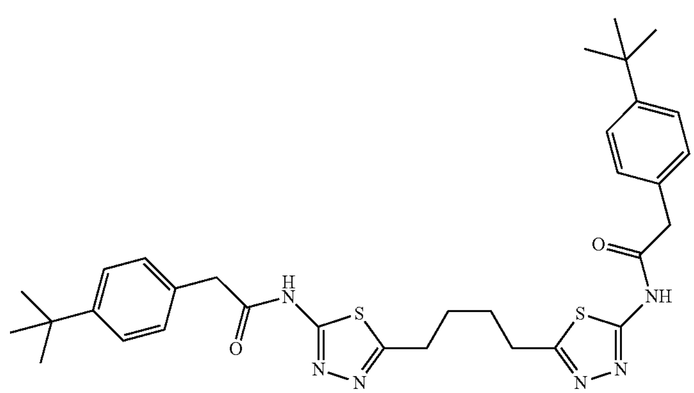 [SMILES: CC(C)(C)c1ccc(CC(=O)Nc2nnc(CCCCc3nnc(NC(=O)Cc4ccc(C(C)(C)C)cc4)s3)s2)cc1] |

TABLE 1-continued
Selected Compounds of Formula I
| Compound ID | Structure |
|---|---|
| 192 | 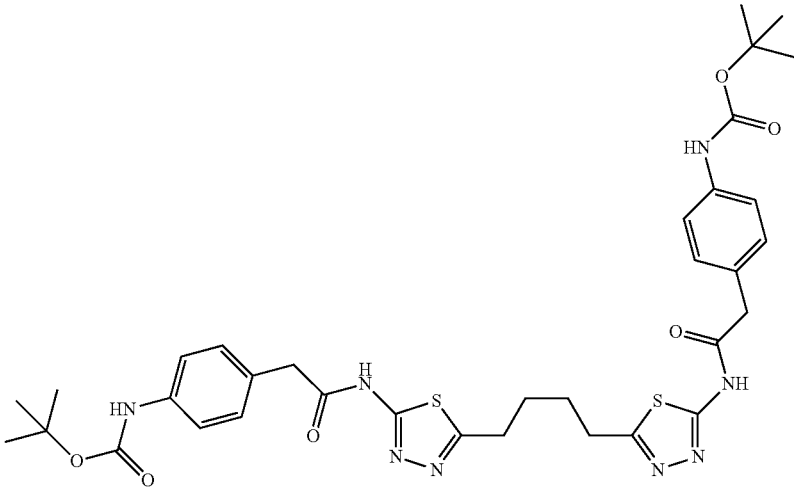 [SMILES: CC(C)(C)OC(=O)Nc1ccc(CC(=O)Nc2nnc(CCCCc3nnc(NC(=O)Cc4ccc(NC(=O)OC(C)(C)C)cc4)s3)s2)cc1] |
| 193 | 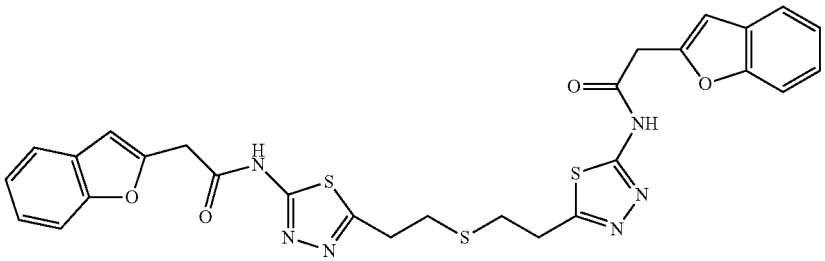 [SMILES: O=C(Cc1cc2ccccc2o1)Nc1nnc(CCSCCc2nnc(NC(=O)Cc3cc4ccccc4o3)s2)s1] |
| 194 | 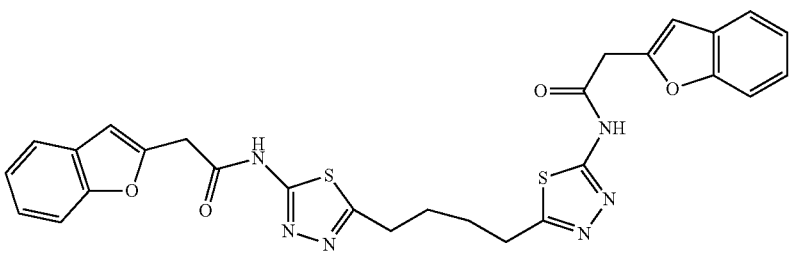 [SMILES: O=C(Cc1cc2ccccc2o1)Nc1nnc(CCCCc2nnc(NC(=O)Cc3cc4ccccc4o3)s2)s1] |
| 195 | 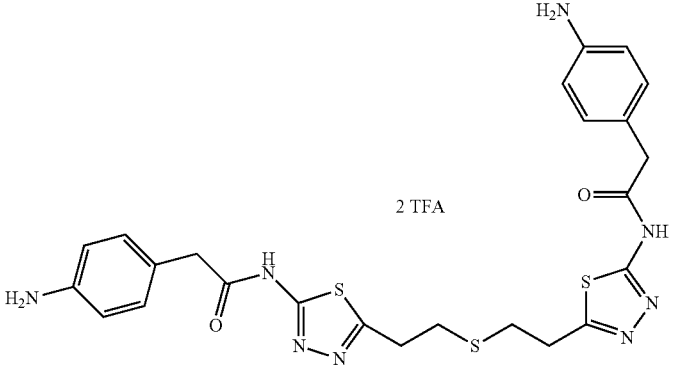 [SMILES: Nc1ccc(CC(=O)Nc2nnc(CCSCCc3nnc(NC(=O)Cc4ccc(N)cc4)s3)s2)cc1] |

TABLE 1-continued
Selected Compounds of Formula I
| Compound ID | Structure |
| --- | --- |
| 196 | 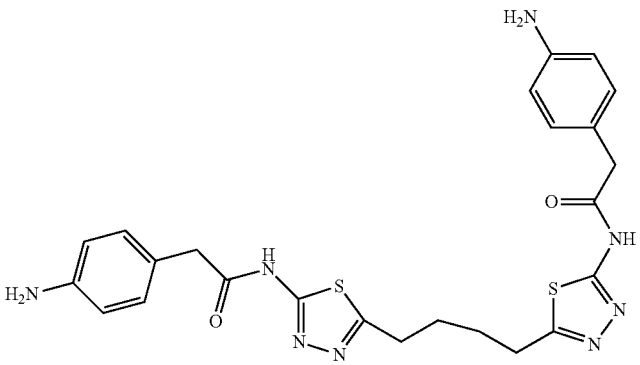<br>2 TFA |
| 197 | 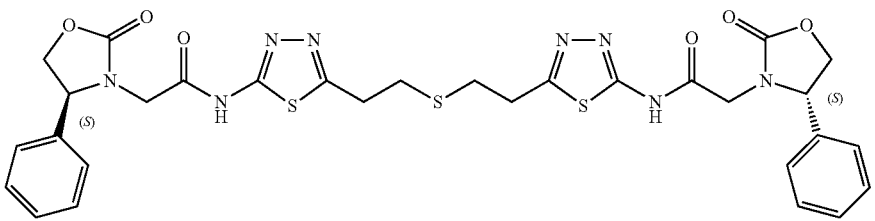 |
| 198 | 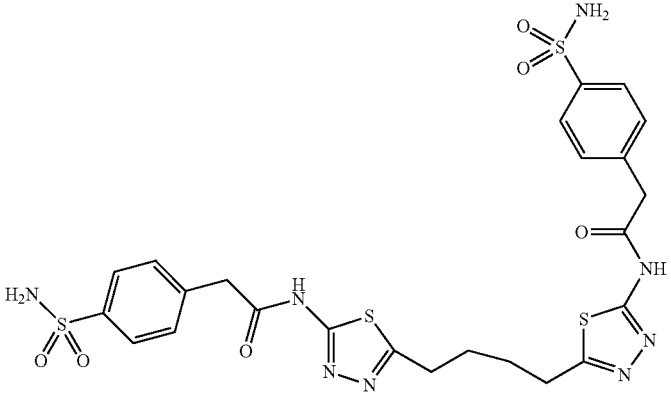 [SMILES: NS(=O)(=O)c1ccc(CC(=O)Nc2nnc(CCCCc3nnc(NC(=O)Cc4ccc(S(N)(=O)=O)cc4)s3)s2)cc1] |
| 199 | 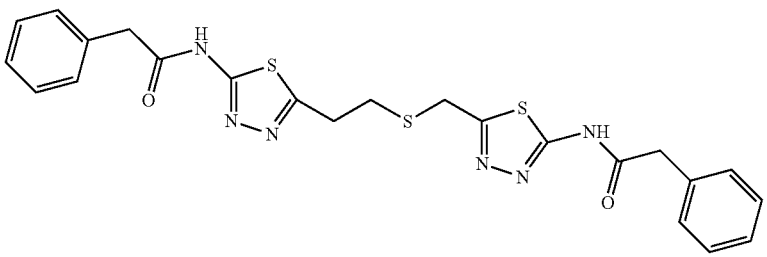 [SMILES: O=C(Cc1ccccc1)Nc1nnc(CCSCc2nnc(NC(=O)Cc3ccccc3)s2)s1] |

TABLE 1-continued
Selected Compounds of Formula I
| Compound ID | Structure |
|---|---|
| 200 | 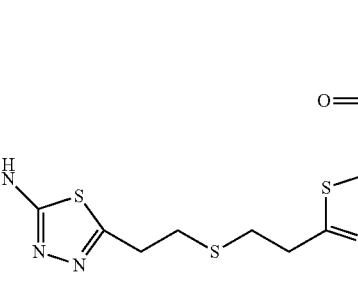 |
| 201 | 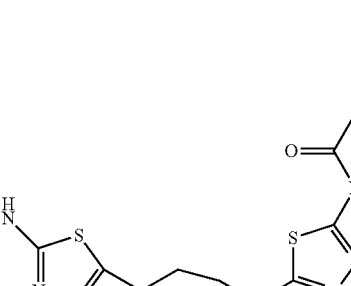 |
| 202 | 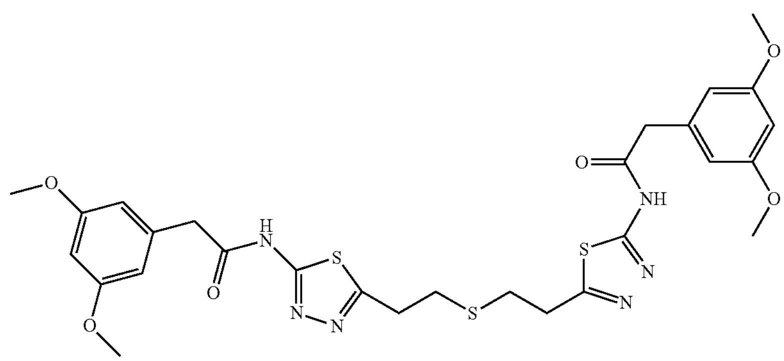 [SMILES: COc1cc(CC(=O)NC(=N)SC(=N)CCSCCc2nnc(NC(=O)Cc3cc(OC)cc(OC)c3)s2)cc(OC)c1] |
| 203 | 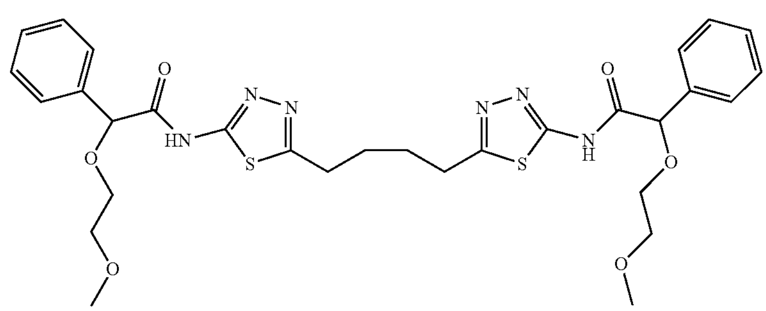 [SMILES: COCCOC(C(=O)Nc1nnc(CCCCc2nnc(NC(=O)C(OCCOC)c3ccccc3)s2)s1)c1ccccc1] |

TABLE 1-continued
Selected Compounds of Formula I
| Compound ID | Structure |
|---|---|
| 204 | 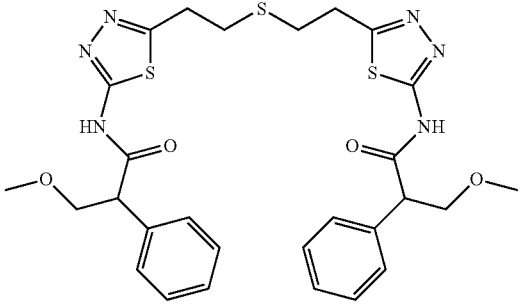 |
| 205 | 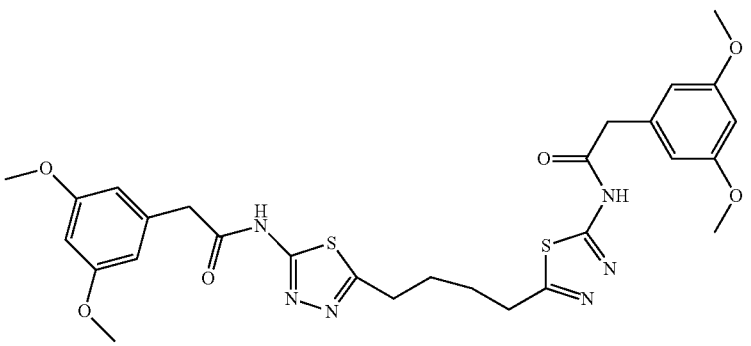 [SMILES: COc1cc(CC(=O)NC(=N)SC(=N)CCCCc2nnc(NC(=O)Cc3cc(OC)cc(OC)c3)s2)cc(OC)c1] |
| 206 | 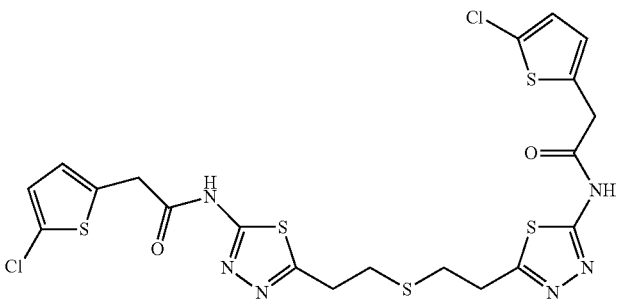 [SMILES: O=C(Cc1ccc(Cl)s1)Nc1nnc(CCSCCc2nnc(NC(=O)Cc3ccc(Cl)s3)s2)s1] |
| 207 | 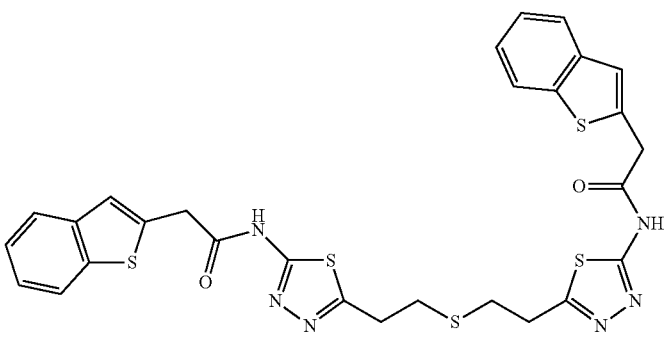 [SMILES: O=C(Cc1cc2ccccc2s1)Nc1nnc(CCSCCc2nnc(NC(=O)Cc3cc4ccccc4s3)s2)s1] |

TABLE 1-continued
Selected Compounds of Formula I
| Compound ID | Structure |
|---|---|
| 208 | 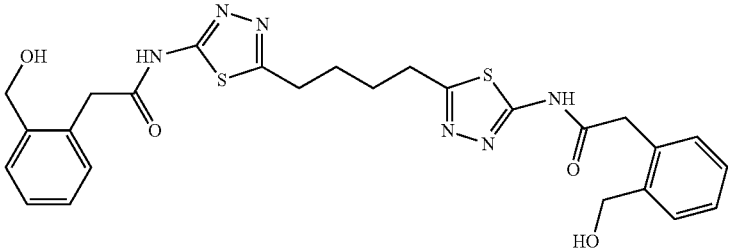 [SMILES: O=C(Cc1ccccc1CO)Nc1nnc(CCCCc2nnc(NC(=O)Cc3ccccc3CO)s2)s1] |
| 209 | 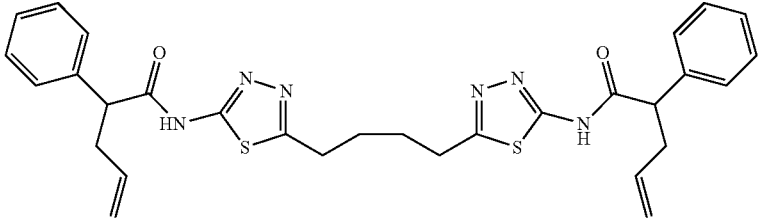 [SMILES: C=CCC(C(=O)Nc1nnc(CCCCc2nnc(NC(=O)C(CC=C)c3ccccc3)s2)s1)c1ccccc1] |
| 210 | 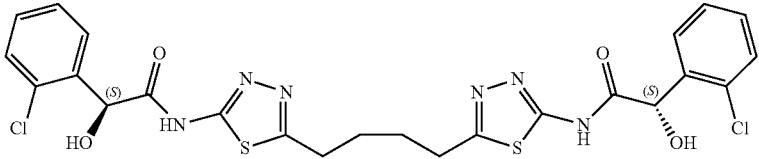 |
| 211 | 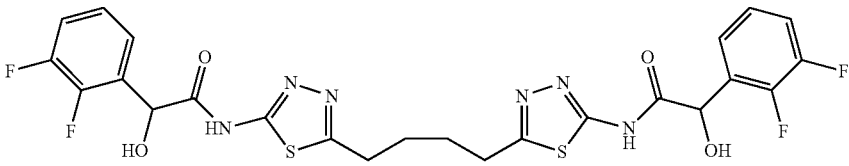 [SMILES: O=C(Nc1nnc(CCCCc2nnc(NC(=O)C(O)c3cccc(F)c3F)s2)s1)C(O)c1cccc(F)c1F] |
| 212 | 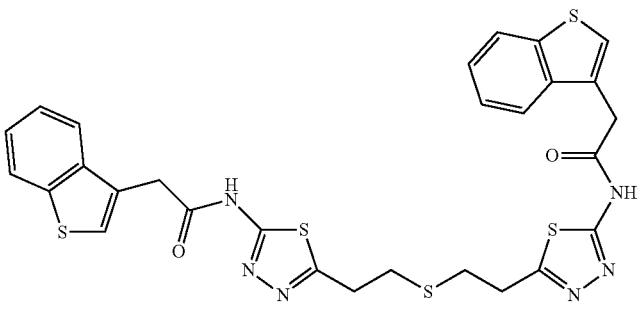 [SMILES: O=C(Cc1csc2ccccc12)Nc1nnc(CCSCCc2nnc(NC(=O)Cc3csc4ccccc34)s2)s1] |
| 213 | 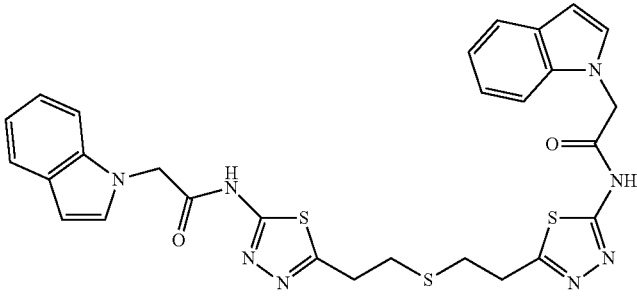 [SMILES: O=C(Cn1ccc2ccccc21)Nc1nnc(CCSCCc2nnc(NC(=O)Cn3ccc4ccccc43)s2)s1] |

TABLE 1-continued

Selected Compounds of Formula I

| Compound ID | Structure |
|---|---|
| 214 | 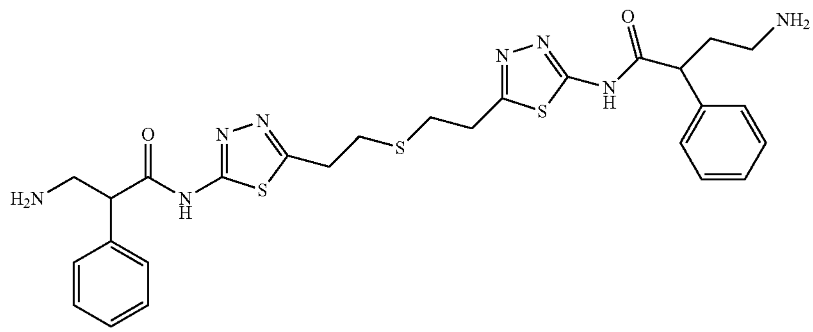 [SMILES: NCCC(C(=O)Nc1nnc(CCSCCc2nnc(NC(=O)C(CN)c3ccccc3)s2)s1)c1ccccc1] |
| 215 | 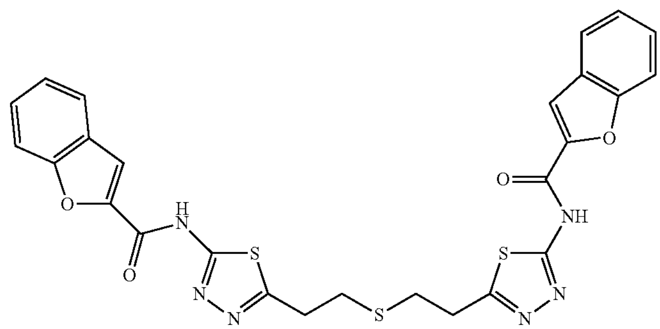 [SMILES: O=C(Nc1nnc(CCSCCc2nnc(NC(=O)c3cc4ccccc4o3)s2)s1)c1cc2ccccc2o1] |
| 216 | 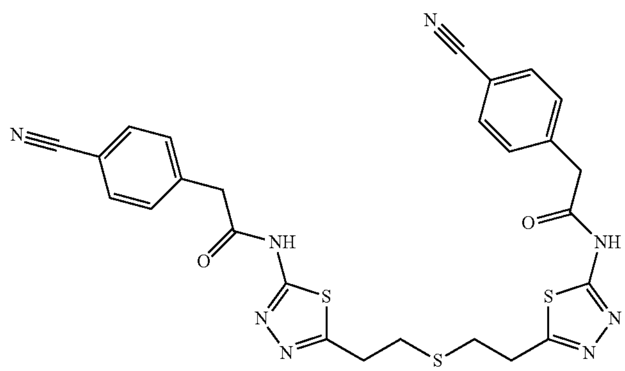 [SMILES: N#Cc1ccc(CC(=O)Nc2nnc(CCSCCc3nnc(NC(=O)Cc4ccc(C#N)cc4)s3)s2)cc1] |
| 217 | 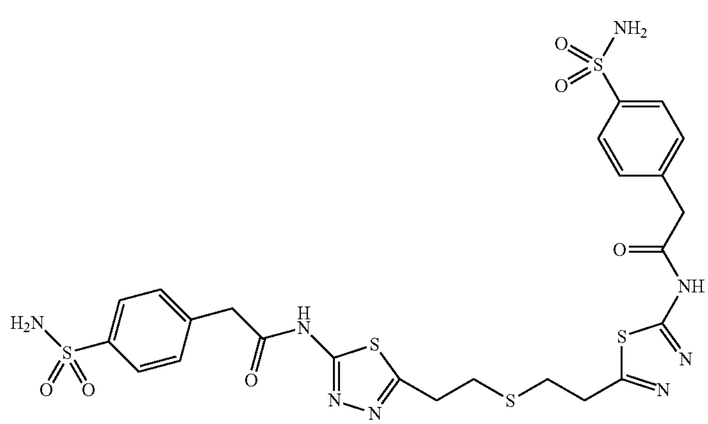 [SMILES: N=C(CCSCCc1nnc(NC(=O)Cc2ccc(S(N)(=O)=O)cc2)s1)SC(=N)NC(=O)Cc1ccc(S(N)(=O)=O)cc1] |

TABLE 1-continued

Selected Compounds of Formula I

| Compound ID | Structure |
| --- | --- |
| 218 | 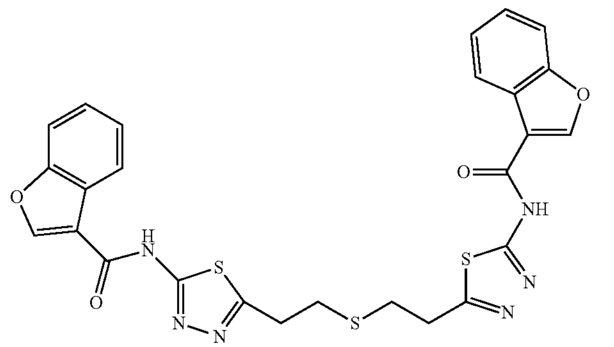 [SMILES: N=C(CCSCCc1nnc(NC(=O)c2coc3ccccc23)s1)SC(=N)NC(=O)c1coc2ccccc12] |
| 219 | 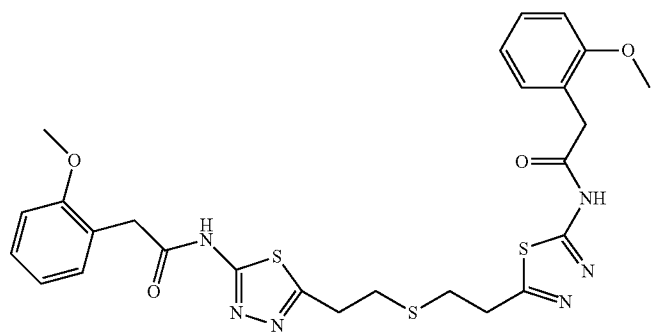 [SMILES: COc1ccccc1CC(=O)NC(=N)SC(=N)CCSCCc1nnc(NC(=O)Cc2ccccc2OC)s1] |
| 220 | 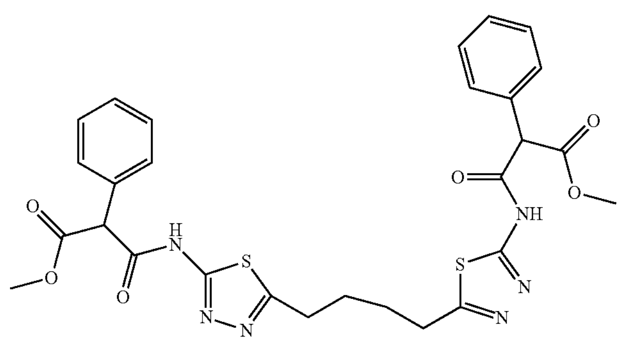 |
| 221 | 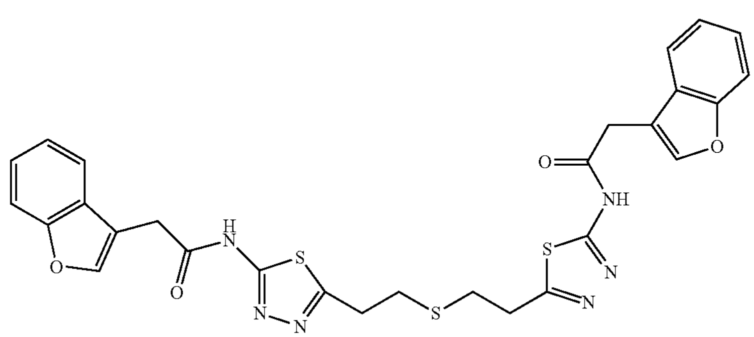 [SMILES: N=C(CCSCCc1nnc(NC(=O)Cc2coc3ccccc23)s1)SC(=N)NC(=O)Cc1coc2ccccc12] |

101 102
TABLE 1-continued
Selected Compounds of Formula I
| Compound ID | Structure |
|---|---|
| 222 | 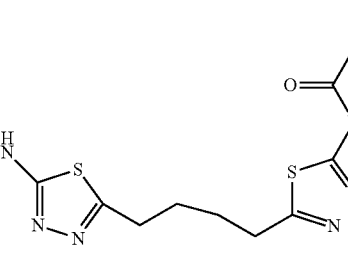 |
| 223 | 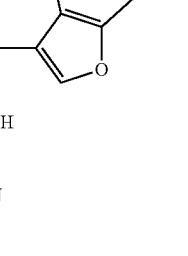 |
| 224 | 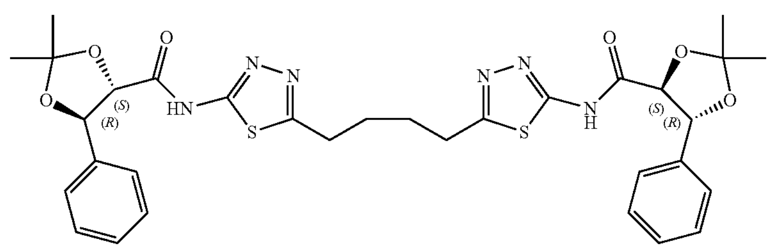 |
| 225 | 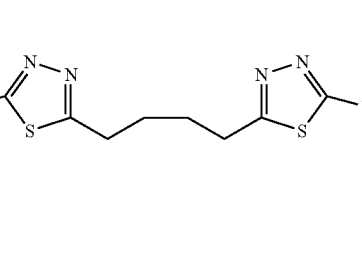 |
| 226 | 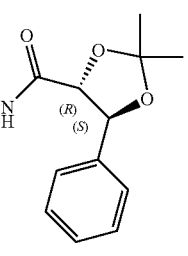 |
| 227 | 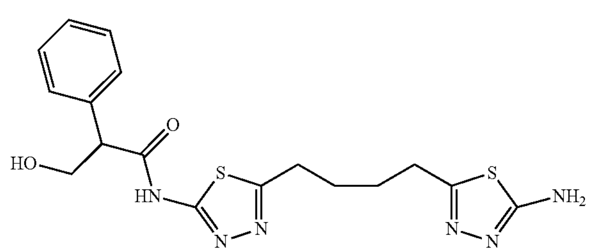 [SMILES: Nc1nnc(CCCCc2nnc(NC(=O)C(CO)c3ccccc3)s2)s1] |

TABLE 1-continued

Selected Compounds of Formula I

| Compound ID | Structure |
|---|---|
| 228 | 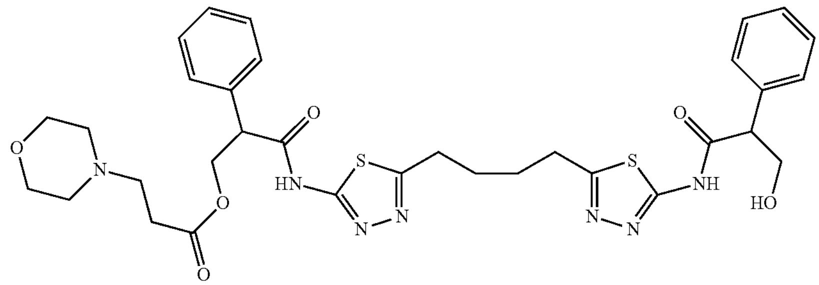 [SMILES: O=C(CCN1CCOCC1)OCC(C(=O)Nc1nnc(CCCCc2nnc(NC(=O)C(CO)c3ccccc3)s2)s1)c1ccccc1] |
| 229 | 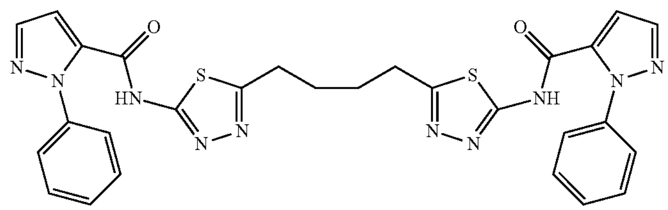 [SMILES: O=C(Nc1nnc(CCCCc2nnc(NC(=O)c3ccnn3-c3ccccc3)s2)s1)c1ccnn1-c1ccccc1] |
| 230 | 2 HCl |
| 231 | 2 HCl |
| 232 | 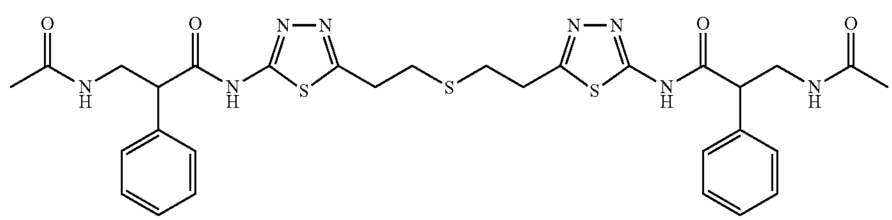 [SMILES: CC(=O)NCC(C(=O)Nc1nnc(CCSCCc2nnc(NC(=O)C(CNC(C)=O)c3ccccc3)s2)s1)c1ccccc1] |
| 233 | 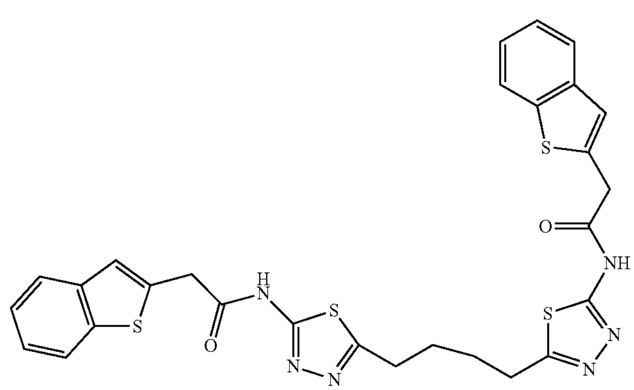 [SMILES: O=C(Cc1cc2ccccc2s1)Nc1nnc(CCCCc2nnc(NC(=O)Cc3cc4ccccc4s3)s2)s1] |

TABLE 1-continued

Selected Compounds of Formula I

| Compound ID | Structure |
|---|---|
| 234 | 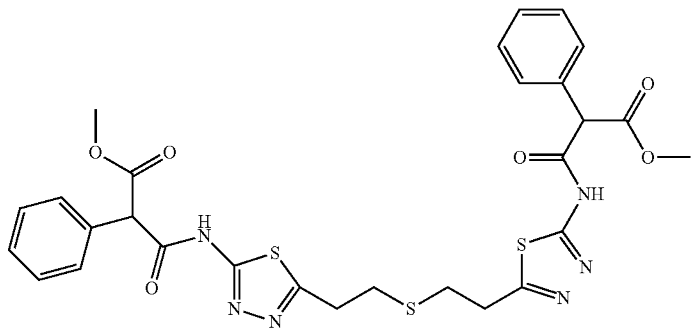 [SMILES: COC(=O)C(C(=O)NC(=N)SC(=N)CCSCCc1nnc(NC(=O)C(C(=O)OC)c2ccccc2)s1)c1ccccc1] |
| 235 | 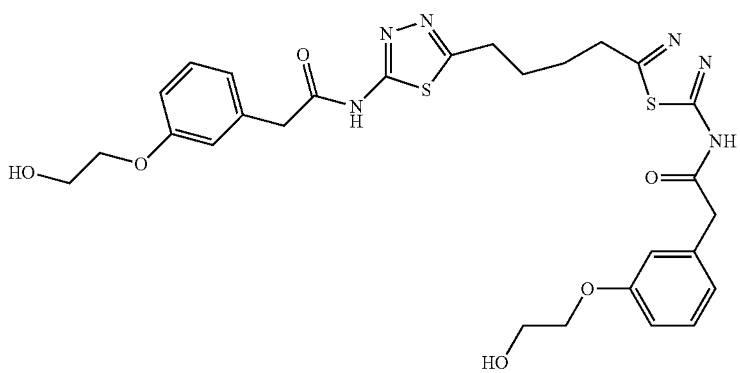 [SMILES: N=C(CCCCc1nnc(NC(=O)Cc2cccc(OCCO)c2)s1)SC(=N)NC(=O)Cc1cccc(OCCO)c1] |
| 236 | 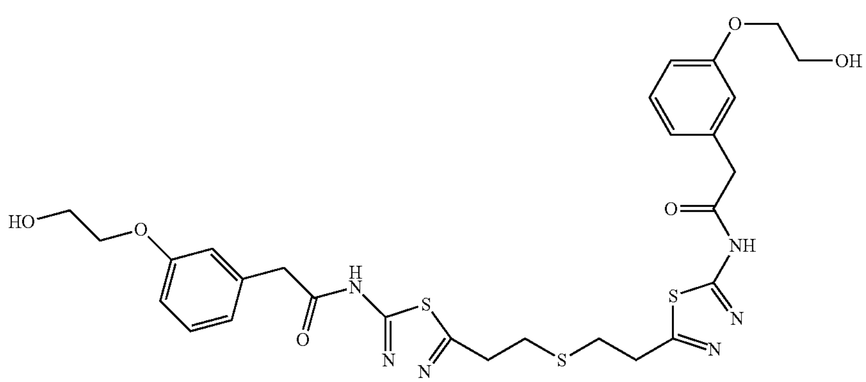 [SMILES: N=C(CCSCCC(=N)SC(=N)NC(=O)Cc1cccc(OCCO)c1)SC(=N)NC(=O)Cc1cccc(OCCO)c1] |
| 237 | 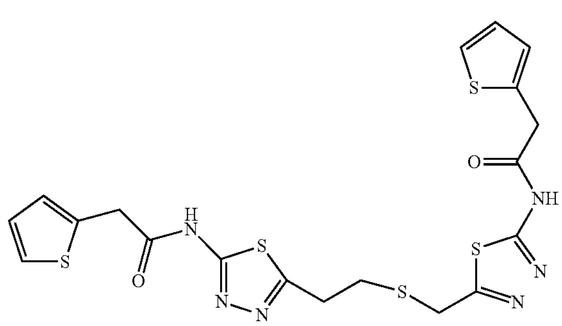 [SMILES: N=C(CSCCc1nnc(NC(=O)Cc2cccs2)s1)SC(=N)NC(=O)Cc1cccs1] |

TABLE 1-continued

Selected Compounds of Formula I

| Compound ID | Structure |
|---|---|
| 238 | 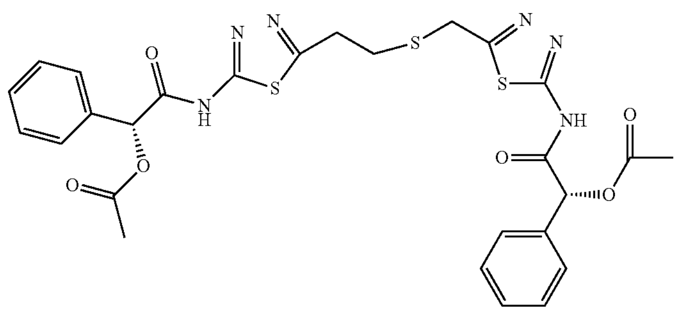 [SMILES: CC(=O)O[C@@H](C(=O)NC(=N)SC(=N)CCSCC(=N)SC(=N)NC(=O)[C@H](OC(C)=O)c1ccccc1)c1ccccc1] |
| 239 | 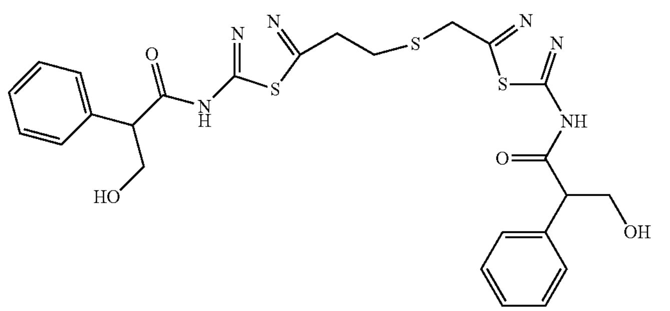 [SMILES: N=C(CCSCC(=N)SC(=N)NC(=O)C(CO)c1ccccc1)SC(=N)NC(=O)C(CO)c1ccccc1] |
| 240 | 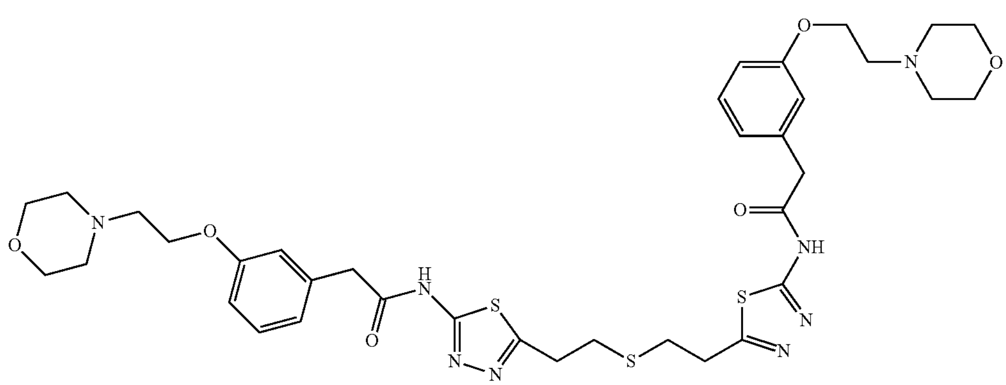 [SMILES: N=C(CCSCCc1nnc(NC(=O)Cc2cccc(OCCN3CCOCC3)c2)s1)SC(=N)NC(=O)Cc1cccc(OCCN2CCOCC2)c1] |
| 241 | 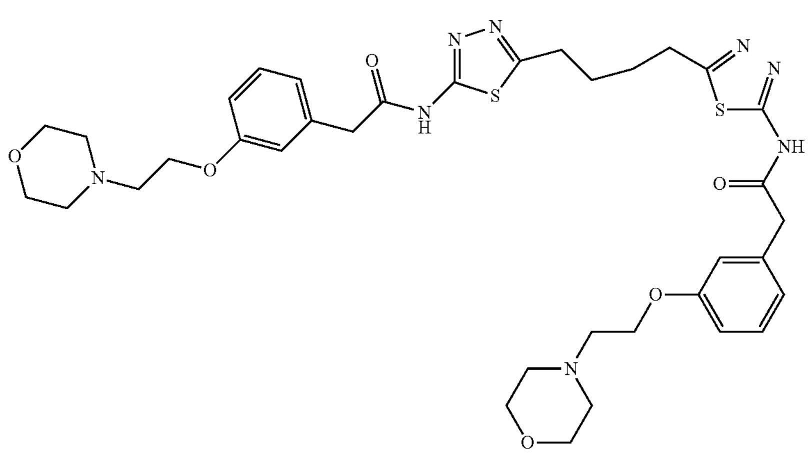 [SMILES: N=C(CCCCc1nnc(NC(=O)Cc2cccc(OCCN3CCOCC3)c2)s1)SC(=N)NC(=O)Cc1cccc(OCCN2CCOCC2)c1] |

TABLE 1-continued

Selected Compounds of Formula I

| Compound ID | Structure |
|---|---|
| 242 | 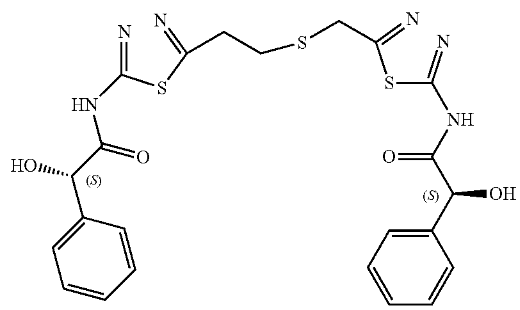 |
| 243 | 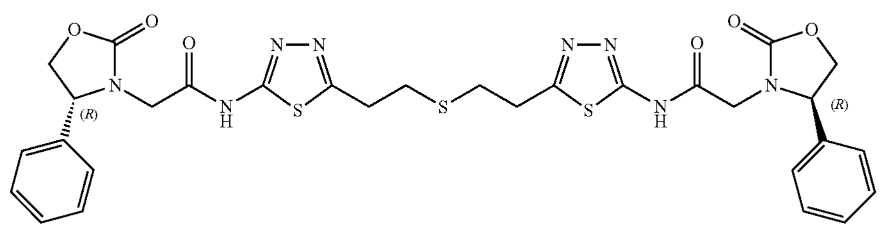 |
| 244 | 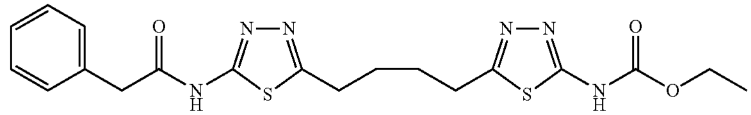 [SMILES: CCOC(=O)Nc1nnc(CCCCc2nnc(NC(=O)Cc3ccccc3)s2)s1] |
| 245 | 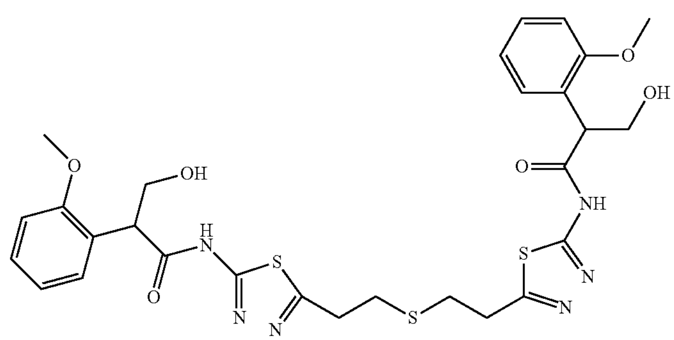 [SMILES: COc1ccccc1C(CO)C(=O)NC(=N)SC(=N)CCSCCC(=N)SC(=N)NC(=O)C(CO)c1ccccc1OC] |
| 246 | 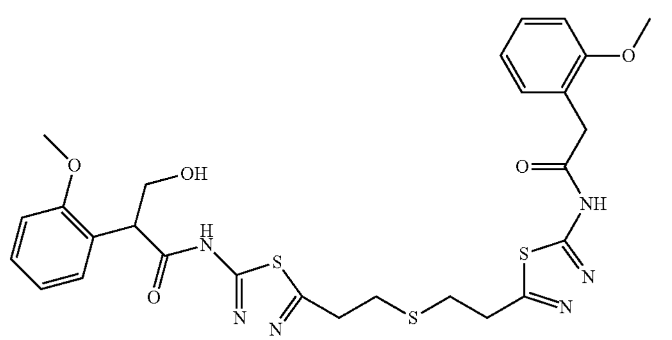 [SMILES: COc1ccccc1CC(=O)NC(=N)SC(=N)CCSCCC(=N)SC(=N)NC(=O)C(CO)c1ccccc1OC] |

TABLE 1-continued
Selected Compounds of Formula I
| Compound ID | Structure |
|---|---|
| 247 | 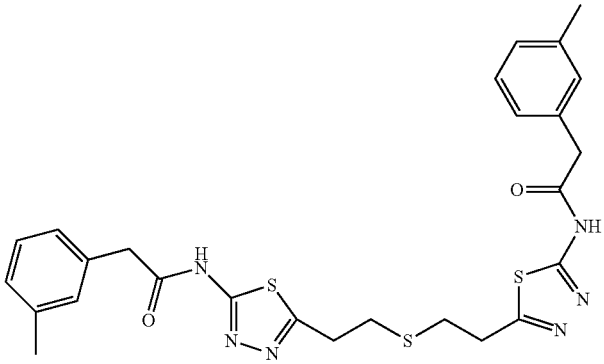 [SMILES: Cc1cccc(CC(=O)NC(=N)SC(=N)CCSCCc2nnc(NC(=O)Cc3cccc(C)c3)s2)c1] |
| 248 | 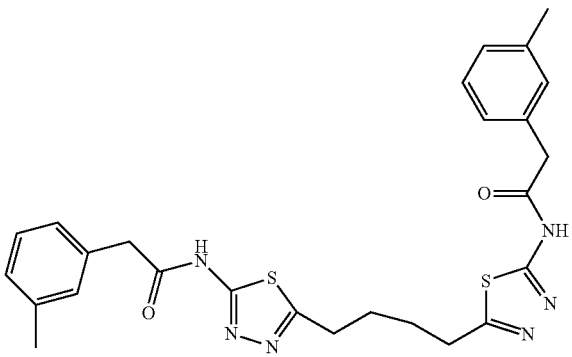 [SMILES: Cc1cccc(CC(=O)NC(=N)SC(=N)CCCCc2nnc(NC(=O)Cc3cccc(C)c3)s2)c1] |
| 249 | 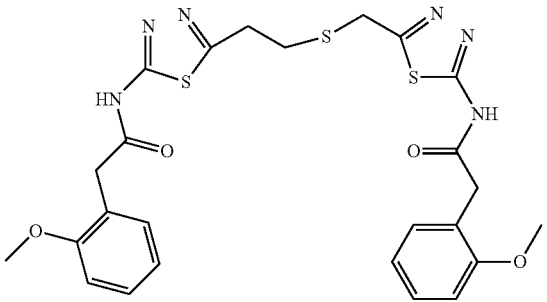 |
| 250 | 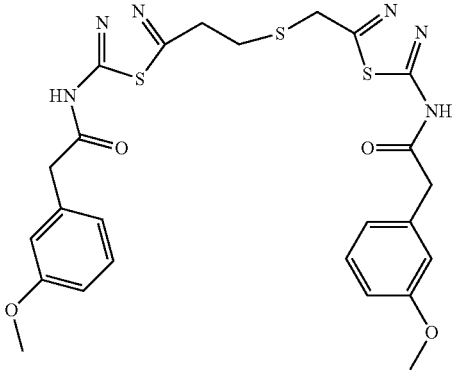 [SMILES: COc1cccc(CC(=O)NC(=N)SC(=N)CCSCC(=N)SC(=N)NC(=O)Cc2cccc(OC)c2)c1] |

TABLE 1-continued

Selected Compounds of Formula I

| Compound ID | Structure |
|---|---|
| 251 | 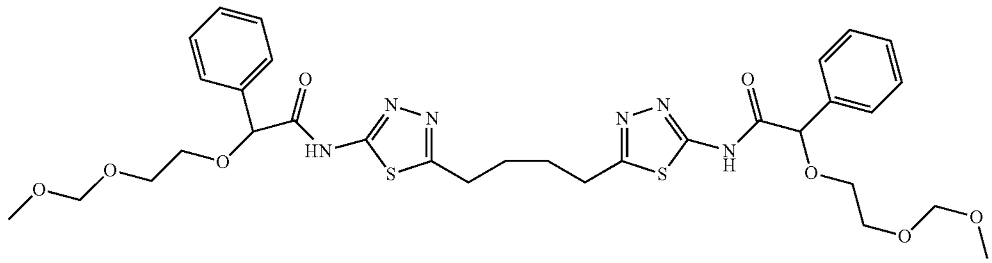 |
| 252 | 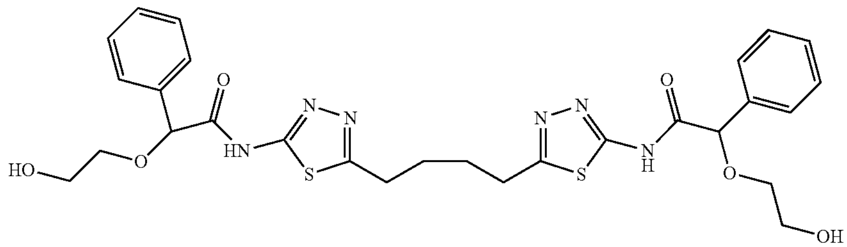 [SMILES: O=C(Nc1nnc(CCCCc2nnc(NC(=O)C(OCCO)c3ccccc3)s2)s1)C(OCCO)c1ccccc1] |
| 253 | 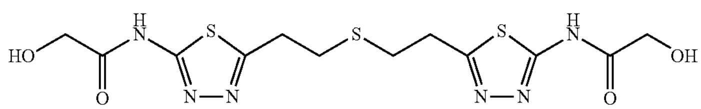 [SMILES: O=C(CO)Nc1nnc(CCSCCc2nnc(NC(=O)CO)s2)s1] |
| 254 | 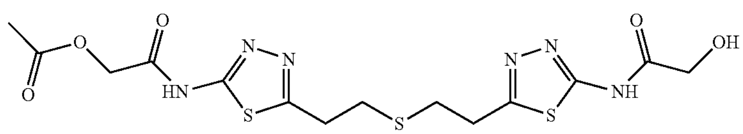 [SMILES: CC(=O)OCC(=O)Nc1nnc(CCSCCc2nnc(NC(=O)CO)s2)s1] |
| 255 | 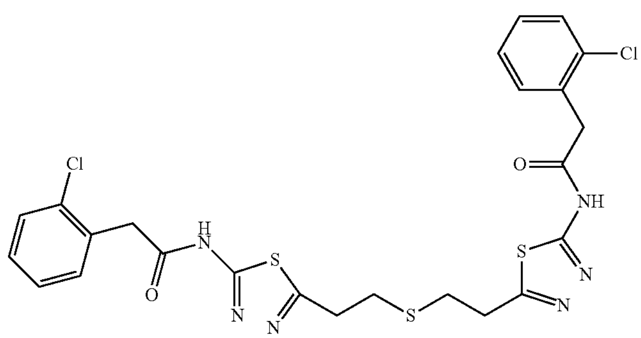 [SMILES: N=C(CCSCCC(=N)SC(=N)NC(=O)Cc1ccccc1Cl)SC(=N)NC(=O)Cc1ccccc1Cl] |
| 256 | 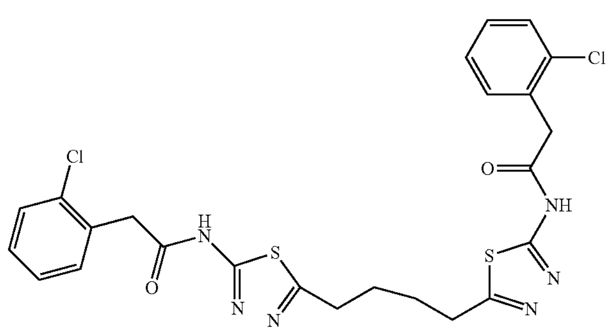 [SMILES: N=C(CCCCC(=N)SC(=N)NC(=O)Cc1ccccc1Cl)SC(=N)NC(=O)Cc1ccccc1Cl] |

TABLE 1-continued

Selected Compounds of Formula I

| Compound ID | Structure |
|---|---|
| 257 | 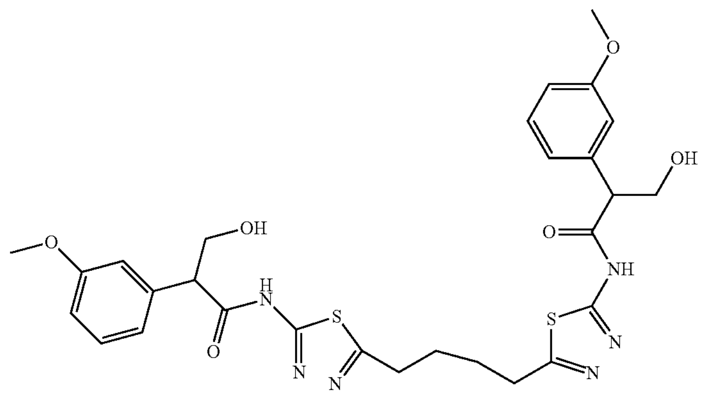 [SMILES: COc1cccc(C(CO)C(=O)NC(=N)SC(=N)CCCCC(=N)SC(=N)NC(=O)C(CO)c2cccc(OC)c2)c1] |
| 258 | 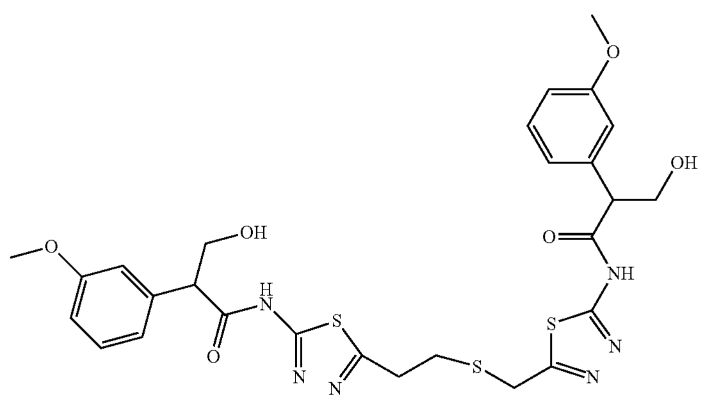 [SMILES: COc1cccc(C(CO)C(=O)NC(=N)SC(=N)CCSCC(=N)SC(=N)NC(=O)C(CO)c2cccc(OC)c2)c1] |
| 259 | 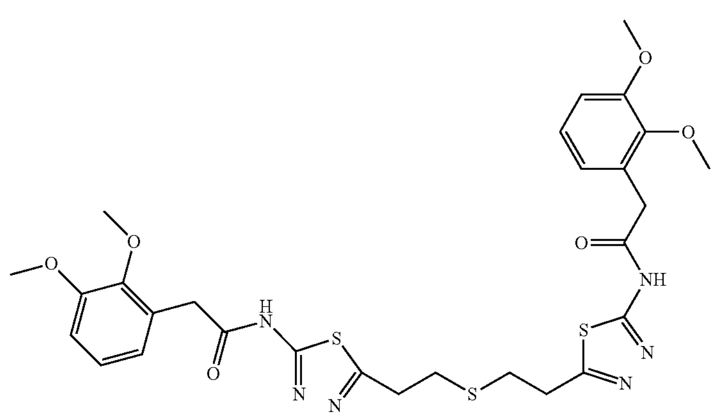 |

TABLE 1-continued
Selected Compounds of Formula I
| Compound ID | Structure |
|---|---|
| 260 | 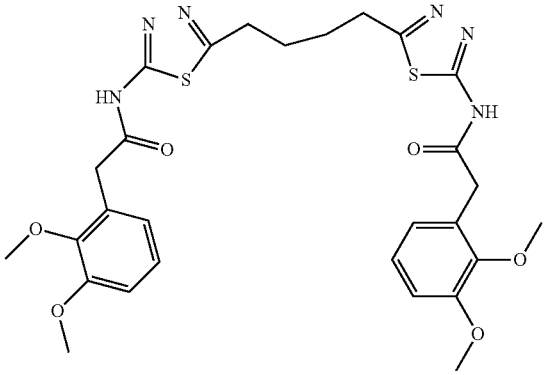 |
| 261 | 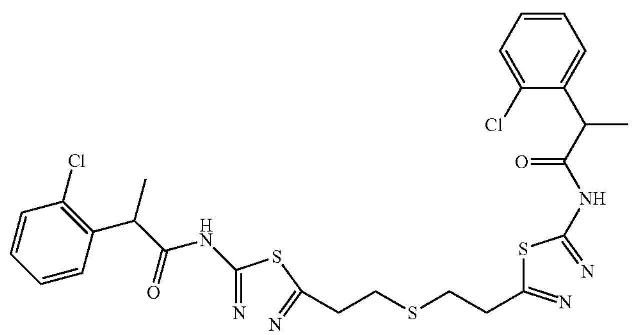 [SMILES: CC(C(=O)NC(=N)SC(=N)CCSCCC(=N)SC(=N)NC(=O)C(C)c1ccccc1Cl)c1ccccc1Cl] |
| 262 | 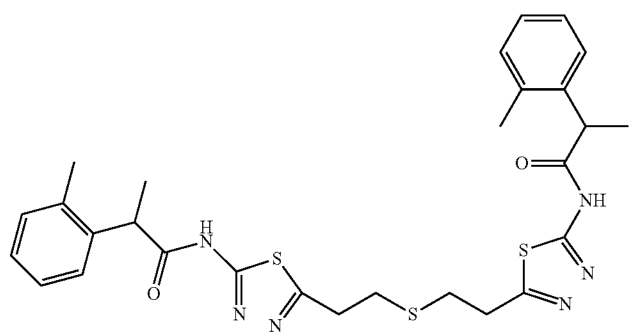 [SMILES: Cc1ccccc1C(C)C(=O)NC(=N)SC(=N)CCSCCC(=N)SC(=N)NC(=O)C(C)c1ccccc1C] |
| 263 | 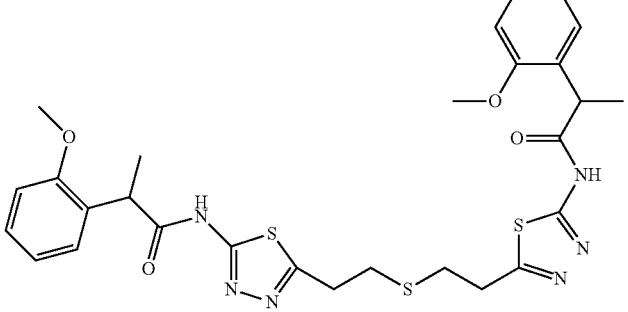 |

TABLE 1-continued

Selected Compounds of Formula I

| Compound ID | Structure |
|---|---|
| 264 | 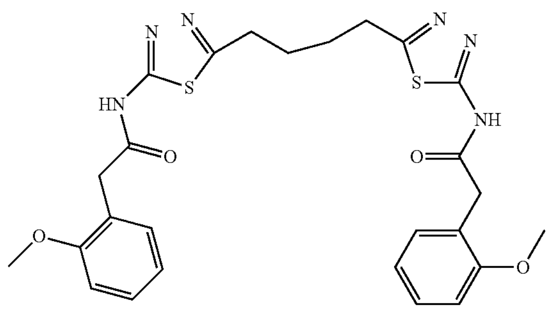 |
| 265 | 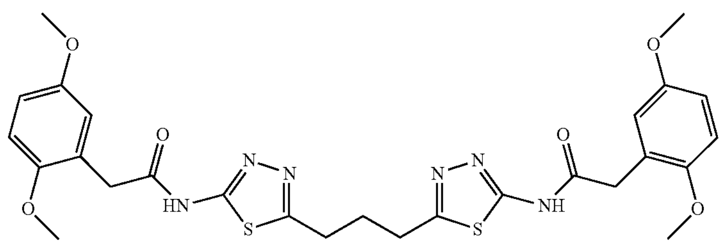 [SMILES: COc1ccc(OC)c(CC(=O)Nc2nnc(CCCc3nnc(NC(=O)Cc4cc(OC)ccc4OC)s3)s2)c1] |
| 266 | 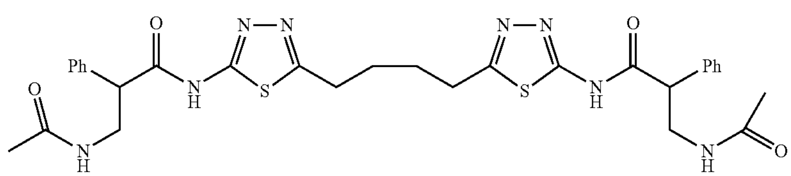 [SMILES: CC(=O)NCC(C(=O)Nc1nnc(CCCCc2nnc(NC(=O)C(CNC(C)=O)c3ccccc3)s2)s1)c1ccccc1] |
| 267 | 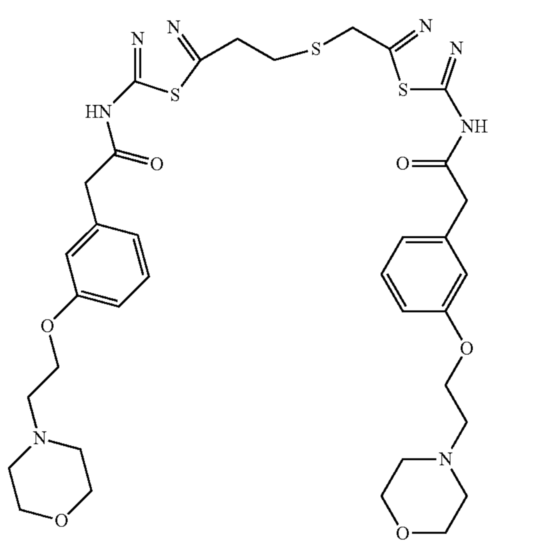 [SMILES: N=C(CCSCC(=N)SC(=N)NC(=O)Cc1cccc(OCCN2CCOCC2)c1)SC(=N)NC(=O)Cc1cccc(OCCN2CCOCC2)c1] |

TABLE 1-continued

Selected Compounds of Formula I

| Compound ID | Structure |
|---|---|
| 268 | 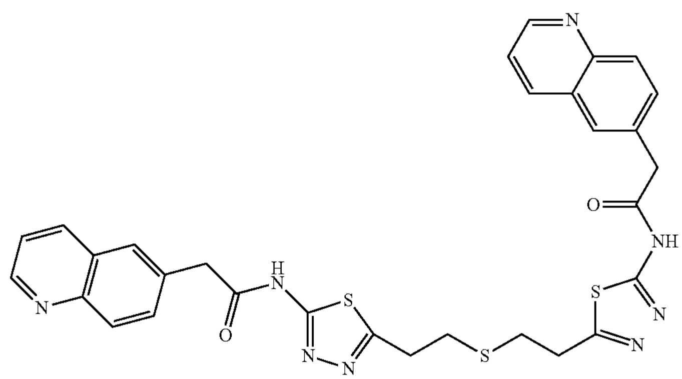 [SMILES: N=C(CCSCCc1nnc(NC(=O)Cc2ccc3ncccc3c2)s1)SC(=N)NC(=O)Cc1ccc2ncccc2c1] |
| 269 | 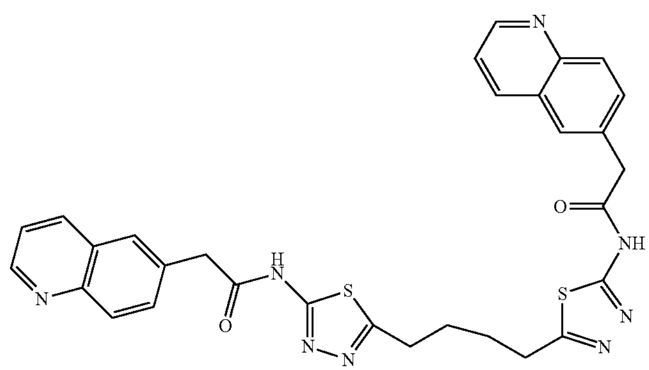 [SMILES: N=C(CCCCc1nnc(NC(=O)Cc2ccc3ncccc3c2)s1)SC(=N)NC(=O)Cc1ccc2ncccc2c1] |
| 270 | 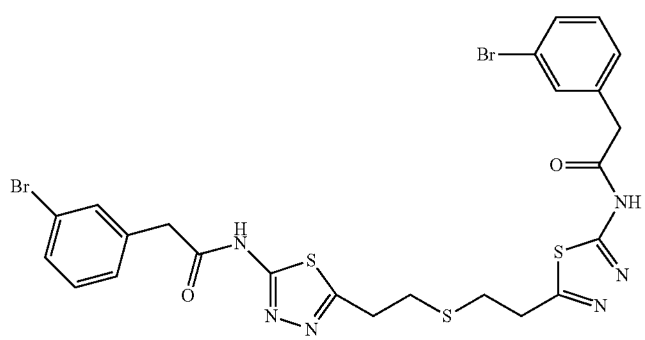 [SMILES: N=C(CCSCCc1nnc(NC(=O)Cc2cccc(Br)c2)s1)SC(=N)NC(=O)Cc1cccc(Br)c1] |
| 271 | 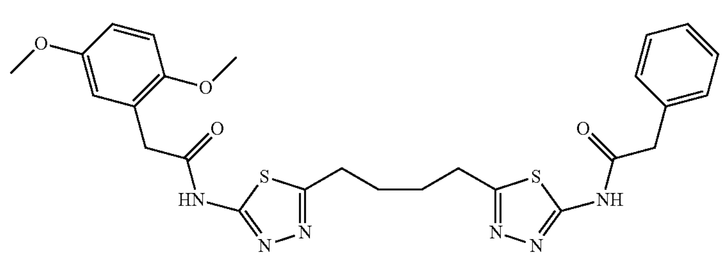 [SMILES: COc1ccc(OC)c(CC(=O)Nc2nnc(CCCCc3nnc(NC(=O)Cc4ccccc4)s3)s2)c1] |

TABLE 1-continued

Selected Compounds of Formula I

| Compound ID | Structure |
|---|---|
| 272 | 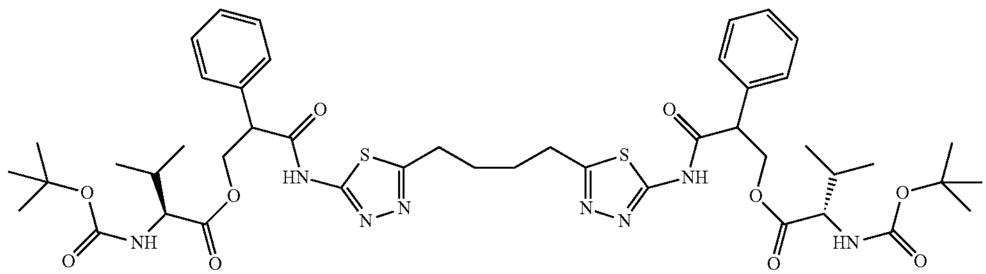 [SMILES: CC(C)[C@H](NC(=O)OC(C)(C)C)C(=O)OCC(C(=O)Nc1nnc(CCCCc2nnc(NC(=O)C(COC(=O)[C@@H](NC(=O)OC(C)(C)C)C(C)C)c3ccccc3)s2)s1)c1ccccc1] |
| 273 | 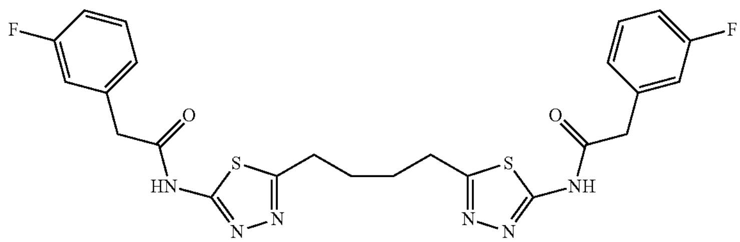 [SMILES: O=C(Cc1cccc(F)c1)Nc1nnc(CCCCc2nnc(NC(=O)Cc3cccc(F)c3)s2)s1] |
| 274 | 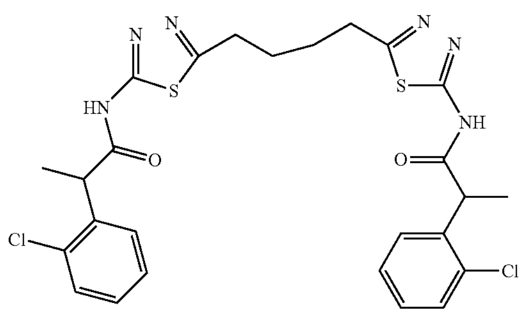 [SMILES: CC(C(=O)NC(=N)SC(=N)CCCCC(=N)SC(=N)NC(=O)C(C)c1ccccc1Cl)c1ccccc1Cl] |
| 275 | 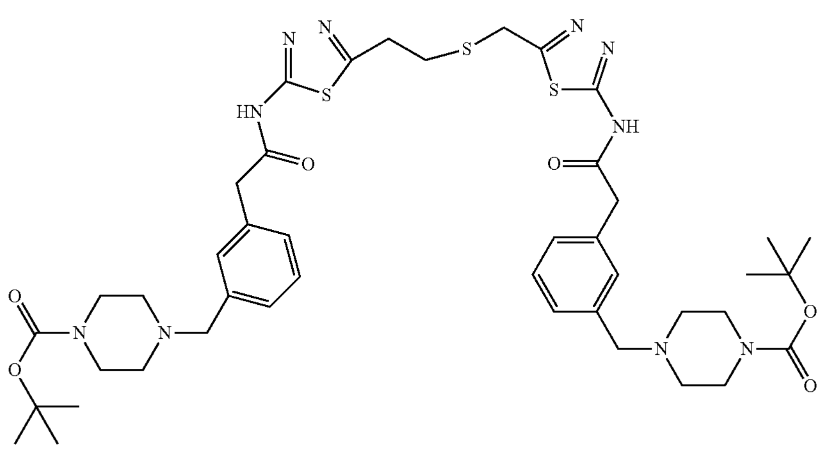 [SMILES: CC(C)(C)OC(=O)N1CCN(Cc2cccc(CC(=O)NC(=N)SC(=N)CCSCC(=N)SC(=N)NC(=O)Cc3cccc(CN4CCN(C(=O)OC(C)(C)C)CC4)c3)c2)CC1] |

TABLE 1-continued
Selected Compounds of Formula I
| Compound ID | Structure |
|---|---|
| 276 | 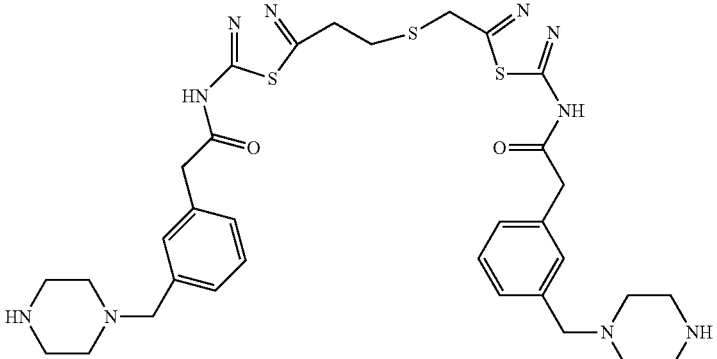<br>2 TFA |
| 277 | 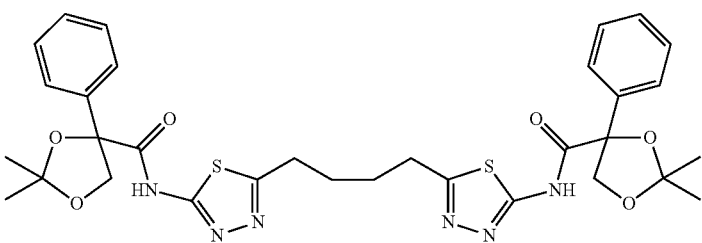 |
| 278 | 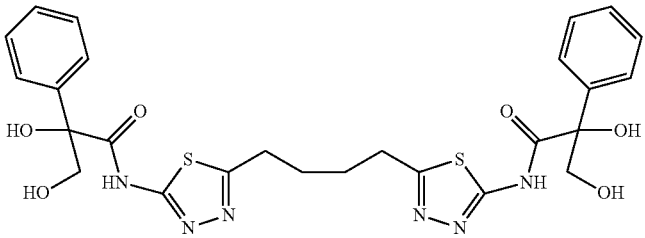 [SMILES: O=C(Nc1nnc(CCCCc2nnc(NC(=O)C(O)(CO)c3ccccc3)s2)s1)C(O)(CO)c1ccccc1] |
| 279 | 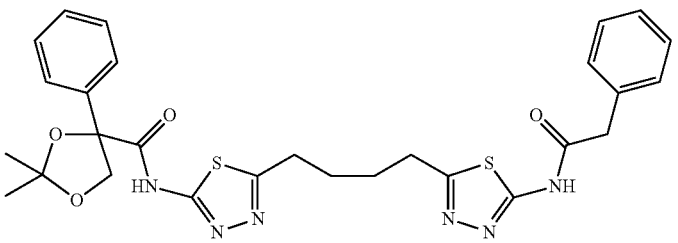 [SMILES: CC1(C)OCC(C(=O)Nc2nnc(CCCCc3nnc(NC(=O)Cc4ccccc4)s3)s2)(c2ccccc2)O1] |
| 280 | 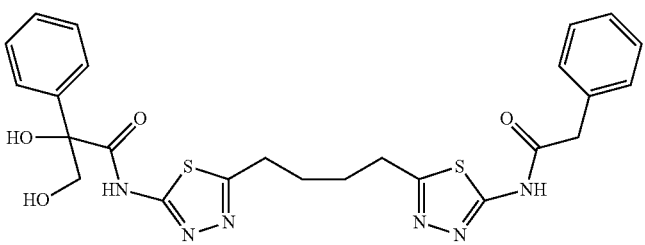 [SMILES: O=C(Cc1ccccc1)Nc1nnc(CCCCc2nnc(NC(=O)C(O)(CO)c3ccccc3)s2)s1] |

TABLE 1-continued

Selected Compounds of Formula I

| Compound ID | Structure |
|---|---|
| 281 | 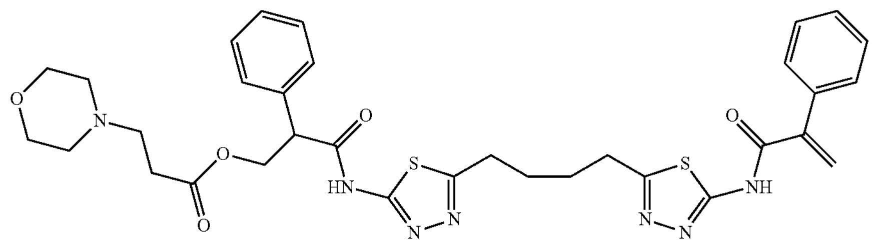 [SMILES: C=C(C(=O)Nc1nnc(CCCCc2nnc(NC(=O)C(COC(=O)CCN3CCOCC3)c3ccccc3)s2)s1)c1ccccc1] |
| 282 | 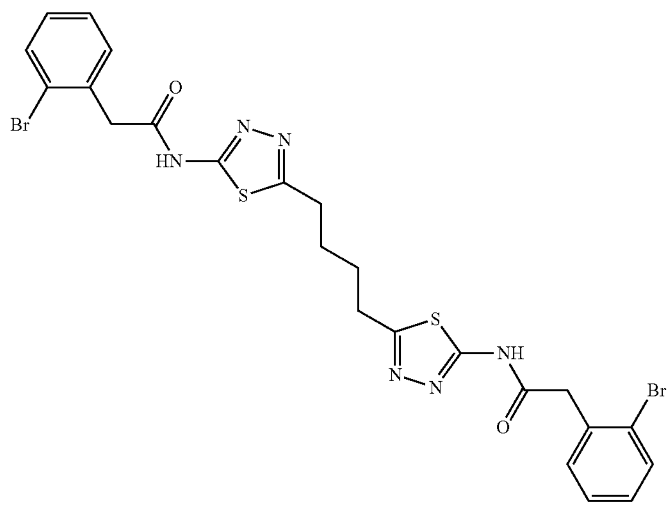 [SMILES: O=C(Cc1ccccc1Br)Nc1nnc(CCCCc2nnc(NC(=O)Cc3ccccc3Br)s2)s1] |
| 283 | 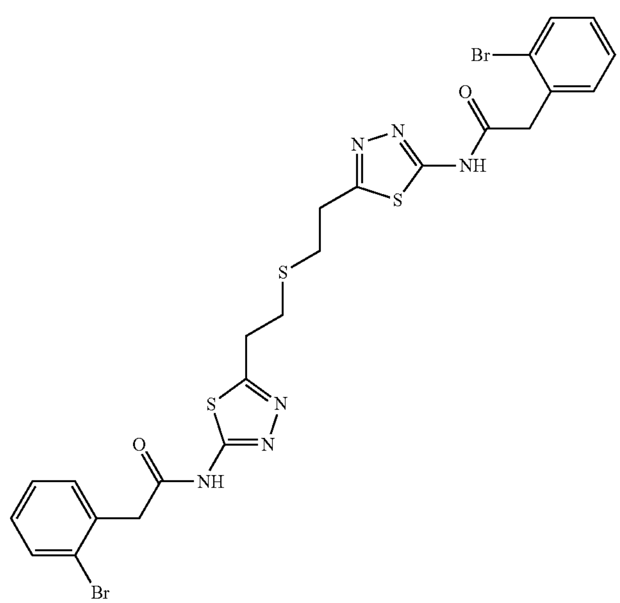 [SMILES: O=C(Cc1ccccc1Br)Nc1nnc(CCSCCc2nnc(NC(=O)Cc3ccccc3Br)s2)s1] |

TABLE 1-continued

Selected Compounds of Formula I

| Compound ID | Structure |
|---|---|
| 284 | 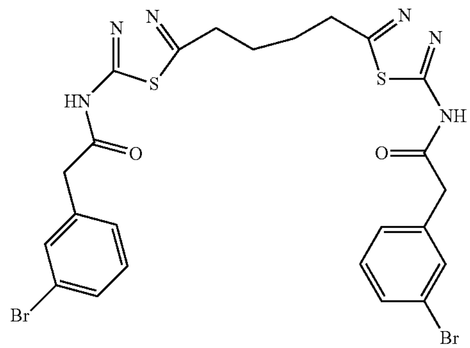 [SMILES: N=C(CCCCC(=N)SC(=N)NC(=O)Cc1cccc(Br)c1)SC(=N)NC(=O)Cc1cccc(Br)c1] |
| 285 | 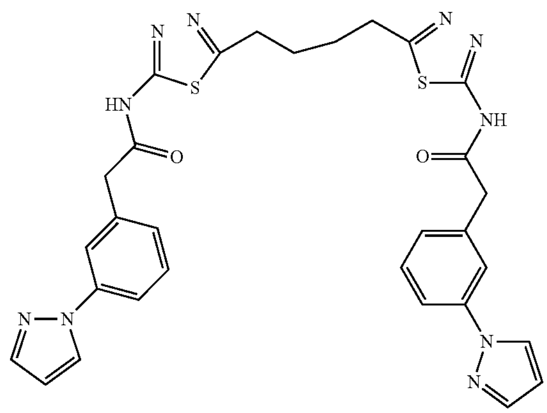 [SMILES: N=C(CCCCC(=N)SC(=N)NC(=O)Cc1cccc(-n2cccn2)c1)SC(=N)NC(=O)Cc1cccc(-n2cccn2)c1] |
| 286 | 2 HCO₂H |
| 287 | 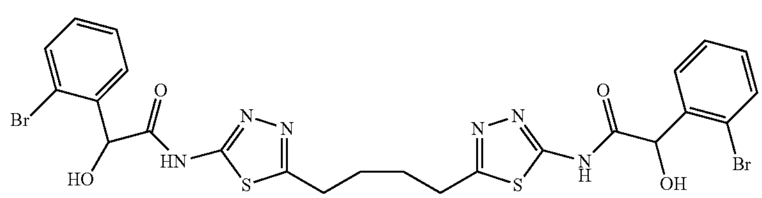 [SMILES: O=C(Nc1nnc(CCCCc2nnc(NC(=O)C(O)c3ccccc3Br)s2)s1)C(O)c1ccccc1Br] |
| 288 | 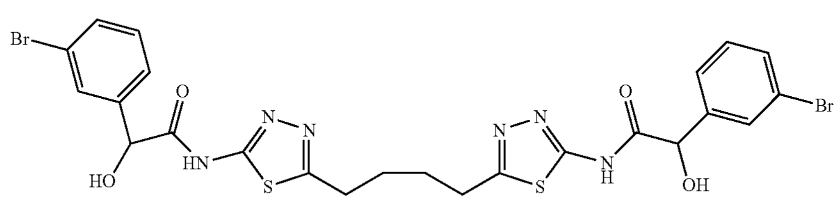 [SMILES: O=C(Nc1nnc(CCCCc2nnc(NC(=O)C(O)c3cccc(Br)c3)s2)s1)C(O)c1cccc(Br)c1] |

TABLE 1-continued

Selected Compounds of Formula I

| Compound ID | Structure |
| --- | --- |
| 289 | 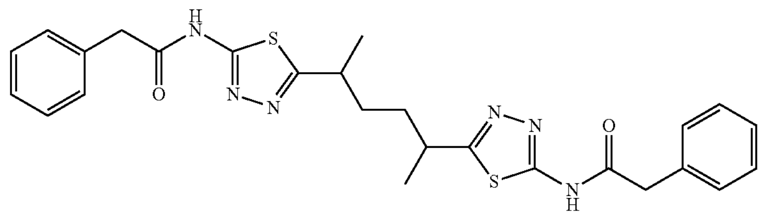 [SMILES: CC(CCC(C)c1nnc(NC(=O)Cc2ccccc2)s1)c1nnc(NC(=O)Cc2ccccc2)s1] |
| 290 | 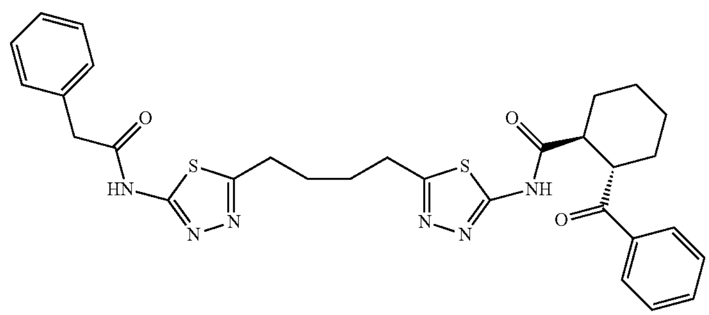 [SMILES: O=C(Cc1ccccc1)Nc1nnc(CCCCc2nnc(NC(=O)[C@H]3CCCC[C@@H]3C(=O)c3ccccc3)s2)s1] |
| 291 | (2 HCl) |
| 292 | 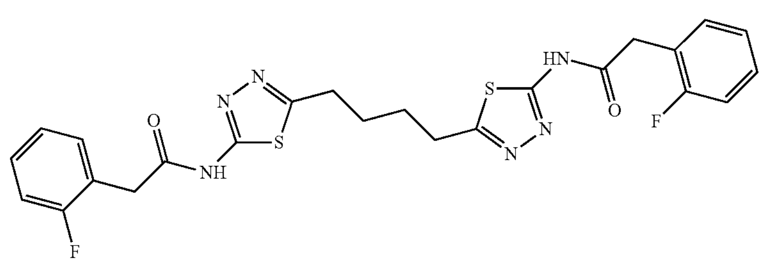 [SMILES: O=C(Cc1ccccc1F)Nc1nnc(CCCCc2nnc(NC(=O)Cc3ccccc3F)s2)s1] |

TABLE 1-continued

Selected Compounds of Formula I

| Compound ID | Structure |
|---|---|
| 293 | 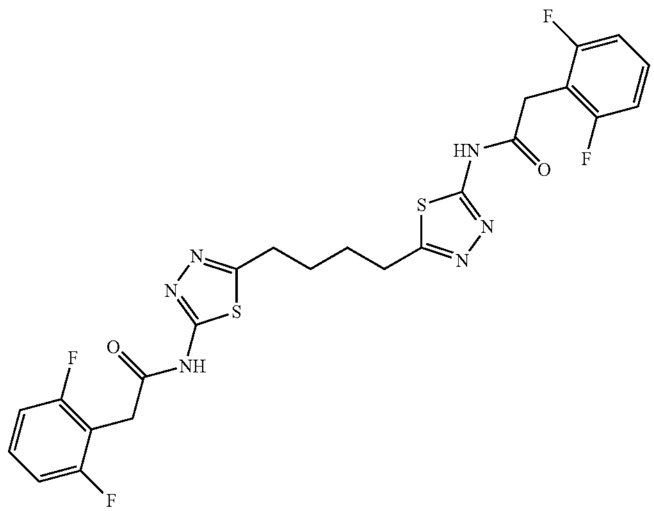 [SMILES: O=C(Cc1c(F)cccc1F)Nc1nnc(CCCCc2nnc(NC(=O)Cc3c(F)cccc3F)s2)s1] |
| 294 | 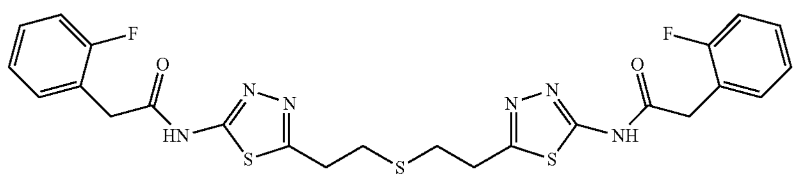 [SMILES: O=C(Cc1ccccc1F)Nc1nnc(CCSCCc2nnc(NC(=O)Cc3ccccc3F)s2)s1] |
| 295 | 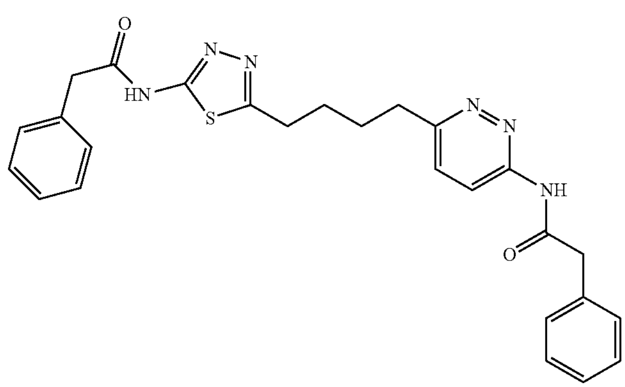 [SMILES: O=C(Cc1ccccc1)Nc1ccc(CCCCc2nnc(NC(=O)Cc3ccccc3)s2)nn1] |
| 296 | 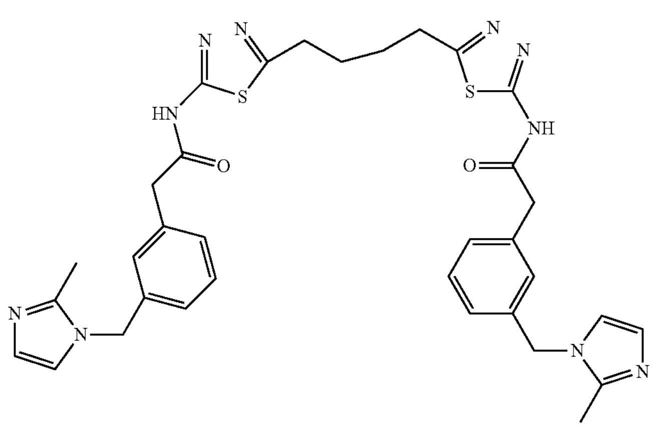 [SMILES: Cc1nccn1Cc1cccc(CC(=O)NC(=N)SC(=N)CCCCC(=N)SC(=N)NC(=O)Cc2cccc(Cn3ccnc3C)c2)c1] |

TABLE 1-continued

Selected Compounds of Formula I

| Compound ID | Structure |
|---|---|
| 297 | 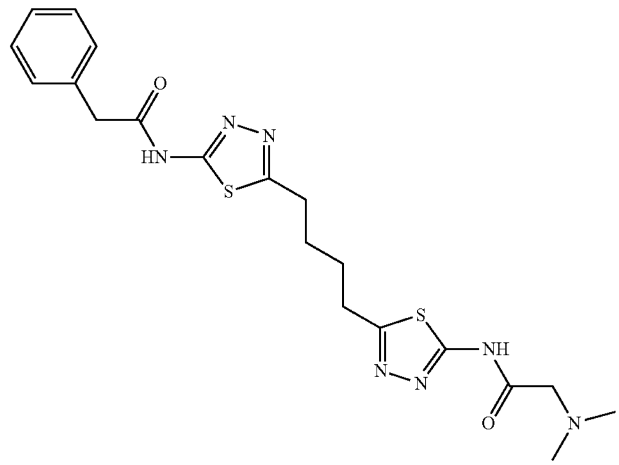 [SMILES: CN(C)CC(=O)Nc1nnc(CCCCc2nnc(NC(=O)Cc3ccccc3)s2)s1] |
| 298 | 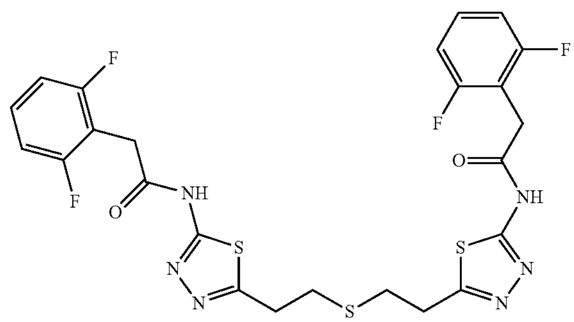 [SMILES: O=C(Cc1c(F)cccc1F)Nc1nnc(CCSCCc2nnc(NC(=O)Cc3c(F)cccc3F)s2)s1] |
| 299 | 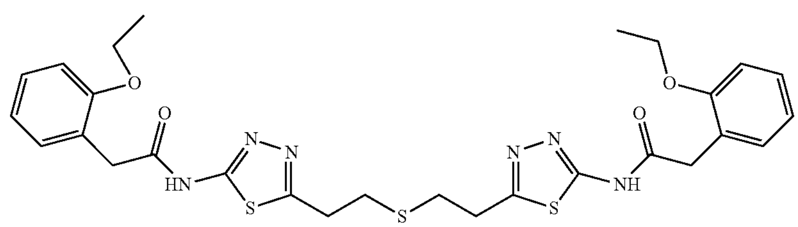 [SMILES: CCOc1ccccc1CC(=O)Nc1nnc(CCSCCc2nnc(NC(=O)Cc3ccccc3OCC)s2)s1] |
| 300 | 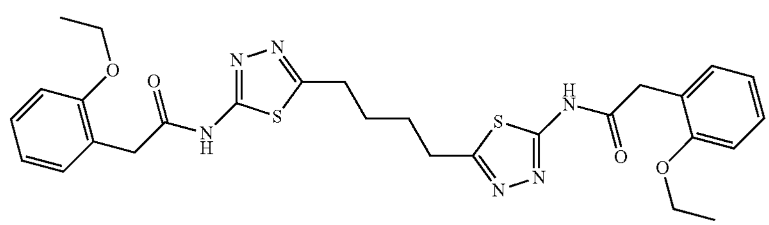 [SMILES: CCOc1ccccc1CC(=O)Nc1nnc(CCCCc2nnc(NC(=O)Cc3ccccc3OCC)s2)s1] |
| 301 | 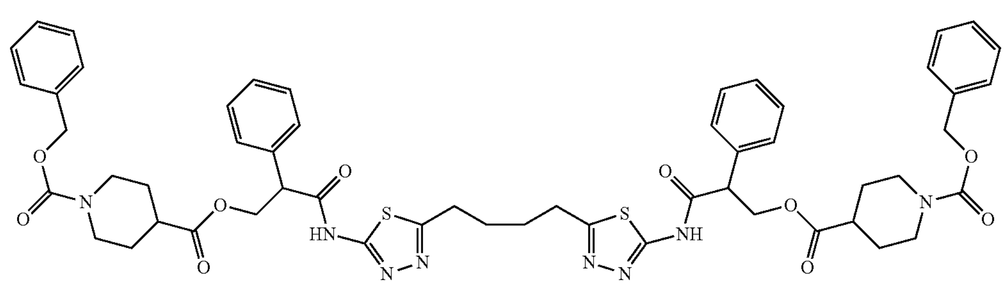 [SMILES: O=C(OCC(C(=O)Nc1nnc(CCCCc2nnc(NC(=O)C(COC(=O)C3CCN(C(=O)OCc4ccccc4)CC3)c3ccccc3)s2)s1)c1ccccc1)C1CCN(C(=O)OCc2ccccc2)CC1] |

TABLE 1-continued

Selected Compounds of Formula I

| Compound ID | Structure |
|---|---|
| 302 | 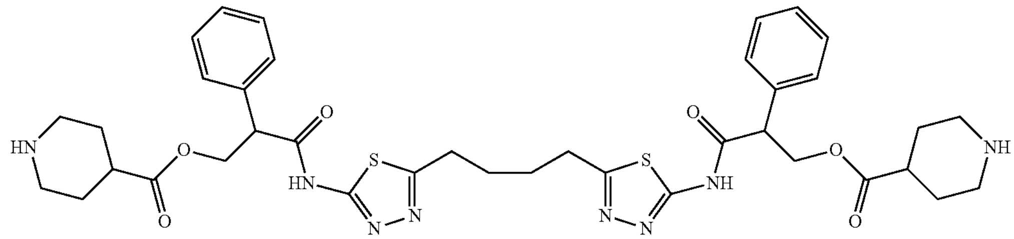 [SMILES: O=C(OCC(C(=O)Nc1nnc(CCCCc2nnc(NC(=O)C(COC(=O)C3CCNCC3)c3ccccc3)s2)s1)c1ccccc1)C1CCNCC1] |
| 303 | 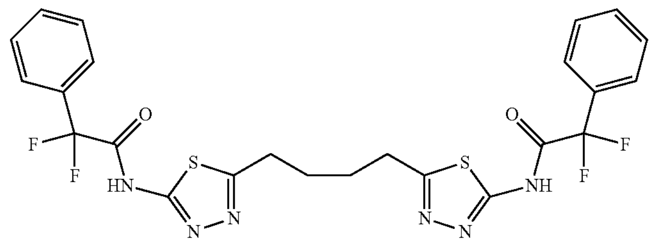 [SMILES: O=C(Nc1nnc(CCCCc2nnc(NC(=O)C(F)(F)c3ccccc3)s2)s1)C(F)(F)c1ccccc1] |
| 304 | 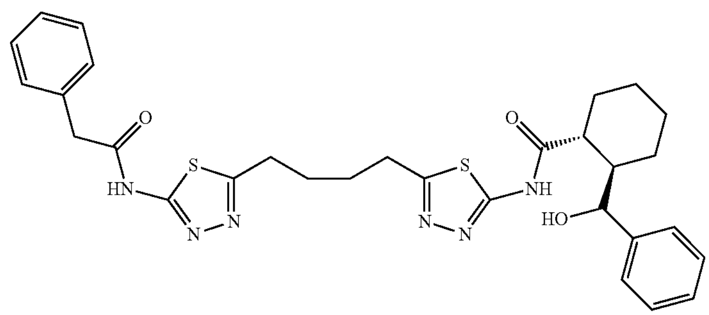 [SMILES: O=C(Cc1ccccc1)Nc1nnc(CCCCc2nnc(NC(=O)[C@@H]3CCCC[C@H]3C(O)c3ccccc3)s2)s1] |
| 305 | 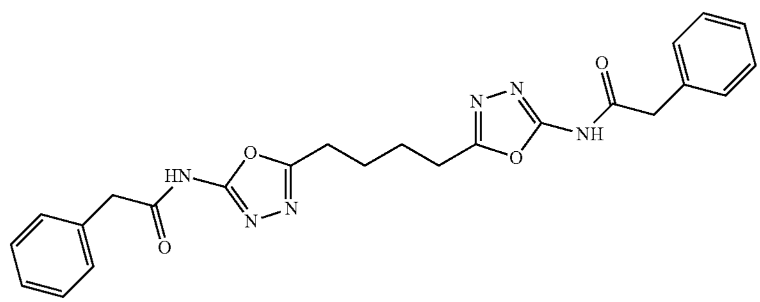 [SMILES: O=C(Cc1ccccc1)Nc1nnc(CCCCc2nnc(NC(=O)Cc3ccccc3)o2)o1] |
| 1038 | 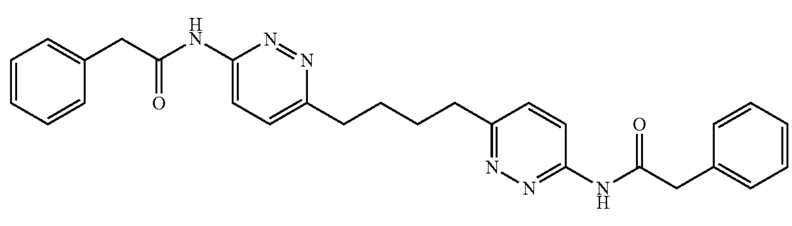 [SMILES: O=C(Cc1ccccc1)Nc1ccc(CCCCc2ccc(NC(=O)Cc3ccccc3)nn2)nn1] |
| 306 | 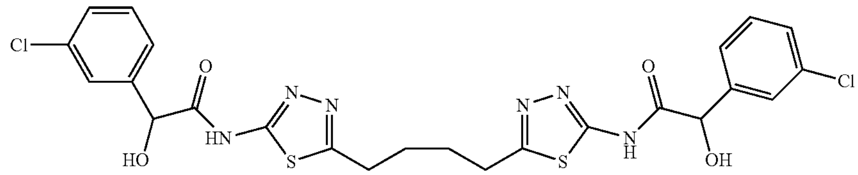 [SMILES: O=C(Nc1nnc(CCCCc2nnc(NC(=O)C(O)c3cccc(Cl)c3)s2)s1)C(O)c1cccc(Cl)c1] |

TABLE 1-continued
Selected Compounds of Formula I
| Compound ID | Structure |
|---|---|
| 307 | 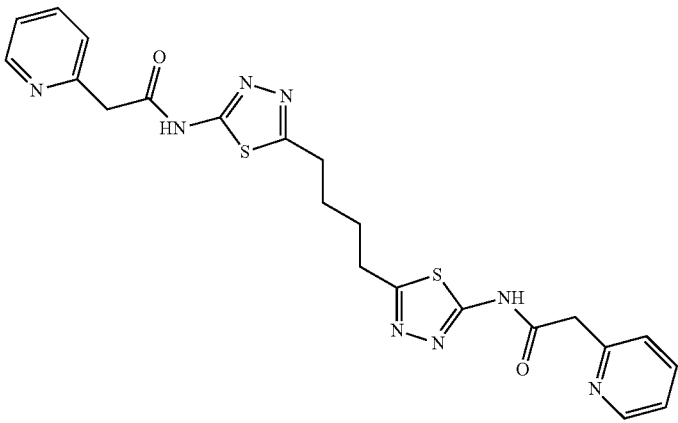 [SMILES: O=C(Cc1ccccn1)Nc1nnc(CCCCc2nnc(NC(=O)Cc3ccccn3)s2)s1] |
| 308 | 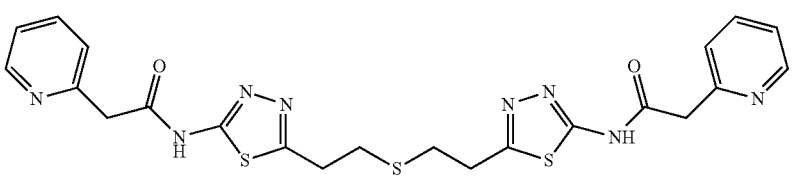 [SMILES: O=C(Cc1ccccn1)Nc1nnc(CCSCCc2nnc(NC(=O)Cc3ccccn3)s2)s1] |
| 309 | 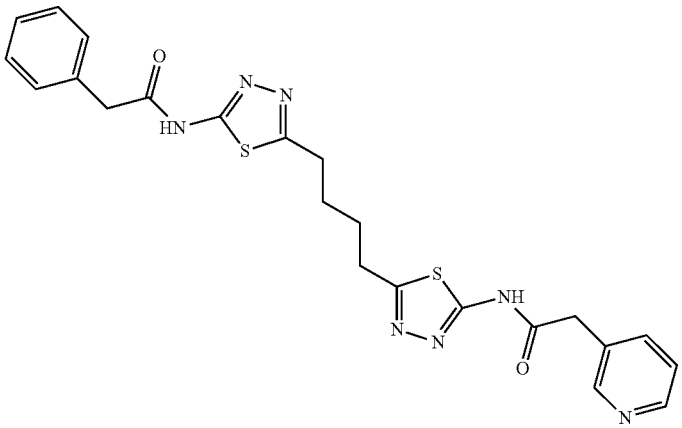 [SMILES: O=C(Cc1ccccc1)Nc1nnc(CCCCc2nnc(NC(=O)Cc3cccnc3)s2)s1] |
| 310 | 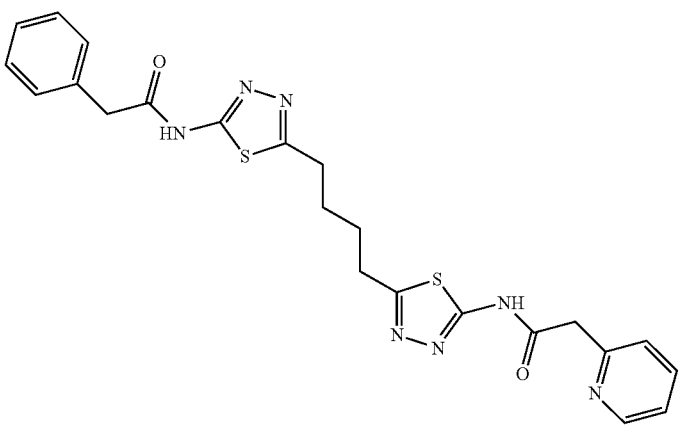 |

TABLE 1-continued

Selected Compounds of Formula I

| Compound ID | Structure |
|---|---|
| 311 | 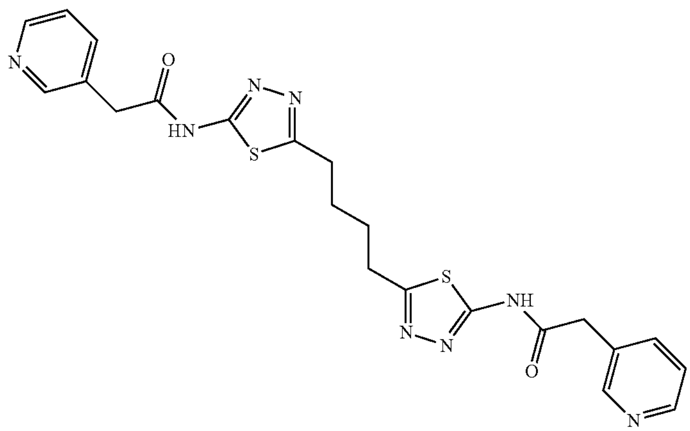 [SMILES: O=C(Cc1cccnc1)Nc1nnc(CCCCc2nnc(NC(=O)Cc3cccnc3)s2)s1] |
| 312 | 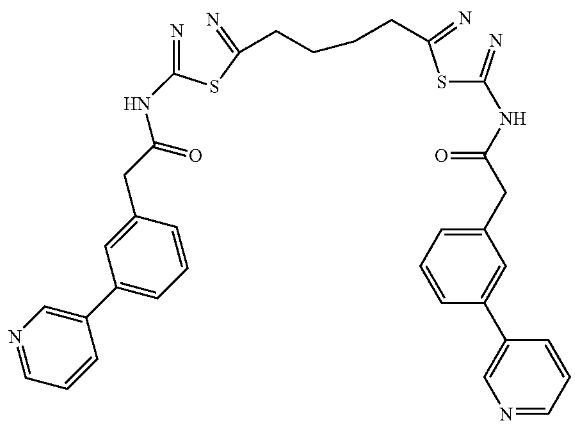 [SMILES: N=C(CCCCC(=N)SC(=N)NC(=O)Cc1cccc(-c2cccnc2)c1)SC(=N)NC(=O)Cc1cccc(-c2cccnc2)c1] |
| 313 | 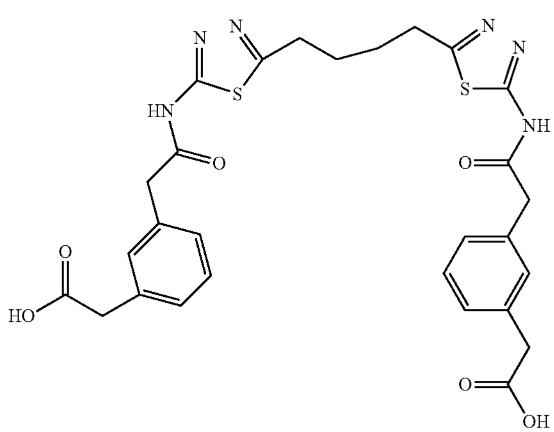 [SMILES: N=C(CCCCC(=N)SC(=N)NC(=O)Cc1cccc(CC(=O)O)c1)SC(=N)NC(=O)Cc1cccc(CC(=O)O)c1] |

TABLE 1-continued
Selected Compounds of Formula I
| Compound ID | Structure |
|---|---|
| 314 | 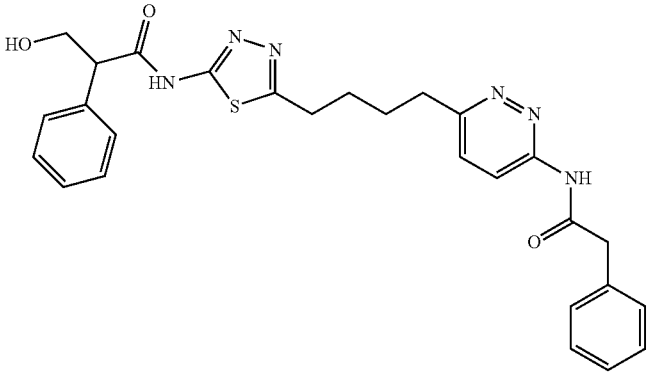 [SMILES: O=C(Cc1ccccc1)Nc1ccc(CCCCc2nnc(NC(=O)C(CO)c3ccccc3)s2)nn1] |
| 315 | 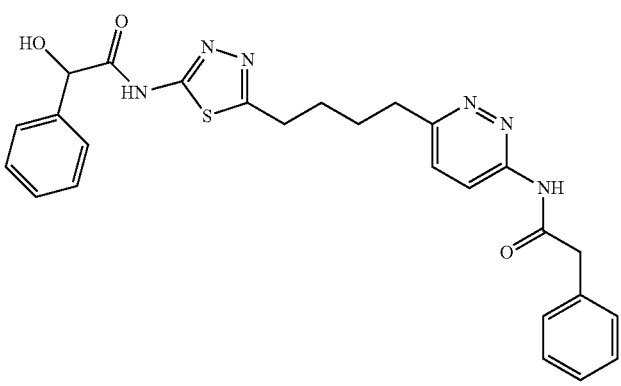 [SMILES: O=C(Cc1ccccc1)Nc1ccc(CCCCc2nnc(NC(=O)C(O)c3ccccc3)s2)nn1] |
| 316 | 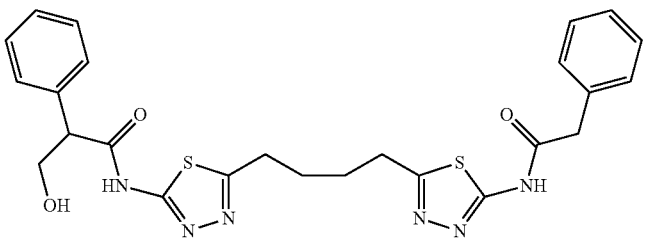 [SMILES: O=C(Cc1ccccc1)Nc1nnc(CCCCc2nnc(NC(=O)C(CO)c3ccccc3)s2)s1] |
| 317 | 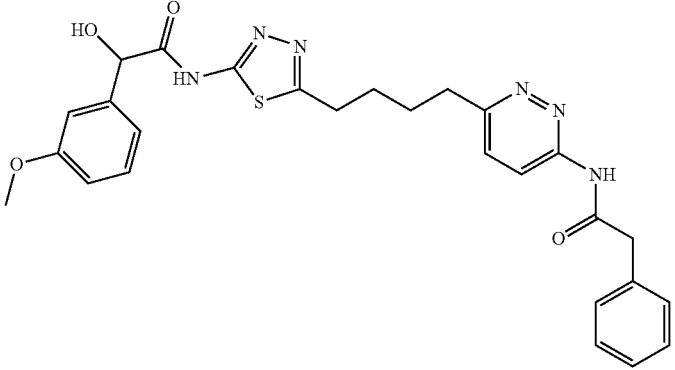 [SMILES: COc1cccc(C(O)C(=O)Nc2nnc(CCCCc3ccc(NC(=O)Cc4ccccc4)nn3)s2)c1] |

TABLE 1-continued
Selected Compounds of Formula I
| Compound ID | Structure |
|---|---|
| 318 | 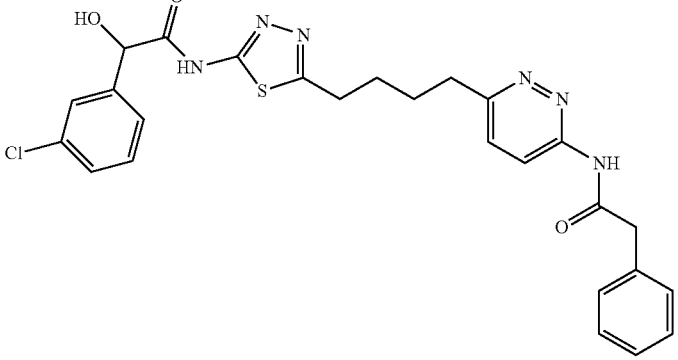 |
| 319 | 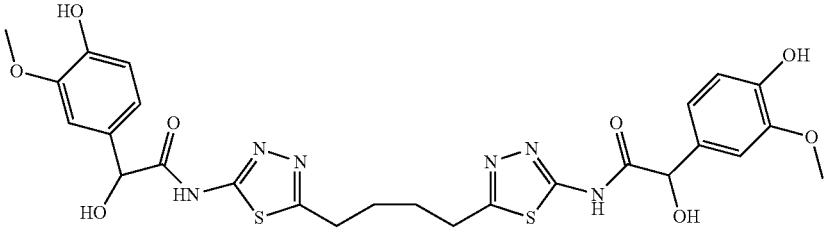 |
| 320 | 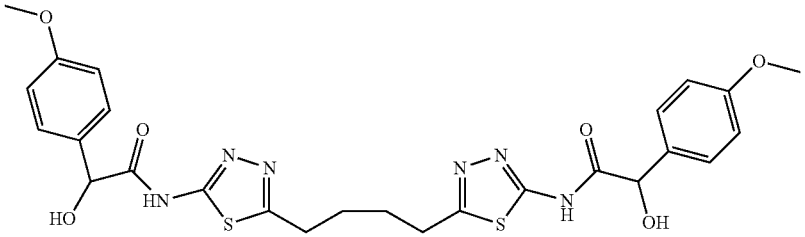 |
| 321 | 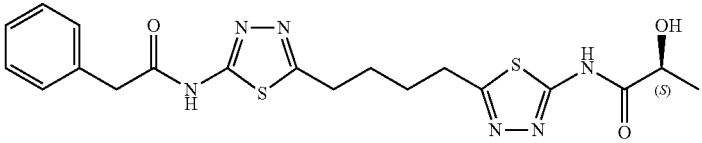 |
| 322 | 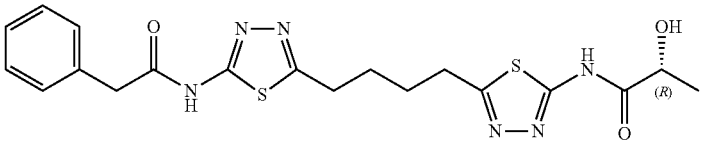 |
| 323 | 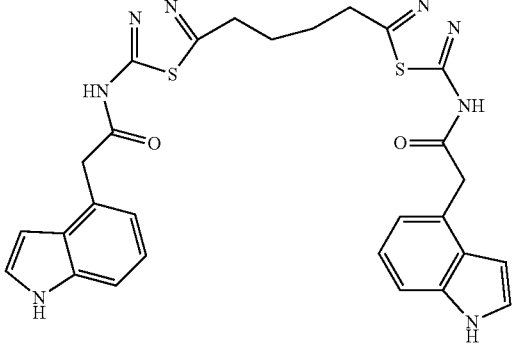 [SMILES: N=C(CCCCC(=N)SC(=N)NC(=O)Cc1cccc2[nH]ccc12)SC(=N)NC(=O)Cc1cccc2[nH]ccc12] |

TABLE 1-continued

Selected Compounds of Formula I

| Compound ID | Structure |
|---|---|
| 324 | 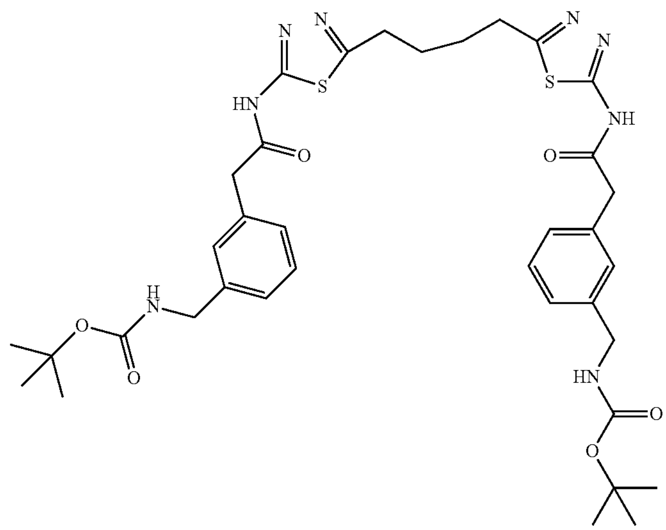 [SMILES: CC(C)(C)OC(=O)NCc1cccc(CC(=O)NC(=N)SC(=N)CCCCC(=N)SC(=N)NC(=O)Cc2cccc(CNC(=O)OC(C)(C)C)c2)c1] |
| 325 | 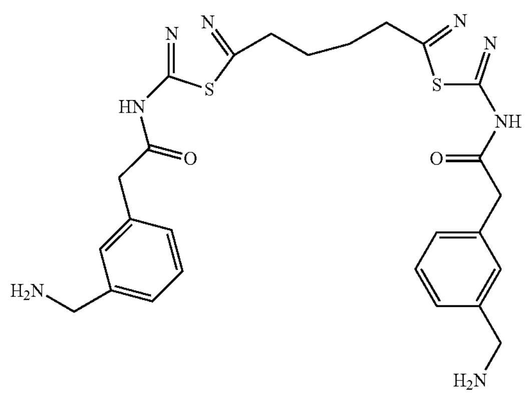 [SMILES: N=C(CCCCC(=N)SC(=N)NC(=O)Cc1cccc(CN)c1)SC(=N)NC(=O)Cc1cccc(CN)c1] |
| 326 | 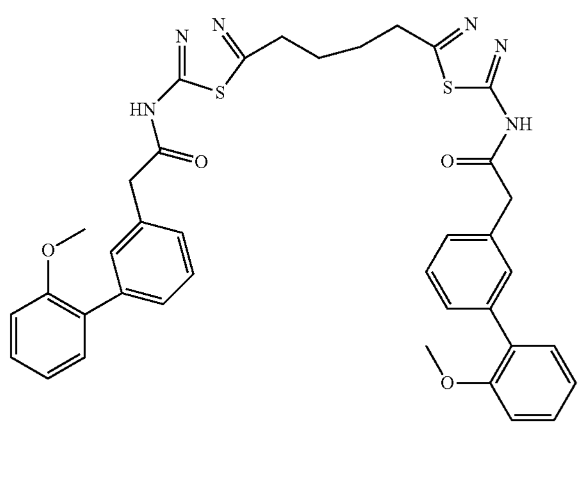 [SMILES: COc1ccccc1-c1cccc(CC(=O)NC(=N)SC(=N)CCCCC(=N)SC(=N)NC(=O)Cc2cccc(-c3ccccc3OC)c2)c1] |

TABLE 1-continued

Selected Compounds of Formula I

| Compound ID | Structure |
|---|---|
| 327 | 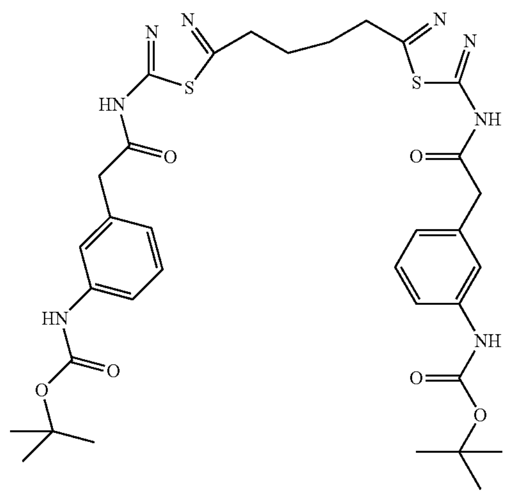 [SMILES: CC(C)(C)OC(=O)Nc1cccc(CC(=O)NC(=N)SC(=N)CCCCC(=N)SC(=N)NC(=O)Cc2cccc(NC(=O)OC(C)(C)C)c2)c1] |
| 328 | 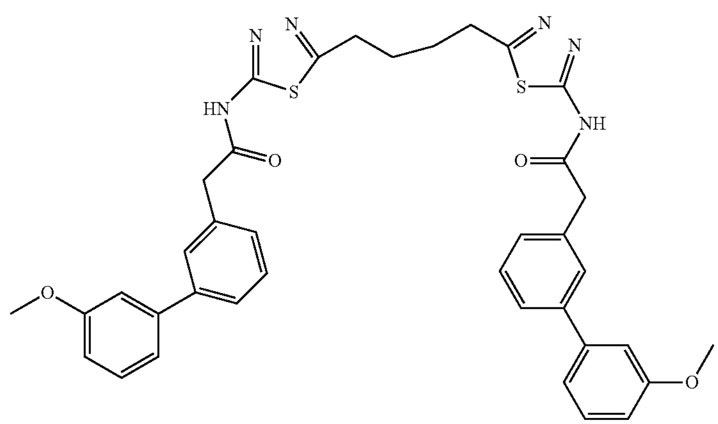 |
| 329 | 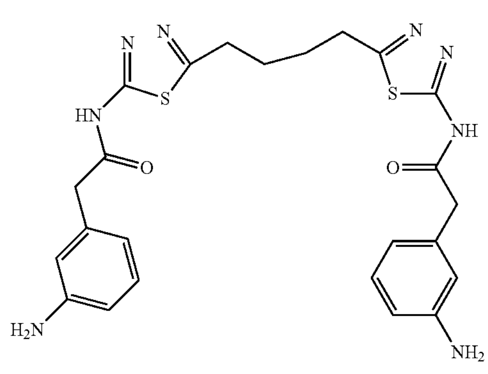 [SMILES: N=C(CCCCC(=N)SC(=N)NC(=O)Cc1cccc(N)c1)SC(=N)NC(=O)Cc1cccc(N)c1] |

TABLE 1-continued

Selected Compounds of Formula I

| Compound ID | Structure |
|---|---|
| 330 | 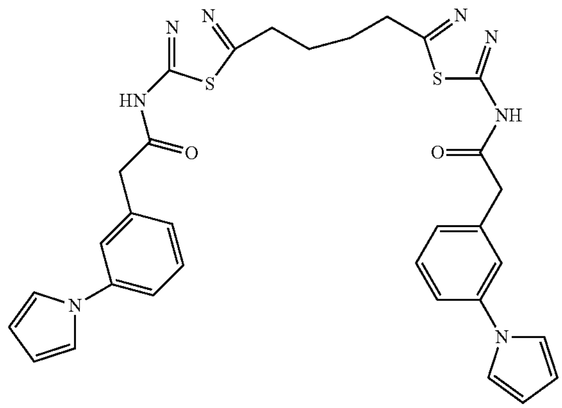 [SMILES: N=C(CCCCC(=N)SC(=N)NC(=O)Cc1cccc(-n2cccc2)c1)SC(=N)NC(=O)Cc1cccc(-n2cccc2)c1] |
| 331 | 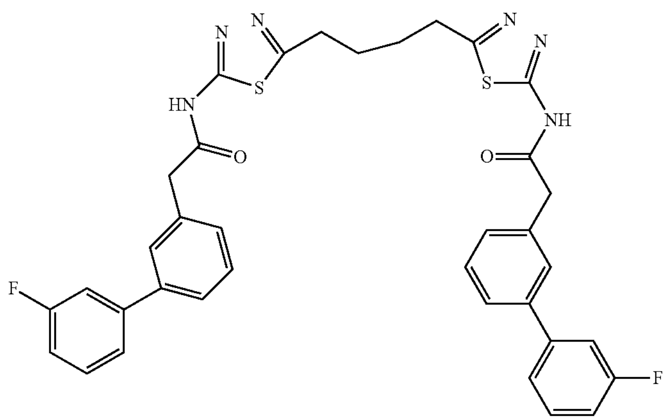 [SMILES: N=C(CCCCC(=N)SC(=N)NC(=O)Cc1cccc(-c2cccc(F)c2)c1)SC(=N)NC(=O)Cc1cccc(-c2cccc(F)c2)c1] |
| 332 | 81% bis ester plus 19% mono ester |
| 333 | 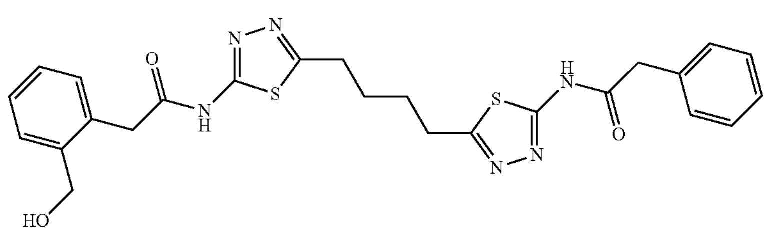 [SMILES: O=C(Cc1ccccc1)Nc1nnc(CCCCc2nnc(NC(=O)Cc3ccccc3CO)s2)s1] |

TABLE 1-continued
Selected Compounds of Formula I
| Compound ID | Structure |
|---|---|
| 334 | 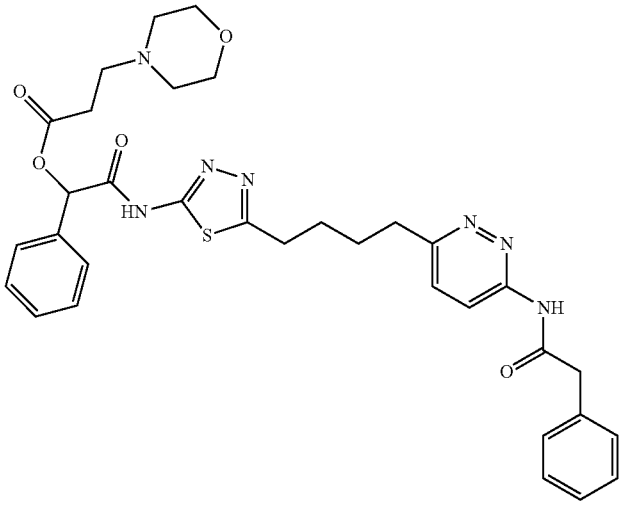 [SMILES: O=C(Cc1ccccc1)Nc1ccc(CCCCc2nnc(NC(=O)C(OC(=O)CCN3CCOCC3)c3ccccc3)s2)nn1] |
| 335 | 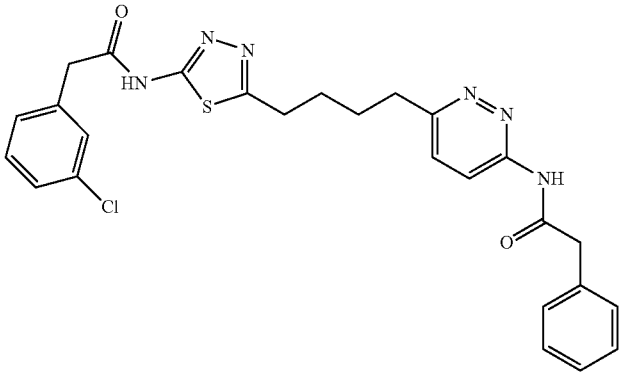 [SMILES: O=C(Cc1ccccc1)Nc1ccc(CCCCc2nnc(NC(=O)Cc3cccc(Cl)c3)s2)nn1] |
| 336 | 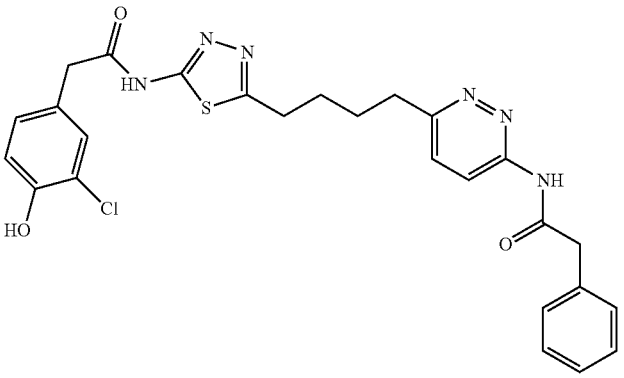 [SMILES: O=C(Cc1ccccc1)Nc1ccc(CCCCc2nnc(NC(=O)Cc3ccc(O)c(Cl)c3)s2)nn1] |

TABLE 1-continued
Selected Compounds of Formula I
| Compound ID | Structure |
|---|---|
| 337 | 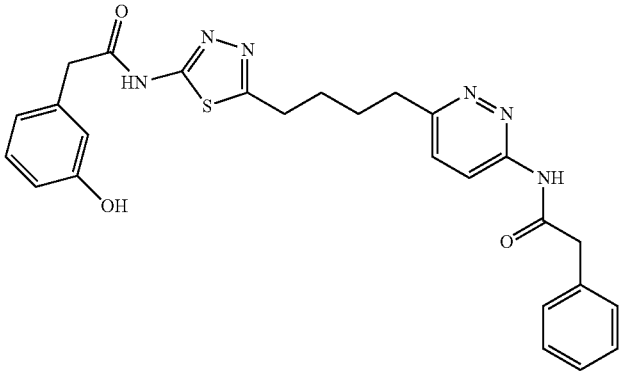 |
| 338 | 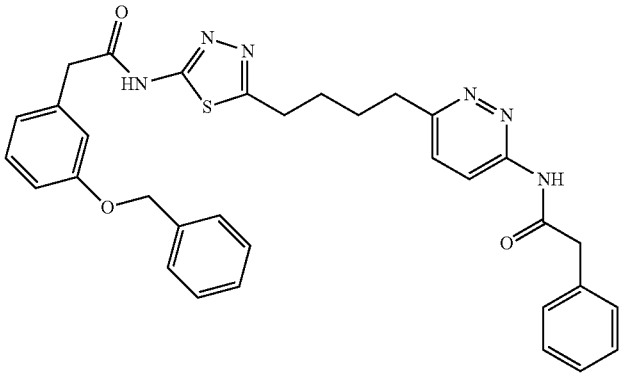 [SMILES: O=C(Cc1ccccc1)Nc1ccc(CCCCc2nnc(NC(=O)Cc3cccc(OCc4ccccc4)c3)s2)nn1] |
| 339 | 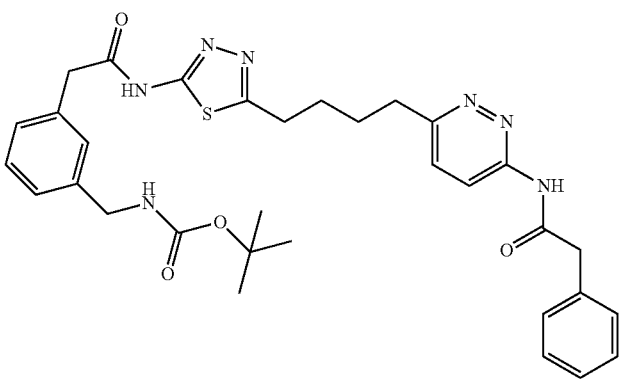 [SMILES: CC(C)(C)OC(=O)NCc1cccc(CC(=O)Nc2nnc(CCCCc3ccc(NC(=O)Cc4ccccc4)nn3)s2)c1] |
| 340 | 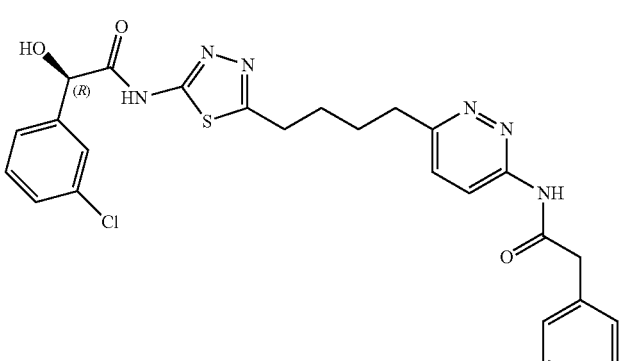 |

TABLE 1-continued
Selected Compounds of Formula I
| Compound ID | Structure |
|---|---|
| 341 | 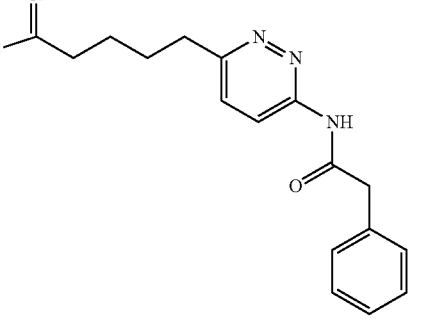 |
| 342 | 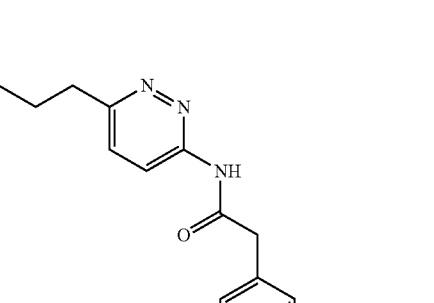 |
| 343 | 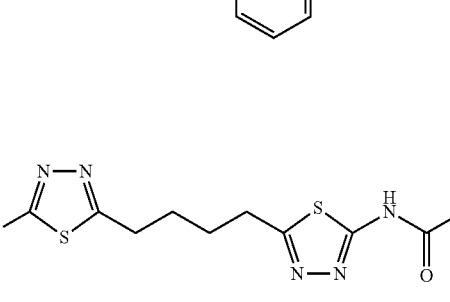 |
| 344 | 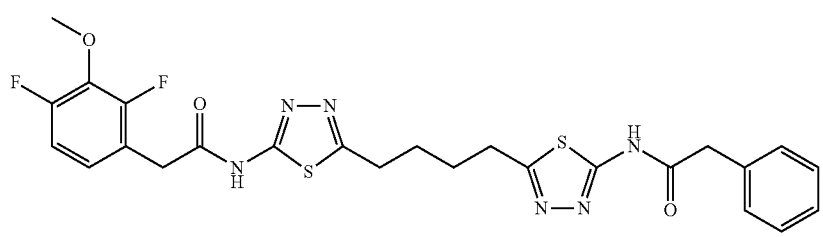 [SMILES: COc1c(F)ccc(CC(=O)Nc2nnc(CCCCc3nnc(NC(=O)Cc4ccccc4)s3)s2)c1F] |
| 345 | 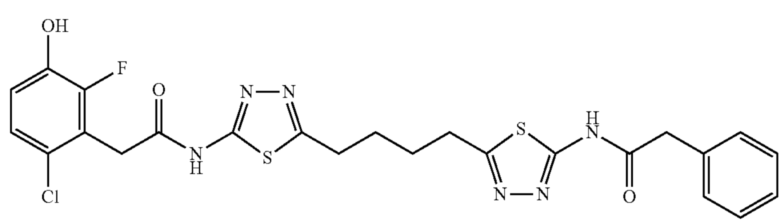 [SMILES: O=C(Cc1ccccc1)Nc1nnc(CCCCc2nnc(NC(=O)Cc3c(Cl)ccc(O)c3F)s2)s1] |

TABLE 1-continued

Selected Compounds of Formula I

| Compound ID | Structure |
|---|---|
| 346 | 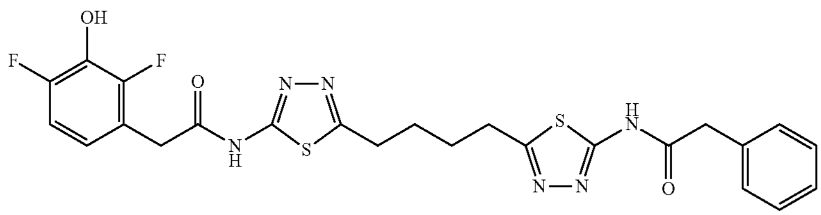 [SMILES: O=C(Cc1ccccc1)Nc1nnc(CCCCc2nnc(NC(=O)Cc3ccc(F)c(O)c3F)s2)s1] |
| 527 | 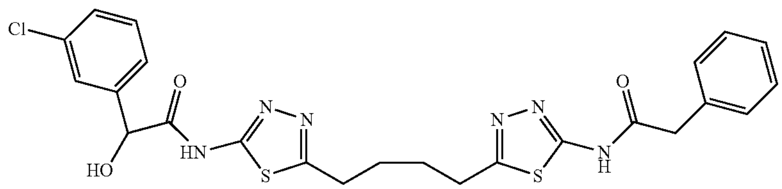 [SMILES: O=C(Cc1ccccc1)Nc1nnc(CCCCc2nnc(NC(=O)C(O)c3cccc(Cl)c3)s2)s1] |
| 347 | 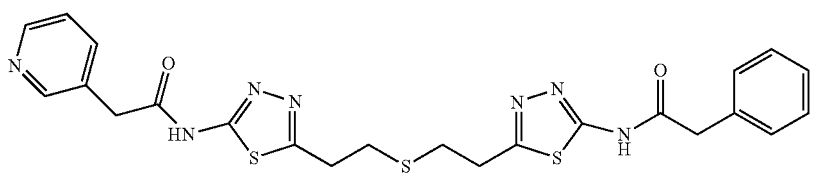 [SMILES: O=C(Cc1ccccc1)Nc1nnc(CCSCCc2nnc(NC(=O)Cc3cccnc3)s2)s1] |
| 348 | 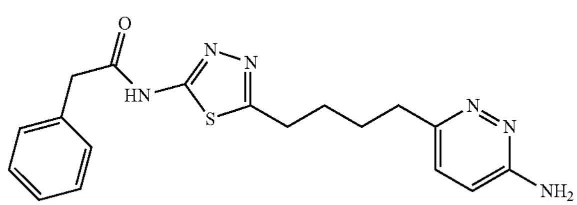 [SMILES: Nc1ccc(CCCCc2nnc(NC(=O)Cc3ccccc3)s2)nn1] |
| 349 | 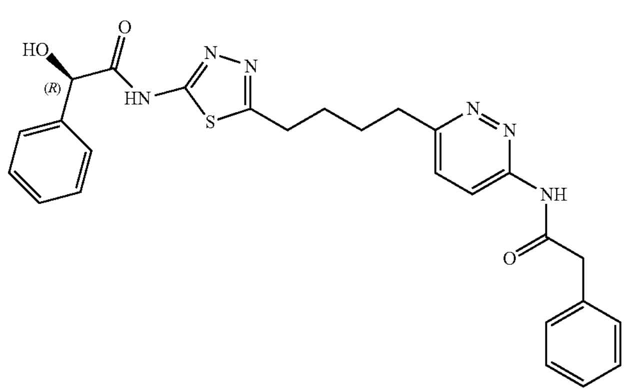 |

TABLE 1-continued

Selected Compounds of Formula I

| Compound ID | Structure |
|---|---|
| 350 | 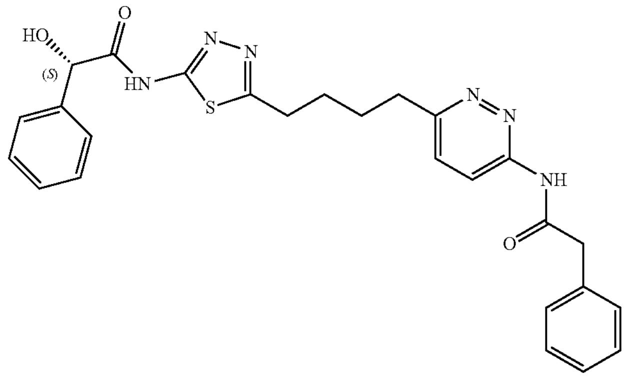 |
| 351 | 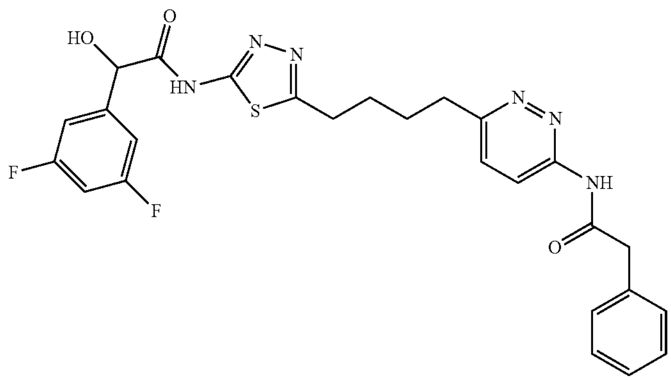 [SMILES: O=C(Cc1ccccc1)Nc1ccc(CCCCc2nnc(NC(=O)C(O)c3cc(F)cc(F)c3)s2)nn1] |
| 352 | 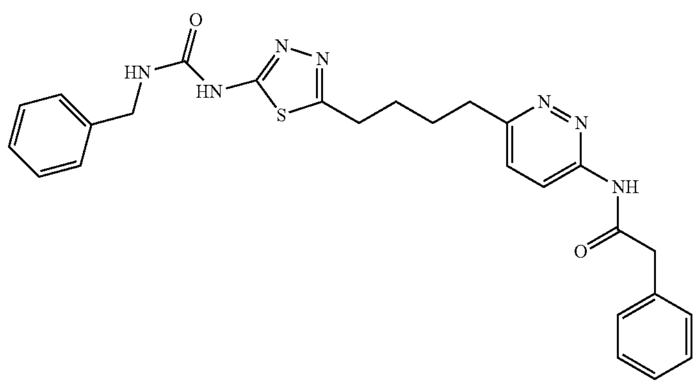 [SMILES: O=C(Cc1ccccc1)Nc1ccc(CCCCc2nnc(NC(=O)NCc3ccccc3)s2)nn1] |
| 353 | 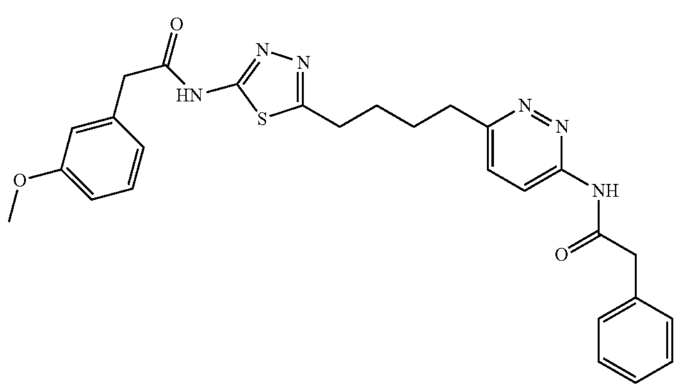 [SMILES: COc1cccc(CC(=O)Nc2nnc(CCCCc3ccc(NC(=O)Cc4ccccc4)nn3)s2)c1] |

TABLE 1-continued
Selected Compounds of Formula I
| Compound ID | Structure |
|---|---|
| 354 | 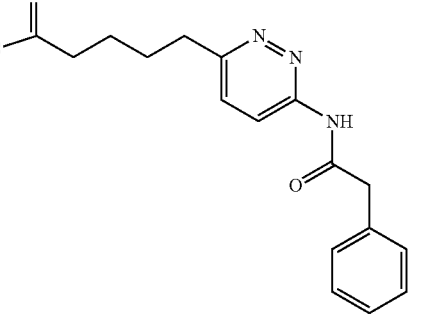 |
| 355 | 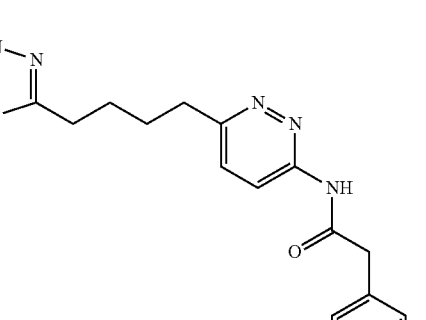 |
| 356 | 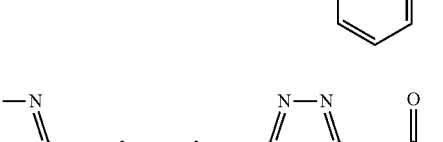 |
| 357 | 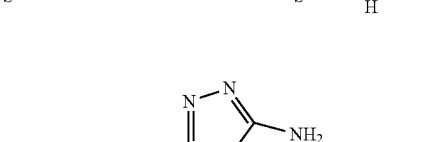 |
| 358 | 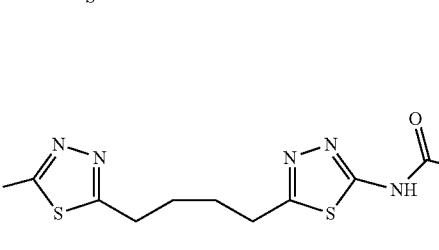 |

TABLE 1-continued

Selected Compounds of Formula I

| Compound ID | Structure |
|---|---|
| 359 | 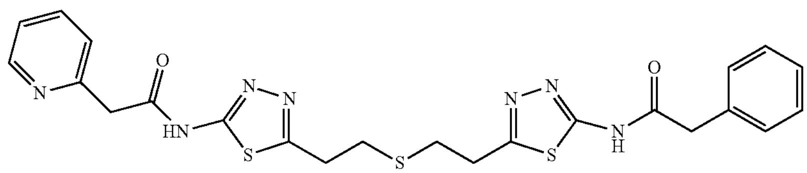 [SMILES: O=C(Cc1ccccc1)Nc1nnc(CCSCCc2nnc(NC(=O)Cc3ccccn3)s2)s1] |
| 360 | 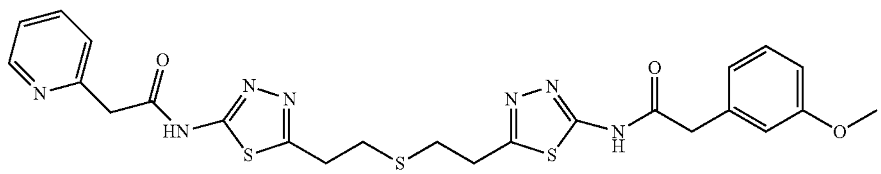 [SMILES: COc1cccc(CC(=O)Nc2nnc(CCSCCc3nnc(NC(=O)Cc4ccccn4)s3)s2)c1] |
| 361 | 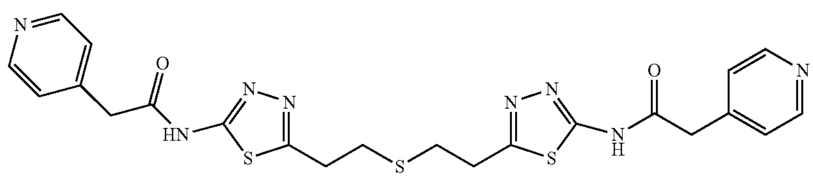 [SMILES: O=C(Cc1ccncc1)Nc1nnc(CCSCCc2nnc(NC(=O)Cc3ccncc3)s2)s1] |
| 1035 | 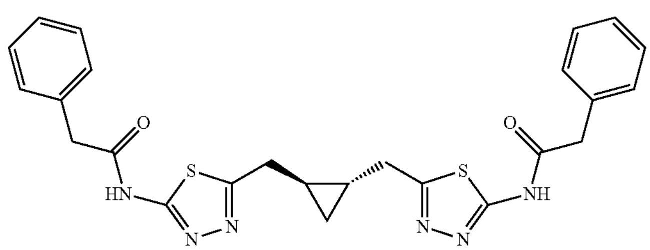 [SMILES: O=C(Cc1ccccc1)Nc1nnc(C[C@@H]2C[C@H]2Cc2nnc(NC(=O)Cc3ccccc3)s2)s1] |
| 362 | 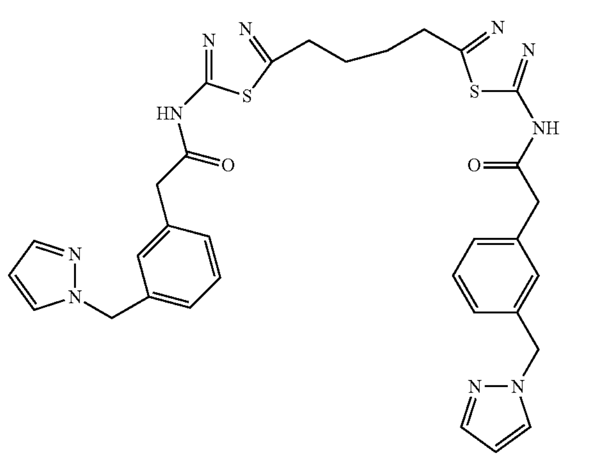 [SMILES: N=C(CCCCC(=N)SC(=N)NC(=O)Cc1cccc(Cn2cccn2)c1)SC(=N)NC(=O)Cc1cccc(Cn2cccn2)c1] |

TABLE 1-continued

Selected Compounds of Formula I

| Compound ID | Structure |
|---|---|
| 363 | 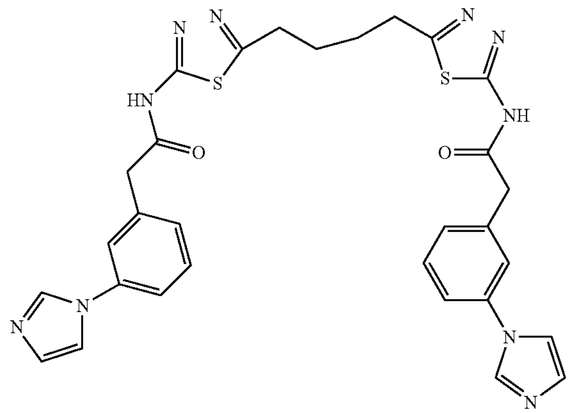 [SMILES: N=C(CCCCC(=N)SC(=N)NC(=O)Cc1cccc(-n2ccnc2)c1)SC(=N)NC(=O)Cc1cccc(-n2ccnc2)c1] |
| 364 | 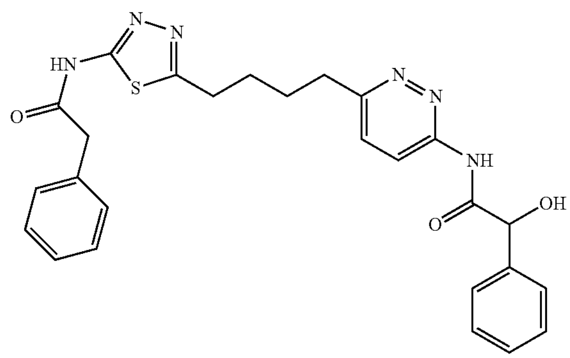 [SMILES: O=C(Cc1ccccc1)Nc1nnc(CCCCc2ccc(NC(=O)C(O)c3ccccc3)nn2)s1] |
| 365 | 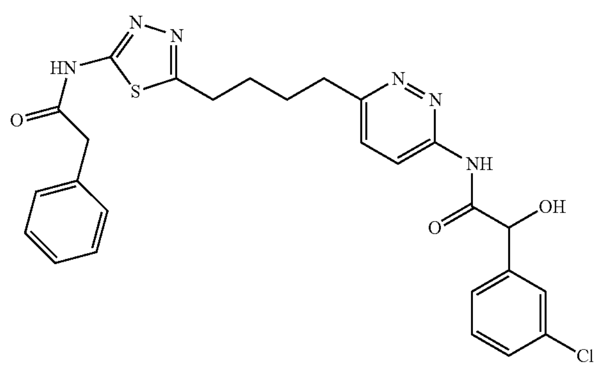 [SMILES: O=C(Cc1ccccc1)Nc1nnc(CCCCc2ccc(NC(=O)C(O)c3cccc(Cl)c3)nn2)s1] |
| 366 | 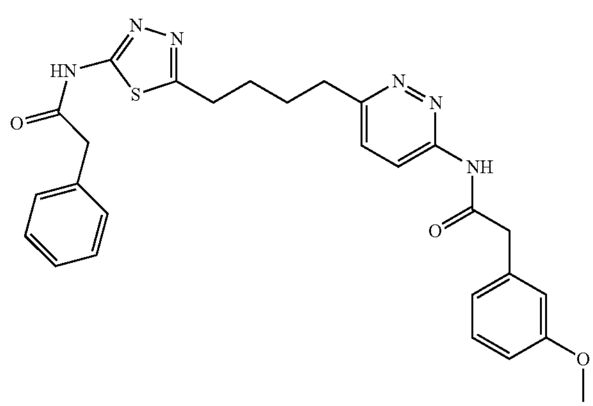 [SMILES: COc1cccc(CC(=O)Nc2ccc(CCCCc3nnc(NC(=O)Cc4ccccc4)s3)nn2)c1] |

TABLE 1-continued

Selected Compounds of Formula I

| Compound ID | Structure |
|---|---|
| 367 | 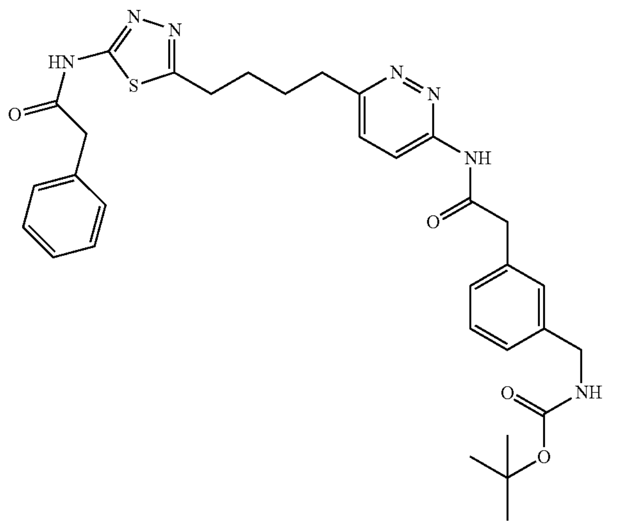 [SMILES: CC(C)(C)OC(=O)NCc1cccc(CC(=O)Nc2ccc(CCCCc3nnc(NC(=O)Cc4ccccc4)s3)nn2)c1] |
| 368 | 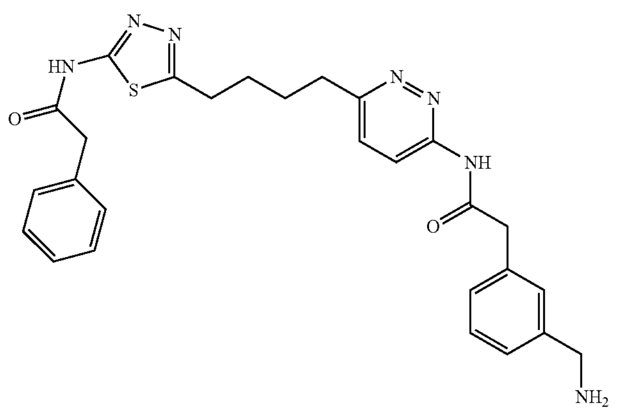 [SMILES: NCc1cccc(CC(=O)Nc2ccc(CCCCc3nnc(NC(=O)Cc4ccccc4)s3)nn2)c1] |
| 369 | 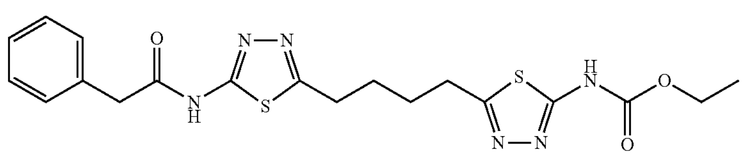 [SMILES: CCOC(=O)Nc1nnc(CCCCc2nnc(NC(=O)Cc3ccccc3)s2)s1] |
| 370 | 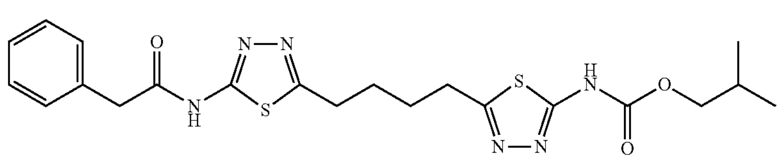 [SMILES: CC(C)COC(=O)Nc1nnc(CCCCc2nnc(NC(=O)Cc3ccccc3)s2)s1] |
| 371 | 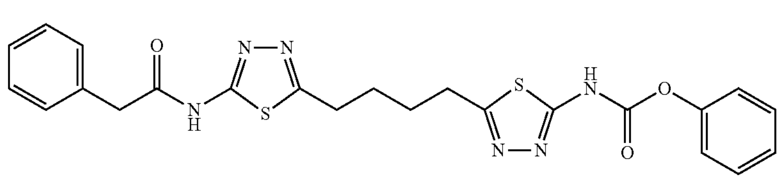 [SMILES: O=C(Cc1ccccc1)Nc1nnc(CCCCc2nnc(NC(=O)Oc3ccccc3)s2)s1] |

TABLE 1-continued

Selected Compounds of Formula I

| Compound ID | Structure |
|---|---|
| 372 | 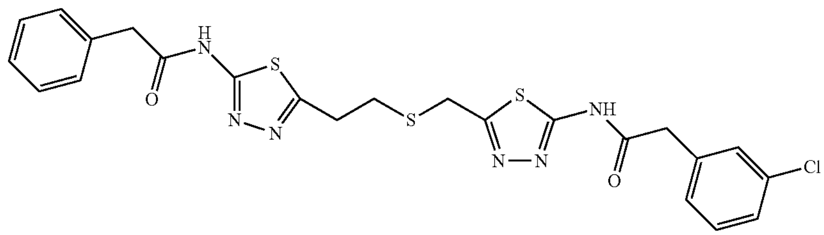 [SMILES: O=C(Cc1ccccc1)Nc1nnc(CCSCc2nnc(NC(=O)Cc3cccc(Cl)c3)s2)s1] |
| 373 | 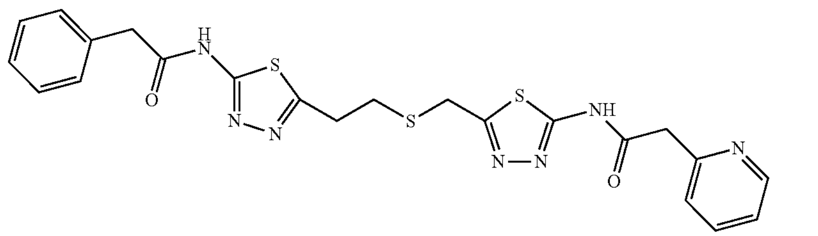 [SMILES: O=C(Cc1ccccc1)Nc1nnc(CCSCc2nnc(NC(=O)Cc3ccccn3)s2)s1] |
| 374 | 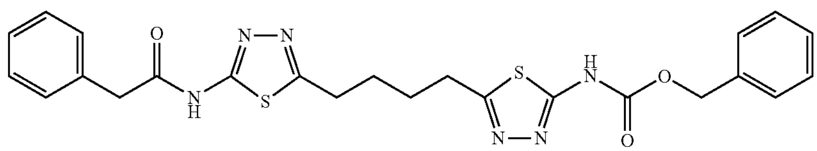 [SMILES: O=C(Cc1ccccc1)Nc1nnc(CCCCc2nnc(NC(=O)OCc3ccccc3)s2)s1] |
| 375 | 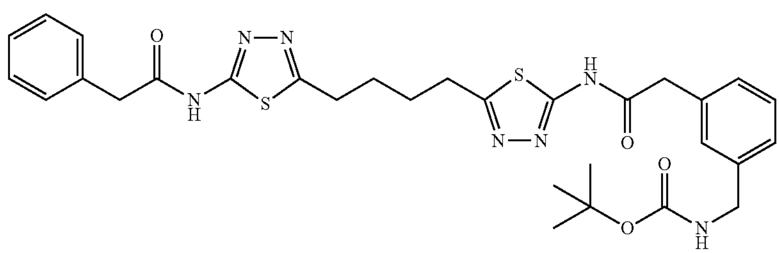 [SMILES: CC(C)(C)OC(=O)NCc1cccc(CC(=O)Nc2nnc(CCCCc3nnc(NC(=O)Cc4ccccc4)s3)s2)c1] |
| 376 | 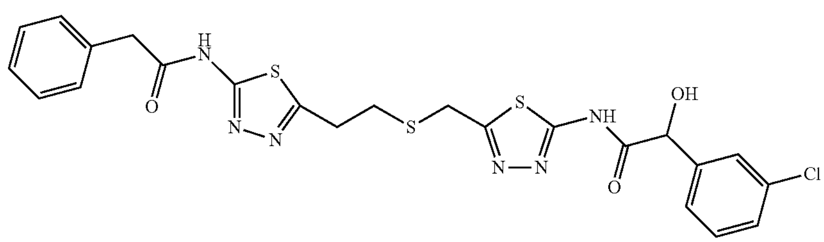 [SMILES: O=C(Cc1ccccc1)Nc1nnc(CCSCc2nnc(NC(=O)C(O)c3cccc(Cl)c3)s2)s1] |
| 377 | 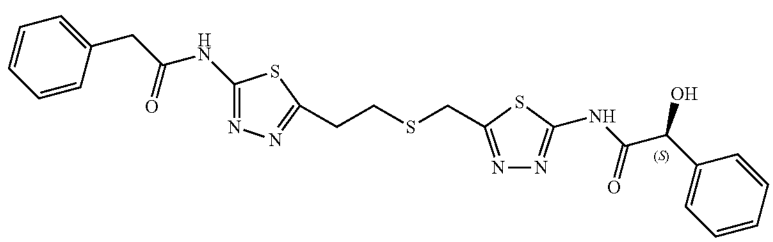 |

TABLE 1-continued

Selected Compounds of Formula I

| Compound ID | Structure |
|---|---|
| 378 | 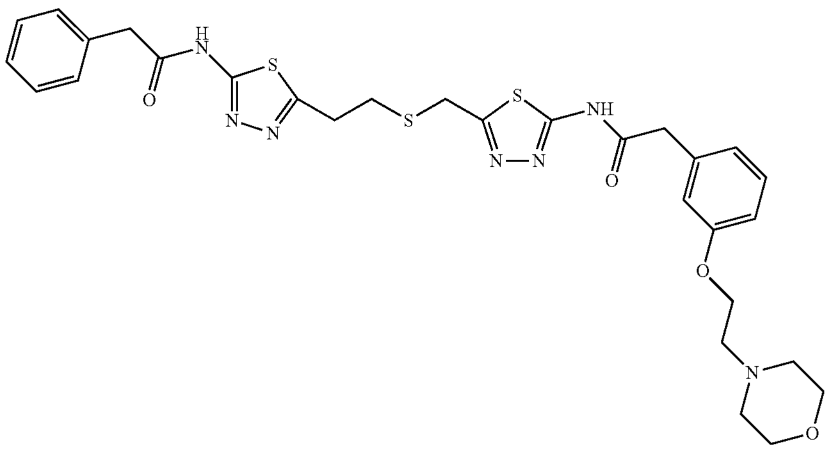 |
| 379 | 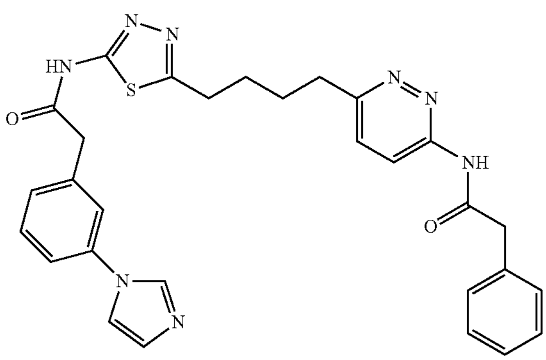 [SMILES: O=C(Cc1ccccc1)Nc1ccc(CCCCc2nnc(NC(=O)Cc3cccc(-n4ccnc4)c3)s2)nn1] |
| 380 | 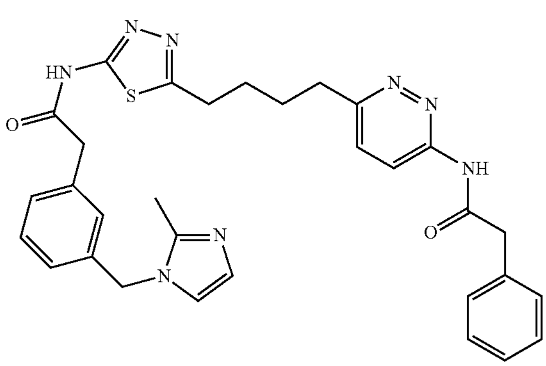 [SMILES: Cc1nccn1Cc1cccc(CC(=O)Nc2nnc(CCCCc3ccc(NC(=O)Cc4ccccc4)nn3)s2)c1] |

TABLE 1-continued
Selected Compounds of Formula I
| Compound ID | Structure |
|---|---|
| 381 | 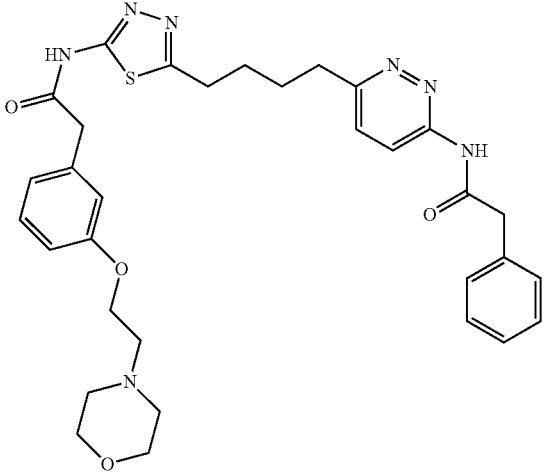 [SMILES: O=C(Cc1ccccc1)Nc1ccc(CCCCc2nnc(NC(=O)Cc3cccc(OCCN4CCOCC4)c3)s2)nn1] |
| 382 | 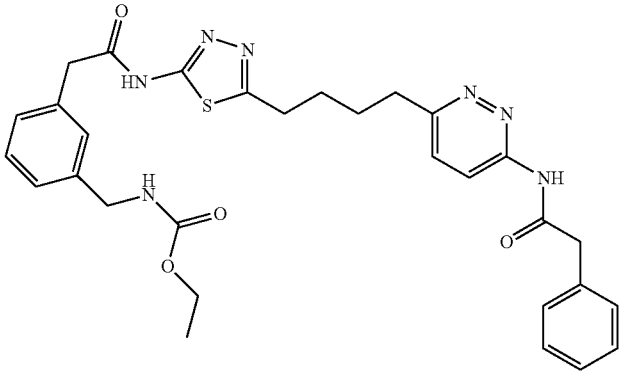 [SMILES: CCOC(=O)NCc1cccc(CC(=O)Nc2nnc(CCCCc3ccc(NC(=O)Cc4ccccc4)nn3)s2)c1] |
| 383 | 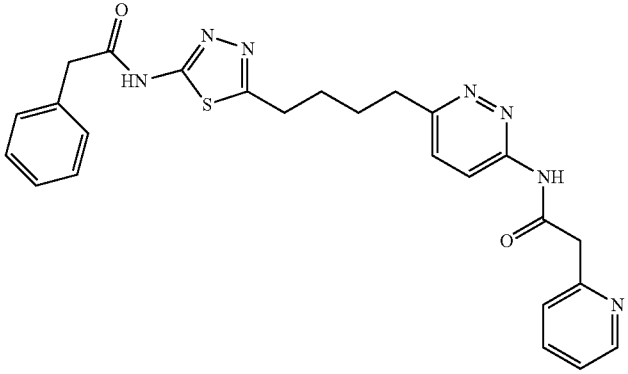 [SMILES: O=C(Cc1ccccn1)Nc1ccc(CCCCc2nnc(NC(=O)Cc3ccccc3)s2)nn1] |

TABLE 1-continued
Selected Compounds of Formula I
| Compound ID | Structure |
|---|---|
| 384 | 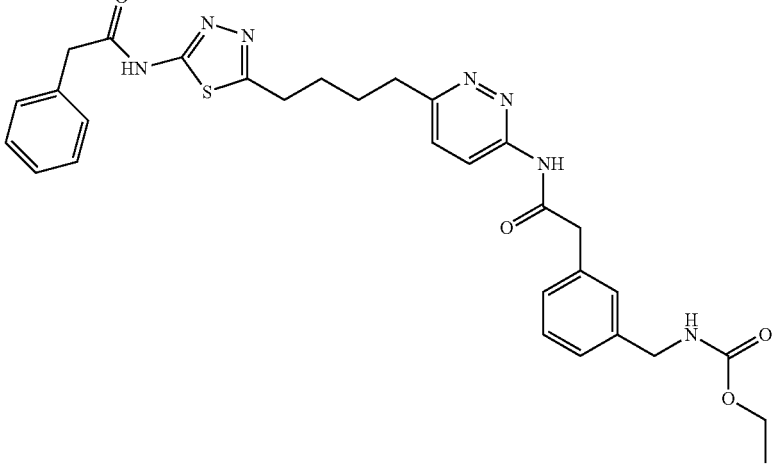 |
| 385 | 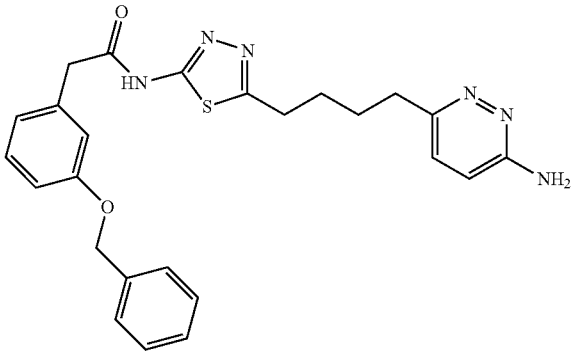 [SMILES: Nc1ccc(CCCCc2nnc(NC(=O)Cc3cccc(OCc4ccccc4)c3)s2)nn1] |
| 386 | 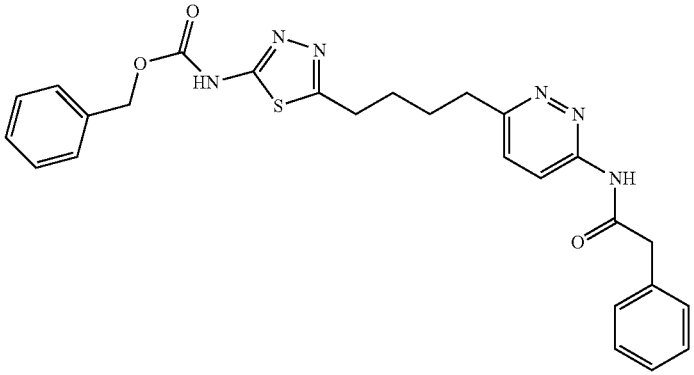 [SMILES: O=C(Cc1ccccc1)Nc1ccc(CCCCc2nnc(NC(=O)OCc3ccccc3)s2)nn1] |
| 387 | 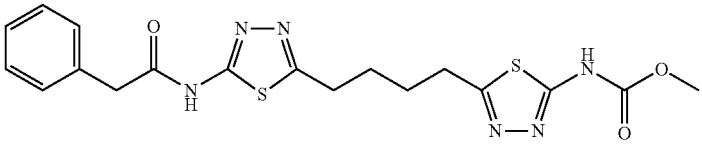 [SMILES: COC(=O)Nc1nnc(CCCCc2nnc(NC(=O)Cc3ccccc3)s2)s1] |
| 388 | 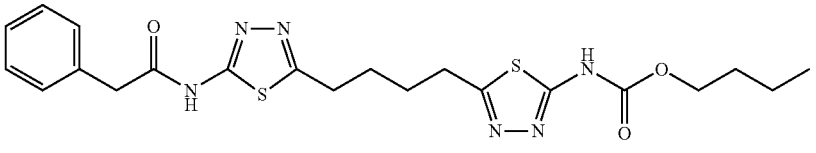 [SMILES: CCCCOC(=O)Nc1nnc(CCCCc2nnc(NC(=O)Cc3ccccc3)s2)s1] |

TABLE 1-continued

Selected Compounds of Formula I

| Compound ID | Structure |
|---|---|
| 389 | 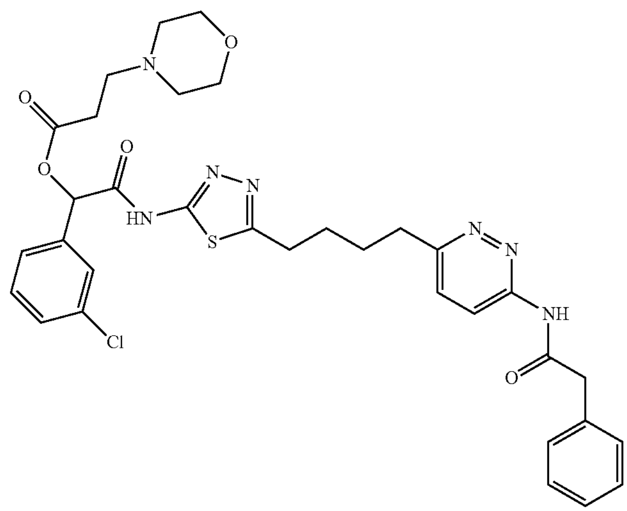 [SMILES: O=C(Cc1ccccc1)Nc1ccc(CCCCc2nnc(NC(=O)C(OC(=O)CCN3CCOCC3)c3cccc(Cl)c3)s2)nn1] |
| 390 | 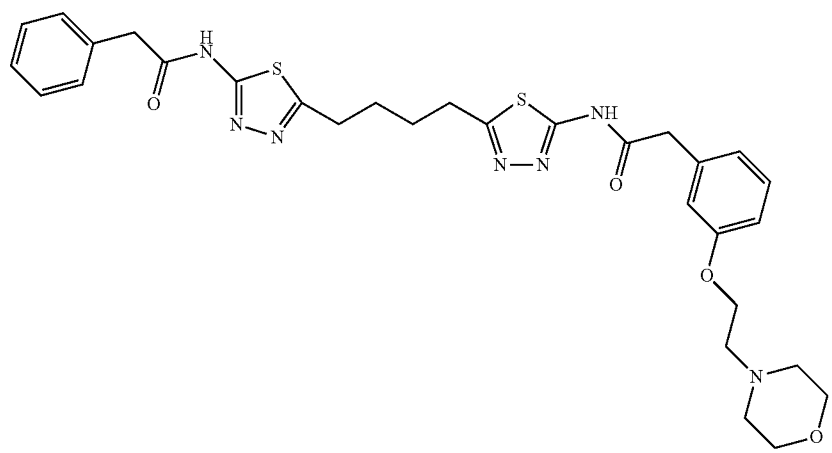 [SMILES: O=C(Cc1ccccc1)Nc1nnc(CCCCc2nnc(NC(=O)Cc3cccc(OCCN4CCOCC4)c3)s2)s1] |
| 391 | 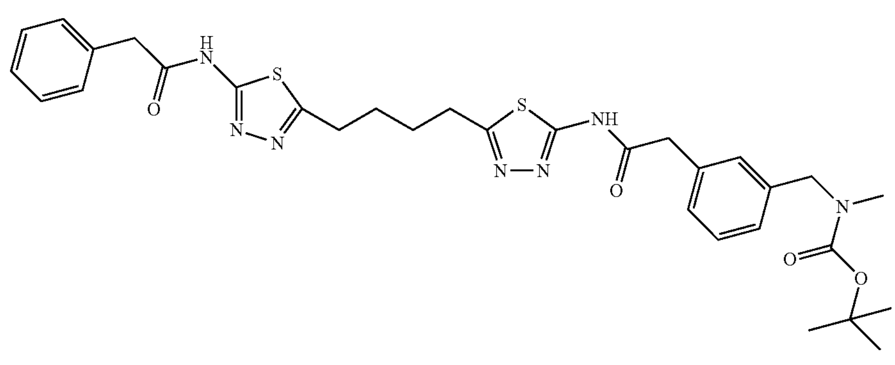 [SMILES: CN(Cc1cccc(CC(=O)Nc2nnc(CCCCc3nnc(NC(=O)Cc4ccccc4)s3)s2)c1)C(=O)OC(C)(C)C] |
| 392 | 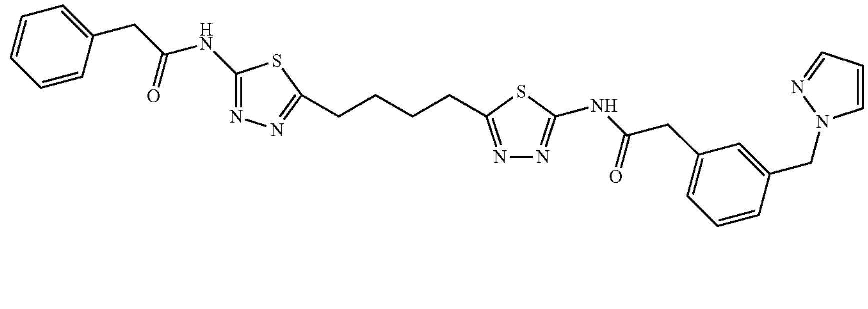 [SMILES: O=C(Cc1ccccc1)Nc1nnc(CCCCc2nnc(NC(=O)Cc3cccc(Cn4cccn4)c3)s2)s1] |

TABLE 1-continued

Selected Compounds of Formula I

| Compound ID | Structure |
|---|---|
| 393 | 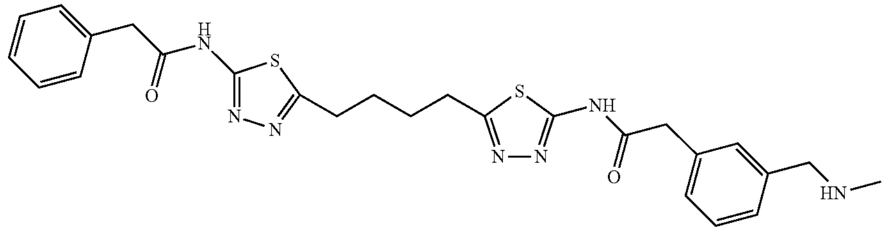 [SMILES: CNCc1cccc(CC(=O)Nc2nnc(CCCCc3nnc(NC(=O)Cc4ccccc4)s3)s2)c1] |
| 394 | 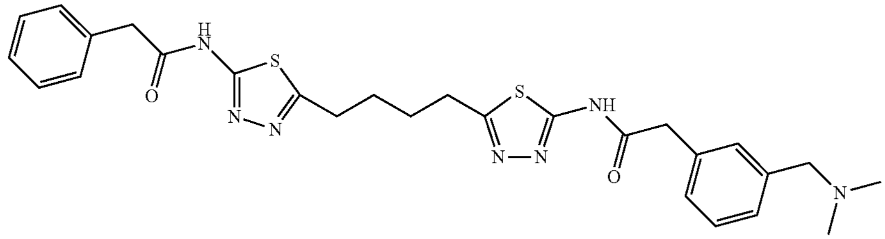 [SMILES: CN(C)Cc1cccc(CC(=O)Nc2nnc(CCCCc3nnc(NC(=O)Cc4ccccc4)s3)s2)c1] |
| 395 | 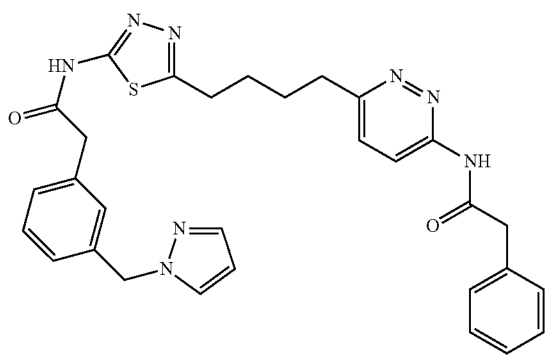 [SMILES: O=C(Cc1ccccc1)Nc1ccc(CCCCc2nnc(NC(=O)Cc3cccc(Cn4cccn4)c3)s2)nn1] |
| 396 | 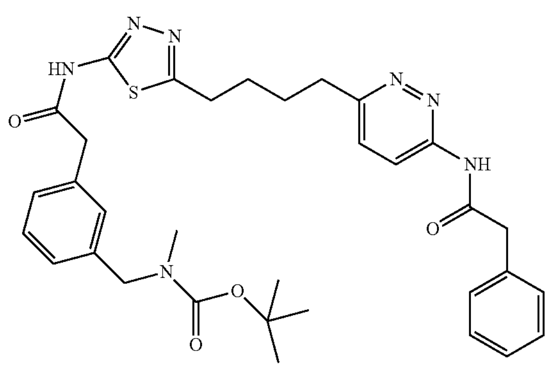 [SMILES: CN(Cc1cccc(CC(=O)Nc2nnc(CCCCc3ccc(NC(=O)Cc4ccccc4)nn3)s2)c1)C(=O)OC(C)(C)C] |
| 397 | 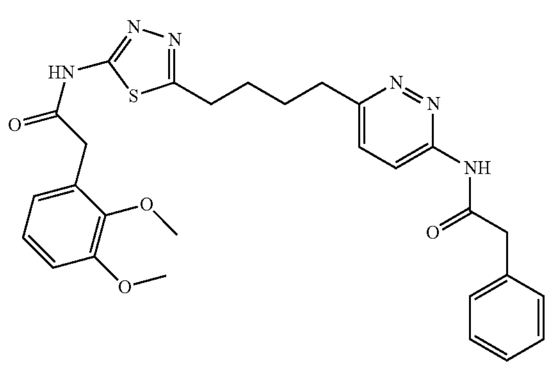 [SMILES: COc1cccc(CC(=O)Nc2nnc(CCCCc3ccc(NC(=O)Cc4ccccc4)nn3)s2)c1OC] |

TABLE 1-continued

Selected Compounds of Formula I

| Compound ID | Structure |
|---|---|
| 398 | 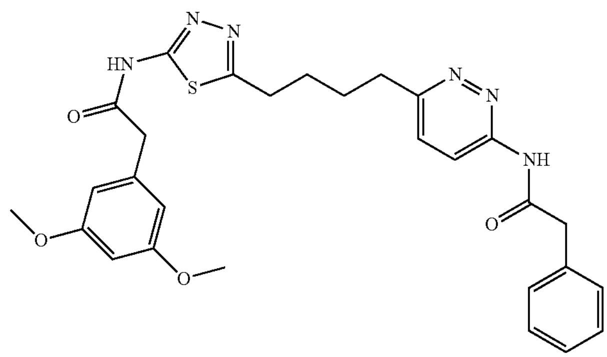 [SMILES: COc1cc(CC(=O)Nc2nnc(CCCCc3ccc(NC(=O)Cc4ccccc4)nn3)s2)cc(OC)c1] |
| 399 | 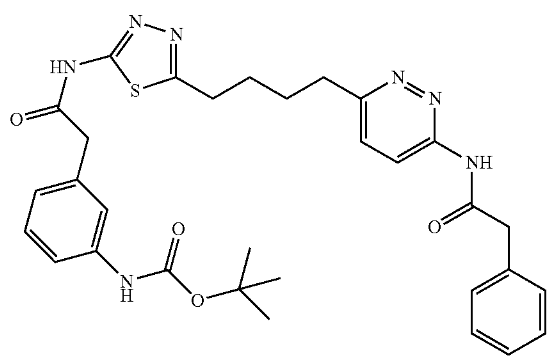 [SMILES: CC(C)(C)OC(=O)Nc1cccc(CC(=O)Nc2nnc(CCCCc3ccc(NC(=O)Cc4ccccc4)nn3)s2)c1] |
| 400 | 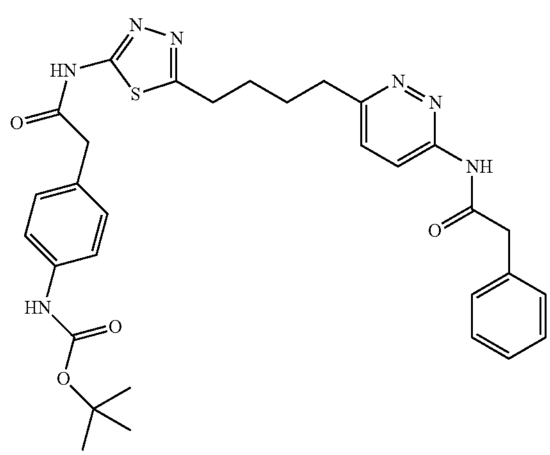 [SMILES: CC(C)(C)OC(=O)Nc1ccc(CC(=O)Nc2nnc(CCCCc3ccc(NC(=O)Cc4ccccc4)nn3)s2)cc1] |

TABLE 1-continued
Selected Compounds of Formula I
| Compound ID | Structure |
|---|---|
| 401 | 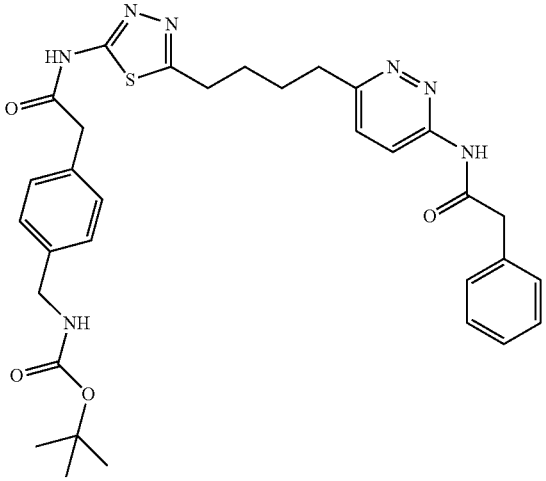 [SMILES: CC(C)(C)OC(=O)NCc1ccc(CC(=O)Nc2nnc(CCCCc3ccc(NC(=O)Cc4ccccc4)nn3)s2)cc1] |
| 402 | 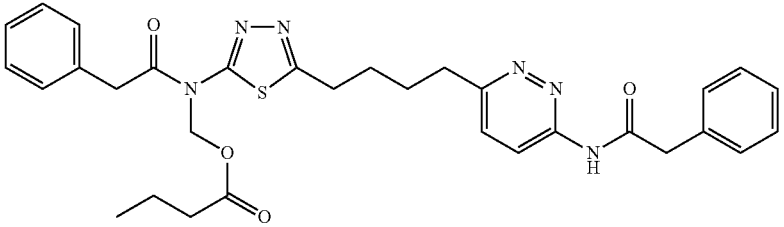 [SMILES: CCCC(=O)OCN(C(=O)Cc1ccccc1)c1nnc(CCCCc2ccc(NC(=O)Cc3ccccc3)nn2)s1] |
| 403 | 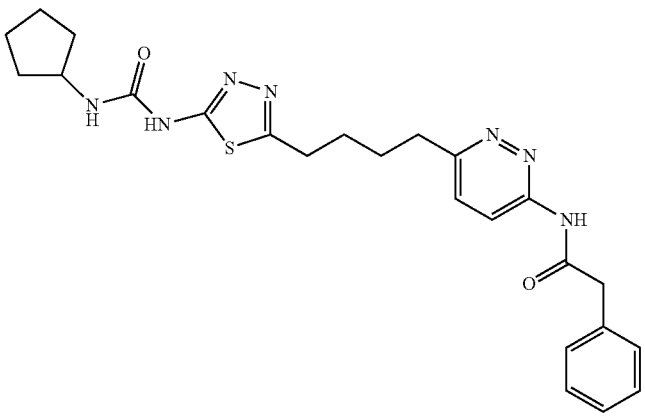 [SMILES: O=C(Cc1ccccc1)Nc1ccc(CCCCc2nnc(NC(=O)NC3CCCC3)s2)nn1] |

TABLE 1-continued

Selected Compounds of Formula I

| Compound ID | Structure |
|---|---|
| 404 | 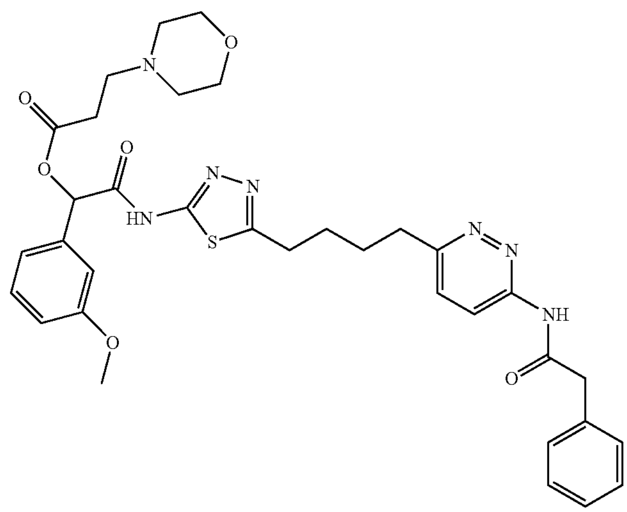 [SMILES: COc1cccc(C(OC(=O)CCN2CCOCC2)C(=O)Nc2nnc(CCCCc3ccc(NC(=O)Cc4ccccc4)nn3)s2)c1] |
| 405 | 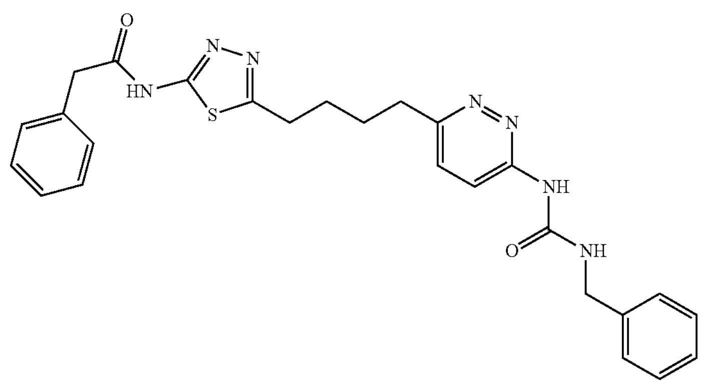 [SMILES: O=C(Cc1ccccc1)Nc1nnc(CCCCc2ccc(NC(=O)NCc3ccccc3)nn2)s1] |
| 406 | 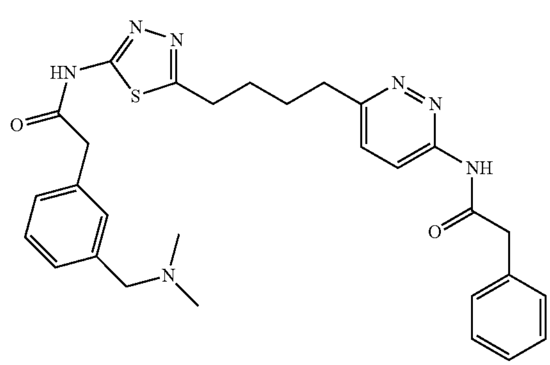 [SMILES: CN(C)Cc1cccc(CC(=O)Nc2nnc(CCCCc3ccc(NC(=O)Cc4ccccc4)nn3)s2)c1] |

TABLE 1-continued
Selected Compounds of Formula I
| Compound ID | Structure |
|---|---|
| 407 | 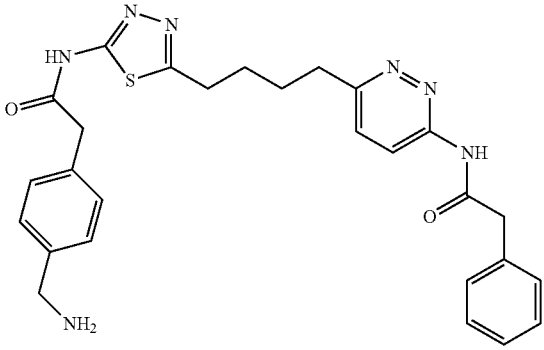 [SMILES: NCc1ccc(CC(=O)Nc2nnc(CCCCc3ccc(NC(=O)Cc4ccccc4)nn3)s2)cc1] |
| 408 | 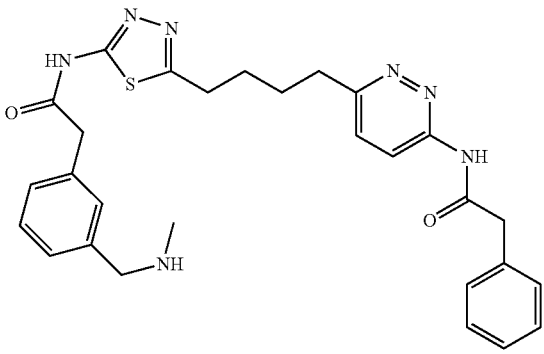 [SMILES: CNCc1cccc(CC(=O)Nc2nnc(CCCCc3ccc(NC(=O)Cc4ccccc4)nn3)s2)c1] |
| 409 | 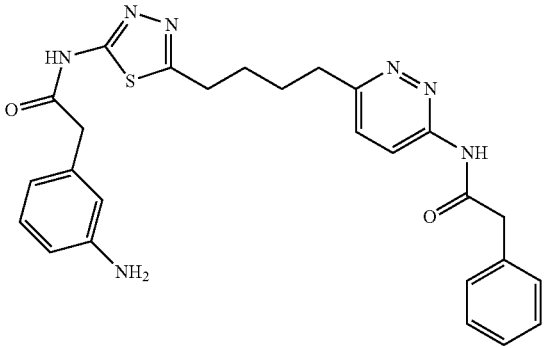 [SMILES: Nc1cccc(CC(=O)Nc2nnc(CCCCc3ccc(NC(=O)Cc4ccccc4)nn3)s2)c1] |
| 410 | 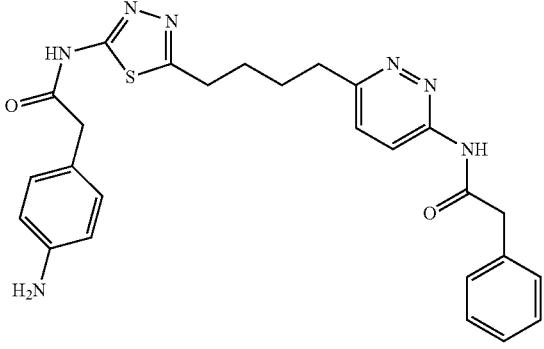 [SMILES: Nc1ccc(CC(=O)Nc2nnc(CCCCc3ccc(NC(=O)Cc4ccccc4)nn3)s2)cc1] |

TABLE 1-continued

Selected Compounds of Formula I

| Compound ID | Structure |
|---|---|
| 411 | 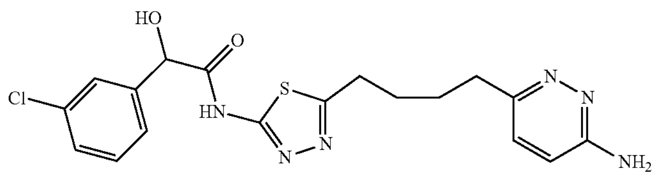 [SMILES: Nc1ccc(CCCCc2nnc(NC(=O)C(O)c3cccc(Cl)c3)s2)nn1] |
| 412 | 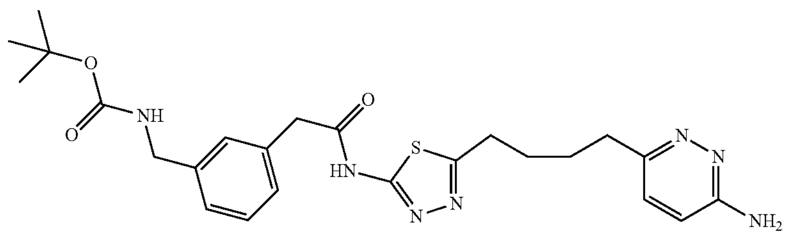 [SMILES: CC(C)(C)OC(=O)NCc1cccc(CC(=O)Nc2nnc(CCCCc3ccc(N)nn3)s2)c1] |
| 413 | 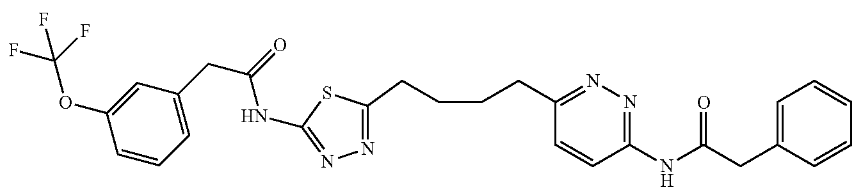 [SMILES: O=C(Cc1ccccc1)Nc1ccc(CCCCc2nnc(NC(=O)Cc3cccc(OC(F)(F)F)c3)s2)nn1] |
| 414 | 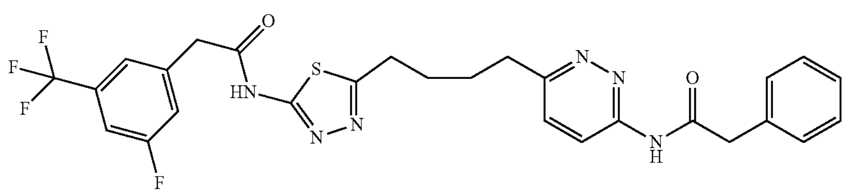 [SMILES: O=C(Cc1ccccc1)Nc1ccc(CCCCc2nnc(NC(=O)Cc3cc(F)cc(C(F)(F)F)c3)s2)nn1] |
| 415 | 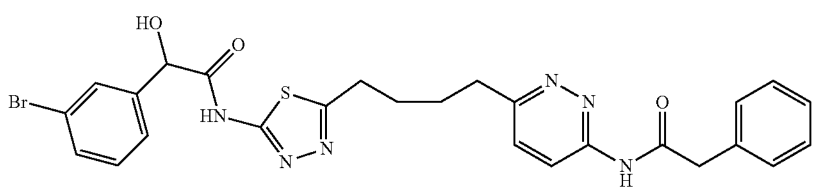 [SMILES: O=C(Cc1ccccc1)Nc1ccc(CCCCc2nnc(NC(=O)C(O)c3cccc(Br)c3)s2)nn1] |
| 416 | 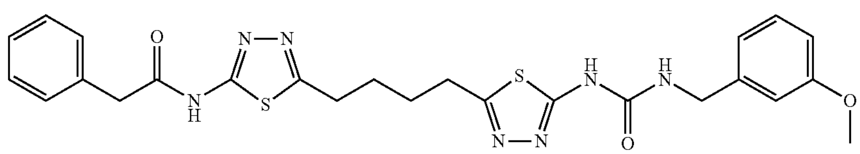 [SMILES: COc1cccc(CNC(=O)Nc2nnc(CCCCc3nnc(NC(=O)Cc4ccccc4)s3)s2)c1] |
| 417 | 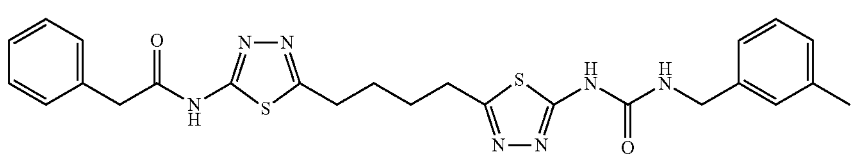 [SMILES: Cc1cccc(CNC(=O)Nc2nnc(CCCCc3nnc(NC(=O)Cc4ccccc4)s3)s2)c1] |

TABLE 1-continued

Selected Compounds of Formula I

| Compound ID | Structure |
|---|---|
| 418 | 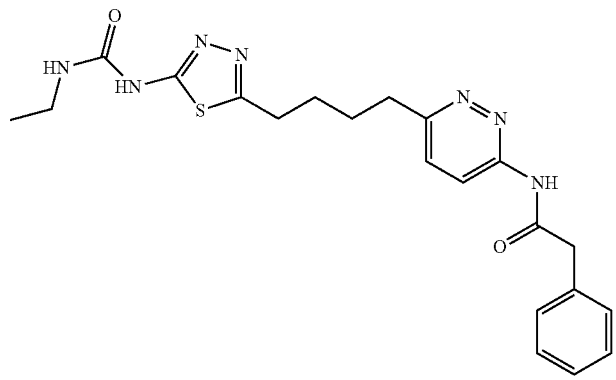 [SMILES: CCNC(=O)Nc1nnc(CCCCc2ccc(NC(=O)Cc3ccccc3)nn2)s1] |
| 419 | 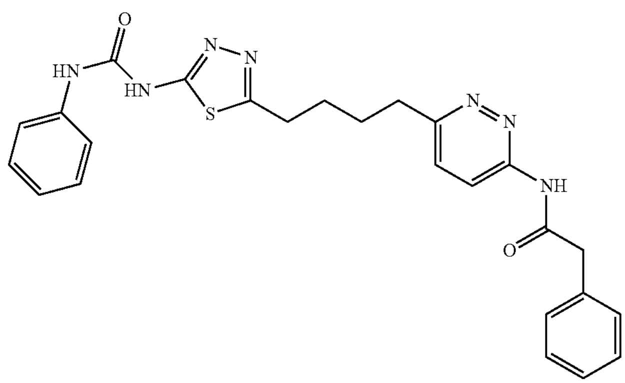 [SMILES: O=C(Cc1ccccc1)Nc1ccc(CCCCc2nnc(NC(=O)Nc3ccccc3)s2)nn1] |
| 420 | 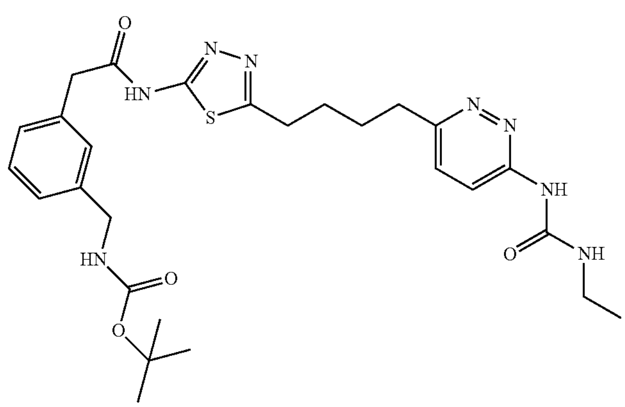 [SMILES: CCNC(=O)Nc1ccc(CCCCc2nnc(NC(=O)Cc3cccc(CNC(=O)OC(C)(C)C)c3)s2)nn1] |
| 421 | 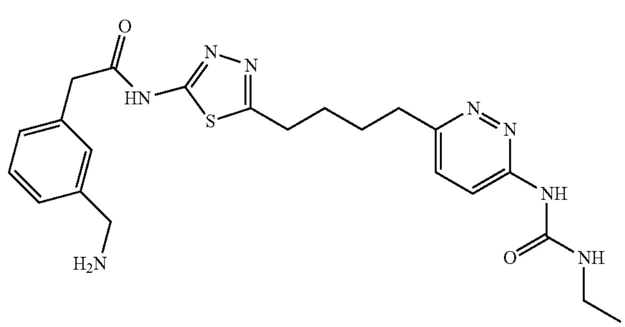 [SMILES: CCNC(=O)Nc1ccc(CCCCc2nnc(NC(=O)Cc3cccc(CN)c3)s2)nn1] |

TABLE 1-continued

Selected Compounds of Formula I

| Compound ID | Structure |
|---|---|
| 422 | 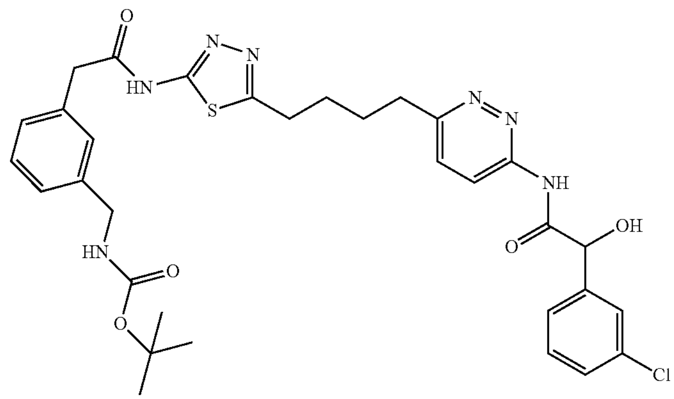 [SMILES: CC(C)(C)OC(=O)NCc1cccc(CC(=O)Nc2nnc(CCCCc3ccc(NC(=O)C(O)c4cccc(Cl)c4)nn3)s2)c1] |
| 423 | 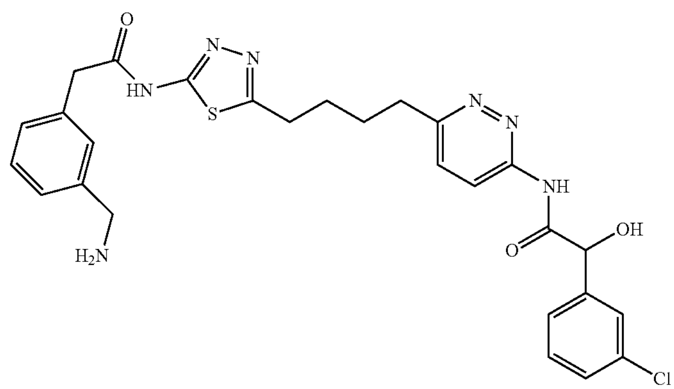 [SMILES: NCc1cccc(CC(=O)Nc2nnc(CCCCc3ccc(NC(=O)C(O)c4cccc(Cl)c4)nn3)s2)c1] |
| 424 | 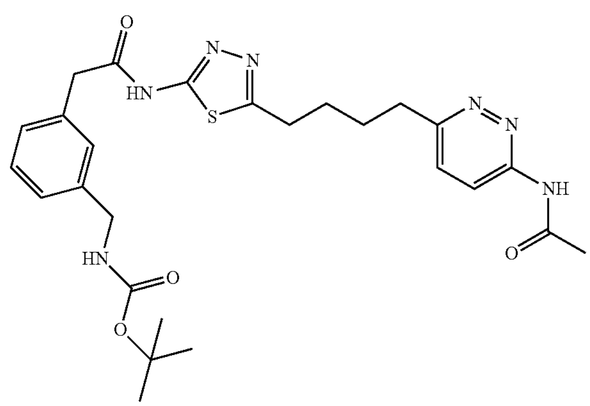 [SMILES: CC(=O)Nc1ccc(CCCCc2nnc(NC(=O)Cc3cccc(CNC(=O)OC(C)(C)C)c3)s2)nn1] |
| 425 | 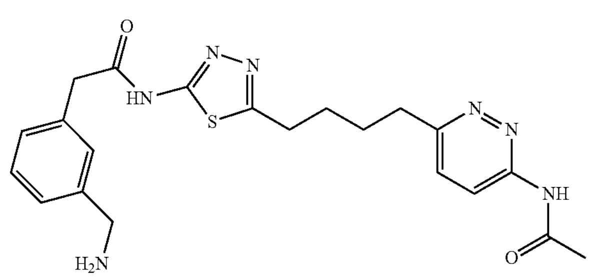 [SMILES: CC(=O)Nc1ccc(CCCCc2nnc(NC(=O)Cc3cccc(CN)c3)s2)nn1] |

TABLE 1-continued
Selected Compounds of Formula I
| Compound ID | Structure |
|---|---|
| 426 | 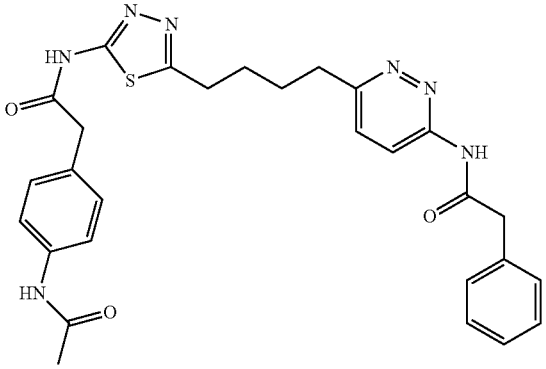 [SMILES: CC(=O)Nc1ccc(CC(=O)Nc2nnc(CCCCc3ccc(NC(=O)Cc4ccccc4)nn3)s2)cc1] |
| 427 | 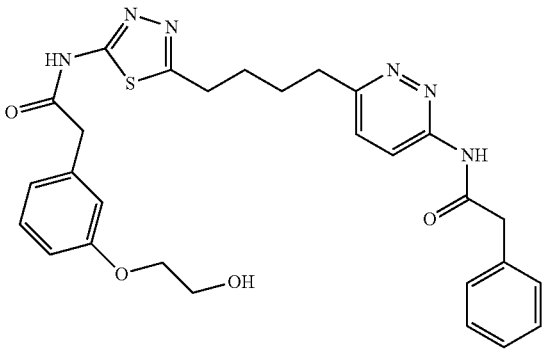 [SMILES: O=C(Cc1ccccc1)Nc1ccc(CCCCc2nnc(NC(=O)Cc3cccc(OCCO)c3)s2)nn1] |
| 428 | 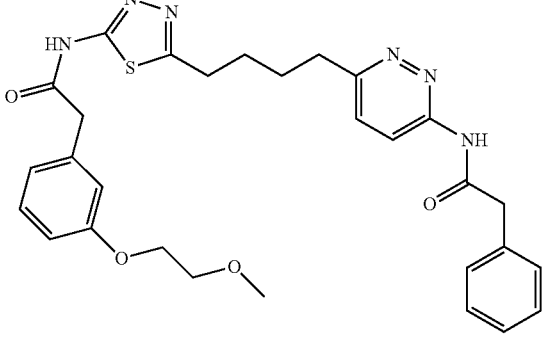 |
| 429 | 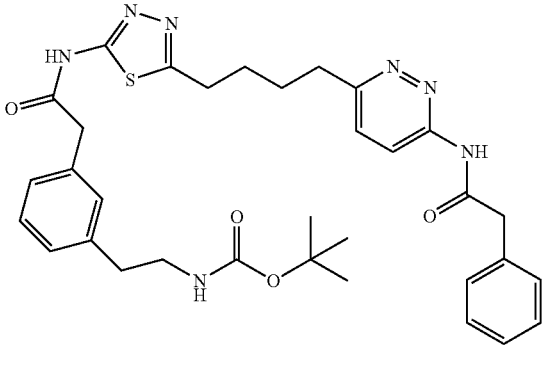 [SMILES: CC(C)(C)OC(=O)NCCc1cccc(CC(=O)Nc2nnc(CCCCc3ccc(NC(=O)Cc4ccccc4)nn3)s2)c1] |

TABLE 1-continued
Selected Compounds of Formula I
| Compound ID | Structure |
|---|---|
| 430 | 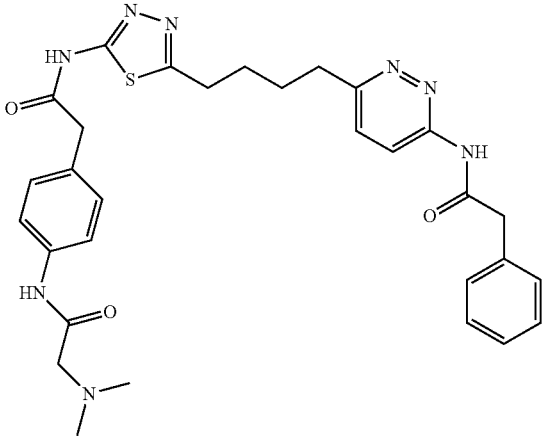 [SMILES: CN(C)CC(=O)Nc1ccc(CC(=O)Nc2nnc(CCCCc3ccc(NC(=O)Cc4ccccc4)nn3)s2)cc1] |
| 431 | 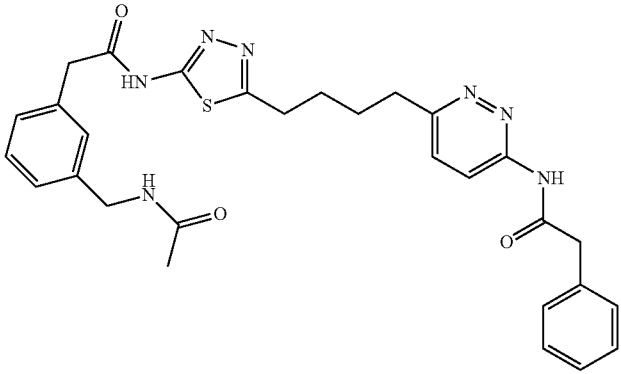 [SMILES: CC(=O)NCc1cccc(CC(=O)Nc2nnc(CCCCc3ccc(NC(=O)Cc4ccccc4)nn3)s2)c1] |
| 432 | 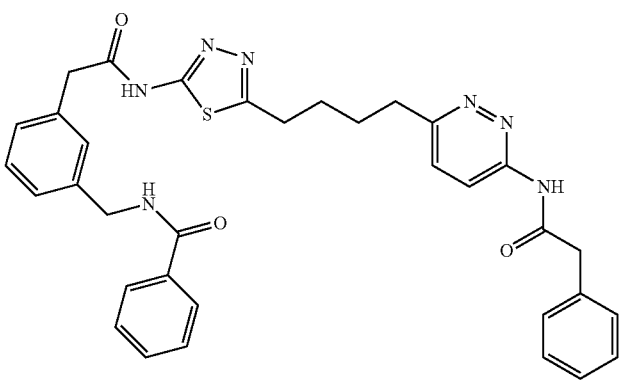 [SMILES: O=C(Cc1ccccc1)Nc1ccc(CCCCc2nnc(NC(=O)Cc3cccc(CNC(=O)c4ccccc4)c3)s2)nn1] |

TABLE 1-continued

Selected Compounds of Formula I

| Compound ID | Structure |
|---|---|
| 433 | 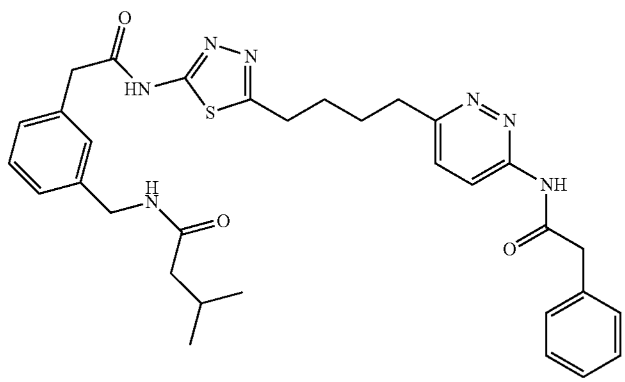 [SMILES: CC(C)CC(=O)NCc1cccc(CC(=O)Nc2nnc(CCCCc3ccc(NC(=O)Cc4ccccc4)nn3)s2)c1] |
| 434 | 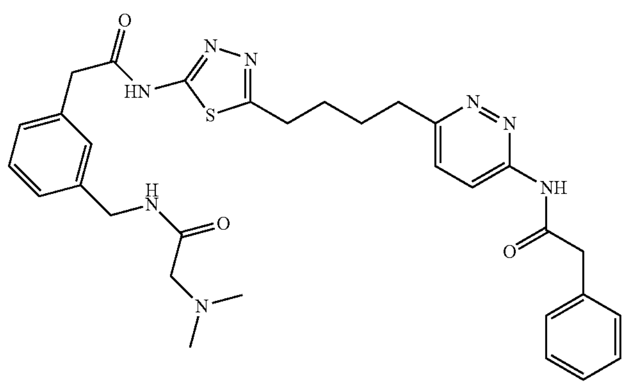 |
| 435 | 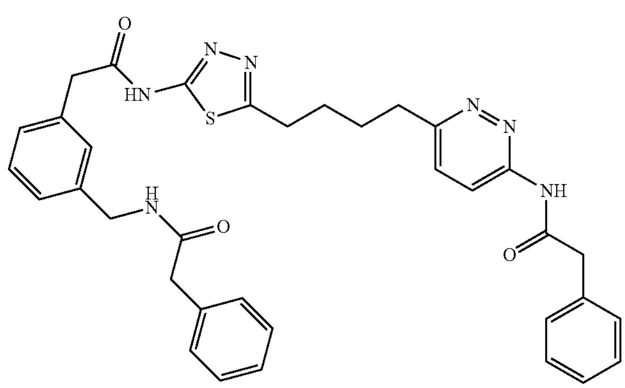 [SMILES: O=C(Cc1ccccc1)NCc1cccc(CC(=O)Nc2nnc(CCCCc3ccc(NC(=O)Cc4ccccc4)nn3)s2)c1] |
| 436 | 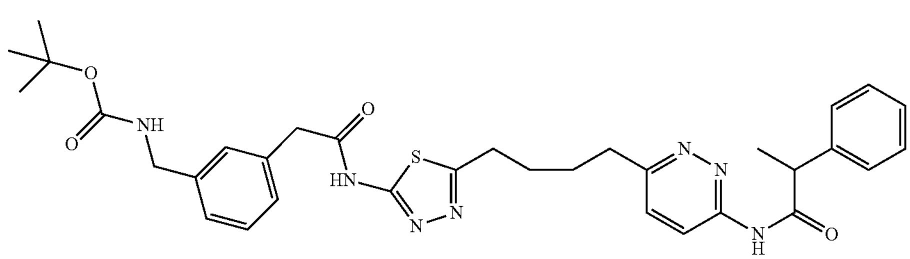 [SMILES: CC(C(=O)Nc1ccc(CCCCc2nnc(NC(=O)Cc3cccc(CNC(=O)OC(C)(C)C)c3)s2)nn1)c1ccccc1] |

TABLE 1-continued

Selected Compounds of Formula I

| Compound ID | Structure |
|---|---|
| 437 | 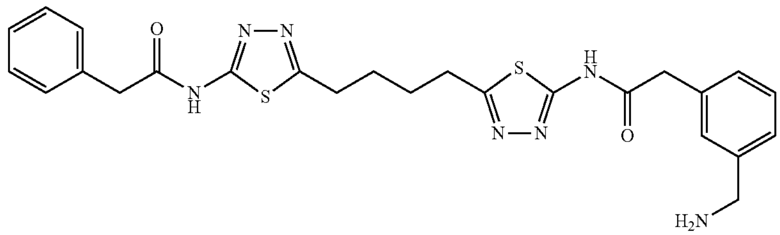 [SMILES: NCc1cccc(CC(=O)Nc2nnc(CCCCc3nnc(NC(=O)Cc4ccccc4)s3)s2)c1] |
| 438 | 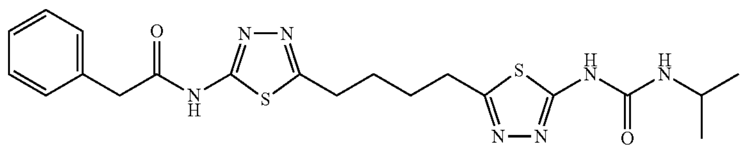 [SMILES: CC(C)NC(=O)Nc1nnc(CCCCc2nnc(NC(=O)Cc3ccccc3)s2)s1] |
| 439 | 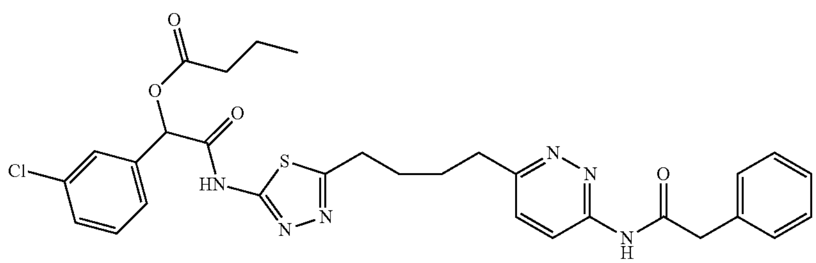 [SMILES: CCCC(=O)OC(C(=O)Nc1nnc(CCCCc2ccc(NC(=O)Cc3ccccc3)nn2)s1)c1cccc(Cl)c1] |
| 440 | 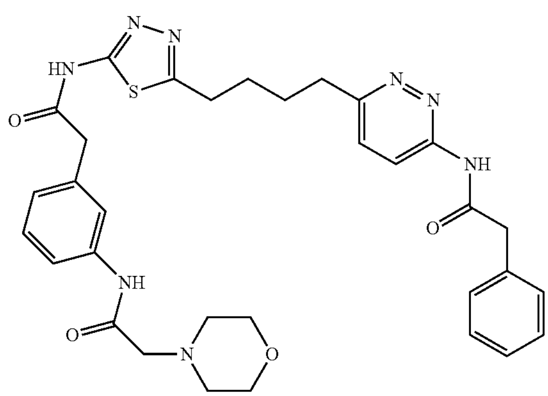 [SMILES: O=C(CN1CCOCC1)Nc1cccc(CC(=O)Nc2nnc(CCCCc3ccc(NC(=O)Cc4ccccc4)nn3)s2)c1] |
| 441 | 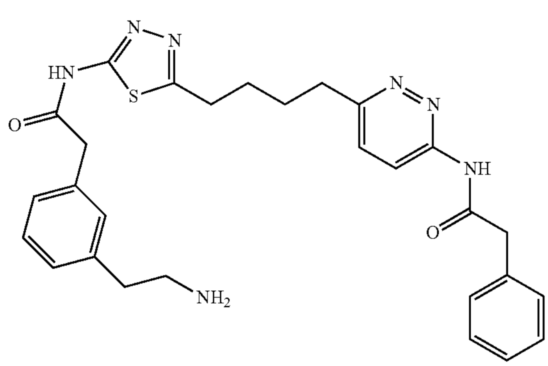 [SMILES: NCCc1cccc(CC(=O)Nc2nnc(CCCCc3ccc(NC(=O)Cc4ccccc4)nn3)s2)c1] |

TABLE 1-continued

Selected Compounds of Formula I

| Compound ID | Structure |
|---|---|
| 442 | 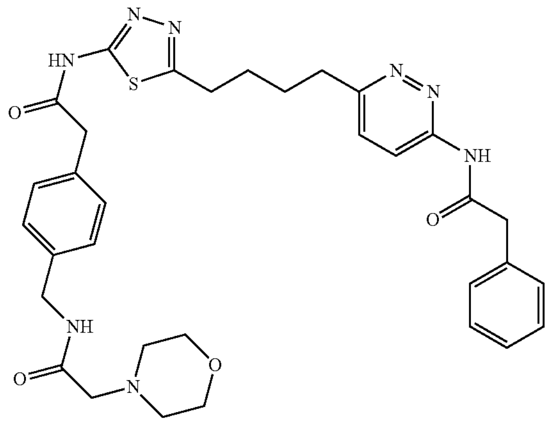 [SMILES: O=C(CN1CCOCC1)NCc1ccc(CC(=O)Nc2nnc(CCCCc3ccc(NC(=O)Cc4ccccc4)nn3)s2)cc1] |
| 443 | 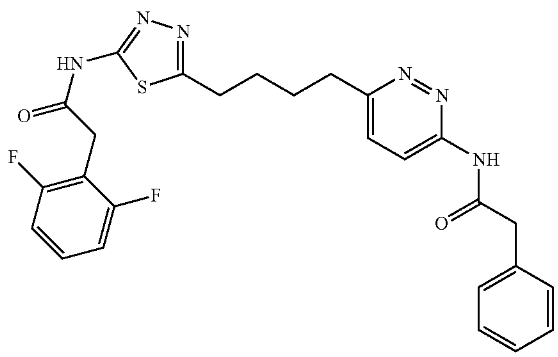 [SMILES: O=C(Cc1ccccc1)Nc1ccc(CCCCc2nnc(NC(=O)Cc3c(F)cccc3F)s2)nn1] |
| 444 | 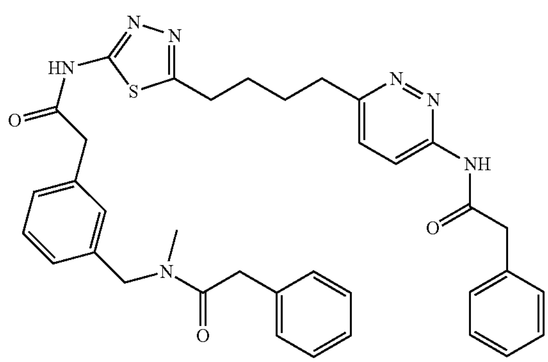 [SMILES: CN(Cc1cccc(CC(=O)Nc2nnc(CCCCc3ccc(NC(=O)Cc4ccccc4)nn3)s2)c1)C(=O)Cc1ccccc1] |
| 445 | 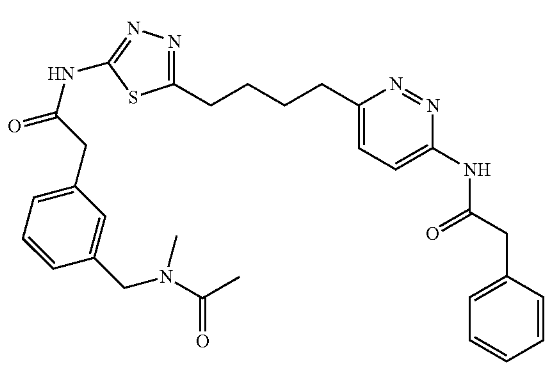 [SMILES: CC(=O)N(C)Cc1cccc(CC(=O)Nc2nnc(CCCCc3ccc(NC(=O)Cc4ccccc4)nn3)s2)c1] |

TABLE 1-continued

Selected Compounds of Formula I

| Compound ID | Structure |
|---|---|
| 446 | 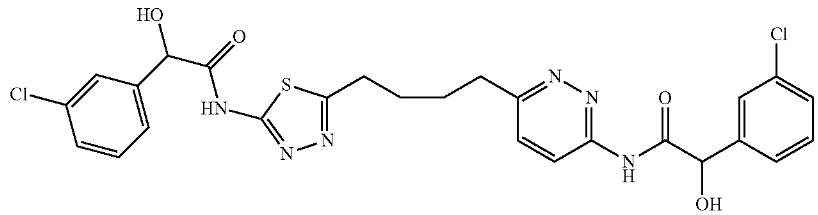 [SMILES: O=C(Nc1ccc(CCCCc2nnc(NC(=O)C(O)c3cccc(Cl)c3)s2)nn1)C(O)c1cccc(Cl)c1] |
| 447 | 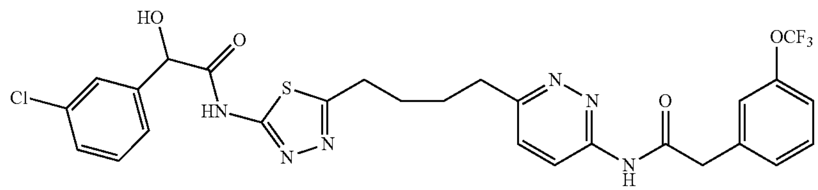 [SMILES: O=C(Cc1cccc(OC(F)(F)F)c1)Nc1ccc(CCCCc2nnc(NC(=O)C(O)c3cccc(Cl)c3)s2)nn1] |
| 448 | 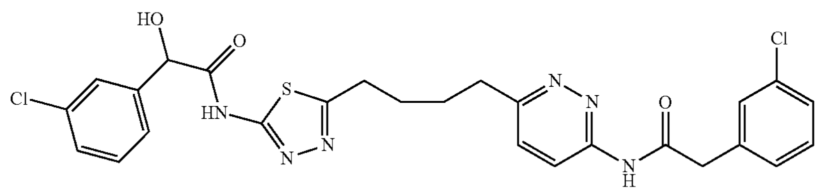 [SMILES: O=C(Cc1cccc(Cl)c1)Nc1ccc(CCCCc2nnc(NC(=O)C(O)c3cccc(Cl)c3)s2)nn1] |
| 449 | 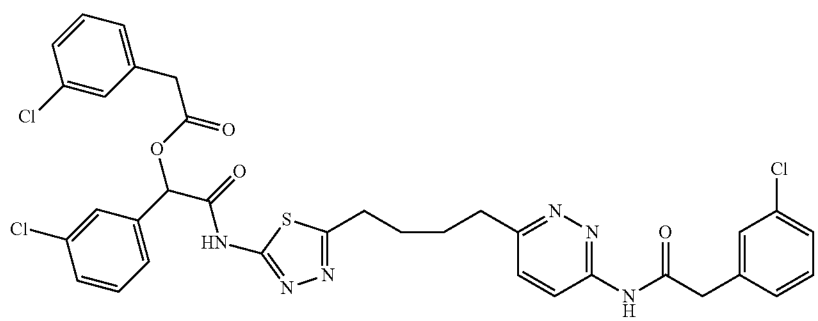 [SMILES: O=C(Cc1cccc(Cl)c1)Nc1ccc(CCCCc2nnc(NC(=O)C(OC(=O)Cc3cccc(Cl)c3)c3cccc(Cl)c3)s2)nn1] |
| 450 | 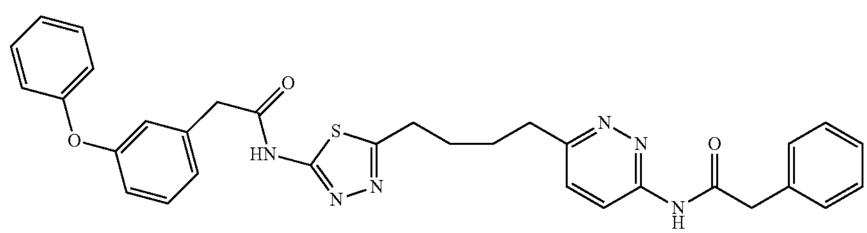 [SMILES: O=C(Cc1ccccc1)Nc1ccc(CCCCc2nnc(NC(=O)Cc3cccc(Oc4ccccc4)c3)s2)nn1] |
| 451 | 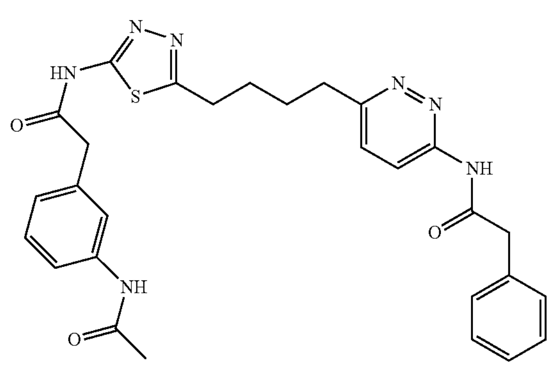 [SMILES: CC(=O)Nc1cccc(CC(=O)Nc2nnc(CCCCc3ccc(NC(=O)Cc4ccccc4)nn3)s2)c1] |

TABLE 1-continued
Selected Compounds of Formula I
| Compound ID | Structure |
|---|---|
| 452 | 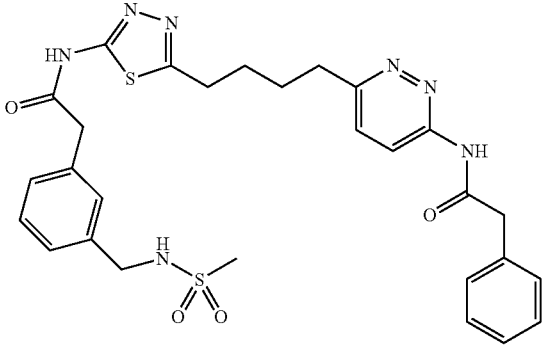 [SMILES: CS(=O)(=O)NCc1cccc(CC(=O)Nc2nnc(CCCCc3ccc(NC(=O)Cc4ccccc4)nn3)s2)c1] |
| 453 | 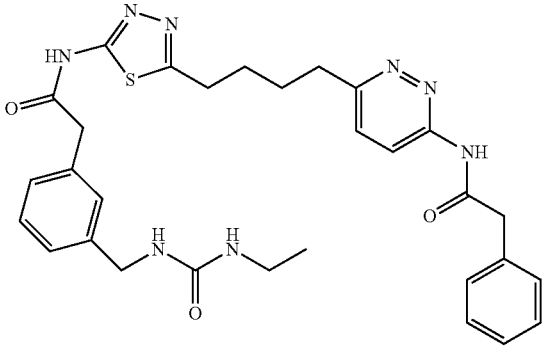 [SMILES: CCNC(=O)NCc1cccc(CC(=O)Nc2nnc(CCCCc3ccc(NC(=O)Cc4ccccc4)nn3)s2)c1] |
| 454 | 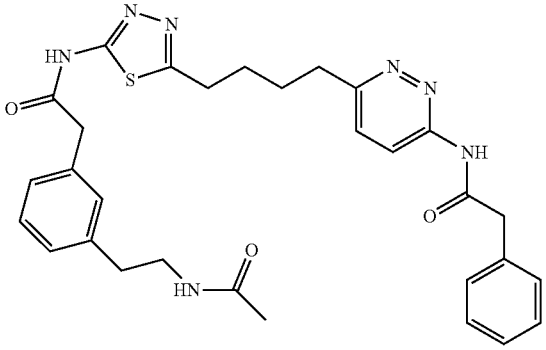 [SMILES: CC(=O)NCCc1cccc(CC(=O)Nc2nnc(CCCCc3ccc(NC(=O)Cc4ccccc4)nn3)s2)c1] |
| 455 | 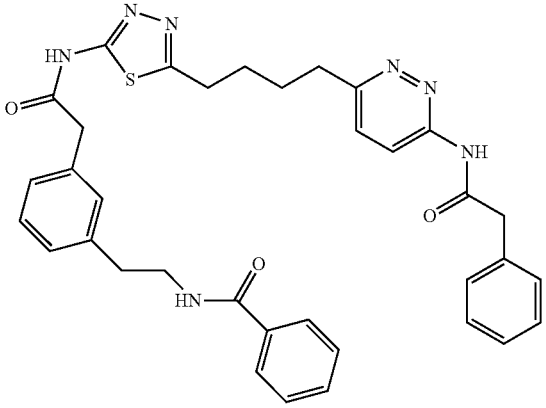 [SMILES: O=C(Cc1ccccc1)Nc1ccc(CCCCc2nnc(NC(=O)Cc3cccc(CCNC(=O)c4ccccc4)c3)s2)nn1] |

TABLE 1-continued

Selected Compounds of Formula I

| Compound ID | Structure |
|---|---|
| 456 | 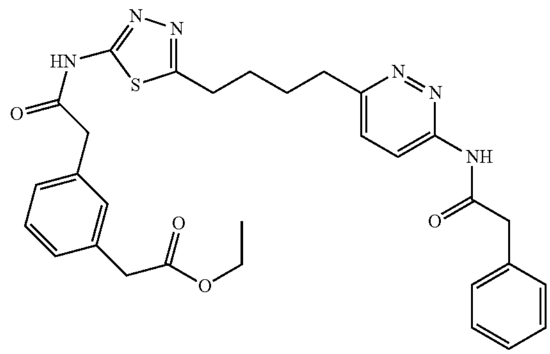 [SMILES: CCOC(=O)Cc1cccc(CC(=O)Nc2nnc(CCCCc3ccc(NC(=O)Cc4ccccc4)nn3)s2)c1] |
| 457 | 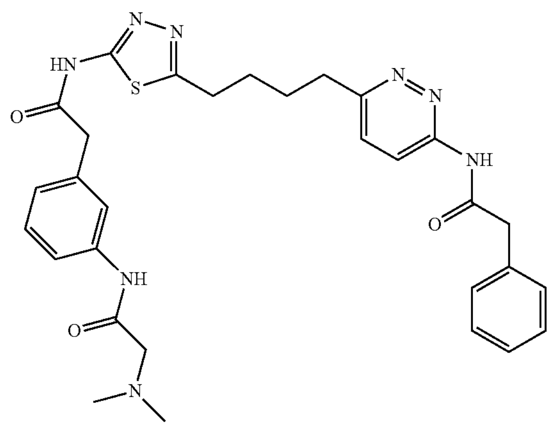 [SMILES: CN(C)CC(=O)Nc1cccc(CC(=O)Nc2nnc(CCCCc3ccc(NC(=O)Cc4ccccc4)nn3)s2)c1] |
| 458 | 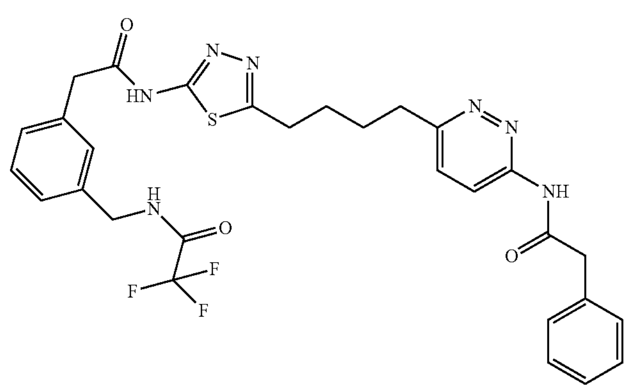 [SMILES: O=C(Cc1ccccc1)Nc1ccc(CCCCc2nnc(NC(=O)Cc3cccc(CNC(=O)C(F)(F)F)c3)s2)nn1] |
| 459 | 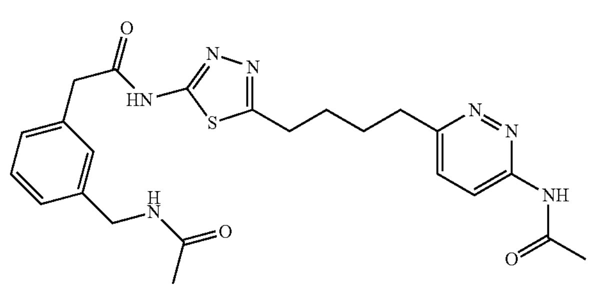 [SMILES: CC(=O)NCc1cccc(CC(=O)Nc2nnc(CCCCc3ccc(NC(C)=O)nn3)s2)c1] |

TABLE 1-continued

Selected Compounds of Formula I

| Compound ID | Structure |
|---|---|
| 460 | 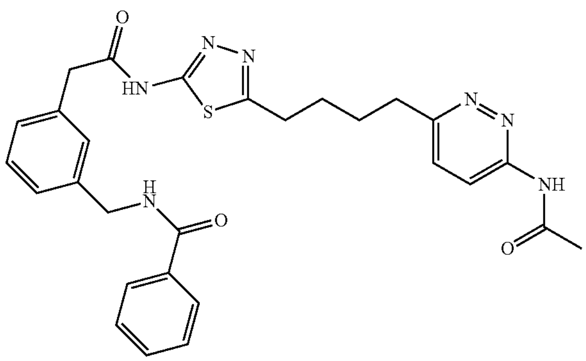 [SMILES: CC(=O)Nc1ccc(CCCCc2nnc(NC(=O)Cc3cccc(CNC(=O)c4ccccc4)c3)s2)nn1] |
| 461 | 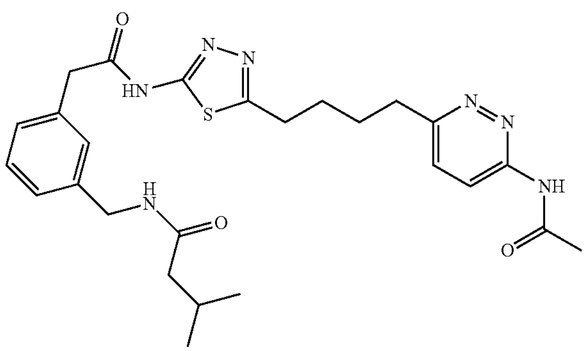 [SMILES: CC(=O)Nc1ccc(CCCCc2nnc(NC(=O)Cc3cccc(CNC(=O)CC(C)C)c3)s2)nn1] |
| 462 | 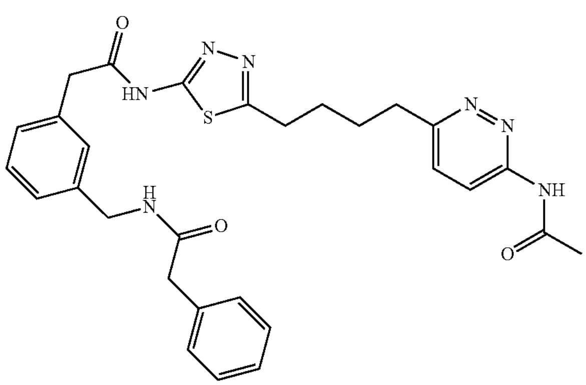 [SMILES: CC(=O)Nc1ccc(CCCCc2nnc(NC(=O)Cc3cccc(CNC(=O)Cc4ccccc4)c3)s2)nn1] |
| 463 | 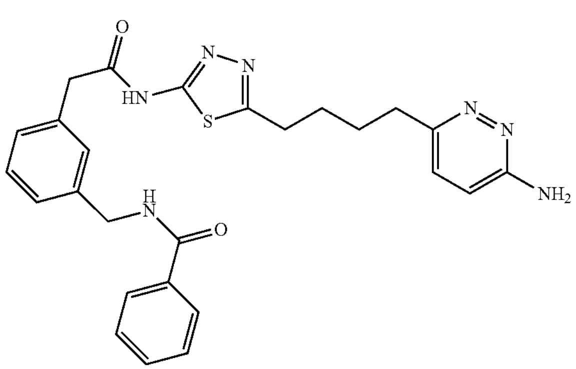 [SMILES: Nc1ccc(CCCCc2nnc(NC(=O)Cc3cccc(CNC(=O)c4ccccc4)c3)s2)nn1] |

TABLE 1-continued

Selected Compounds of Formula I

| Compound ID | Structure |
|---|---|
| 464 | 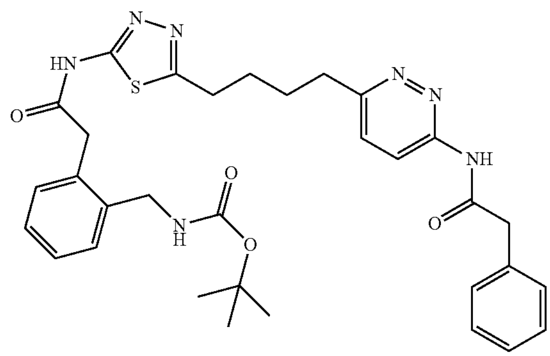 [SMILES: CC(C)(C)OC(=O)NCc1ccccc1CC(=O)Nc1nnc(CCCCc2ccc(NC(=O)Cc3ccccc3)nn2)s1] |
| 465 | 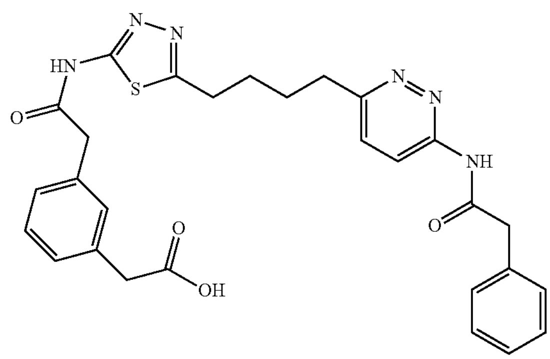 [SMILES: O=C(O)Cc1cccc(CC(=O)Nc2nnc(CCCCc3ccc(NC(=O)Cc4ccccc4)nn3)s2)c1] |
| 466 | 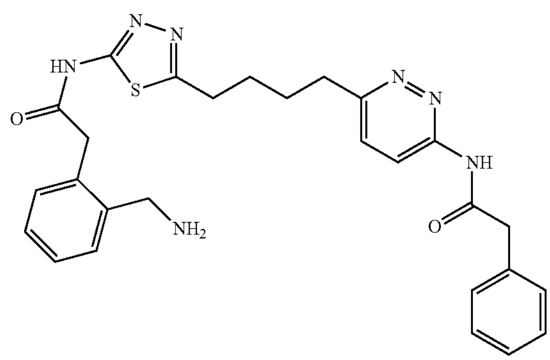 [SMILES: NCc1ccccc1CC(=O)Nc1nnc(CCCCc2ccc(NC(=O)Cc3ccccc3)nn2)s1] |
| 467 | 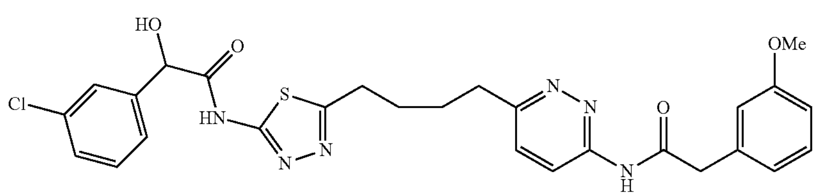 [SMILES: COc1cccc(CC(=O)Nc2ccc(CCCCc3nnc(NC(=O)C(O)c4cccc(Cl)c4)s3)nn2)c1] |
| 468 | 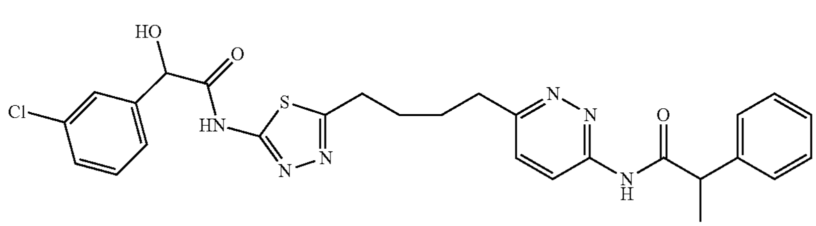 [SMILES: CC(C(=O)Nc1ccc(CCCCc2nnc(NC(=O)C(O)c3cccc(Cl)c3)s2)nn1)c1ccccc1] |

TABLE 1-continued

Selected Compounds of Formula I

| Compound ID | Structure |
|---|---|
| 469 | 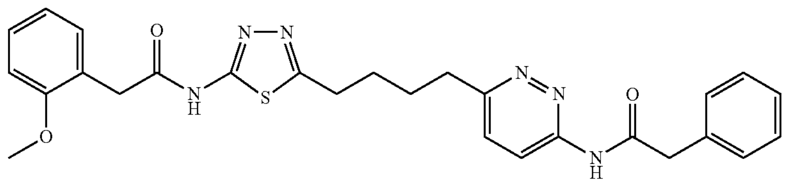 [SMILES: COc1ccccc1CC(=O)Nc1nnc(CCCCc2ccc(NC(=O)Cc3ccccc3)nn2)s1] |
| 470 | 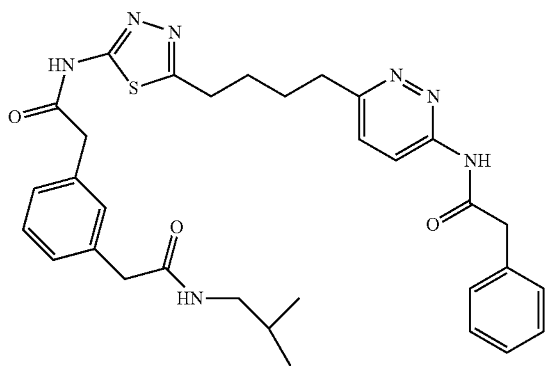 [SMILES: CC(C)CNC(=O)Cc1cccc(CC(=O)Nc2nnc(CCCCc3ccc(NC(=O)Cc4ccccc4)nn3)s2)c1] |
| 471 | 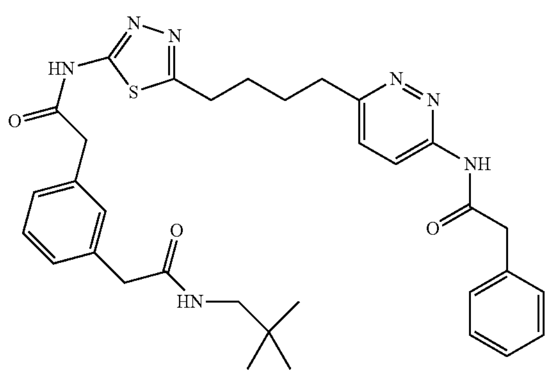 [SMILES: CC(C)(C)CNC(=O)Cc1cccc(CC(=O)Nc2nnc(CCCCc3ccc(NC(=O)Cc4ccccc4)nn3)s2)c1] |
| 472 | 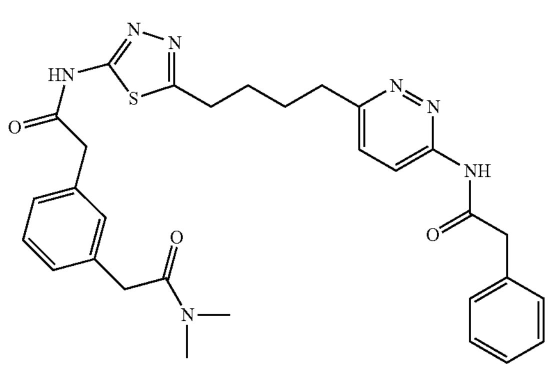 [SMILES: CN(C)C(=O)Cc1cccc(CC(=O)Nc2nnc(CCCCc3ccc(NC(=O)Cc4ccccc4)nn3)s2)c1] |

TABLE 1-continued
Selected Compounds of Formula I
| Compound ID | Structure |
|---|---|
| 473 | 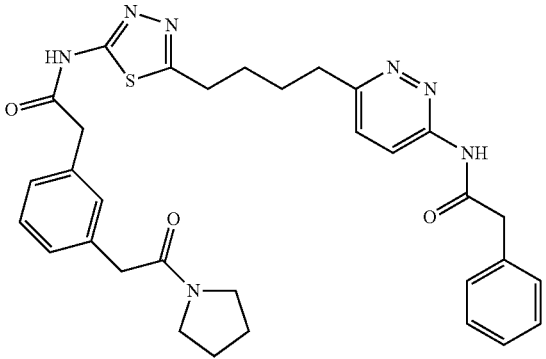 [SMILES: O=C(Cc1ccccc1)Nc1ccc(CCCCc2nnc(NC(=O)Cc3cccc(CC(=O)N4CCCC4)c3)s2)nn1] |
| 474 | 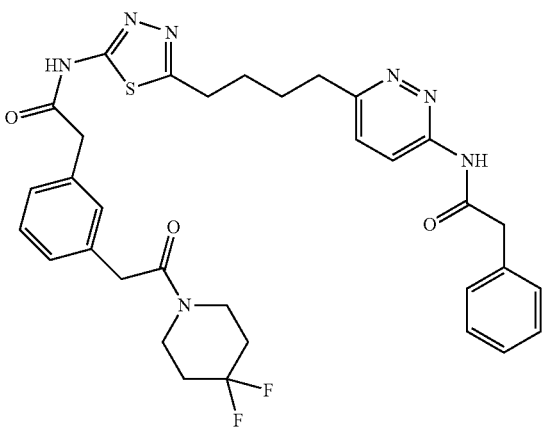 [SMILES: O=C(Cc1ccccc1)Nc1ccc(CCCCc2nnc(NC(=O)Cc3cccc(CC(=O)N4CCC(F)(F)CC4)c3)s2)nn1] |
| 475 | 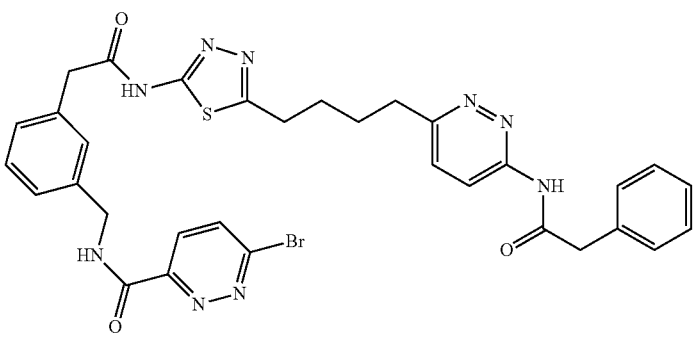 [SMILES: O=C(Cc1ccccc1)Nc1ccc(CCCCc2nnc(NC(=O)Cc3cccc(CNC(=O)c4ccc(Br)nn4)c3)s2)nn1] |
| 476 | 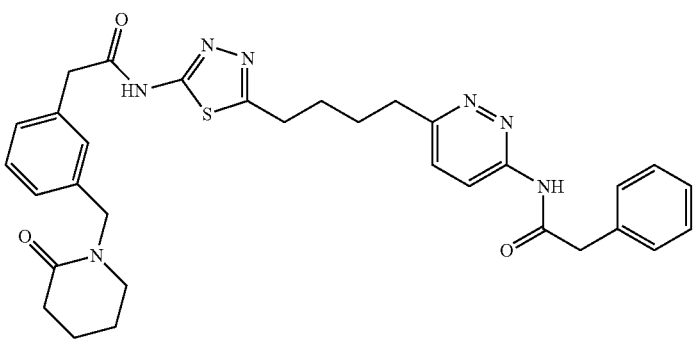 [SMILES: O=C(Cc1ccccc1)Nc1ccc(CCCCc2nnc(NC(=O)Cc3cccc(CN4CCCCC4=O)c3)s2)nn1] |

TABLE 1-continued
Selected Compounds of Formula I
| Compound ID | Structure |
|---|---|
| 477 | 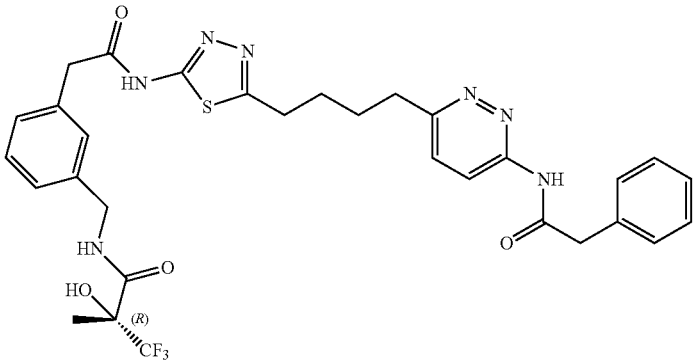 |
| 478 | 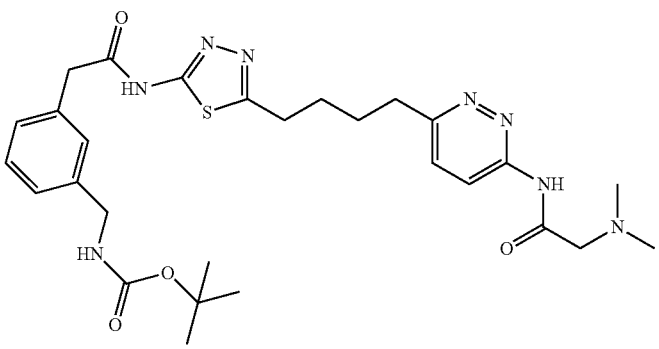 [SMILES: CN(C)CC(=O)Nc1ccc(CCCCc2nnc(NC(=O)Cc3cccc(CNC(=O)OC(C)(C)C)c3)s2)nn1] |
| 479 | 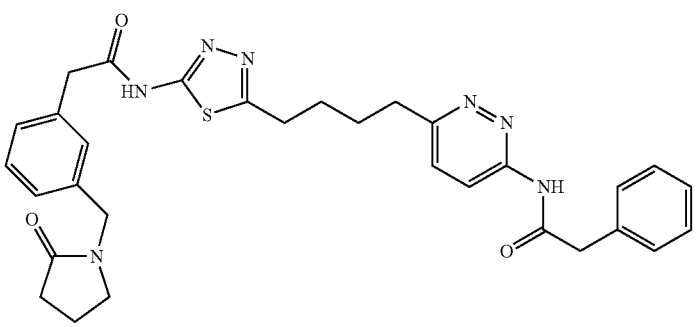 [SMILES: O=C(Cc1ccccc1)Nc1ccc(CCCCc2nnc(NC(=O)Cc3cccc(CN4CCCC4=O)c3)s2)nn1] |
| 480 | 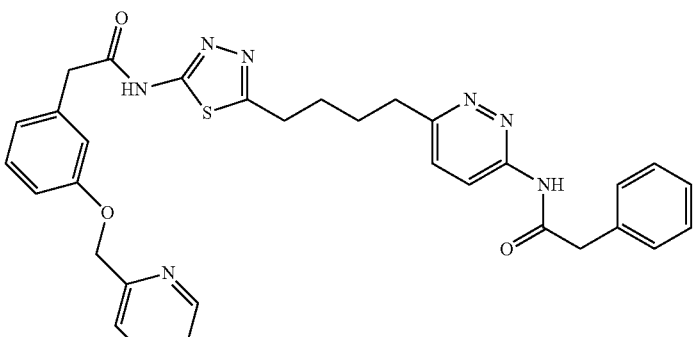 |

TABLE 1-continued

Selected Compounds of Formula I

| Compound ID | Structure |
|---|---|
| 481 | 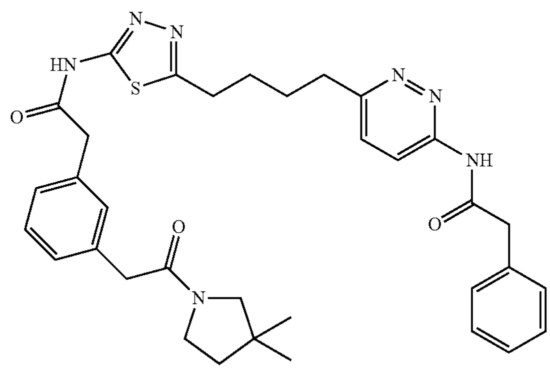 [SMILES: CC1(C)CCN(C(=O)Cc2cccc(CC(=O)Nc3nnc(CCCCc4ccc(NC(=O)Cc5ccccc5)nn4)s3)c2)C1] |
| 482 | 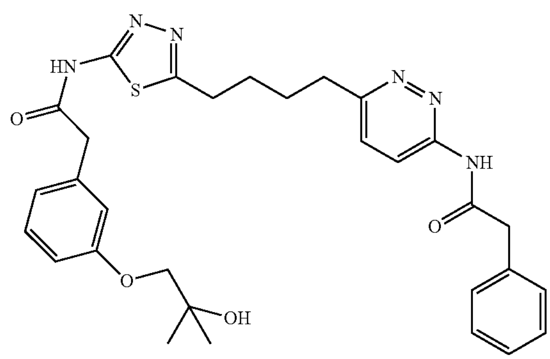 [SMILES: CC(C)(O)COc1cccc(CC(=O)Nc2nnc(CCCCc3ccc(NC(=O)Cc4ccccc4)nn3)s2)c1] |
| 483 | 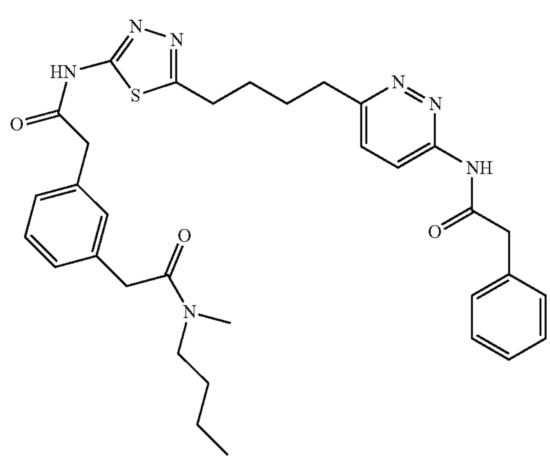 [SMILES: CCCCN(C)C(=O)Cc1cccc(CC(=O)Nc2nnc(CCCCc3ccc(NC(=O)Cc4ccccc4)nn3)s2)c1] |

TABLE 1-continued
Selected Compounds of Formula I
| Compound ID | Structure |
|---|---|
| 484 | 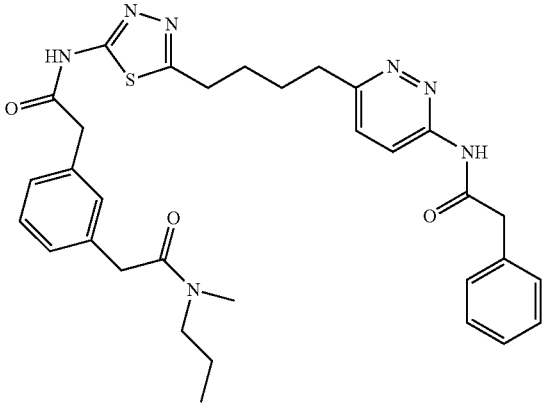 [SMILES: CCCN(C)C(=O)Cc1cccc(CC(=O)Nc2nnc(CCCCc3ccc(NC(=O)Cc4ccccc4)nn3)s2)c1] |
| 485 | 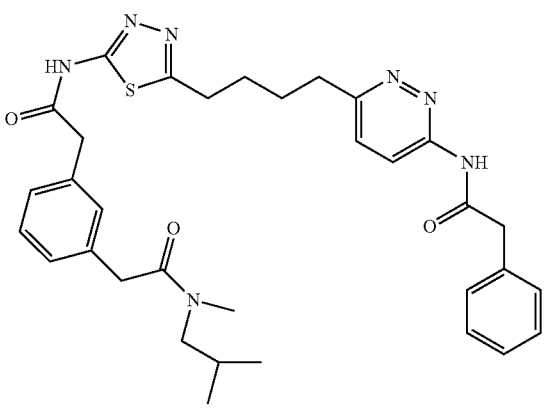 [SMILES: CC(C)CN(C)C(=O)Cc1cccc(CC(=O)Nc2nnc(CCCCc3ccc(NC(=O)Cc4ccccc4)nn3)s2)c1] |
| 486 | 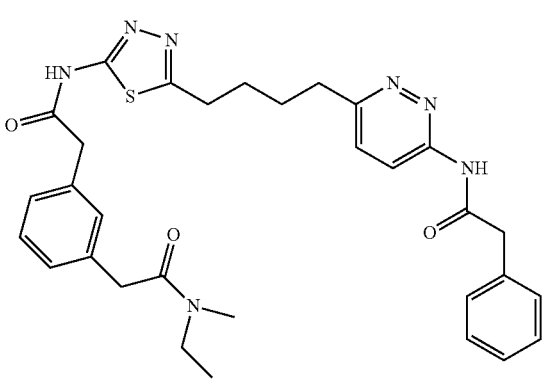 [SMILES: CCN(C)C(=O)Cc1cccc(CC(=O)Nc2nnc(CCCCc3ccc(NC(=O)Cc4ccccc4)nn3)s2)c1] |
| 487 | 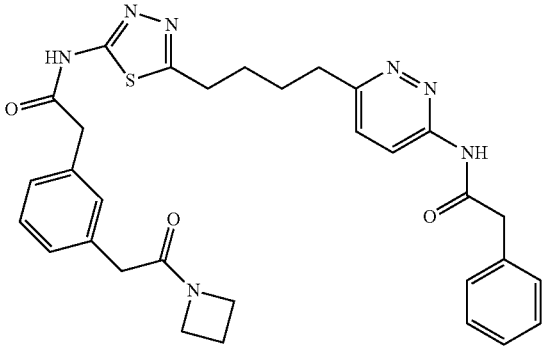 [SMILES: O=C(Cc1ccccc1)Nc1ccc(CCCCc2nnc(NC(=O)Cc3cccc(CC(=O)N4CCC4)c3)s2)nn1] |

TABLE 1-continued
Selected Compounds of Formula I
| Compound ID | Structure |
|---|---|
| 488 | 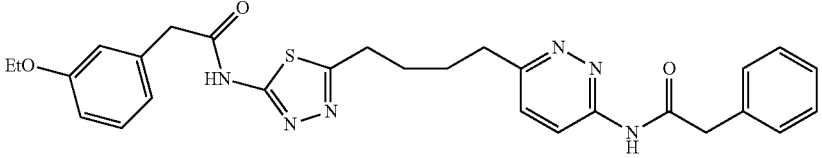 [SMILES: CCOc1cccc(CC(=O)Nc2nnc(CCCCc3ccc(NC(=O)Cc4ccccc4)nn3)s2)c1] |
| 489 | 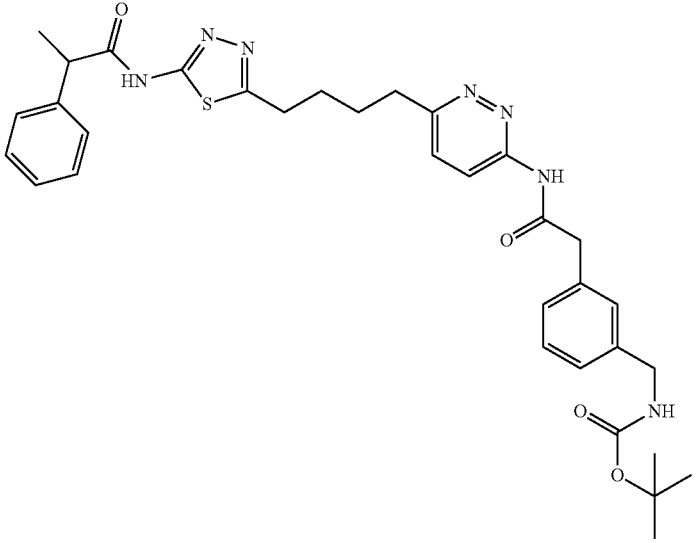 [SMILES: CC(C(=O)Nc1nnc(CCCCc2ccc(NC(=O)Cc3cccc(CNC(=O)OC(C)(C)C)c3)nn2)s1)c1ccccc1] |
| 490 | 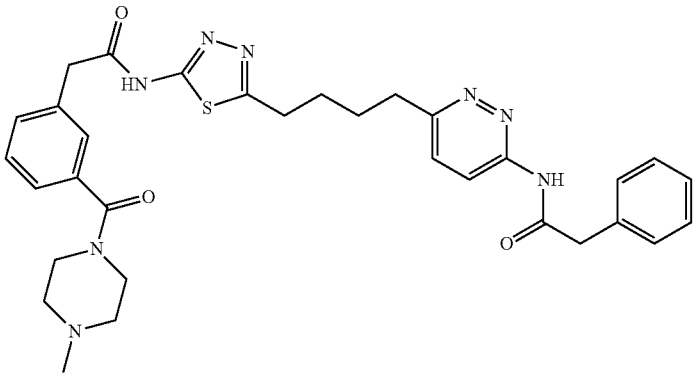 [SMILES: CN1CCN(C(=O)c2cccc(CC(=O)Nc3nnc(CCCCc4ccc(NC(=O)Cc5ccccc5)nn4)s3)c2)CC1] |
| 491 | 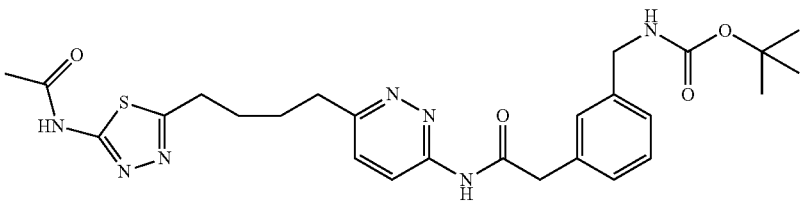 [SMILES: CC(=O)Nc1nnc(CCCCc2ccc(NC(=O)Cc3cccc(CNC(=O)OC(C)(C)C)c3)nn2)s1] |

TABLE 1-continued
Selected Compounds of Formula I
| Compound ID | Structure |
|---|---|
| 492 | 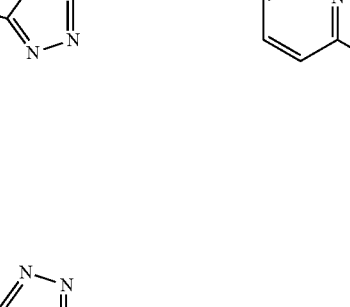 |
| 493 | 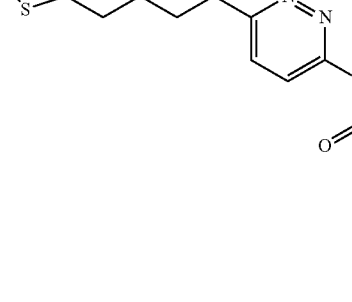 |
| 494 | 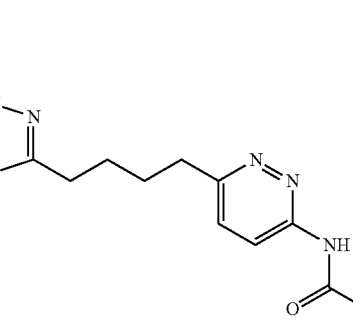 |
| 495 | 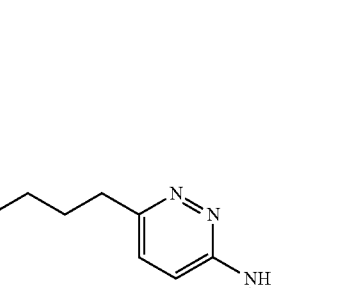 |

TABLE 1-continued

Selected Compounds of Formula I

| Compound ID | Structure |
|---|---|
| 496 | 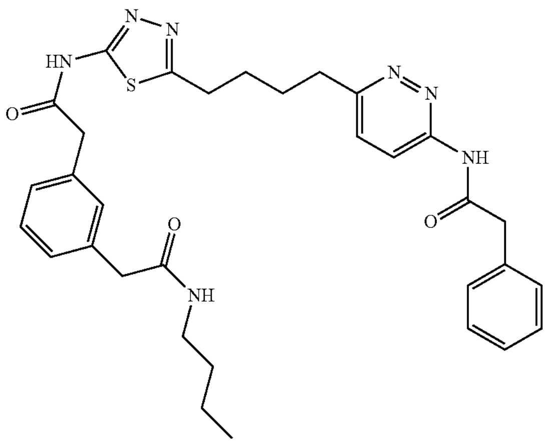 [SMILES: CCCCNC(=O)Cc1cccc(CC(=O)Nc2nnc(CCCCc3ccc(NC(=O)Cc4ccccc4)nn3)s2)c1] |
| 497 | 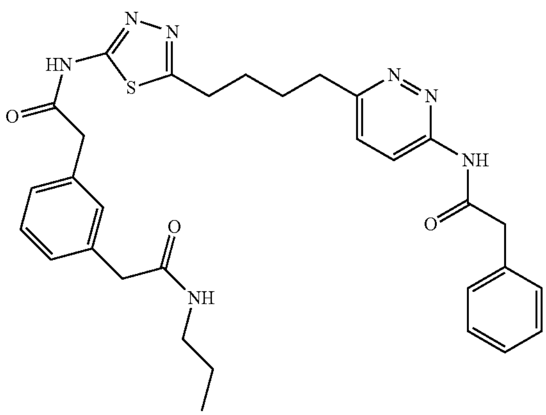 [SMILES: CCCNC(=O)Cc1cccc(CC(=O)Nc2nnc(CCCCc3ccc(NC(=O)Cc4ccccc4)nn3)s2)c1] |
| 498 | 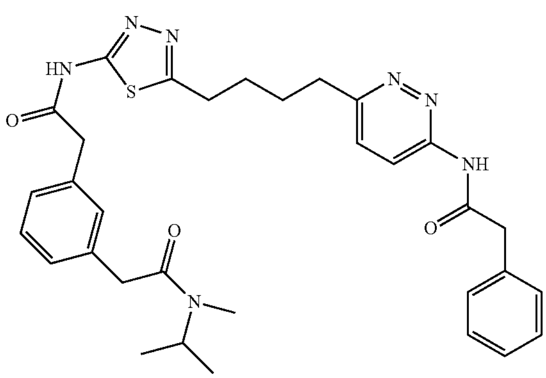 [SMILES: CC(C)N(C)C(=O)Cc1cccc(CC(=O)Nc2nnc(CCCCc3ccc(NC(=O)Cc4ccccc4)nn3)s2)c1] |
| 499 | 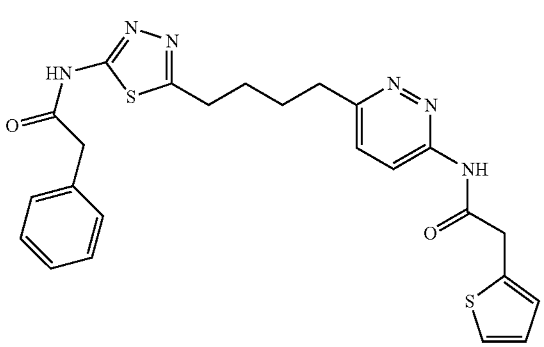 [SMILES: O=C(Cc1cccs1)Nc1ccc(CCCCc2nnc(NC(=O)Cc3ccccc3)s2)nn1] |

TABLE 1-continued
Selected Compounds of Formula I
| Compound ID | Structure |
|---|---|
| 500 | 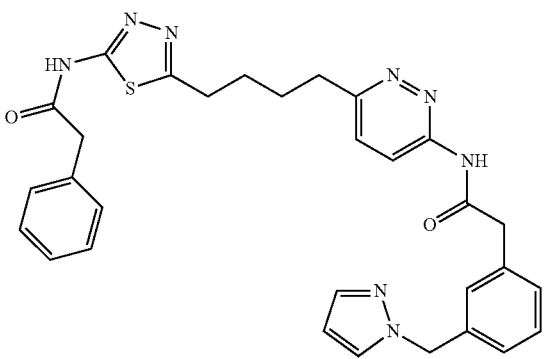 [SMILES: O=C(Cc1cccc(Cn2cccn2)c1)Nc1ccc(CCCCc2nnc(NC(=O)Cc3ccccc3)s2)nn1] |
| 501 | 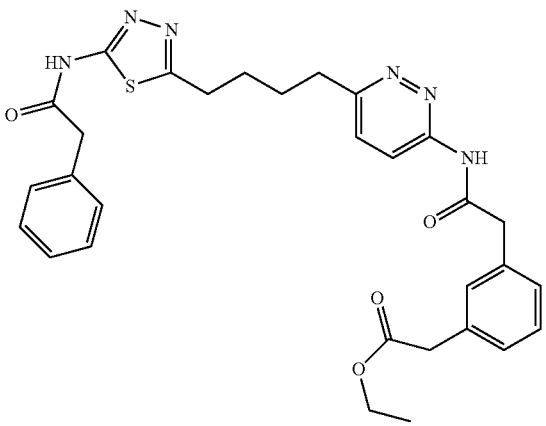 [SMILES: CCOC(=O)Cc1cccc(CC(=O)Nc2ccc(CCCCc3nnc(NC(=O)Cc4ccccc4)s3)nn2)c1] |
| 502 | 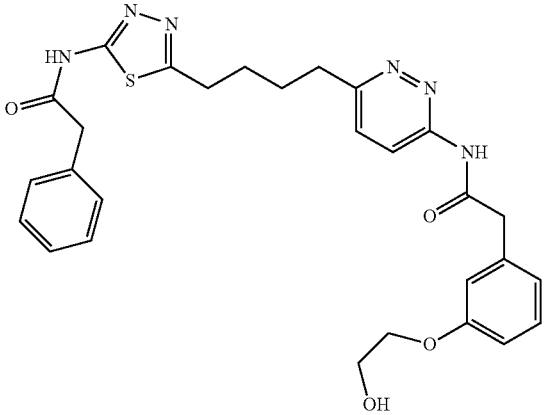 [SMILES: O=C(Cc1cccc(OCCO)c1)Nc1ccc(CCCCc2nnc(NC(=O)Cc3ccccc3)s2)nn1] |

TABLE 1-continued

Selected Compounds of Formula I

| Compound ID | Structure |
|---|---|
| 503 | 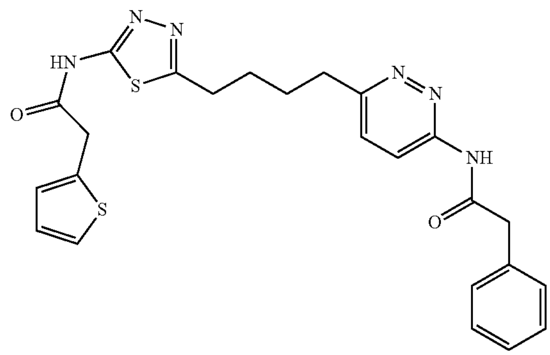 [SMILES: O=C(Cc1ccccc1)Nc1ccc(CCCCc2nnc(NC(=O)Cc3cccs3)s2)nn1] |
| 504 | 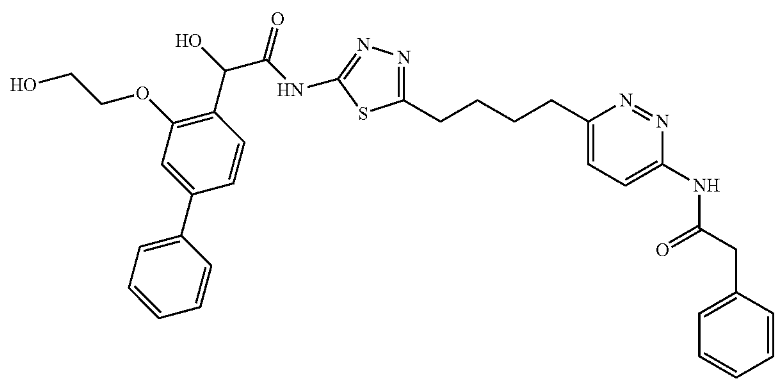 [SMILES: O=C(Cc1ccccc1)Nc1ccc(CCCCc2nnc(NC(=O)C(O)c3ccc(-c4ccccc4)cc3OCCO)s2)nn1] |
| 505 | 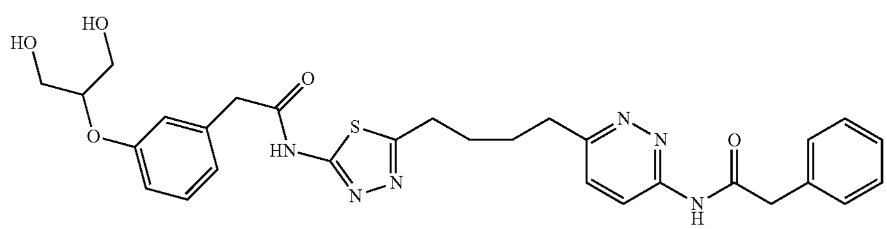 [SMILES: O=C(Cc1ccccc1)Nc1ccc(CCCCc2nnc(NC(=O)Cc3cccc(OC(CO)CO)c3)s2)nn1] |
| 506 | 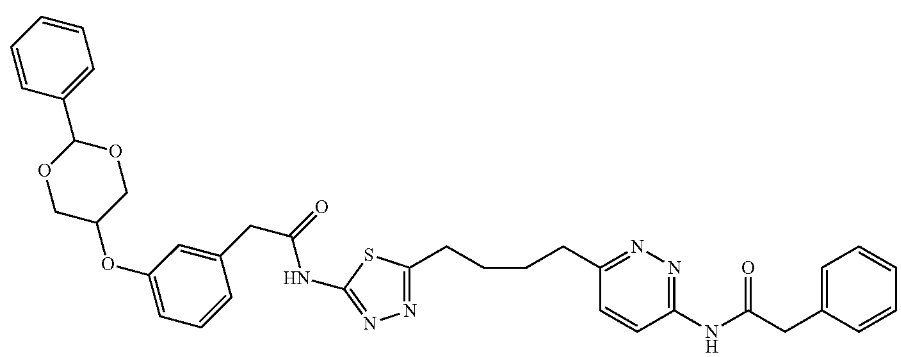 [SMILES: O=C(Cc1ccccc1)Nc1ccc(CCCCc2nnc(NC(=O)Cc3cccc(OC4COC(c5ccccc5)OC4)c3)s2)nn1] |

TABLE 1-continued

Selected Compounds of Formula I

| Compound ID | Structure |
|---|---|
| 507 | 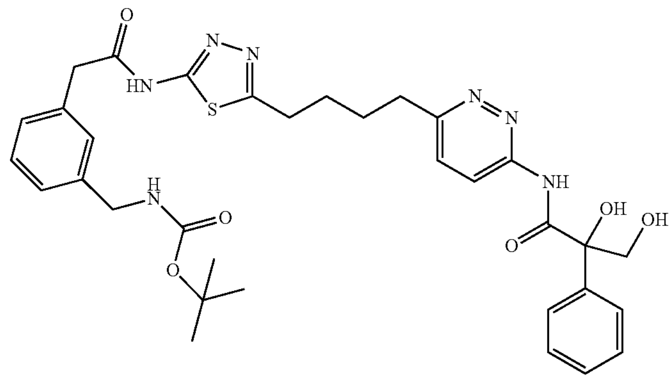 [SMILES: CC(C)(C)OC(=O)NCc1cccc(CC(=O)Nc2nnc(CCCCc3ccc(NC(=O)C(O)(CO)c4ccccc4)nn3)s2)c1] |
| 508 | 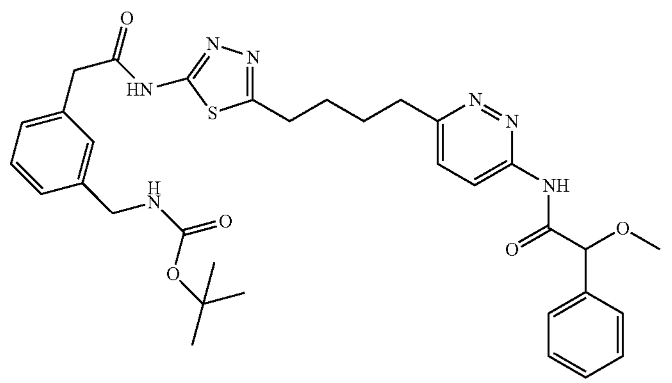 [SMILES: COC(C(=O)Nc1ccc(CCCCc2nnc(NC(=O)Cc3cccc(CNC(=O)OC(C)(C)C)c3)s2)nn1)c1ccccc1] |
| 509 | 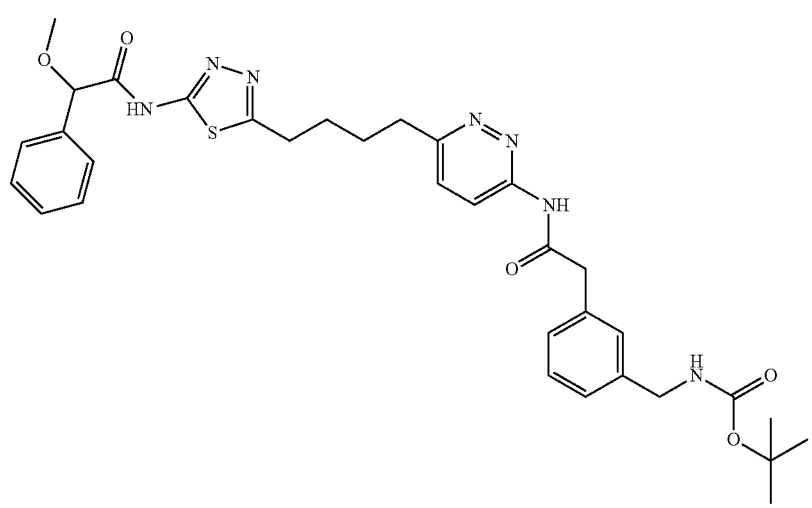 [SMILES: COC(C(=O)Nc1nnc(CCCCc2ccc(NC(=O)Cc3cccc(CNC(=O)OC(C)(C)C)c3)nn2)s1)c1ccccc1] |

TABLE 1-continued

Selected Compounds of Formula I

| Compound ID | Structure |
|---|---|
| 510 | 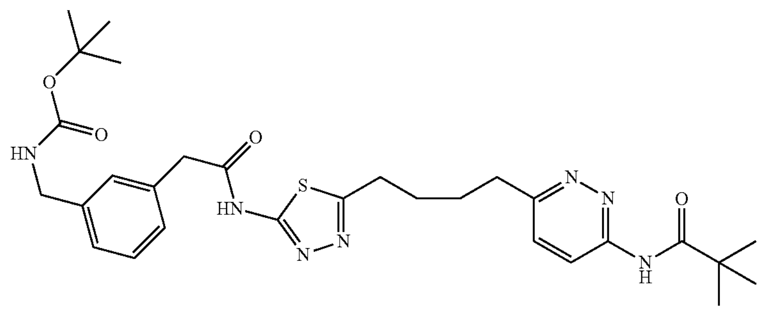 [SMILES: CC(C)(C)OC(=O)NCc1cccc(CC(=O)Nc2nnc(CCCCc3ccc(NC(=O)C(C)(C)C)nn3)s2)c1] |
| 511 | 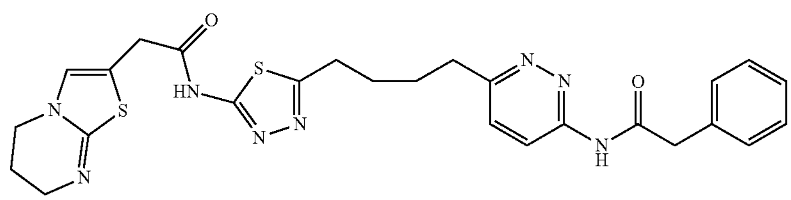 [SMILES: O=C(Cc1ccccc1)Nc1ccc(CCCCc2nnc(NC(=O)CC3=CN4CCCN=C4S3)s2)nn1] |
| 512 | 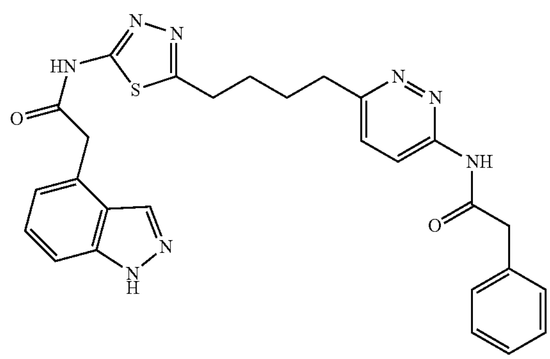 [SMILES: O=C(Cc1ccccc1)Nc1ccc(CCCCc2nnc(NC(=O)Cc3cccc4[nH]ncc34)s2)nn1] |
| 513 | 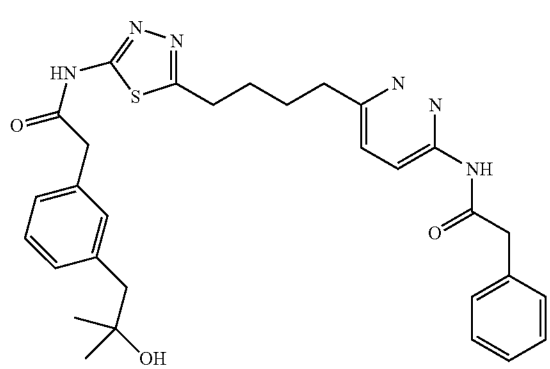 [SMILES: CC(C)(O)Cc1cccc(CC(=O)Nc2nnc(CCCC/C(N)=C/C=C(\N)NC(=O)Cc3ccccc3)s2)c1] |

US 10,441,587 B2
241                                                                                         242
TABLE 1-continued
Selected Compounds of Formula I
| Compound ID | Structure |
|---|---|
| 514 | 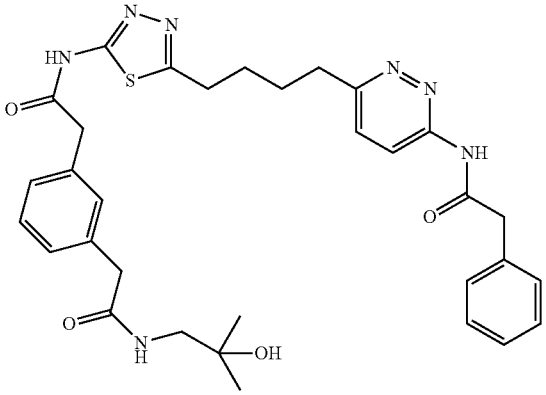 [SMILES: CC(C)(O)CNC(=O)Cc1cccc(CC(=O)Nc2nnc(CCCCc3ccc(NC(=O)Cc4ccccc4)nn3)s2)c1] |
| 515 | 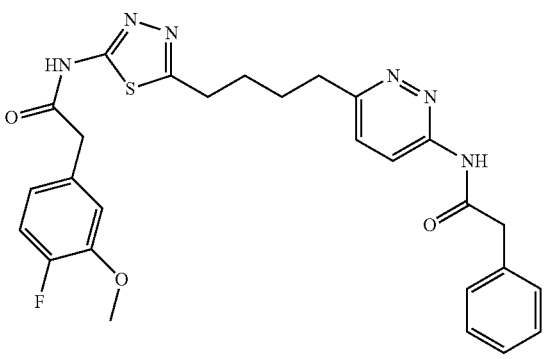 [SMILES: COc1cc(CC(=O)Nc2nnc(CCCCc3ccc(NC(=O)Cc4ccccc4)nn3)s2)ccc1F] |
| 516 | 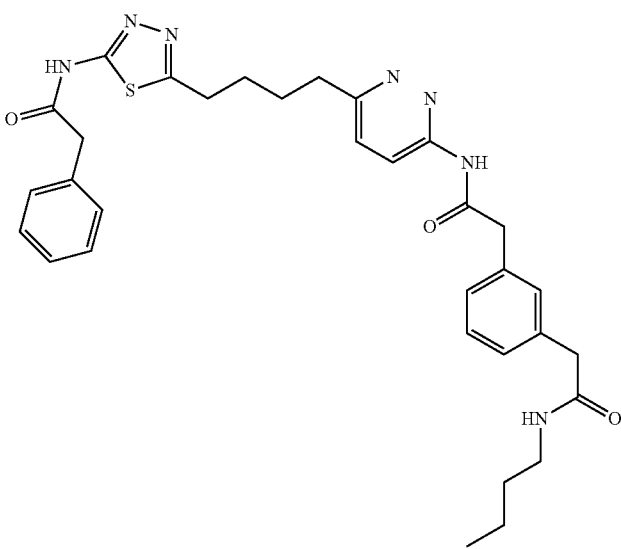 [SMILES: CCCCNC(=O)Cc1cccc(CC(=O)N/C(N)=C/C=C(\N)CCCCc2nnc(NC(=O)Cc3ccccc3)s2)c1] |

TABLE 1-continued
Selected Compounds of Formula I
| Compound ID | Structure |
|---|---|
| 517 | 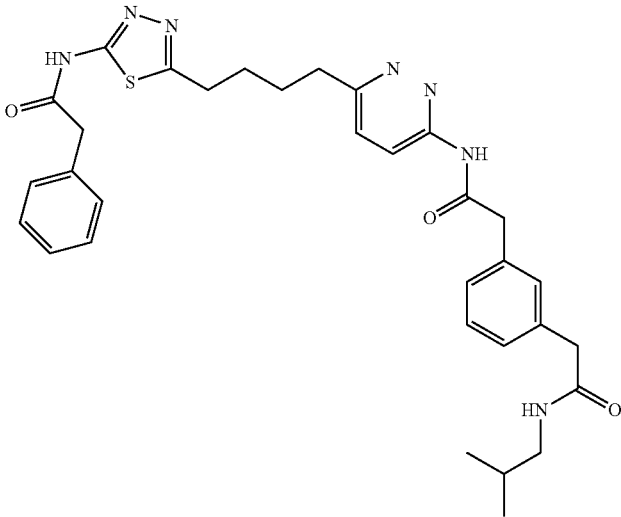 [SMILES: CC(C)CNC(=O)Cc1cccc(CC(=O)N/C(N)=C/C=C(\N)CCCCc2nnc(NC(=O)Cc3ccccc3)s2)c1] |
| 518 | 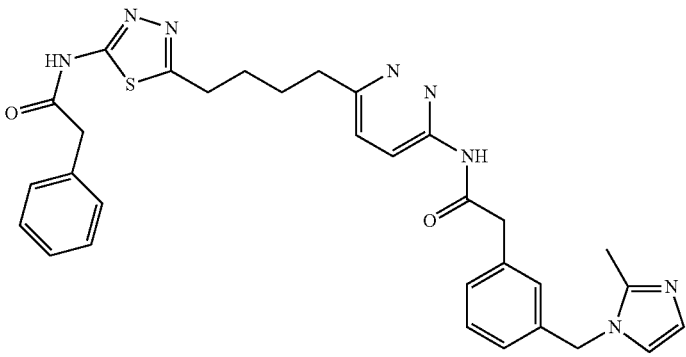 [SMILES: Cc1nccn1Cc1cccc(CC(=O)N/C(N)=C/C=C(\N)CCCCc2nnc(NC(=O)Cc3ccccc3)s2)c1] |
| 519 | 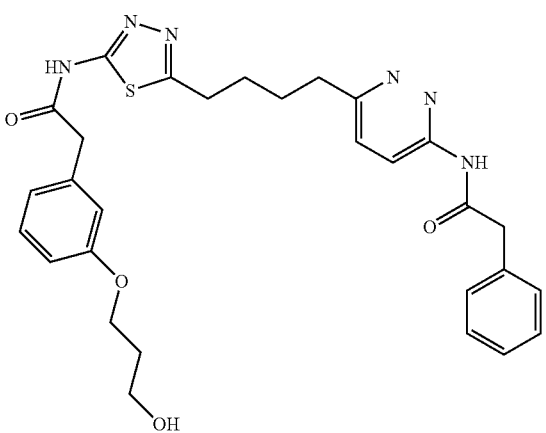 [SMILES: N/C(=C\C=C(/N)NC(=O)Cc1ccccc1)CCCCc1nnc(NC(=O)Cc2cccc(OCCCO)c2)s1] |
| 520 | 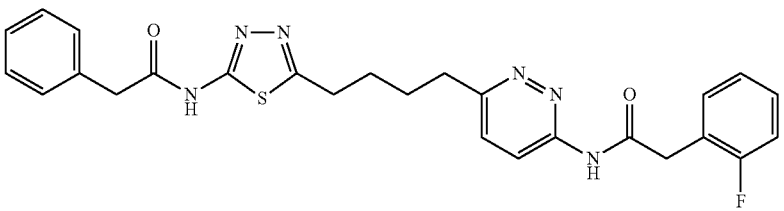 |

TABLE 1-continued

Selected Compounds of Formula I

| Compound ID | Structure |
|---|---|
| 521 | 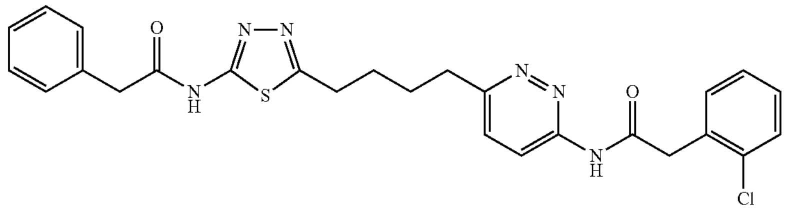 [SMILES: O=C(Cc1ccccc1F)Nc1ccc(CCCCc2nnc(NC(=O)Cc3ccccc3)s2)nn1] |
| 522 | 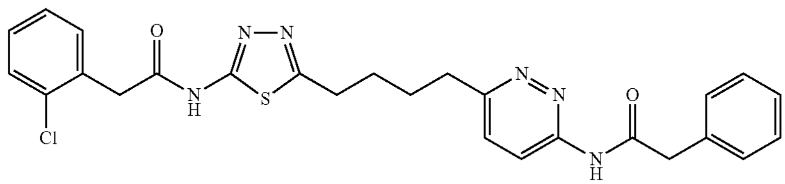 |
| 523 | 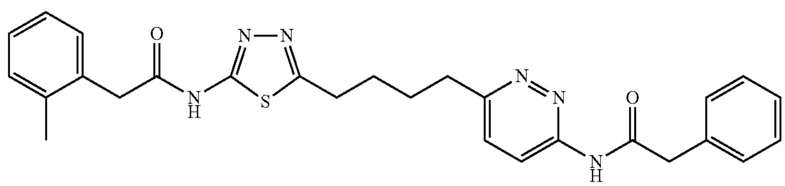 |
| 524 | 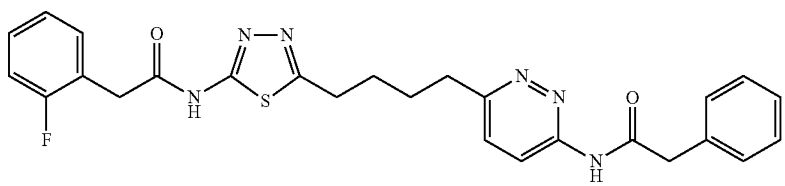 [SMILES: Cc1ccccc1CC(=O)Nc1nnc(CCCCc2ccc(NC(=O)Cc3ccccc3)nn2)s1] |
| 525 | 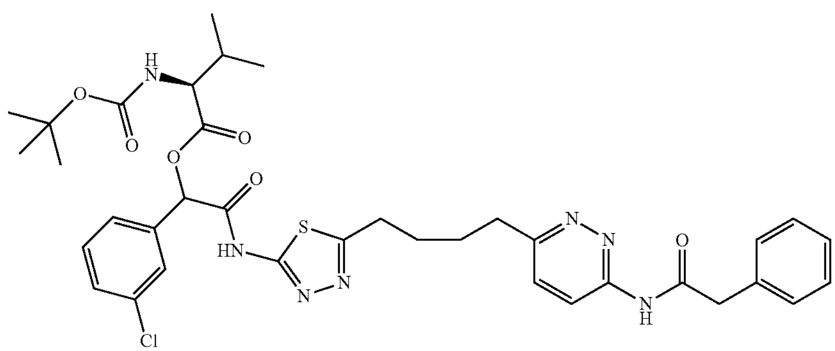 [SMILES: CC(C)[C@H](NC(=O)OC(C)(C)C)C(=O)OC(C(=O)Nc1nnc(CCCCc2ccc(NC(=O)Cc3ccccc3)nn2)s1)c1cccc(Cl)c1] |
| 526 | 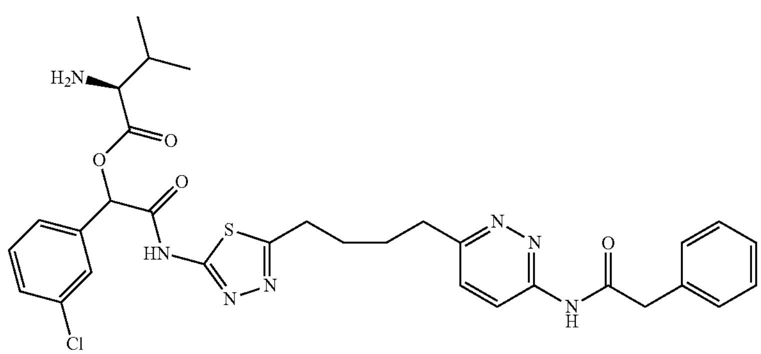 [SMILES: CC(C)[C@H](N)C(=O)OC(C(=O)Nc1nnc(CCCCc2ccc(NC(=O)Cc3ccccc3)nn2)s1)c1cccc(Cl)c1] |

TABLE 1-continued
Selected Compounds of Formula I
| Compound ID | Structure |
|---|---|
| 528 | 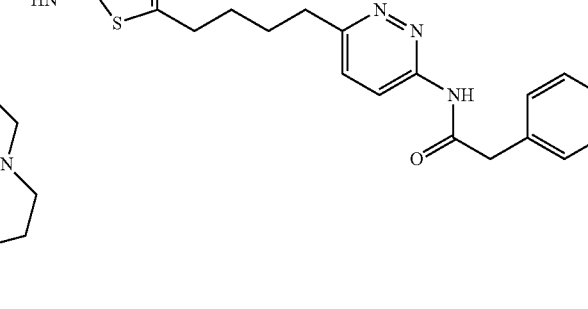 |
| 529 | 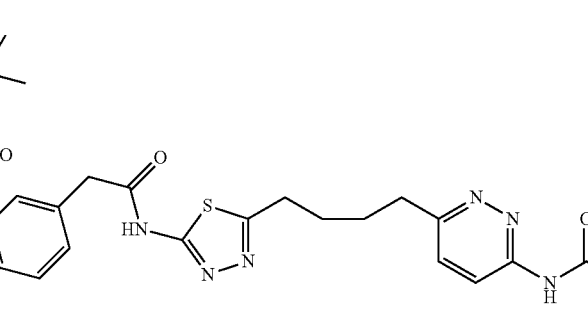 |
| 530 | 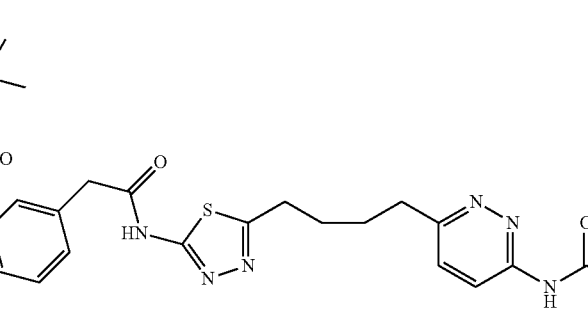 |
| 531 | 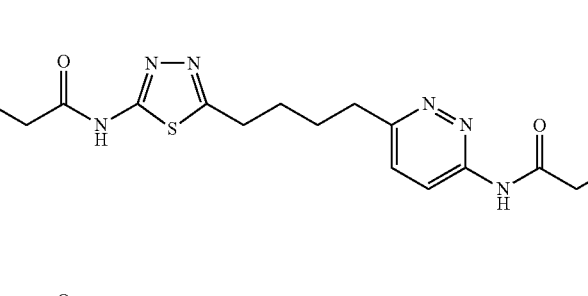 |
| 532 | 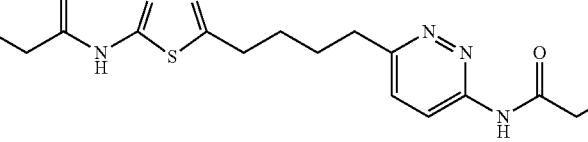 |

TABLE 1-continued
Selected Compounds of Formula I
| Compound ID | Structure |
|---|---|
| 533 | 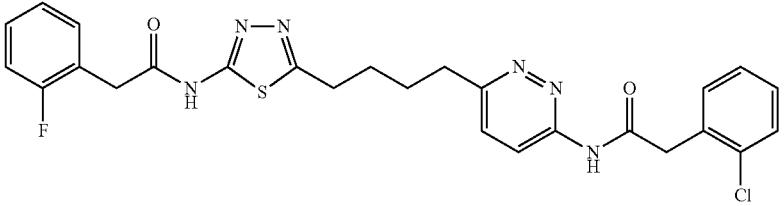 [SMILES: O=C(Cc1ccccc1Cl)Nc1ccc(CCCCc2nnc(NC(=O)Cc3ccccc3F)s2)nn1] |
| 534 | 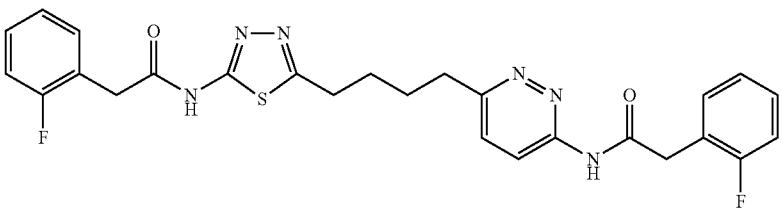 [SMILES: O=C(Cc1ccccc1F)Nc1ccc(CCCCc2nnc(NC(=O)Cc3ccccc3F)s2)nn1] |
| 535 | 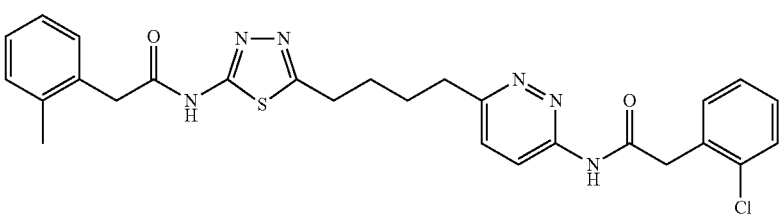 [SMILES: Cc1ccccc1CC(=O)Nc1nnc(CCCCc2ccc(NC(=O)Cc3ccccc3Cl)nn2)s1] |
| 536 | 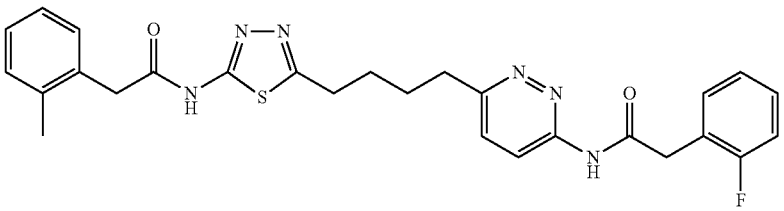 [SMILES: Cc1ccccc1CC(=O)Nc1nnc(CCCCc2ccc(NC(=O)Cc3ccccc3F)nn2)s1] |
| 537 | 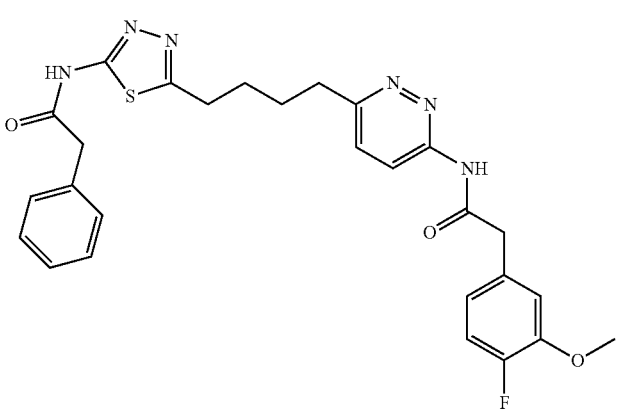 [SMILES: COc1cc(CC(=O)Nc2ccc(CCCCc3nnc(NC(=O)Cc4ccccc4)s3)nn2)ccc1F] |

TABLE 1-continued

Selected Compounds of Formula I

| Compound ID | Structure |
|---|---|
| 538 | 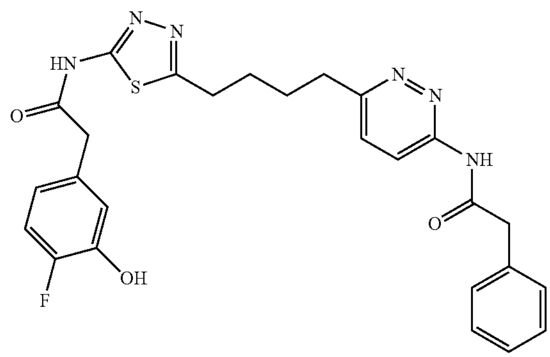 [SMILES: O=C(Cc1ccccc1)Nc1ccc(CCCCc2nnc(NC(=O)Cc3ccc(F)c(O)c3)s2)nn1] |
| 539 | 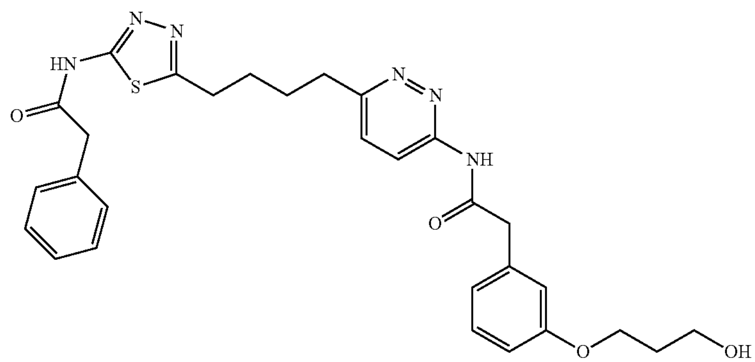 [SMILES: O=C(Cc1cccc(OCCCO)c1)Nc1ccc(CCCCc2nnc(NC(=O)Cc3ccccc3)s2)nn1] |
| 540 | 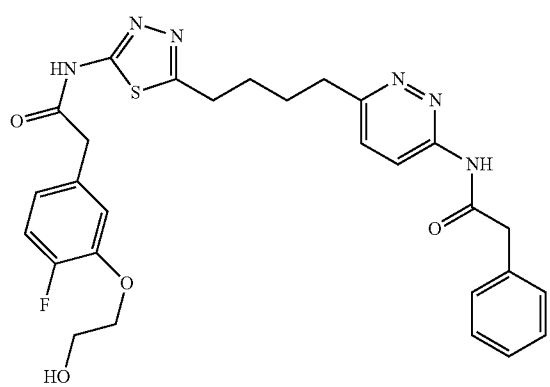 [SMILES: O=C(Cc1ccccc1)Nc1ccc(CCCCc2nnc(NC(=O)Cc3ccc(F)c(OCCO)c3)s2)nn1] |
| 541 | 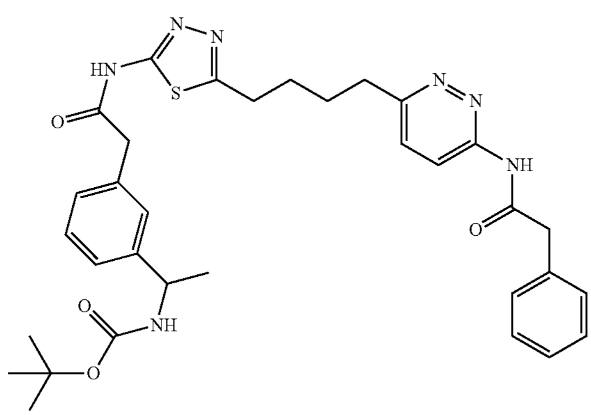 [SMILES: CC(NC(=O)OC(C)(C)C)c1cccc(CC(=O)Nc2nnc(CCCCc3ccc(NC(=O)Cc4ccccc4)nn3)s2)c1] |

TABLE 1-continued
Selected Compounds of Formula I
| Compound ID | Structure |
|---|---|
| 542 | 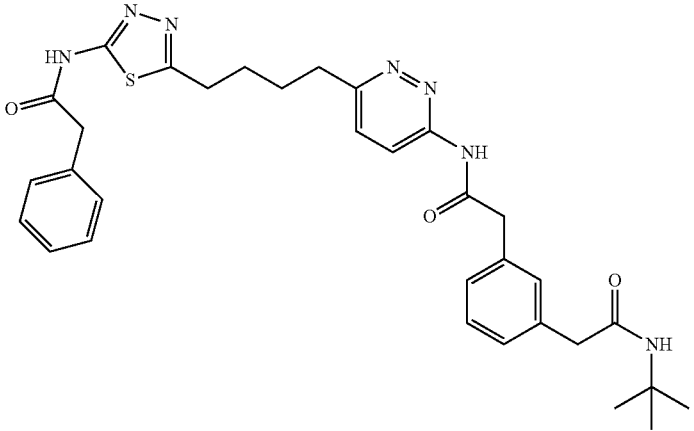 [SMILES: CC(C)(C)NC(=O)Cc1cccc(CC(=O)Nc2ccc(CCCCc3nnc(NC(=O)Cc4ccccc4)s3)nn2)c1] |
| 543 | 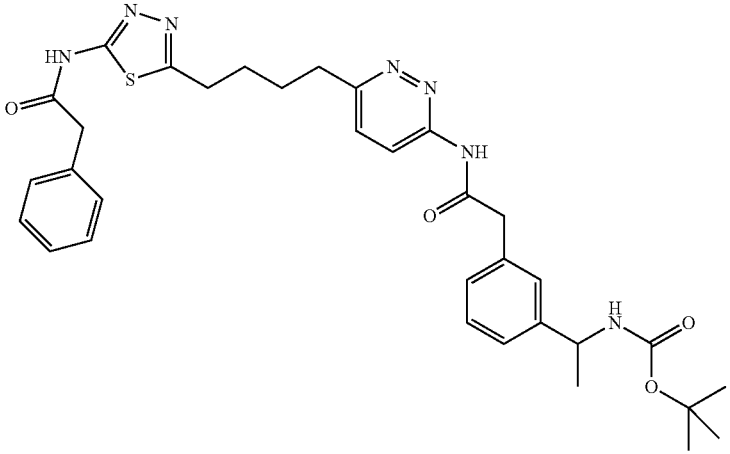 [SMILES: CC(NC(=O)OC(C)(C)C)c1cccc(CC(=O)Nc2ccc(CCCCc3nnc(NC(=O)Cc4ccccc4)s3)nn2)c1] |
| 544 | 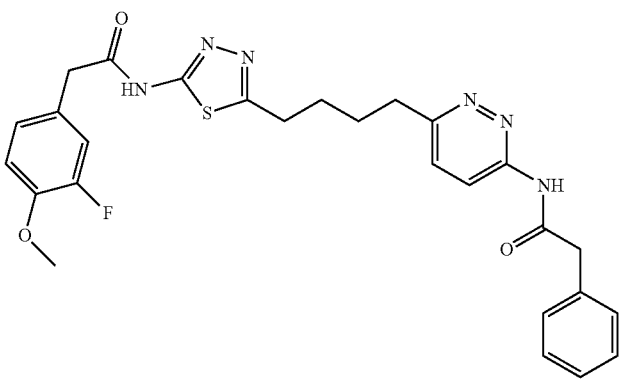 [SMILES: COc1ccc(CC(=O)Nc2nnc(CCCCc3ccc(NC(=O)Cc4ccccc4)nn3)s2)cc1F] |

TABLE 1-continued
Selected Compounds of Formula I
| Compound ID | Structure |
|---|---|
| 545 | 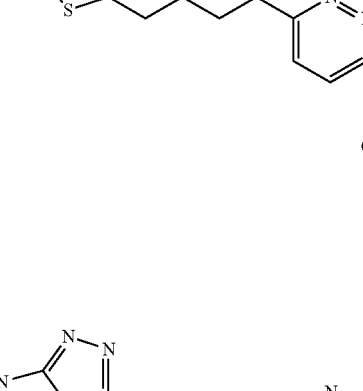 |
| 546 | 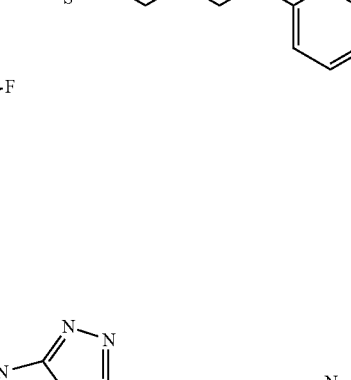 |
| 547 | 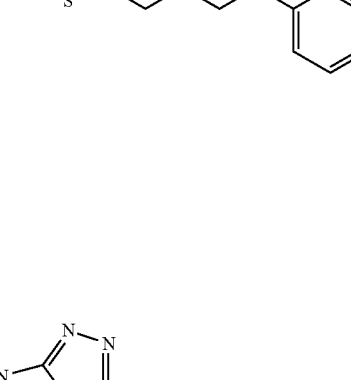 |
| 548 | 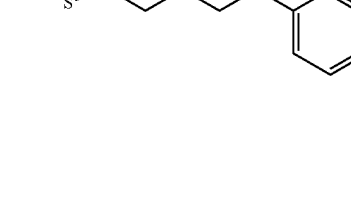 |

TABLE 1-continued

Selected Compounds of Formula I

| Compound ID | Structure |
|---|---|
| 549 | 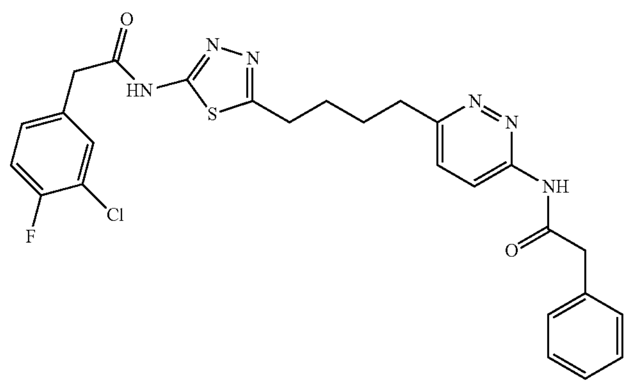 [SMILES: O=C(Cc1ccccc1)Nc1ccc(CCCCc2nnc(NC(=O)Cc3ccc(F)c(Cl)c3)s2)nn1] |
| 550 | 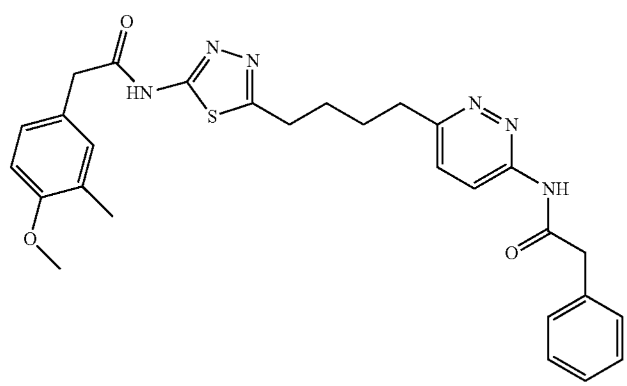 [SMILES: COc1ccc(CC(=O)Nc2nnc(CCCCc3ccc(NC(=O)Cc4ccccc4)nn3)s2)cc1C] |
| 551 | 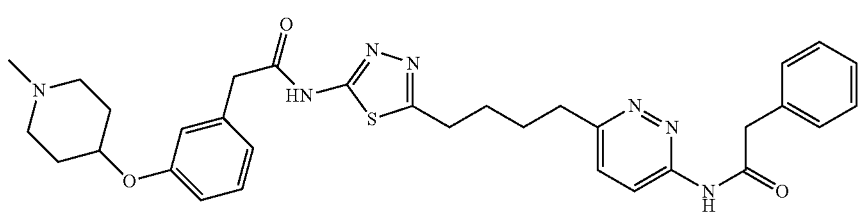 [SMILES: CN1CCC(Oc2cccc(CC(=O)Nc3nnc(CCCCc4ccc(NC(=O)Cc5ccccc5)nn4)s3)c2)CC1] |
| 552 | 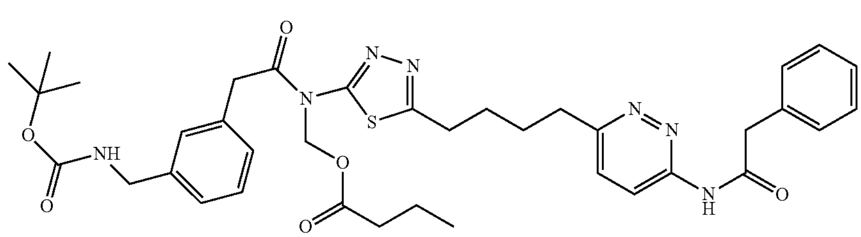 [SMILES: CCCC(=O)OCN(C(=O)Cc1cccc(CNC(=O)OC(C)(C)C)c1)c1nnc(CCCCc2ccc(NC(=O)Cc3ccccc3)nn2)s1] |

TABLE 1-continued

Selected Compounds of Formula I

| Compound ID | Structure |
|---|---|
| 553 | 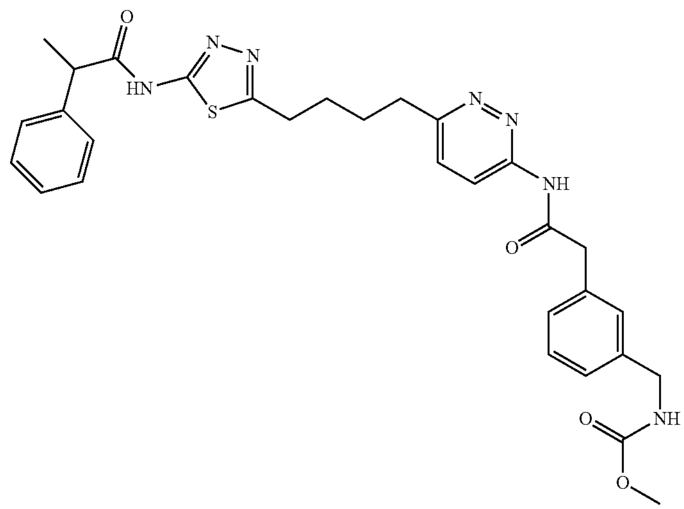 [SMILES: COC(=O)NCc1cccc(CC(=O)Nc2ccc(CCCCc3nnc(NC(=O)C(C)c4ccccc4)s3)nn2)c1] |
| 554 | 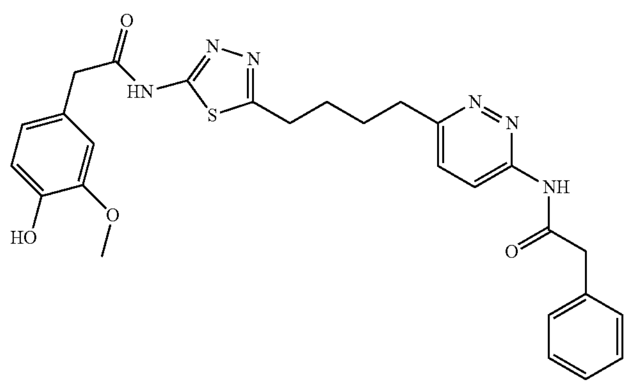 [SMILES: COc1cc(CC(=O)Nc2nnc(CCCCc3ccc(NC(=O)Cc4ccccc4)nn3)s2)ccc1O] |
| 555 | 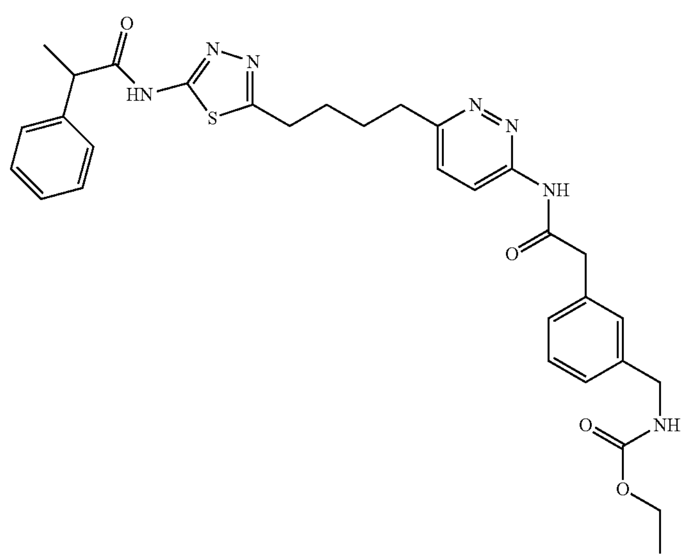 [SMILES: CCOC(=O)NCc1cccc(CC(=O)Nc2ccc(CCCCc3nnc(NC(=O)C(C)c4ccccc4)s3)nn2)c1] |

TABLE 1-continued

Selected Compounds of Formula I

| Compound ID | Structure |
|---|---|
| 556 | 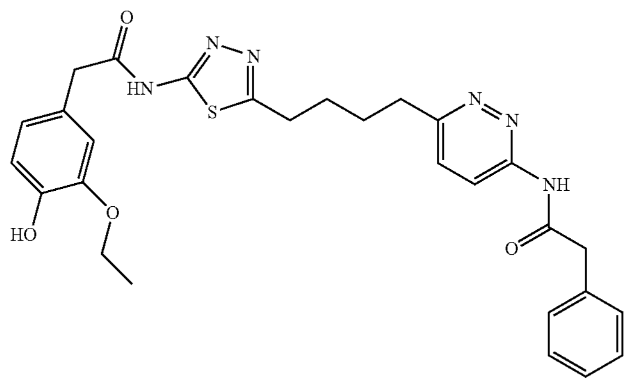 [SMILES: CCOc1cc(CC(=O)Nc2nnc(CCCCc3ccc(NC(=O)Cc4ccccc4)nn3)s2)ccc1O] |
| 557 | 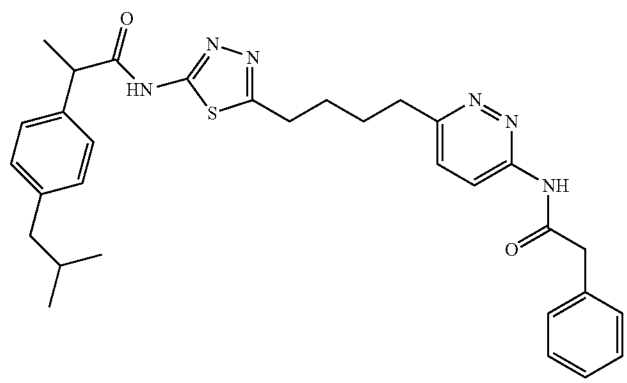 [SMILES: CC(C)Cc1ccc(C(C)C(=O)Nc2nnc(CCCCc3ccc(NC(=O)Cc4ccccc4)nn3)s2)cc1] |
| 558 | 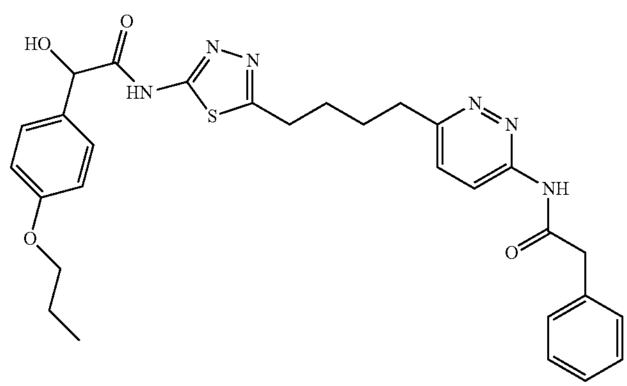 [SMILES: CCCOc1ccc(C(O)C(=O)Nc2nnc(CCCCc3ccc(NC(=O)Cc4ccccc4)nn3)s2)cc1] |
| 559 | 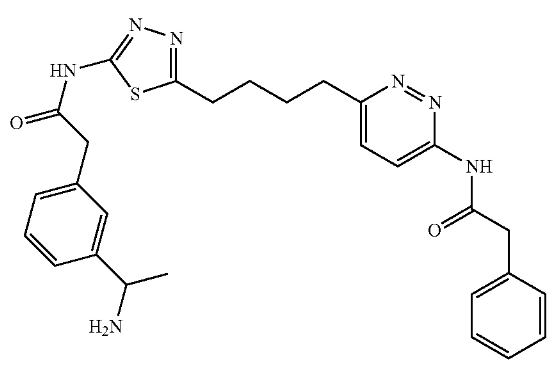 [SMILES: CC(N)c1cccc(CC(=O)Nc2nnc(CCCCc3ccc(NC(=O)Cc4ccccc4)nn3)s2)c1] |

TABLE 1-continued

Selected Compounds of Formula I

| Compound ID | Structure |
|---|---|
| 560 | 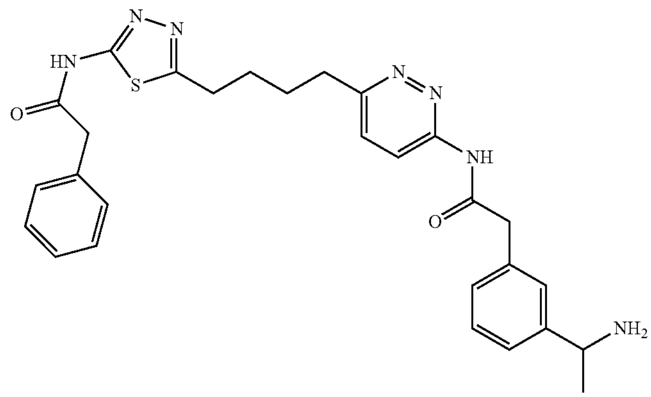 [SMILES: CC(N)c1cccc(CC(=O)Nc2ccc(CCCCc3nnc(NC(=O)Cc4ccccc4)s3)nn2)c1] |
| 561 | 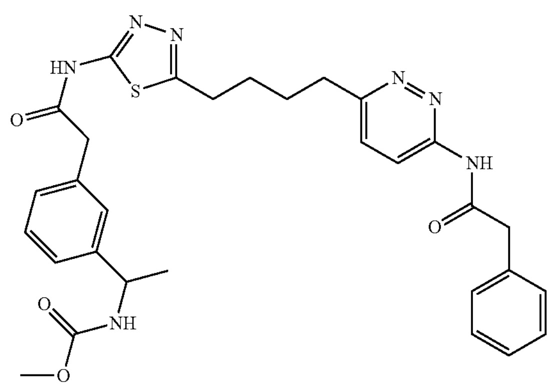 [SMILES: COC(=O)NC(C)c1cccc(CC(=O)Nc2nnc(CCCCc3ccc(NC(=O)Cc4ccccc4)nn3)s2)c1] |
| 562 | 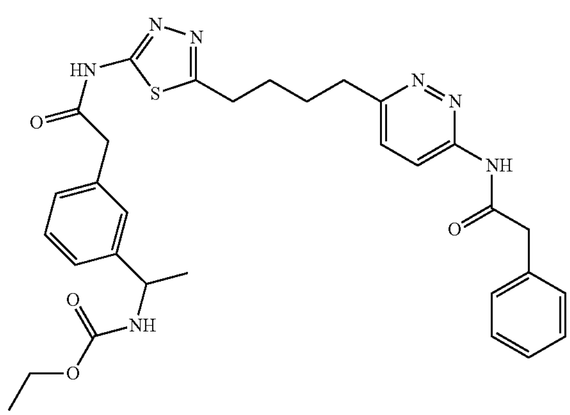 [SMILES: CCOC(=O)NC(C)c1cccc(CC(=O)Nc2nnc(CCCCc3ccc(NC(=O)Cc4ccccc4)nn3)s2)c1] |

TABLE 1-continued

Selected Compounds of Formula I

| Compound ID | Structure |
|---|---|
| 563 | 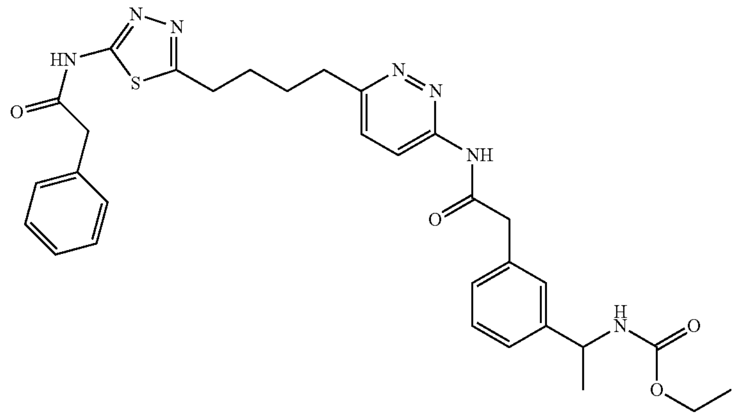 [SMILES: CCOC(=O)NC(C)c1cccc(CC(=O)Nc2ccc(CCCCc3nnc(NC(=O)Cc4ccccc4)s3)nn2)c1] |
| 564 | 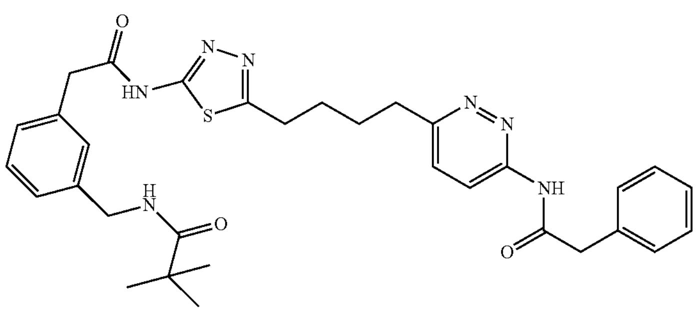 [SMILES: CC(C)(C)C(=O)NCc1cccc(CC(=O)Nc2nnc(CCCCc3ccc(NC(=O)Cc4ccccc4)nn3)s2)c1] |
| 565 | 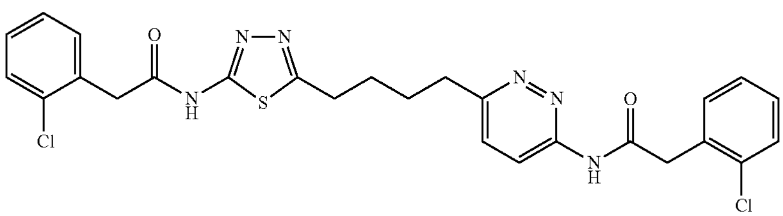 |
| 566 | 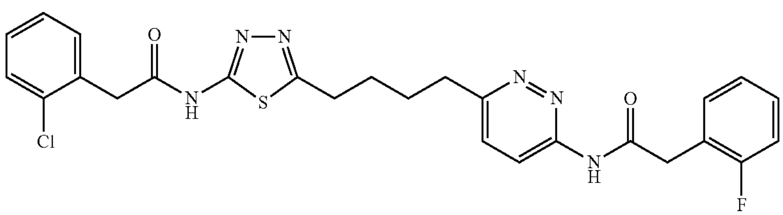 [SMILES: O=C(Cc1ccccc1F)Nc1ccc(CCCCc2nnc(NC(=O)Cc3ccccc3Cl)s2)nn1] |
| 567 | 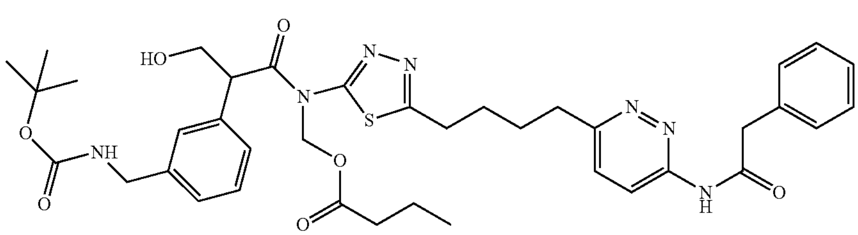 [SMILES: CCCC(=O)OCN(C(=O)C(CO)c1cccc(CNC(=O)OC(C)(C)C)c1)c1nnc(CCCCc2ccc(NC(=O)Cc3ccccc3)nn2)s1] |

TABLE 1-continued
Selected Compounds of Formula I
| Compound ID | Structure |
|---|---|
| 568 | 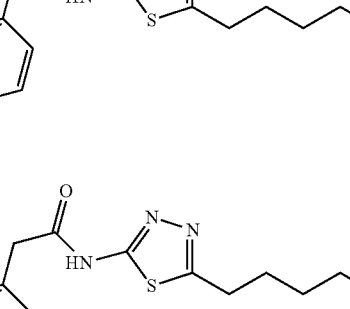 |
| 569 | 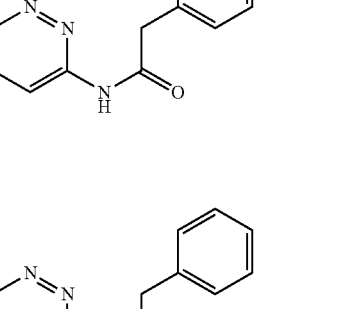 |
| 570 | 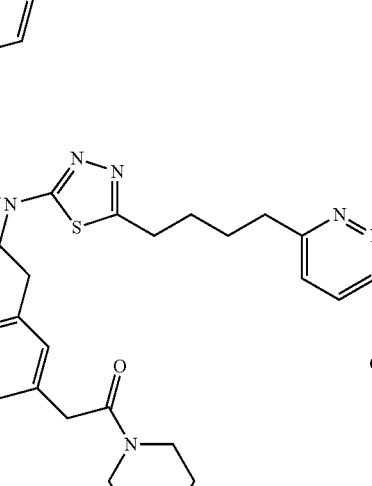 |
| 571 | 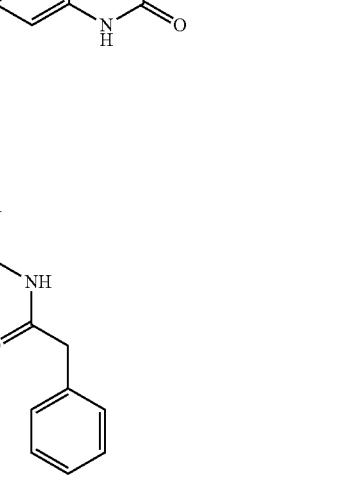 |
| 572 | 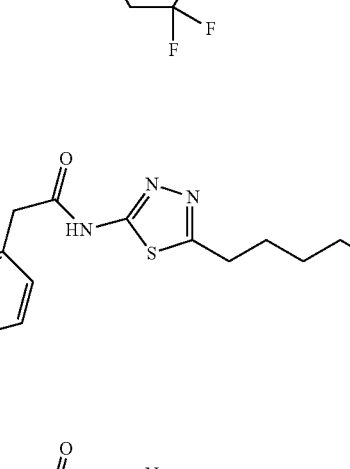 |

TABLE 1-continued
Selected Compounds of Formula I
| Compound ID | Structure |
|---|---|
| 573 | 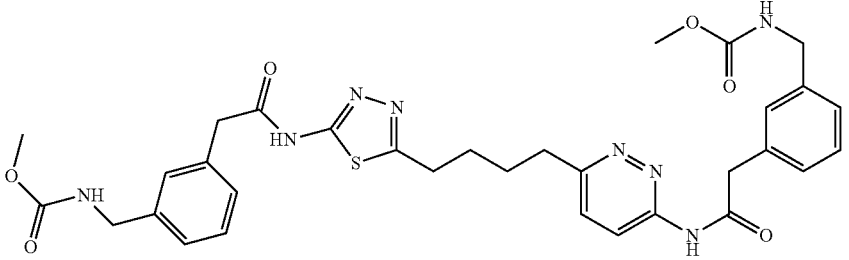 [SMILES: COC(=O)NCc1cccc(CC(=O)Nc2ccc(CCCCc3nnc(NC(=O)Cc4cccc(CNC(=O)OC)c4)s3)nn2)c1] |
| 574 | 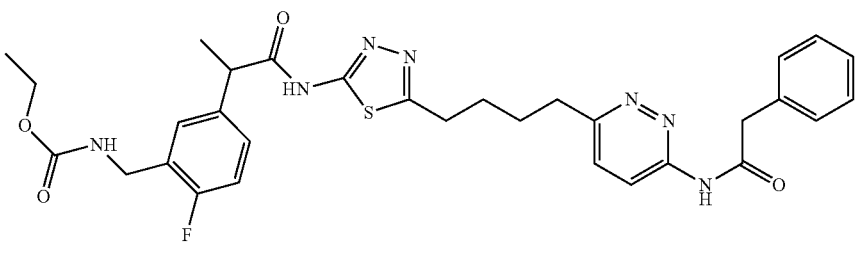 [SMILES: CCOC(=O)NCc1cc(C(C)C(=O)Nc2nnc(CCCCc3ccc(NC(=O)Cc4ccccc4)nn3)s2)ccc1F] |
| 575 | 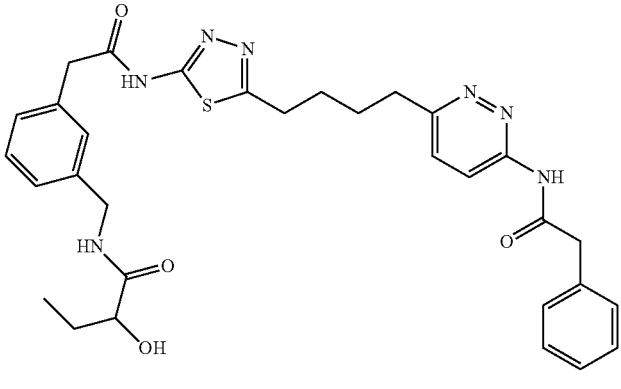 [SMILES: CCC(O)C(=O)NCc1cccc(CC(=O)Nc2nnc(CCCCc3ccc(NC(=O)Cc4ccccc4)nn3)s2)c1] |
| 576 | 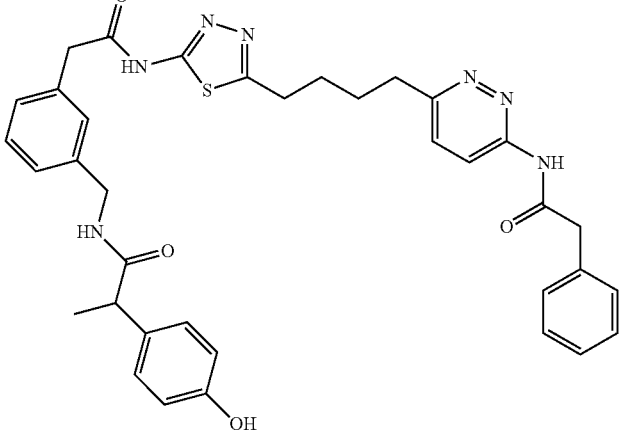 |

TABLE 1-continued

Selected Compounds of Formula I

| Compound ID | Structure |
|---|---|
| 577 | 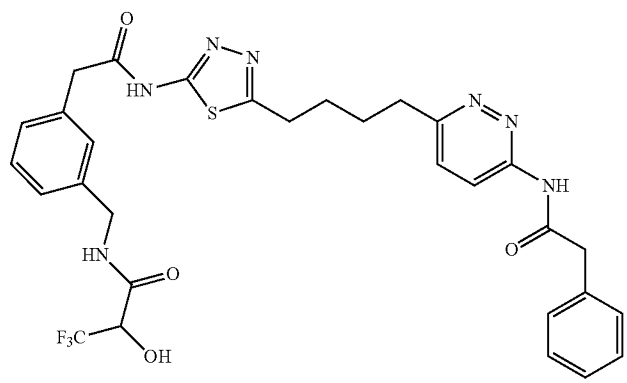 [SMILES: O=C(Cc1ccccc1)Nc1ccc(CCCCc2nnc(NC(=O)Cc3cccc(CNC(=O)C(O)C(F)(F)F)c3)s2)nn1] |
| 578 | 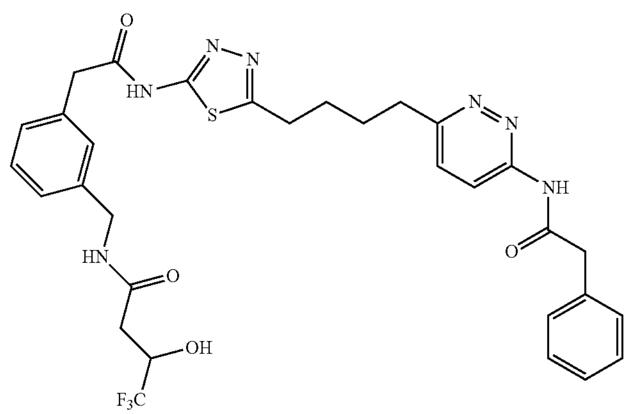 [SMILES: O=C(CC(O)C(F)(F)F)NCc1cccc(CC(=O)Nc2nnc(CCCCc3ccc(NC(=O)Cc4ccccc4)nn3)s2)c1] |
| 579 | 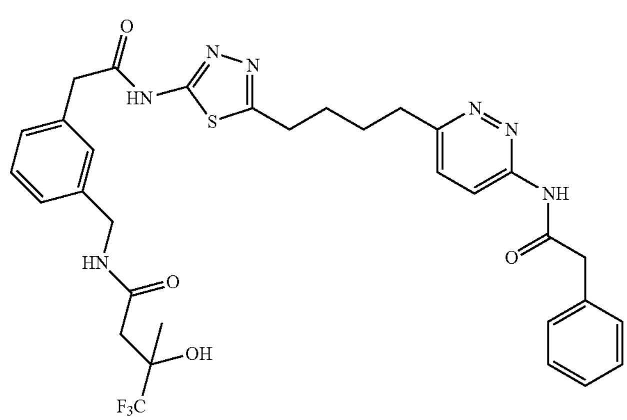 [SMILES: CC(O)(CC(=O)NCc1cccc(CC(=O)Nc2nnc(CCCCc3ccc(NC(=O)Cc4ccccc4)nn3)s2)c1)C(F)(F)F] |

TABLE 1-continued

Selected Compounds of Formula I

| Compound ID | Structure |
|---|---|
| 580 | 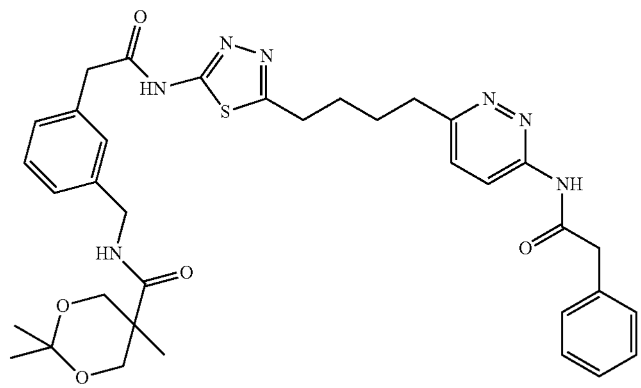 [SMILES: CC1(C)OCC(C)(C(=O)NCc2cccc(CC(=O)Nc3nnc(CCCCc4ccc(NC(=O)Cc5ccccc5)nn4)s3)c2)CO1] |
| 581 | 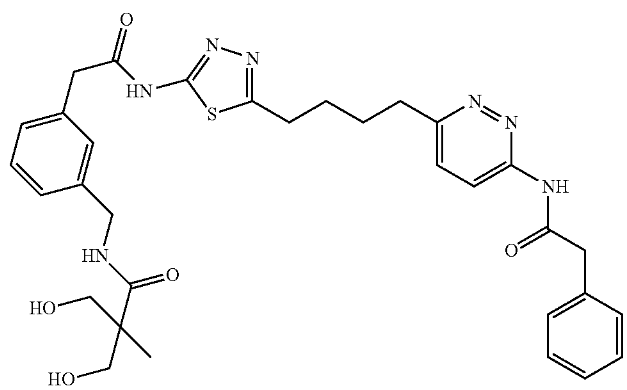 [SMILES: CC(CO)(CO)C(=O)NCc1cccc(CC(=O)Nc2nnc(CCCCc3ccc(NC(=O)Cc4ccccc4)nn3)s2)c1] |
| 582 | 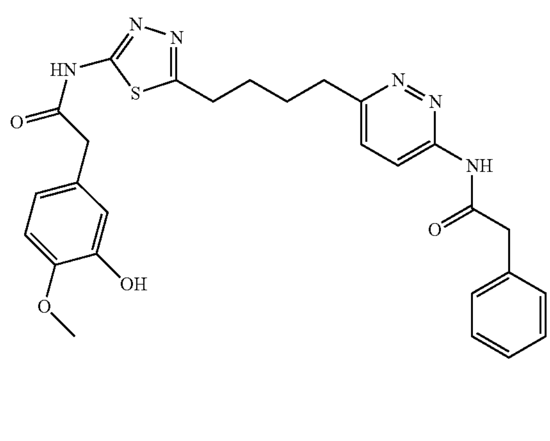 [SMILES: COc1ccc(CC(=O)Nc2nnc(CCCCc3ccc(NC(=O)Cc4ccccc4)nn3)s2)cc1O] |

TABLE 1-continued

Selected Compounds of Formula I

| Compound ID | Structure |
|---|---|
| 583 | 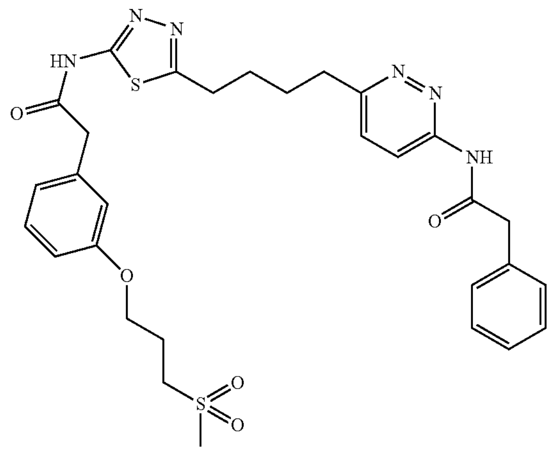 [SMILES: CS(=O)(=O)CCCOc1cccc(CC(=O)Nc2nnc(CCCCc3ccc(NC(=O)Cc4ccccc4)nn3)s2)c1] |
| 584 | 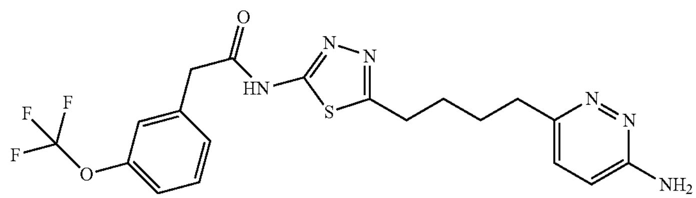 [SMILES: Nc1ccc(CCCCc2nnc(NC(=O)Cc3cccc(OC(F)(F)F)c3)s2)nn1] |
| 585 | 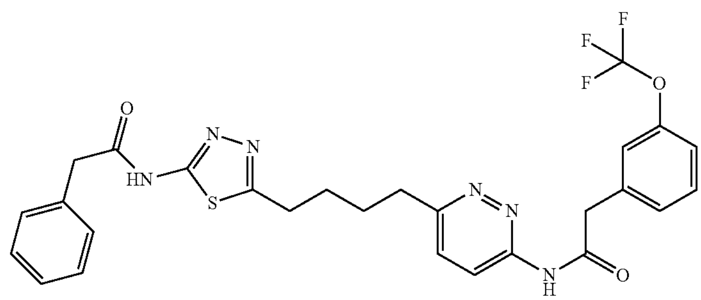 [SMILES: O=C(Cc1cccc(OC(F)(F)F)c1)Nc1ccc(CCCCc2nnc(NC(=O)Cc3ccccc3)s2)nn1] |
| 586 | 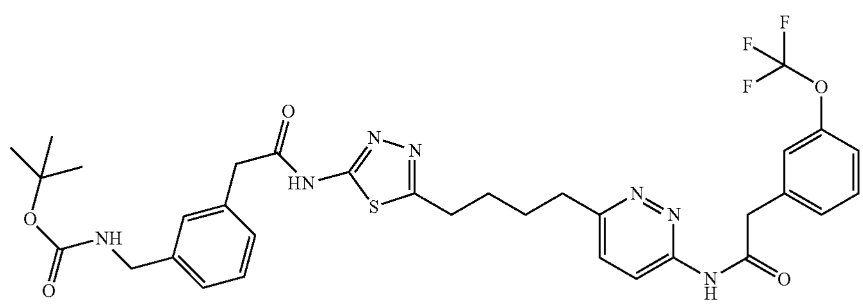 [SMILES: CC(C)(C)OC(=O)NCc1cccc(CC(=O)Nc2nnc(CCCCc3ccc(NC(=O)Cc4cccc(OC(F)(F)F)c4)nn3)s2)c1] |
| 587 | 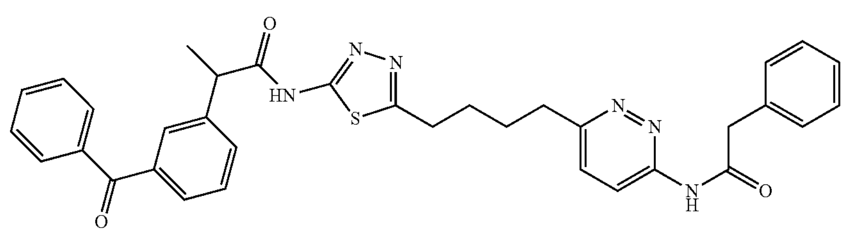 [SMILES: CC(C(=O)Nc1nnc(CCCCc2ccc(NC(=O)Cc3ccccc3)nn2)s1)c1cccc(C(=O)c2ccccc2)c1] |

TABLE 1-continued

Selected Compounds of Formula I

| Compound ID | Structure |
|---|---|
| 588 | 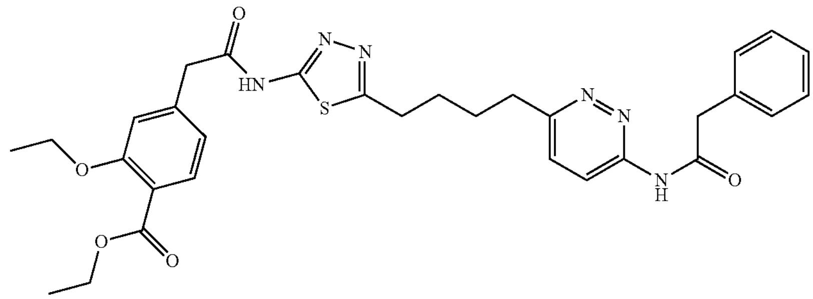 [SMILES: CCOC(=O)c1ccc(CC(=O)Nc2nnc(CCCCc3ccc(NC(=O)Cc4ccccc4)nn3)s2)cc1OCC] |
| 589 | 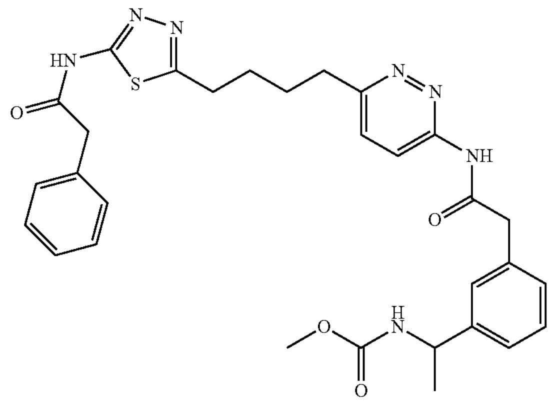 [SMILES: COC(=O)NC(C)c1cccc(CC(=O)Nc2ccc(CCCCc3nnc(NC(=O)Cc4ccccc4)s3)nn2)c1] |
| 590 | 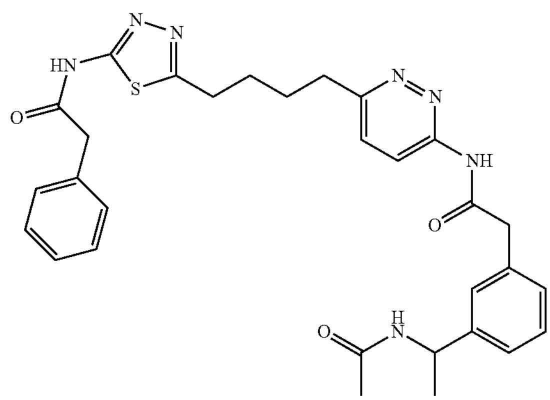 [SMILES: CC(=O)NC(C)c1cccc(CC(=O)Nc2ccc(CCCCc3nnc(NC(=O)Cc4ccccc4)s3)nn2)c1] |
| 591 | 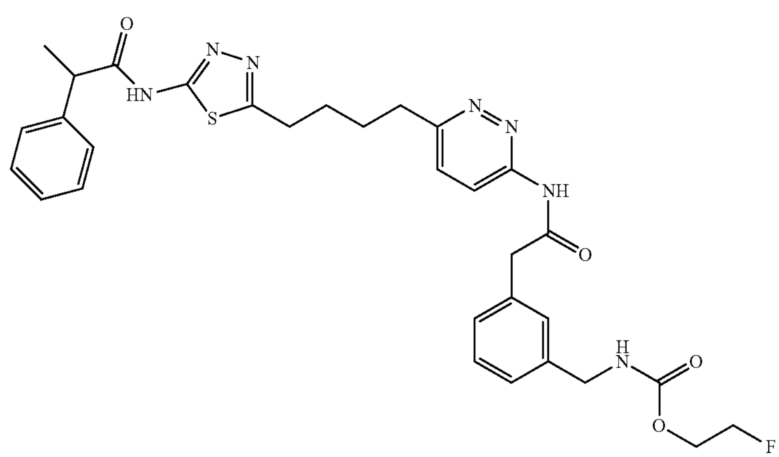 [SMILES: CC(C(=O)Nc1nnc(CCCCc2ccc(NC(=O)Cc3cccc(CNC(=O)OCCF)c3)nn2)s1)c1ccccc1] |

TABLE 1-continued

Selected Compounds of Formula I

| Compound ID | Structure |
|---|---|
| 592 | 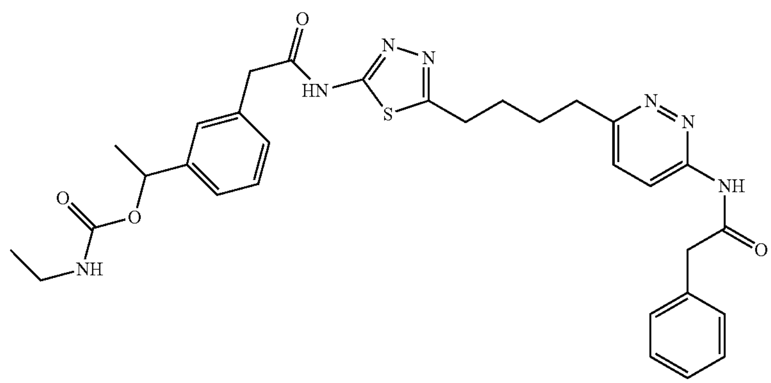 [SMILES: CCNC(=O)OC(C)c1cccc(CC(=O)Nc2nnc(CCCCc3ccc(NC(=O)Cc4ccccc4)nn3)s2)c1] |
| 593 | 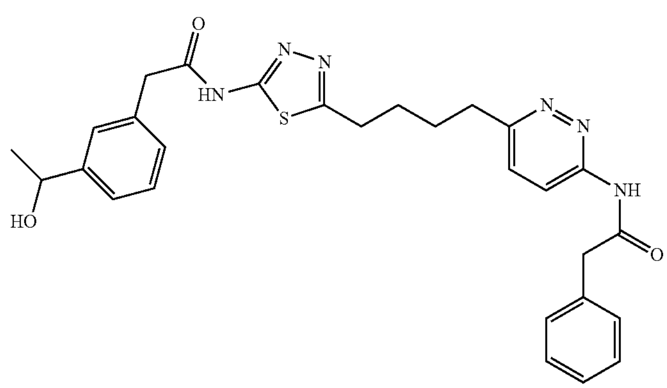 [SMILES: CC(O)c1cccc(CC(=O)Nc2nnc(CCCCc3ccc(NC(=O)Cc4ccccc4)nn3)s2)c1] |
| 594 | 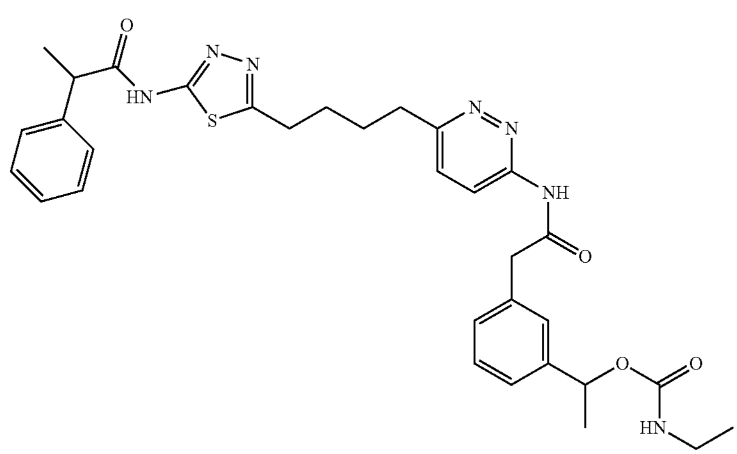 [SMILES: CCNC(=O)OC(C)c1cccc(CC(=O)Nc2ccc(CCCCc3nnc(NC(=O)C(C)c4ccccc4)s3)nn2)c1] |

TABLE 1-continued
Selected Compounds of Formula I
| Compound ID | Structure |
|---|---|
| 595 | 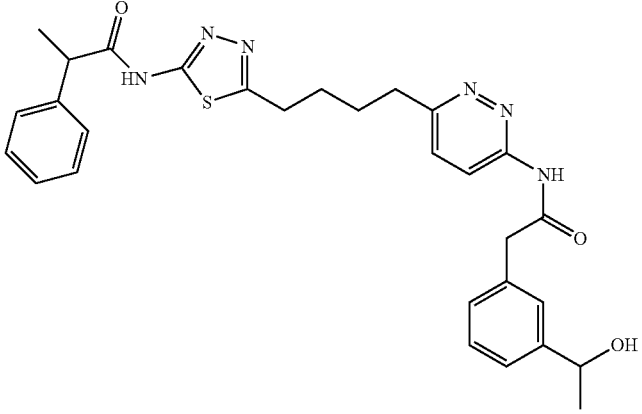 [SMILES: CC(O)c1cccc(CC(=O)Nc2ccc(CCCCc3nnc(NC(=O)C(C)c4ccccc4)s3)nn2)c1] |
| 596 | 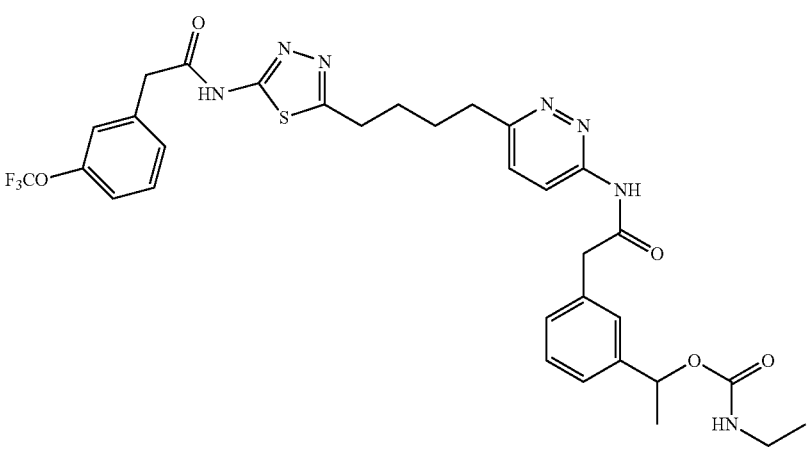 [SMILES: CCNC(=O)OC(C)c1cccc(CC(=O)Nc2ccc(CCCCc3nnc(NC(=O)Cc4cccc(OC(F)(F)F)c4)s3)nn2)c1] |
| 597 | 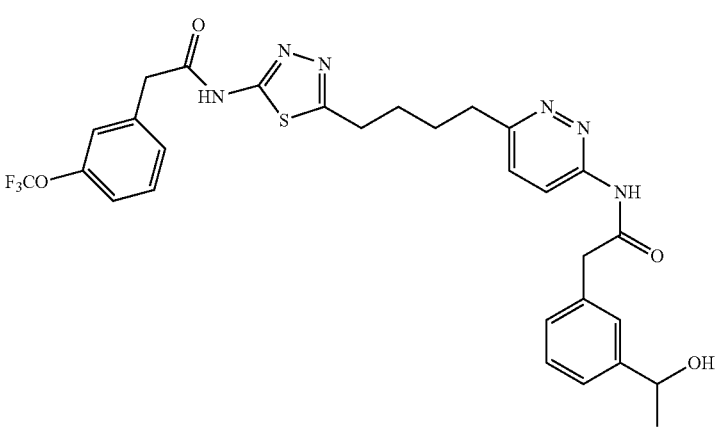 [SMILES: CC(O)c1cccc(CC(=O)Nc2ccc(CCCCc3nnc(NC(=O)Cc4cccc(OC(F)(F)F)c4)s3)nn2)c1] |

TABLE 1-continued
Selected Compounds of Formula I
| Compound ID | Structure |
|---|---|
| 598 | 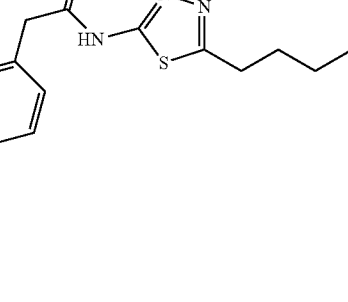 |
| 599 | 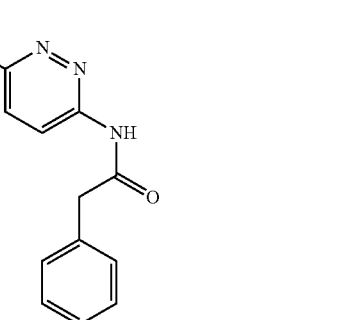 |
| 600 | 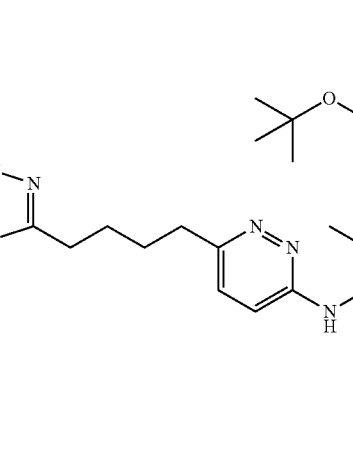 |
| 601 | 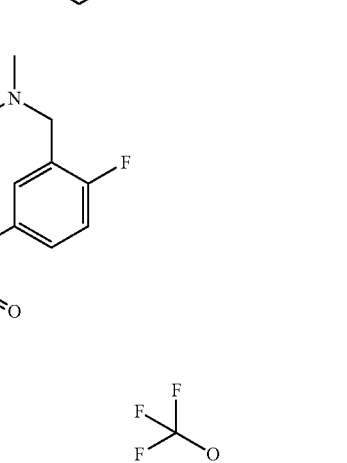 |

TABLE 1-continued
Selected Compounds of Formula I
| Compound ID | Structure |
|---|---|
| 602 | 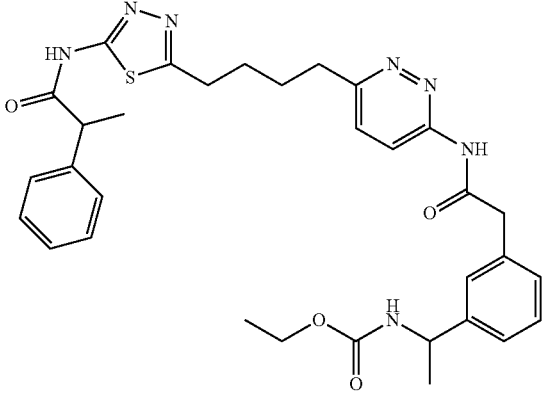 [SMILES: CCOC(=O)NC(C)c1cccc(CC(=O)Nc2ccc(CCCCc3nnc(NC(=O)C(C)c4ccccc4)s3)nn2)c1] |
| 603 | 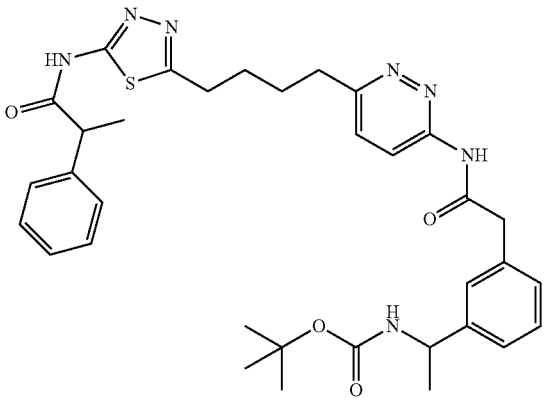 [SMILES: CC(NC(=O)OC(C)(C)C)c1cccc(CC(=O)Nc2ccc(CCCCc3nnc(NC(=O)C(C)c4ccccc4)s3)nn2)c1] |
| 604 | 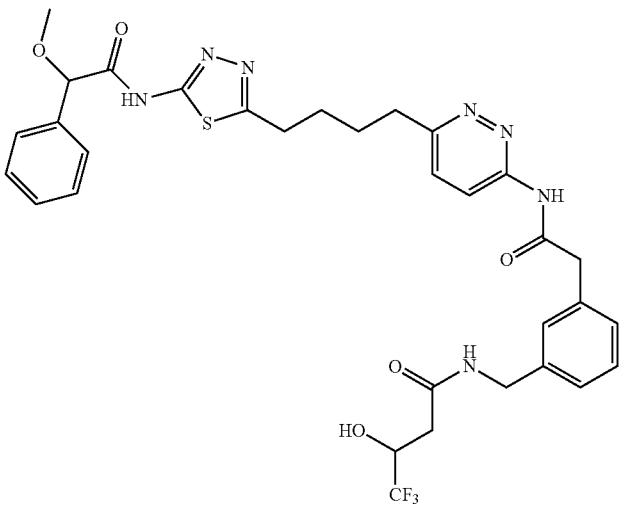 [SMILES: COC(C(=O)Nc1nnc(CCCCc2ccc(NC(=O)Cc3cccc(CNC(=O)CC(O)C(F)(F)F)c3)nn2)s1)c1ccccc1] |

TABLE 1-continued
Selected Compounds of Formula I
| Compound ID | Structure |
|---|---|
| 605 | 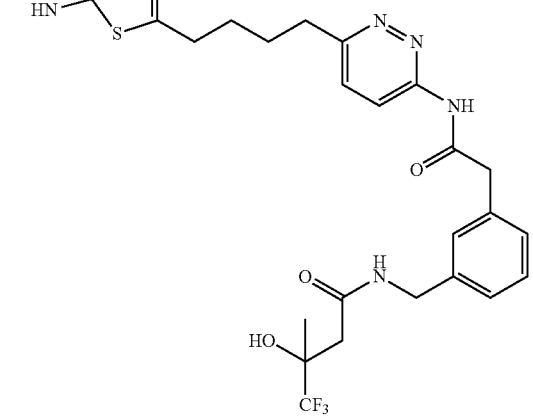 |
| 606 | 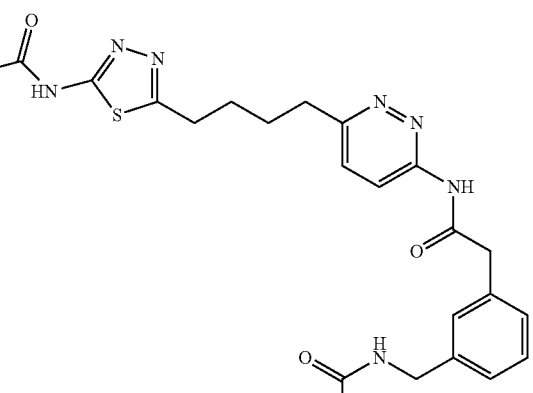 |
| 607 | 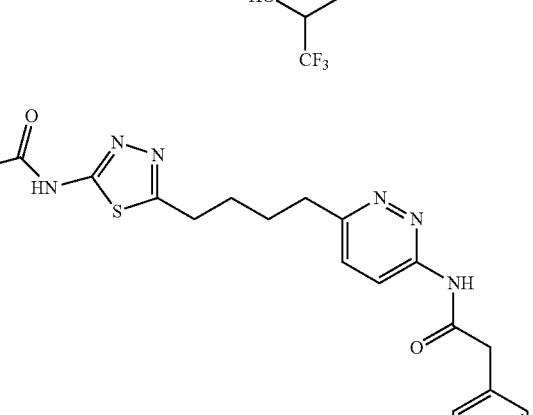 |

TABLE 1-continued
Selected Compounds of Formula I
| Compound ID | Structure |
|---|---|
| 608 | 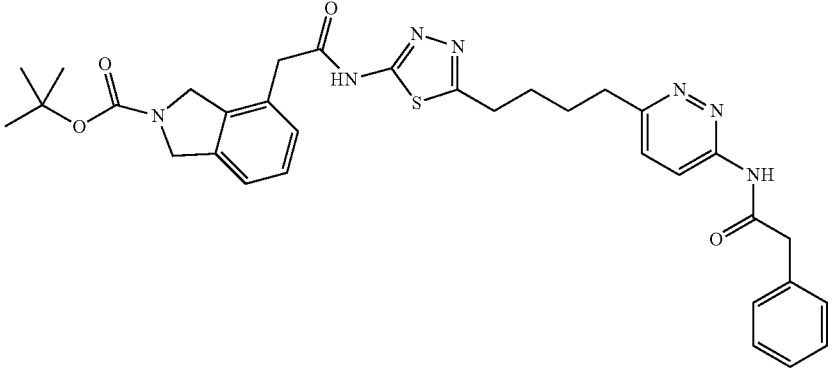 [SMILES: CC(C)(C)OC(=O)N1Cc2cccc(CC(=O)Nc3nnc(CCCCc4ccc(NC(=O)Cc5ccccc5)nn4)s3)c2C1] |
| 609 | 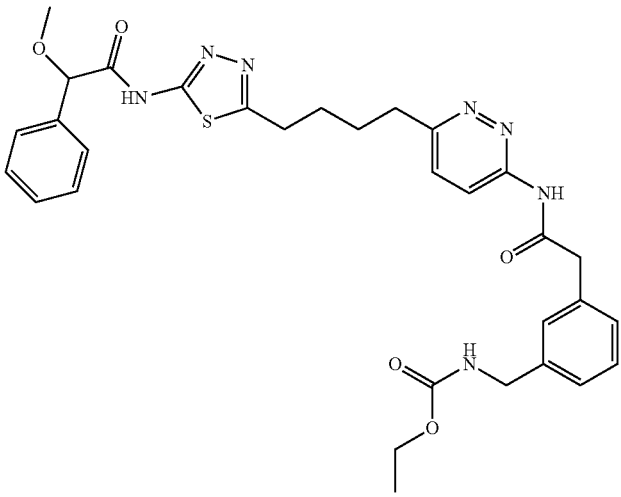 [SMILES: CCOC(=O)NCc1cccc(CC(=O)Nc2ccc(CCCCc3nnc(NC(=O)C(OC)c4ccccc4)s3)nn2)c1] |
| 610 | 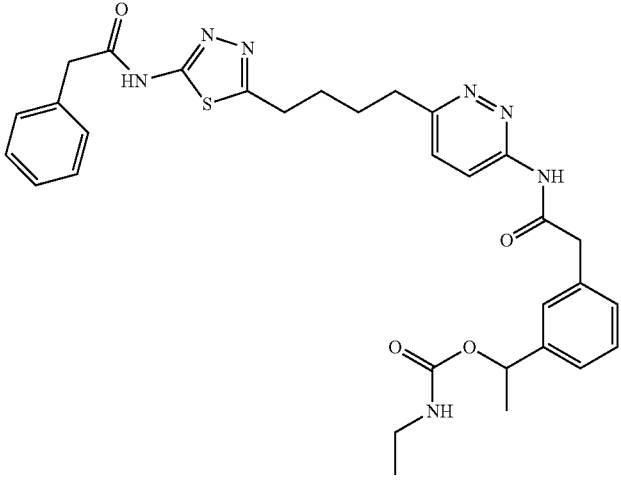 [SMILES: CCNC(=O)OC(C)c1cccc(CC(=O)Nc2ccc(CCCCc3nnc(NC(=O)Cc4ccccc4)s3)nn2)c1] |

TABLE 1-continued
Selected Compounds of Formula I
| Compound ID | Structure |
|---|---|
| 611 | 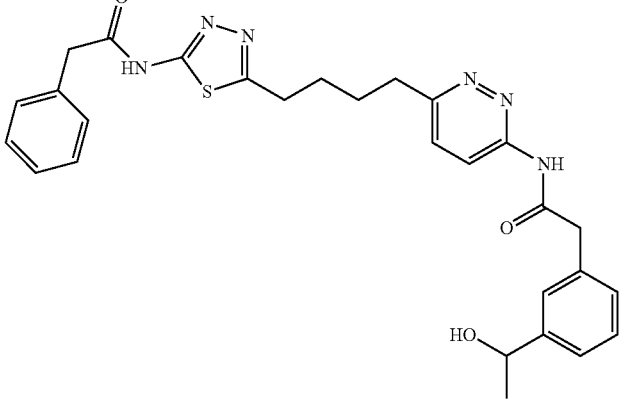 |
| 612 | 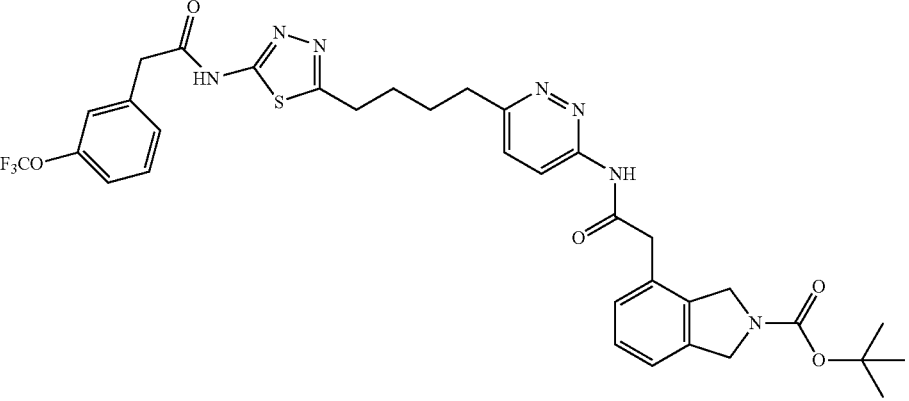 [SMILES: CC(C)(C)OC(=O)N1Cc2cccc(CC(=O)Nc3ccc(CCCCc4nnc(NC(=O)Cc5cccc(OC(F)(F)F)c5)s4)nn3)c2C1] |
| 613 | 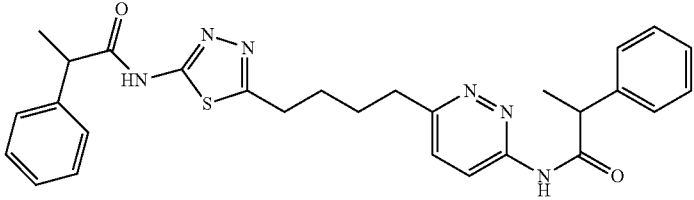 [SMILES: CC(C(=O)Nc1ccc(CCCCc2nnc(NC(=O)C(C)c3ccccc3)s2)nn1)c1ccccc1] |
| 614 | 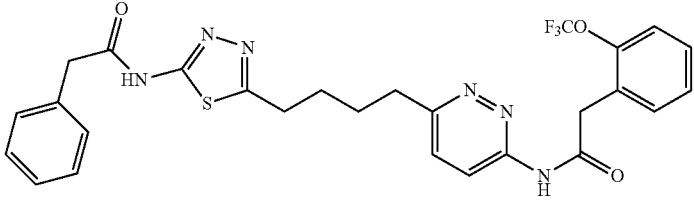 [SMILES: O=C(Cc1ccccc1OC(F)(F)F)Nc1ccc(CCCCc2nnc(NC(=O)Cc3ccccc3)s2)nn1] |
| 615 | 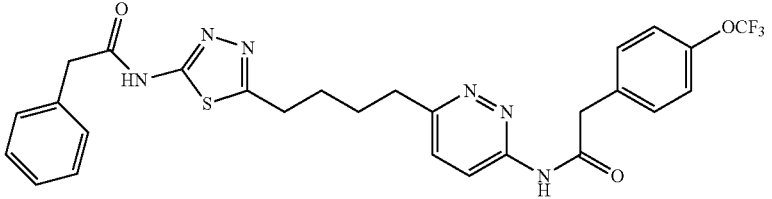 [SMILES: O=C(Cc1ccc(OC(F)(F)F)cc1)Nc1ccc(CCCCc2nnc(NC(=O)Cc3ccccc3)s2)nn1] |

TABLE 1-continued
Selected Compounds of Formula I
| Compound ID | Structure |
|---|---|
| 616 | 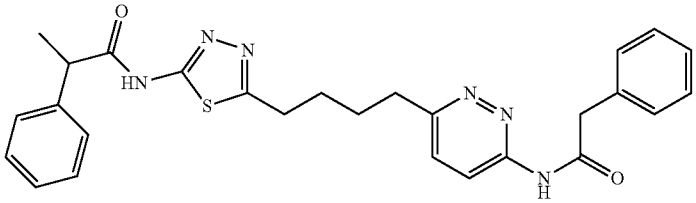 [SMILES: CC(C(=O)Nc1nnc(CCCCc2ccc(NC(=O)Cc3ccccc3)nn2)s1)c1ccccc1] |
| 617 | 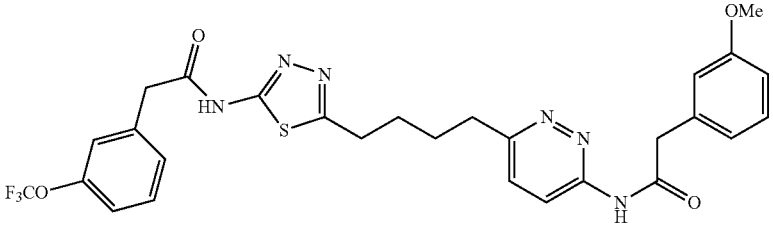 [SMILES: COc1cccc(CC(=O)Nc2ccc(CCCCc3nnc(NC(=O)Cc4cccc(OC(F)(F)F)c4)s3)nn2)c1] |
| 618 | 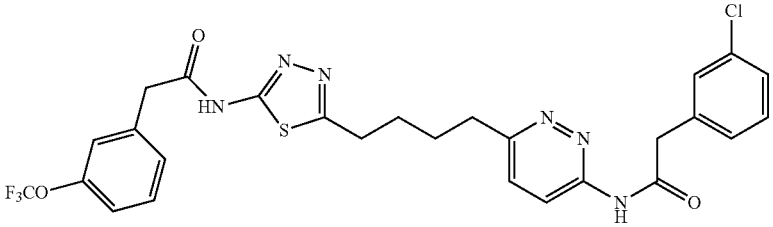 [SMILES: O=C(Cc1cccc(Cl)c1)Nc1ccc(CCCCc2nnc(NC(=O)Cc3cccc(OC(F)(F)F)c3)s2)nn1] |
| 619 | 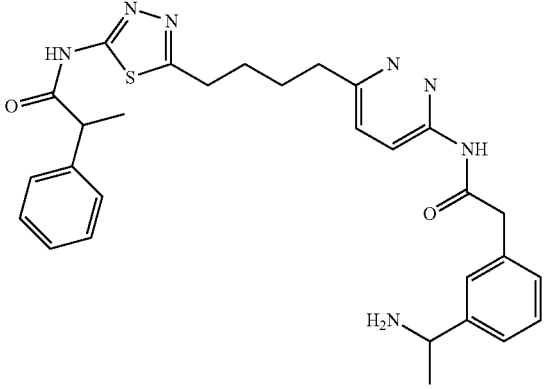 [SMILES: CC(N)c1cccc(CC(=O)N/C(N)=C/C=C(\N)CCCCc2nnc(NC(=O)C(C)c3ccccc3)s2)c1] |
| 620 | 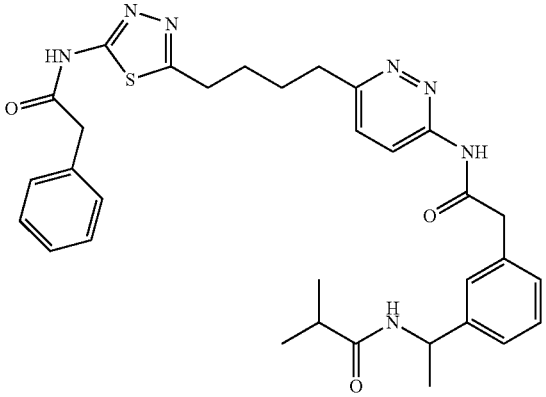 [SMILES: CC(C)C(=O)NC(C)c1cccc(CC(=O)Nc2ccc(CCCCc3nnc(NC(=O)Cc4ccccc4)s3)nn2)c1] |

TABLE 1-continued
Selected Compounds of Formula I
| Compound ID | Structure |
|---|---|
| 621 | 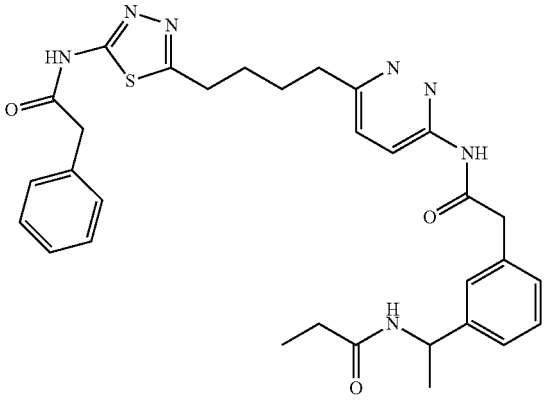 [SMILES: CCC(=O)NC(C)c1cccc(CC(=O)N/C(N)=C/C=C(\N)CCCCc2nnc(NC(=O)Cc3ccccc3)s2)c1] |
| 622 | 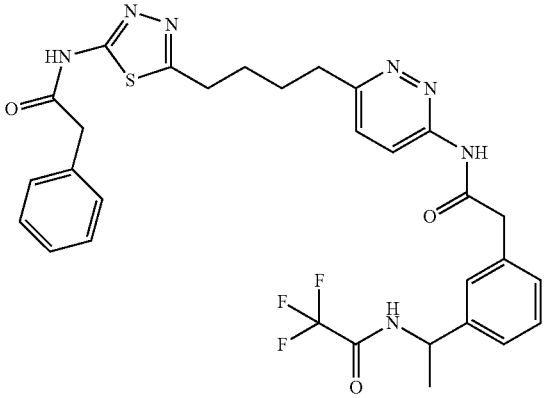 [SMILES: CC(NC(=O)C(F)(F)F)c1cccc(CC(=O)Nc2ccc(CCCCc3nnc(NC(=O)Cc4ccccc4)s3)nn2)c1] |
| 623 | 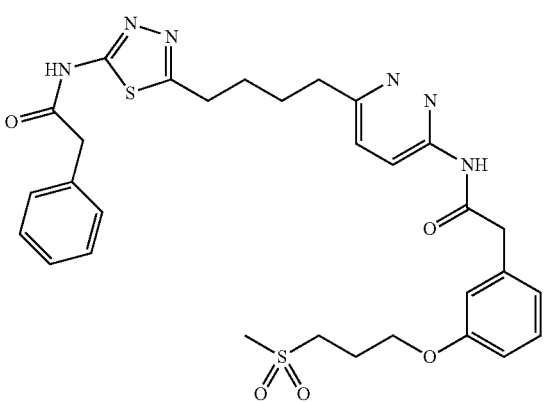 [SMILES: CS(=O)(=O)CCCOc1cccc(CC(=O)N/C(N)=C/C=C(\N)CCCCc2nnc(NC(=O)Cc3ccccc3)s2)c1] |

TABLE 1-continued
Selected Compounds of Formula I
| Compound ID | Structure |
|---|---|
| 624 | 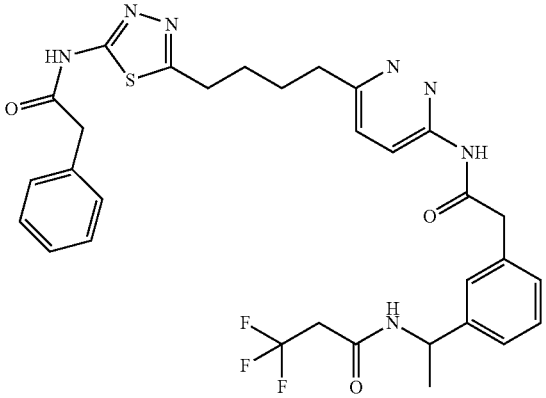 [SMILES: CC(NC(=O)CC(F)(F)F)c1cccc(CC(=O)N/C(N)=C/C=C(\N)CCCCc2nnc(NC(=O)Cc3ccccc3)s2)c1] |
| 625 | 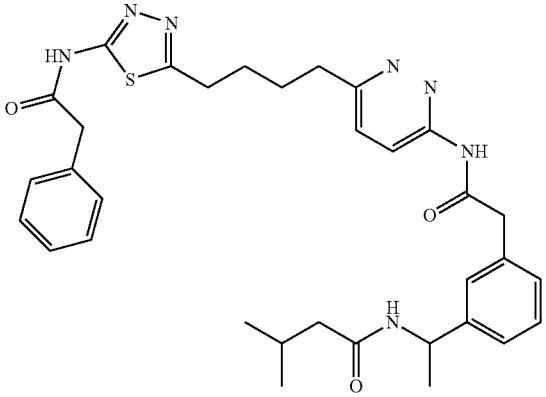 [SMILES: CC(C)CC(=O)NC(C)c1cccc(CC(=O)N/C(N)=C/C=C(\N)CCCCc2nnc(NC(=O)Cc3ccccc3)s2)c1] |
| 626 | 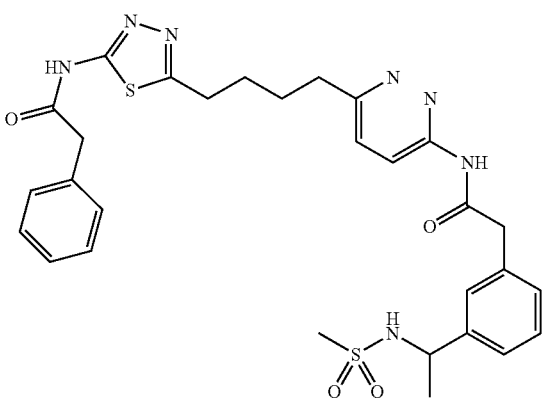 [SMILES: CC(NS(C)(=O)=O)c1cccc(CC(=O)N/C(N)=C/C=C(\N)CCCCc2nnc(NC(=O)Cc3ccccc3)s2)c1] |

TABLE 1-continued
Selected Compounds of Formula I
| Compound ID | Structure |
|---|---|
| 627 | 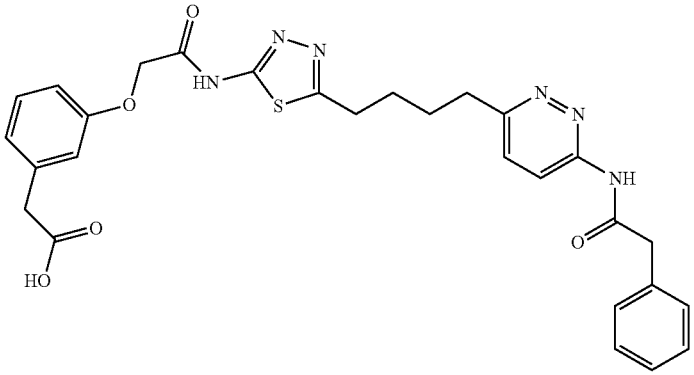 [SMILES: O=C(O)Cc1cccc(OCC(=O)Nc2nnc(CCCCc3ccc(NC(=O)Cc4ccccc4)nn3)s2)c1] |
| 628 | 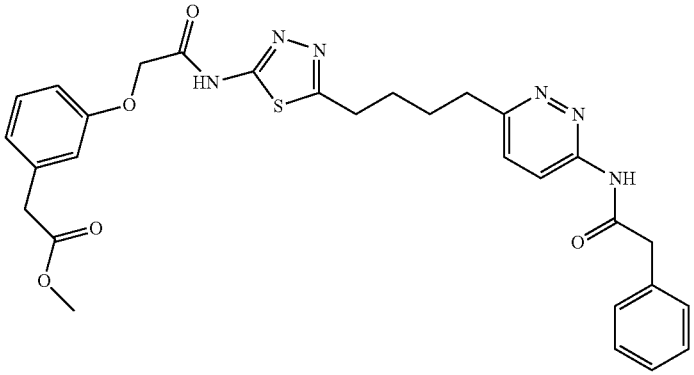 [SMILES: COC(=O)Cc1cccc(OCC(=O)Nc2nnc(CCCCc3ccc(NC(=O)Cc4ccccc4)nn3)s2)c1] |
| 629 | 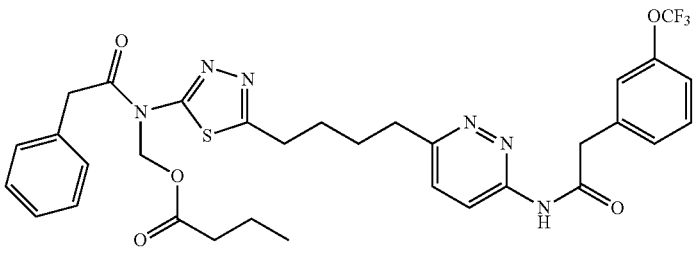 [SMILES: CCCC(=O)OCN(C(=O)Cc1ccccc1)c1nnc(CCCCc2ccc(NC(=O)Cc3cccc(OC(F)(F)F)c3)nn2)s1] |
| 630 | 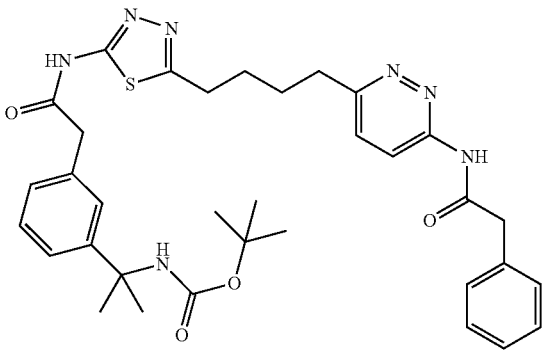 [SMILES: CC(C)(C)OC(=O)NC(C)(C)c1cccc(CC(=O)Nc2nnc(CCCCc3ccc(NC(=O)Cc4ccccc4)nn3)s2)c1] |

TABLE 1-continued

Selected Compounds of Formula I

| Compound ID | Structure |
|---|---|
| 631 | 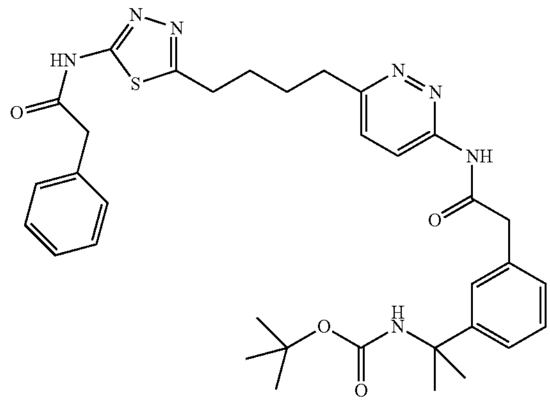 [SMILES: CC(C)(C)OC(=O)NC(C)(C)c1cccc(CC(=O)Nc2ccc(CCCCc3nnc(NC(=O)Cc4ccccc4)s3)nn2)c1] |
| 632 | 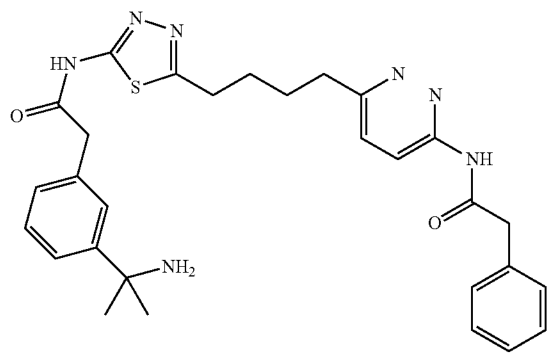 [SMILES: CC(C)(N)c1cccc(CC(=O)Nc2nnc(CCCC/C(N)=C/C=C(\N)NC(=O)Cc3ccccc3)s2)c1] |
| 633 | 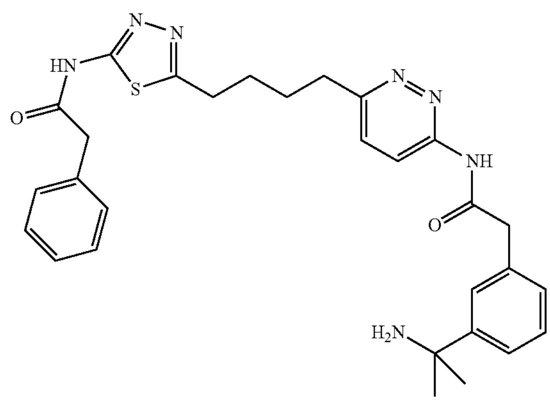 [SMILES: CC(C)(N)c1cccc(CC(=O)Nc2ccc(CCCCc3nnc(NC(=O)Cc4ccccc4)s3)nn2)c1] |
| 634 | 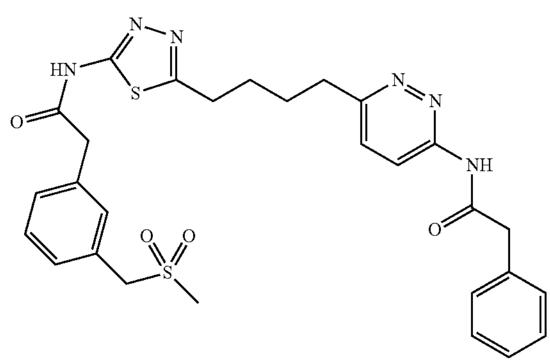 [SMILES: CS(=O)(=O)Cc1cccc(CC(=O)Nc2nnc(CCCCc3ccc(NC(=O)Cc4ccccc4)nn3)s2)c1] |

TABLE 1-continued
Selected Compounds of Formula I
| Compound ID | Structure |
|---|---|
| 635 | 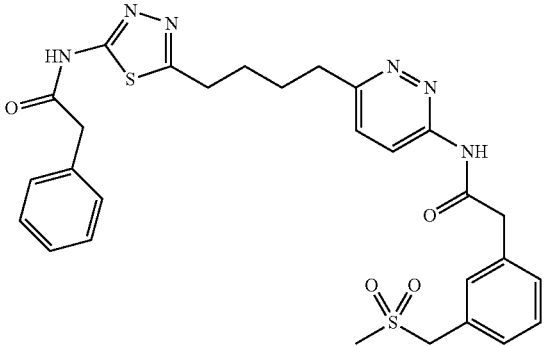 [SMILES: CS(=O)(=O)Cc1cccc(CC(=O)Nc2ccc(CCCCc3nnc(NC(=O)Cc4ccccc4)s3)nn2)c1] |
| 636 | 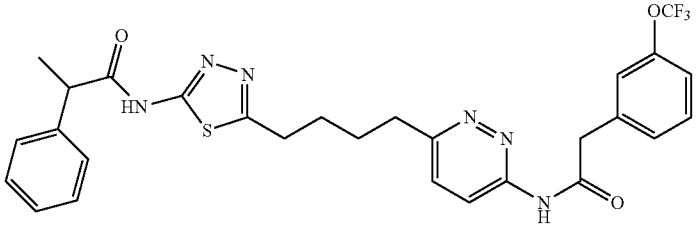 [SMILES: CC(C(=O)Nc1nnc(CCCCc2ccc(NC(=O)Cc3cccc(OC(F)(F)F)c3)nn2)s1)c1ccccc1] |
| 637 | 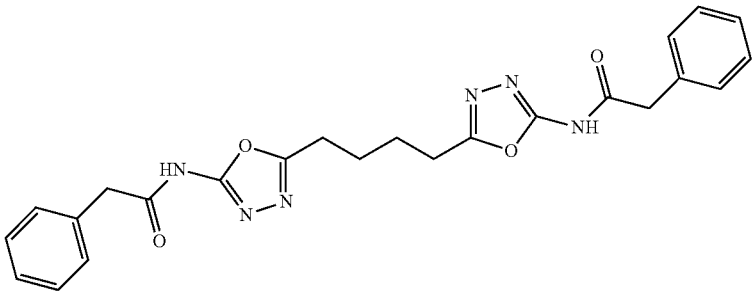 [SMILES: O=C(Cc1ccccc1)Nc1nnc(CCCCc2nnc(NC(=O)Cc3ccccc3)o2)o1] |
| 638 | 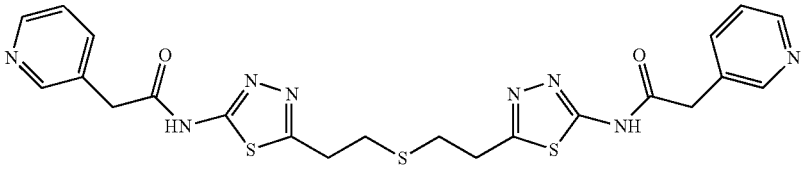 [SMILES: O=C(Cc1cccnc1)Nc1nnc(CCSCCc2nnc(NC(=O)Cc3cccnc3)s2)s1] |
| 639 | 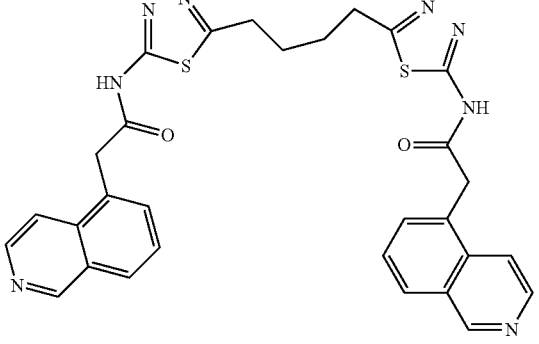 |

TABLE 1-continued

Selected Compounds of Formula I

| Compound ID | Structure |
|---|---|
| 640 | 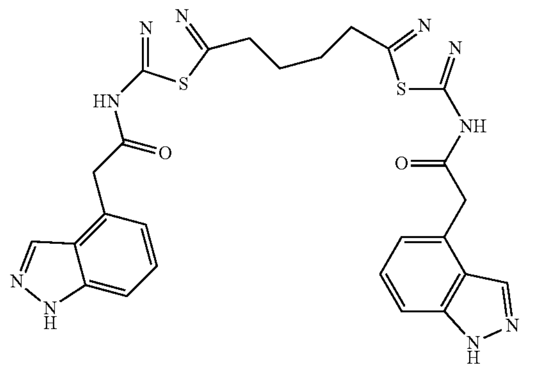 [SMILES: N=C(CCCCC(=N)SC(=N)NC(=O)Cc1cccc2[nH]ncc12)SC(=N)NC(=O)Cc1cccc2[nH]ncc12] |
| 641 | 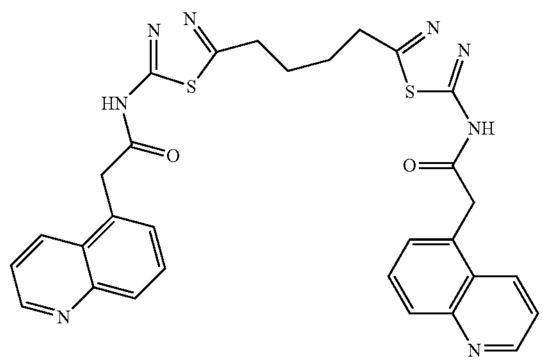 [SMILES: N=C(CCCCC(=N)SC(=N)NC(=O)Cc1cccc2ncccc12)SC(=N)NC(=O)Cc1cccc2ncccc12] |
| 644 | 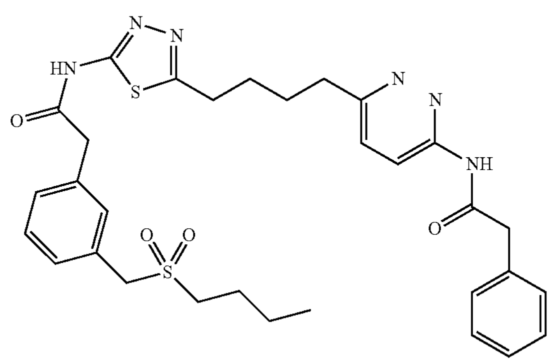 [SMILES: CCCCS(=O)(=O)Cc1cccc(CC(=O)Nc2nnc(CCCC/C(N)=C/C=C(\N)NC(=O)Cc3ccccc3)s2)c1] |
| 645 | 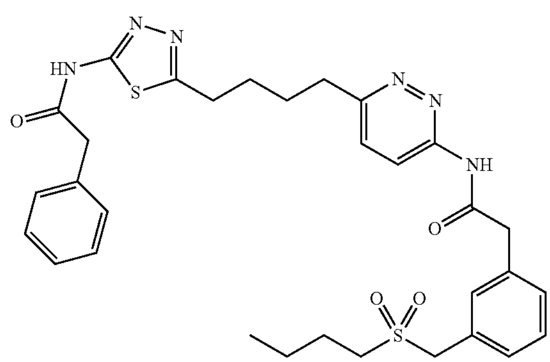 [SMILES: CCCCS(=O)(=O)Cc1cccc(CC(=O)Nc2ccc(CCCCc3nnc(NC(=O)Cc4ccccc4)s3)nn2)c1] |

TABLE 1-continued
Selected Compounds of Formula I
| Compound ID | Structure |
| --- | --- |
| 646 | 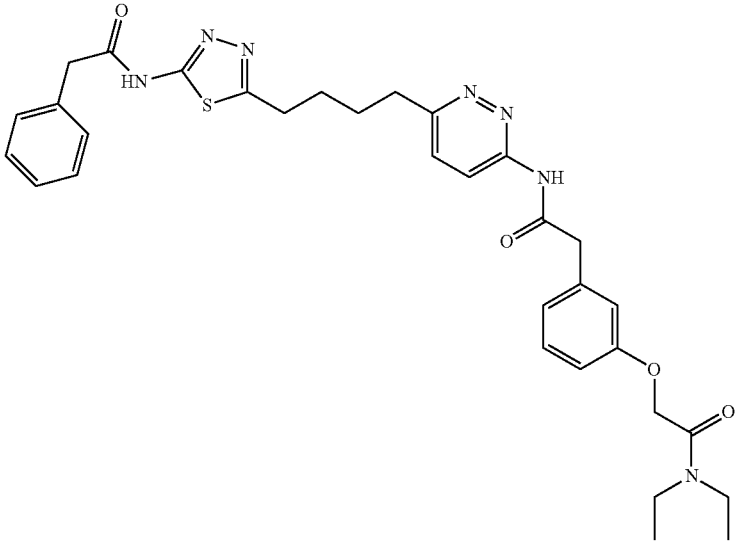 [SMILES: CCN(CC)C(=O)COc1cccc(CC(=O)Nc2ccc(CCCCc3nnc(NC(=O)Cc4ccccc4)s3)nn2)c1] |
| 647 | 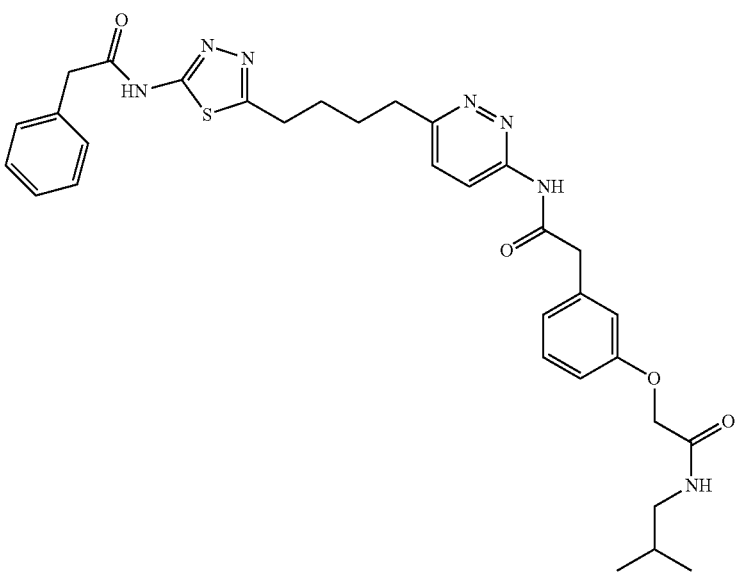 [SMILES: CC(C)CNC(=O)COc1cccc(CC(=O)Nc2ccc(CCCCc3nnc(NC(=O)Cc4ccccc4)s3)nn2)c1] |
| 648 | 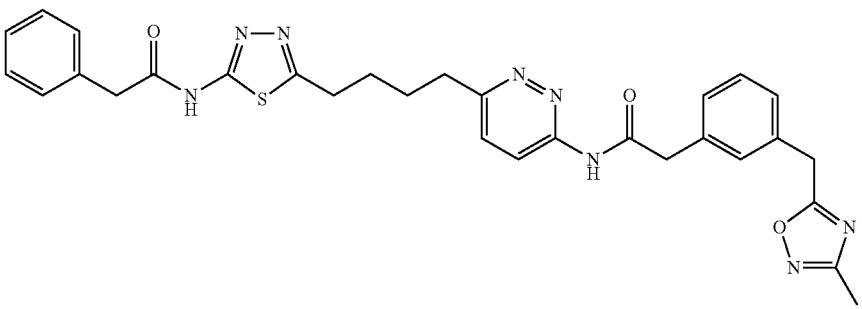 [SMILES: Cc1noc(Cc2cccc(CC(=O)Nc3ccc(CCCCc4nnc(NC(=O)Cc5ccccc5)s4)nn3)c2)n1] |

TABLE 1-continued

Selected Compounds of Formula I

| Compound ID | Structure |
|---|---|
| 649 | 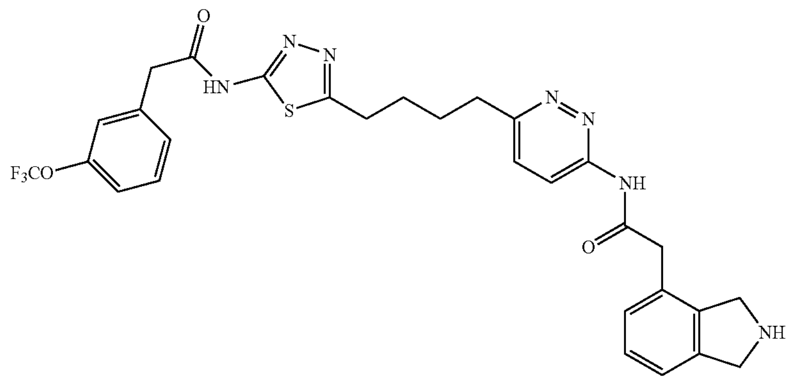 [SMILES: O=C(Cc1cccc2c1CNC2)Nc1ccc(CCCCc2nnc(NC(=O)Cc3cccc(OC(F)(F)F)c3)s2)nn1] |
| 650 | 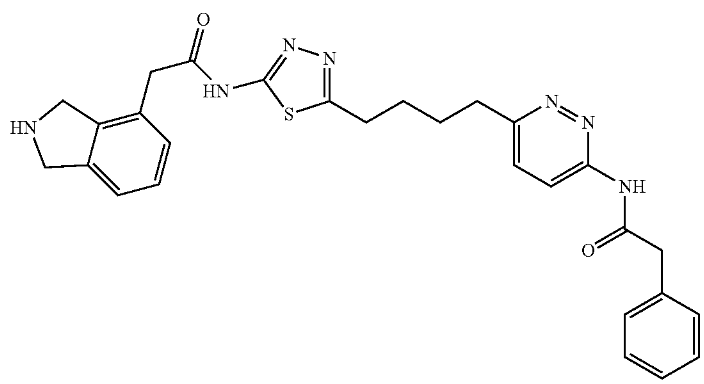 [SMILES: O=C(Cc1ccccc1)Nc1ccc(CCCCc2nnc(NC(=O)Cc3cccc4c3CNC4)s2)nn1] |
| 651 | 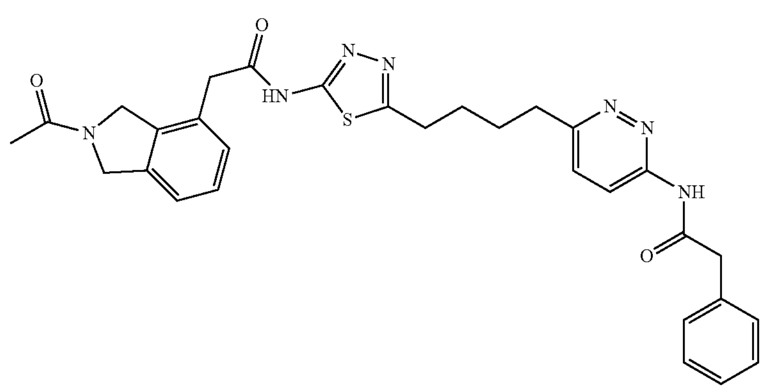 [SMILES: CC(=O)N1Cc2cccc(CC(=O)Nc3nnc(CCCCc4ccc(NC(=O)Cc5ccccc5)nn4)s3)c2C1] |
| 652 | 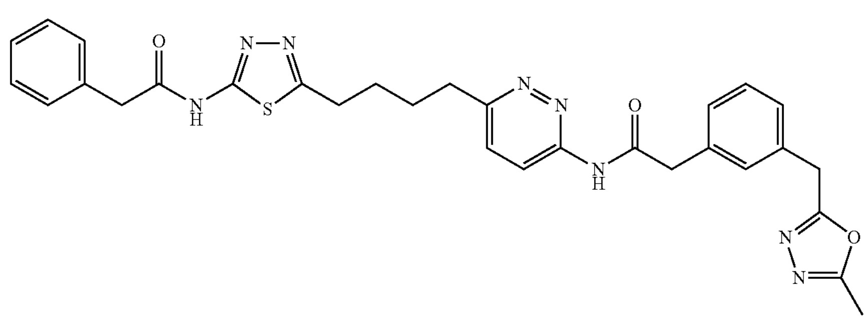 [SMILES: Cc1nnc(Cc2cccc(CC(=O)Nc3ccc(CCCCc4nnc(NC(=O)Cc5ccccc5)s4)nn3)c2)o1] |

TABLE 1-continued

Selected Compounds of Formula I

| Compound ID | Structure |
|---|---|
| 653 | 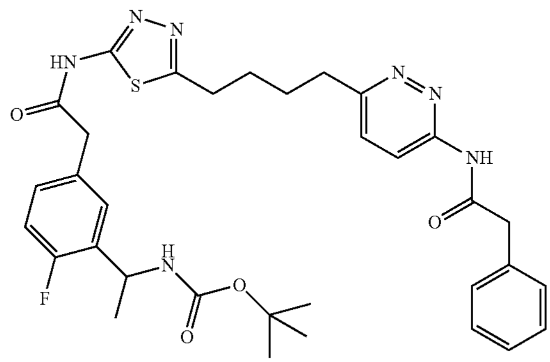 [SMILES: CC(NC(=O)OC(C)(C)C)c1cc(CC(=O)Nc2nnc(CCCCc3ccc(NC(=O)Cc4ccccc4)nn3)s2)ccc1F] |
| 654 | 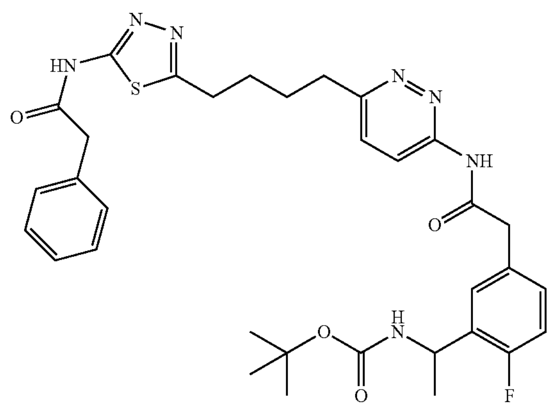 [SMILES: CC(NC(=O)OC(C)(C)C)c1cc(CC(=O)Nc2ccc(CCCCc3nnc(NC(=O)Cc4ccccc4)s3)nn2)ccc1F] |
| 655 | 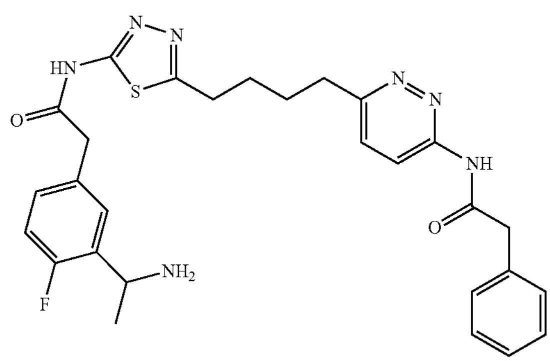 [SMILES: CC(N)c1cc(CC(=O)Nc2nnc(CCCCc3ccc(NC(=O)Cc4ccccc4)nn3)s2)ccc1F] |
| 656 | 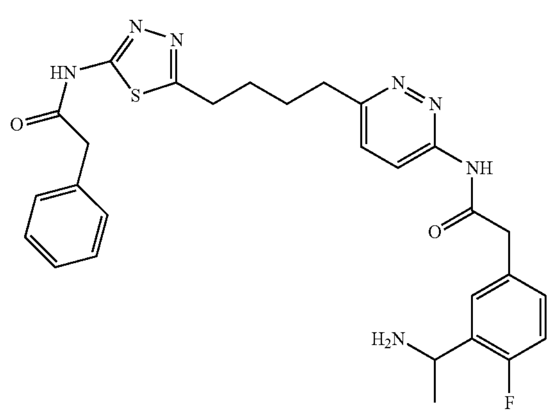 [SMILES: CC(N)c1cc(CC(=O)Nc2ccc(CCCCc3nnc(NC(=O)Cc4ccccc4)s3)nn2)ccc1F] |

TABLE 1-continued

Selected Compounds of Formula I

| Compound ID | Structure |
|---|---|
| 657 | 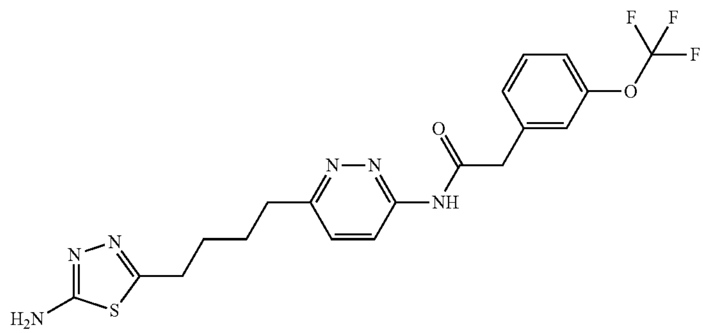 [SMILES: Nc1nnc(CCCCc2ccc(NC(=O)Cc3cccc(OC(F)(F)F)c3)nn2)s1] |
| 658 | 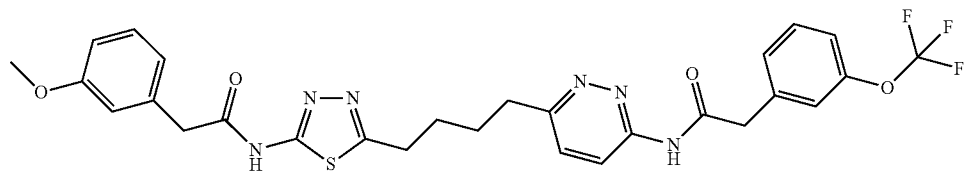 [SMILES: COc1cccc(CC(=O)Nc2nnc(CCCCc3ccc(NC(=O)Cc4cccc(OC(F)(F)F)c4)nn3)s2)c1] |
| 659 | 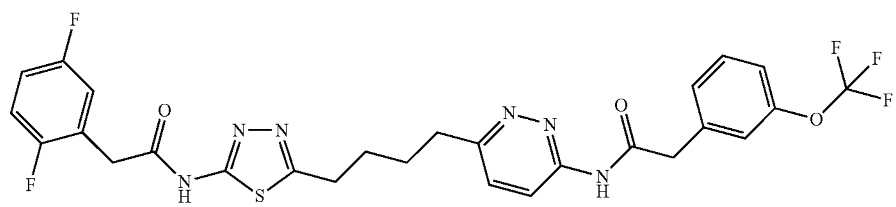 [SMILES: O=C(Cc1cccc(OC(F)(F)F)c1)Nc1ccc(CCCCc2nnc(NC(=O)Cc3cc(F)ccc3F)s2)nn1] |
| 660 | 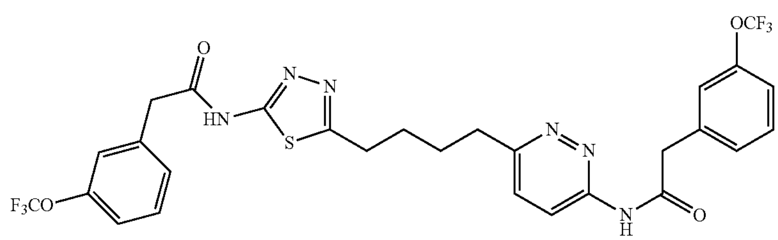 [SMILES: O=C(Cc1cccc(OC(F)(F)F)c1)Nc1ccc(CCCCc2nnc(NC(=O)Cc3cccc(OC(F)(F)F)c3)s2)nn1] |
| 661 | 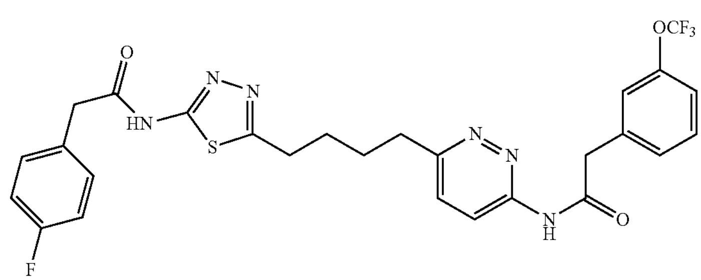 [SMILES: O=C(Cc1cccc(OC(F)(F)F)c1)Nc1ccc(CCCCc2nnc(NC(=O)Cc3ccc(F)cc3)s2)nn1] |
| 662 | 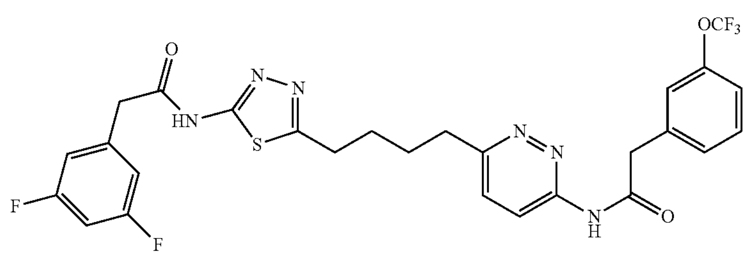 [SMILES: O=C(Cc1cccc(OC(F)(F)F)c1)Nc1ccc(CCCCc2nnc(NC(=O)Cc3cc(F)cc(F)c3)s2)nn1] |

TABLE 1-continued
Selected Compounds of Formula I
| Compound ID | Structure |
|---|---|
| 663 | 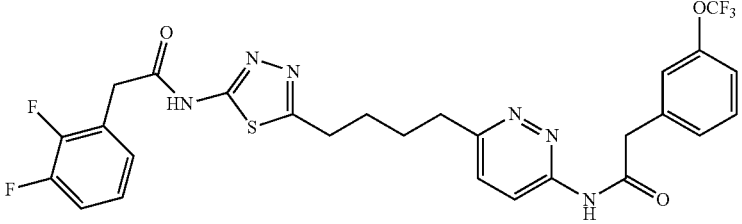 [SMILES: O=C(Cc1cccc(OC(F)(F)F)c1)Nc1ccc(CCCCc2nnc(NC(=O)Cc3cccc(F)c3F)s2)nn1] |
| 664 | 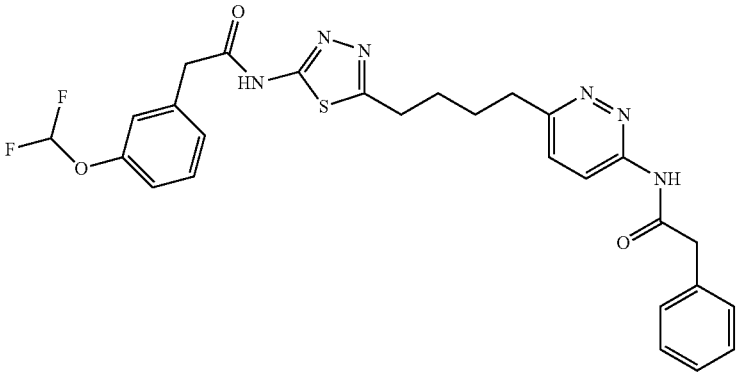 [SMILES: O=C(Cc1ccccc1)Nc1ccc(CCCCc2nnc(NC(=O)Cc3cccc(OC(F)F)c3)s2)nn1] |
| 665 | 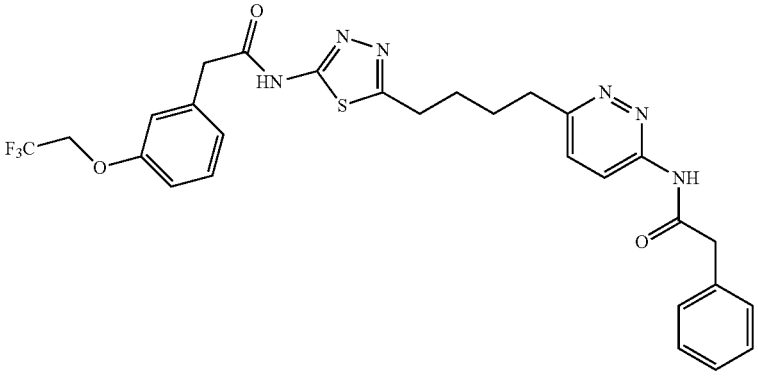 [SMILES: O=C(Cc1ccccc1)Nc1ccc(CCCCc2nnc(NC(=O)Cc3cccc(OCC(F)(F)F)c3)s2)nn1] |
| 666 | 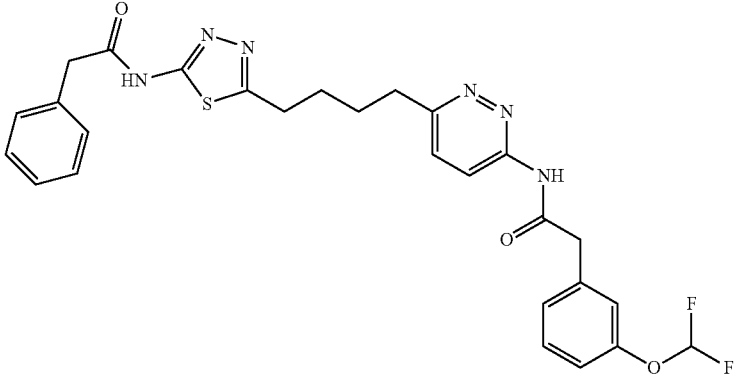 [SMILES: O=C(Cc1cccc(OC(F)F)c1)Nc1ccc(CCCCc2nnc(NC(=O)Cc3ccccc3)s2)nn1] |

TABLE 1-continued
Selected Compounds of Formula I
| Compound ID | Structure |
|---|---|
| 667 | 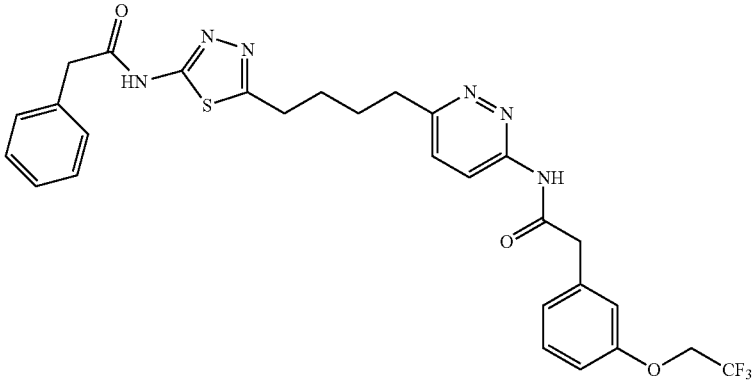 [SMILES: O=C(Cc1cccc(OCC(F)(F)F)c1)Nc1ccc(CCCCc2nnc(NC(=O)Cc3ccccc3)s2)nn1] |
| 668 | 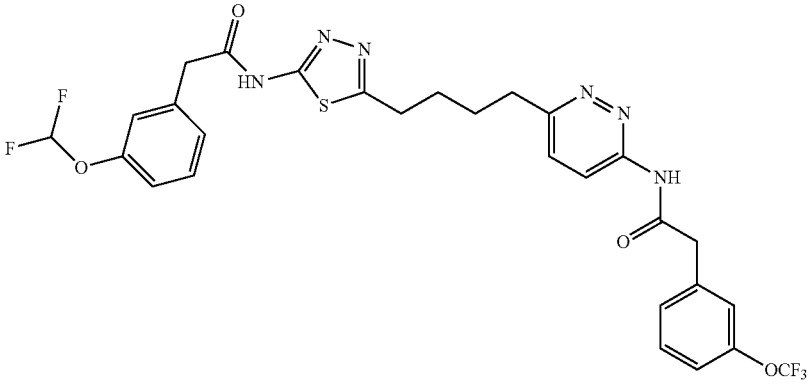 [SMILES: O=C(Cc1cccc(OC(F)(F)F)c1)Nc1ccc(CCCCc2nnc(NC(=O)Cc3cccc(OC(F)F)c3)s2)nn1] |
| 669 | 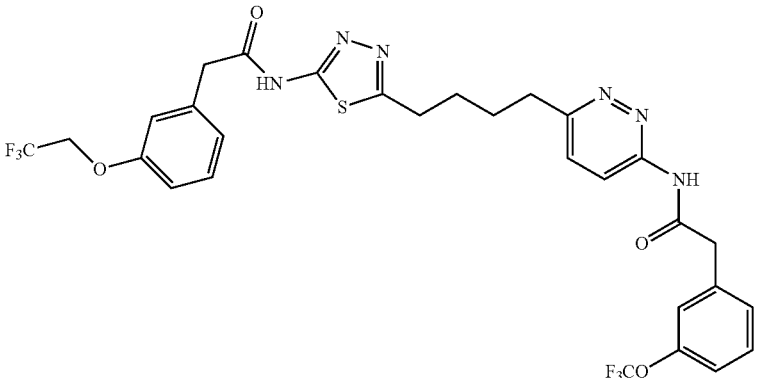 [SMILES: O=C(Cc1cccc(OC(F)(F)F)c1)Nc1ccc(CCCCc2nnc(NC(=O)Cc3cccc(OCC(F)(F)F)c3)s2)nn1] |
| 670 | 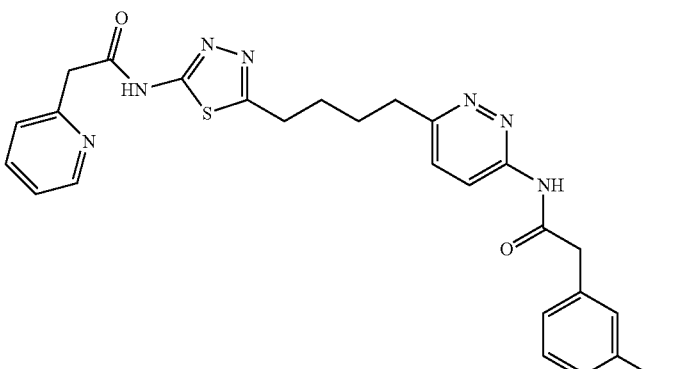 |

TABLE 1-continued

Selected Compounds of Formula I

| Compound ID | Structure |
|---|---|
| 671 | 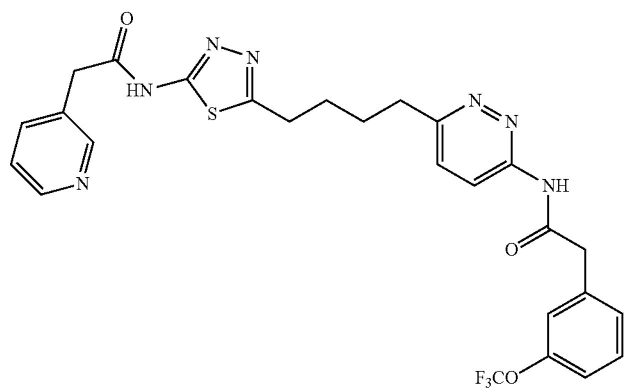 [SMILES: O=C(Cc1cccc(OC(F)(F)F)c1)Nc1ccc(CCCCc2nnc(NC(=O)Cc3cccnc3)s2)nn1] |
| 672 | 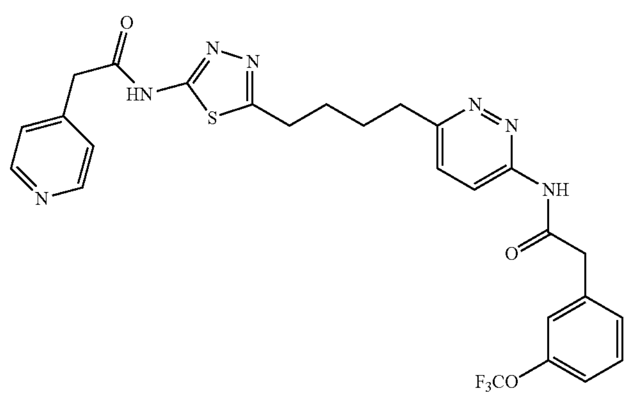 [SMILES: O=C(Cc1cccc(OC(F)(F)F)c1)Nc1ccc(CCCCc2nnc(NC(=O)Cc3ccncc3)s2)nn1] |
| 673 | 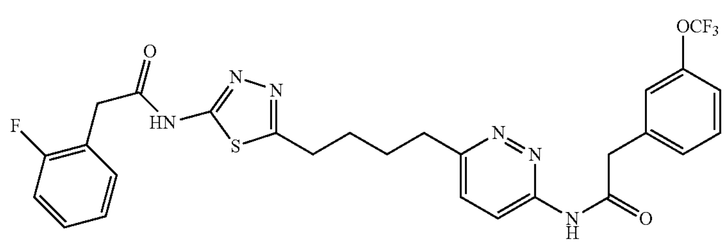 [SMILES: O=C(Cc1cccc(OC(F)(F)F)c1)Nc1ccc(CCCCc2nnc(NC(=O)Cc3ccccc3F)s2)nn1] |
| 674 | 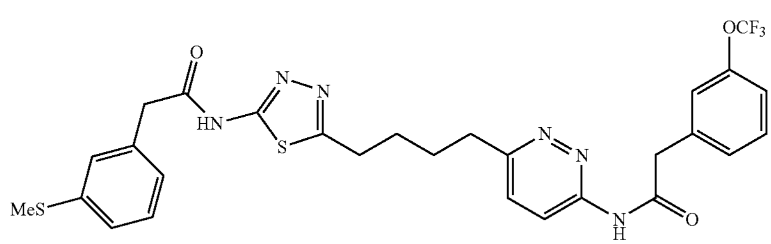 [SMILES: CSc1cccc(CC(=O)Nc2nnc(CCCCc3ccc(NC(=O)Cc4cccc(OC(F)(F)F)c4)nn3)s2)c1] |

TABLE 1-continued

Selected Compounds of Formula I

| Compound ID | Structure |
|---|---|
| 675 | 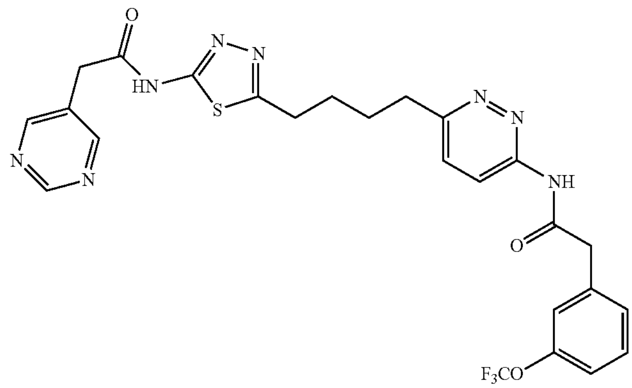 [SMILES: O=C(Cc1cccc(OC(F)(F)F)c1)Nc1ccc(CCCCc2nnc(NC(=O)Cc3cncnc3)s2)nn1] |
| 676 | 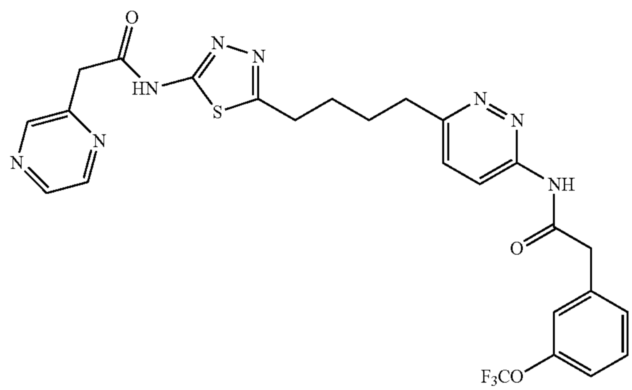 [SMILES: O=C(Cc1cccc(OC(F)(F)F)c1)Nc1ccc(CCCCc2nnc(NC(=O)Cc3cnccn3)s2)nn1] |
| 677 | 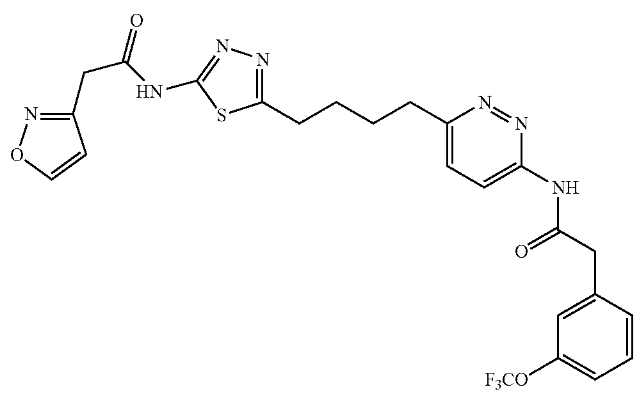 [SMILES: O=C(Cc1cccc(OC(F)(F)F)c1)Nc1ccc(CCCCc2nnc(NC(=O)Cc3ccon3)s2)nn1] |
| 678 | 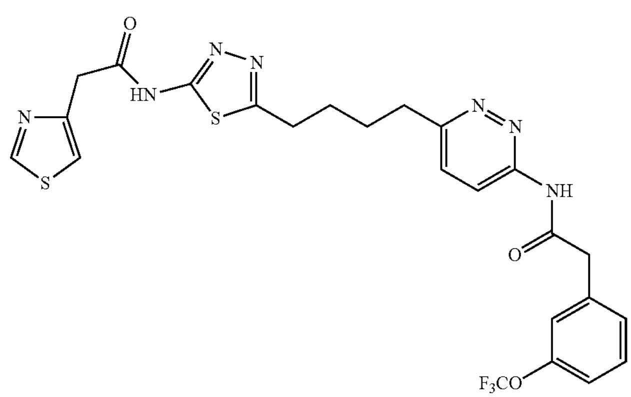 [SMILES: O=C(Cc1cccc(OC(F)(F)F)c1)Nc1ccc(CCCCc2nnc(NC(=O)Cc3cscn3)s2)nn1] |

US 10,441,587 B2
323                                                                                         324
TABLE 1-continued
Selected Compounds of Formula I
| Compound ID | Structure |
|---|---|
679 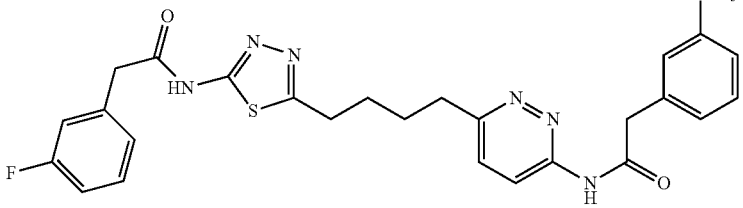
680 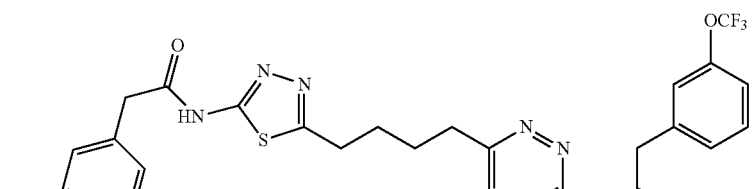
681 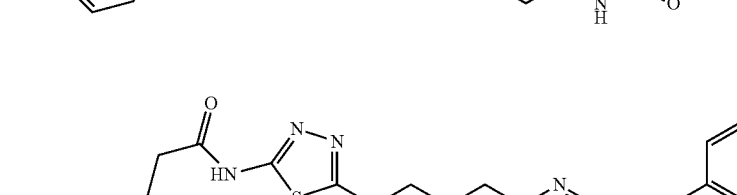
682 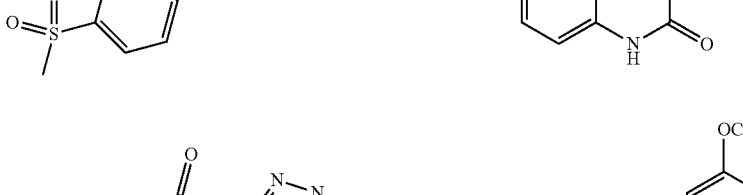
683 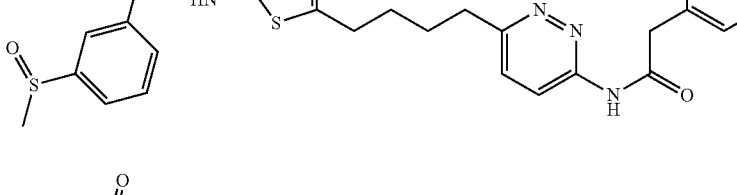

TABLE 1-continued
Selected Compounds of Formula I
| Compound ID | Structure |
|---|---|
| 684 | 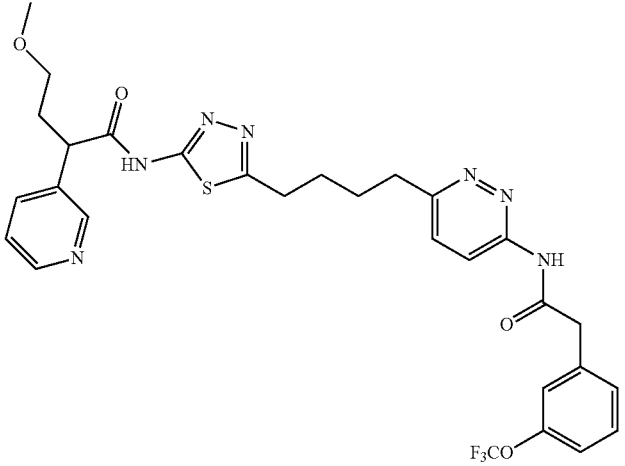 [SMILES: COCCC(C(=O)Nc1nnc(CCCCc2ccc(NC(=O)Cc3cccc(OC(F)(F)F)c3)nn2)s1)c1cccnc1] |
| 685 | 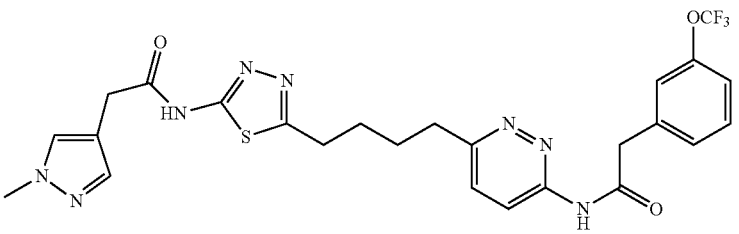 |
| 686 | 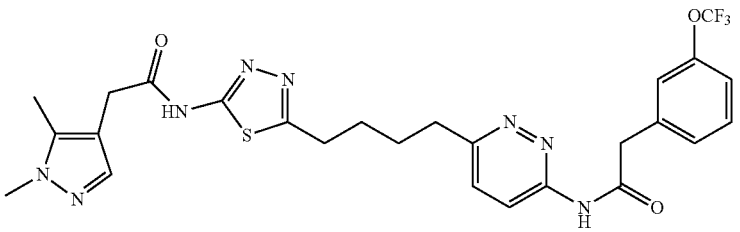 [SMILES: Cc1c(CC(=O)Nc2nnc(CCCCc3ccc(NC(=O)Cc4cccc(OC(F)(F)F)c4)nn3)s2)cnn1C] |
| 687 | 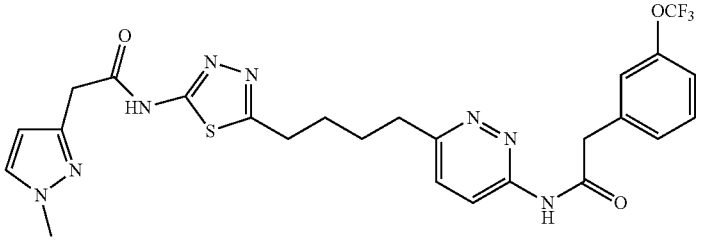 [SMILES: Cn1ccc(CC(=O)Nc2nnc(CCCCc3ccc(NC(=O)Cc4cccc(OC(F)(F)F)c4)nn3)s2)n1] |
| 688 | 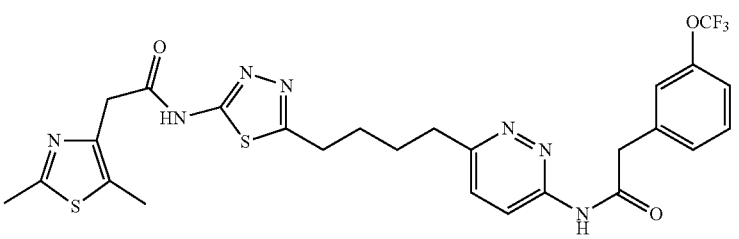 [SMILES: Cc1nc(CC(=O)Nc2nnc(CCCCc3ccc(NC(=O)Cc4cccc(OC(F)(F)F)c4)nn3)s2)c(C)s1] |

TABLE 1-continued
Selected Compounds of Formula I
| Compound ID | Structure |
|---|---|
| 689 | 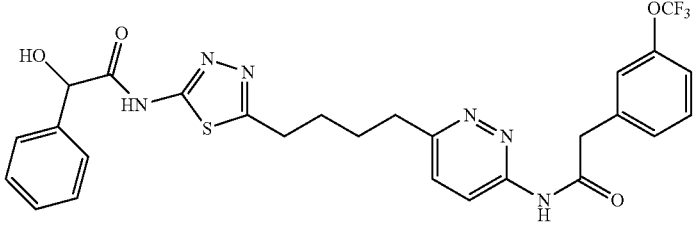 [SMILES: O=C(Cc1cccc(OC(F)(F)F)c1)Nc1ccc(CCCCc2nnc(NC(=O)C(O)c3ccccc3)s2)nn1] |
| 690 | 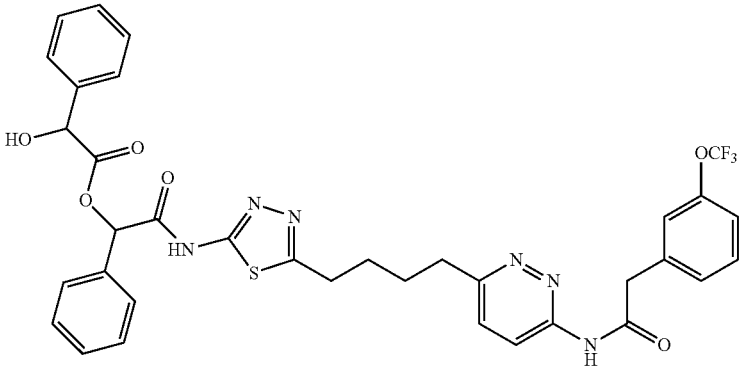 [SMILES: O=C(Cc1cccc(OC(F)(F)F)c1)Nc1ccc(CCCCc2nnc(NC(=O)C(OC(=O)C(O)c3ccccc3)c3ccccc3)s2)nn1] |
| 692 | 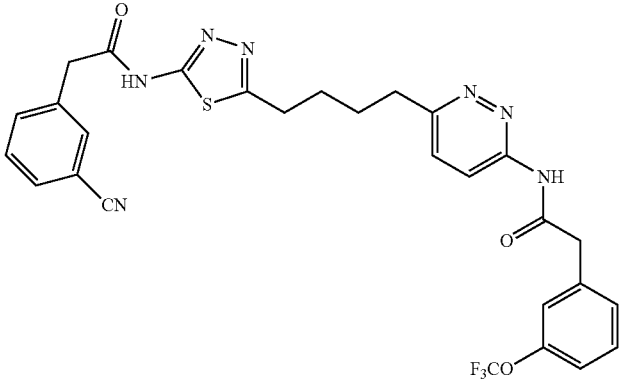 [SMILES: N#Cc1cccc(CC(=O)Nc2nnc(CCCCc3ccc(NC(=O)Cc4cccc(OC(F)(F)F)c4)nn3)s2)c1] |
| 693 | 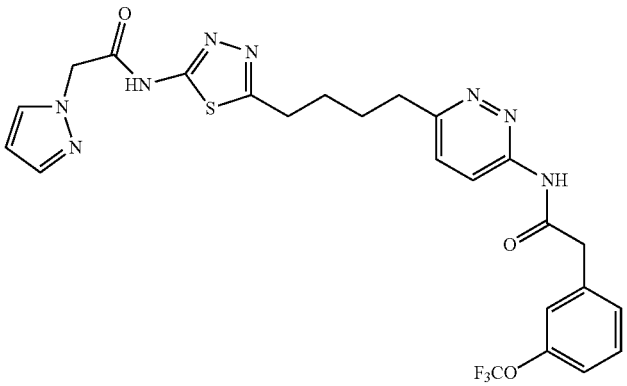 [SMILES: O=C(Cc1cccc(OC(F)(F)F)c1)Nc1ccc(CCCCc2nnc(NC(=O)Cn3cccn3)s2)nn1] |

TABLE 1-continued

Selected Compounds of Formula I

| Compound ID | Structure |
|---|---|
| 694 | 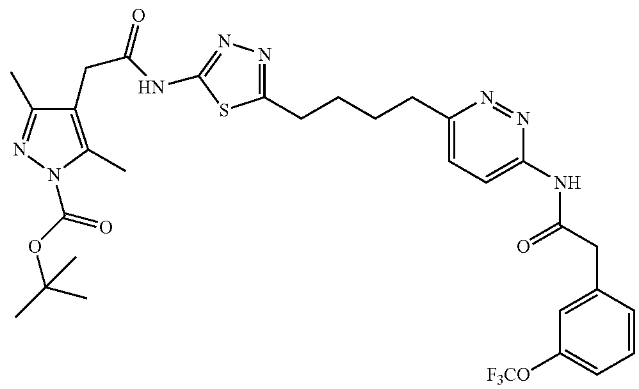 [SMILES: Cc1nn(C(=O)OC(C)(C)C)c(C)c1CC(=O)Nc1nnc(CCCCc2ccc(NC(=O)Cc3cccc(OC(F)(F)F)c3)nn2)s1] |
| 695 | 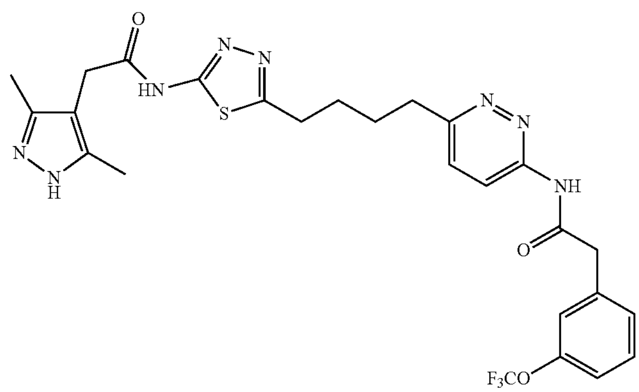 [SMILES: Cc1n[nH]c(C)c1CC(=O)Nc1nnc(CCCCc2ccc(NC(=O)Cc3cccc(OC(F)(F)F)c3)nn2)s1] |
| 696 | 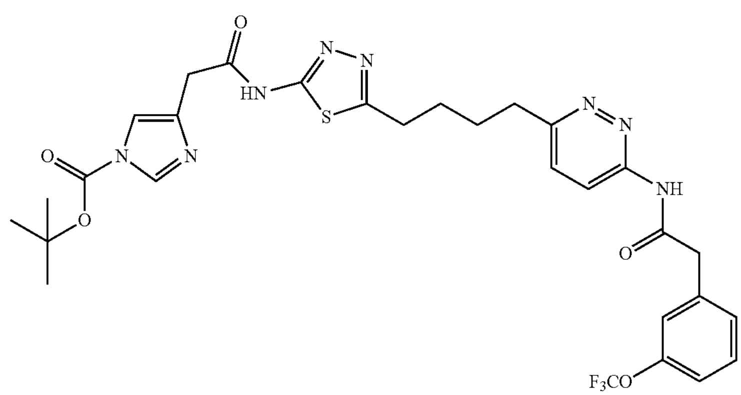 [SMILES: CC(C)(C)OC(=O)n1cnc(CC(=O)Nc2nnc(CCCCc3ccc(NC(=O)Cc4cccc(OC(F)(F)F)c4)nn3)s2)c1] |
| 697 | 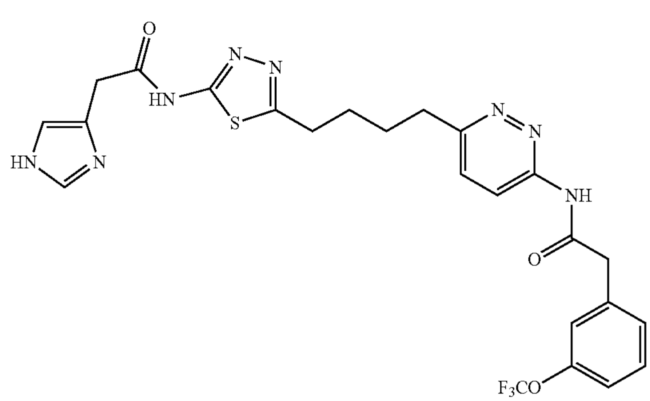 [SMILES: O=C(Cc1cccc(OC(F)(F)F)c1)Nc1ccc(CCCCc2nnc(NC(=O)Cc3c[nH]cn3)s2)nn1] |

TABLE 1-continued
Selected Compounds of Formula I
| Compound ID | Structure |
|---|---|
| 698 | 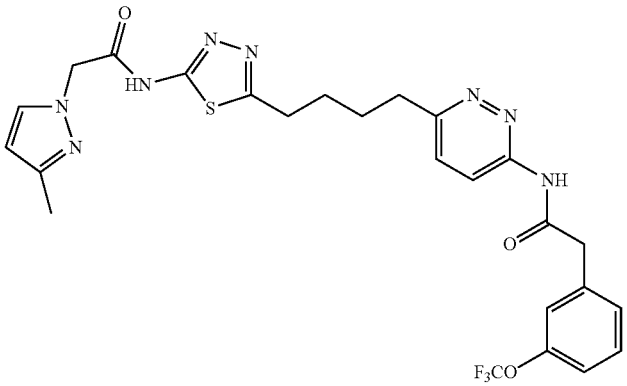 [SMILES: Cc1ccn(CC(=O)Nc2nnc(CCCCc3ccc(NC(=O)Cc4cccc(OC(F)(F)F)c4)nn3)s2)n1] |
| 699 | 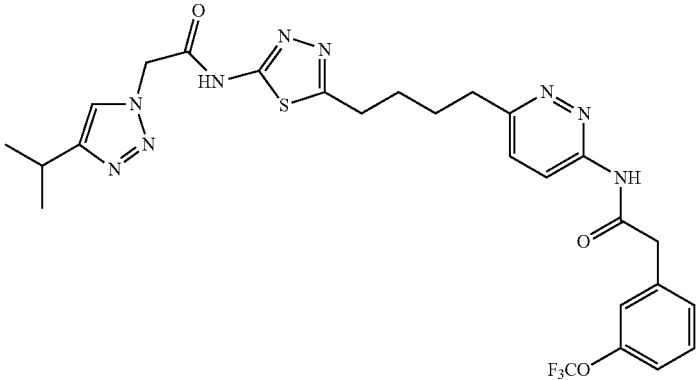 [SMILES: CC(C)c1cn(CC(=O)Nc2nnc(CCCCc3ccc(NC(=O)Cc4cccc(OC(F)(F)F)c4)nn3)s2)nn1] |
| 700 | 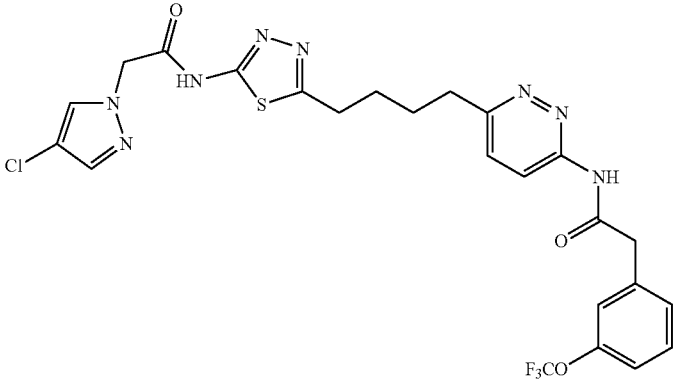 [SMILES: O=C(Cc1cccc(OC(F)(F)F)c1)Nc1ccc(CCCCc2nnc(NC(=O)Cn3cc(Cl)cn3)s2)nn1] |

TABLE 1-continued
Selected Compounds of Formula I
| Compound ID | Structure |
|---|---|
| 701 | 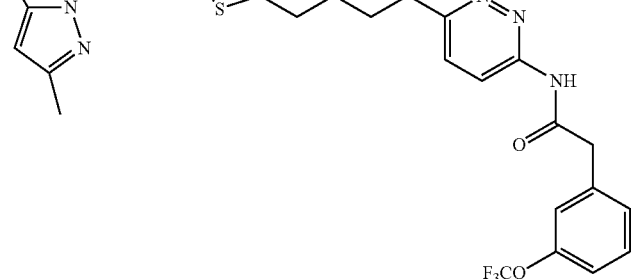 |
| 702 | 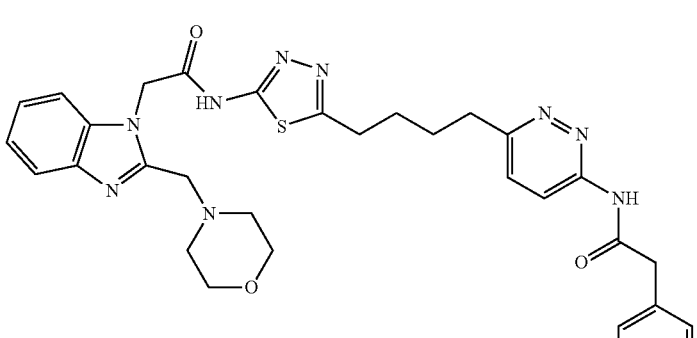 |
| 703 | 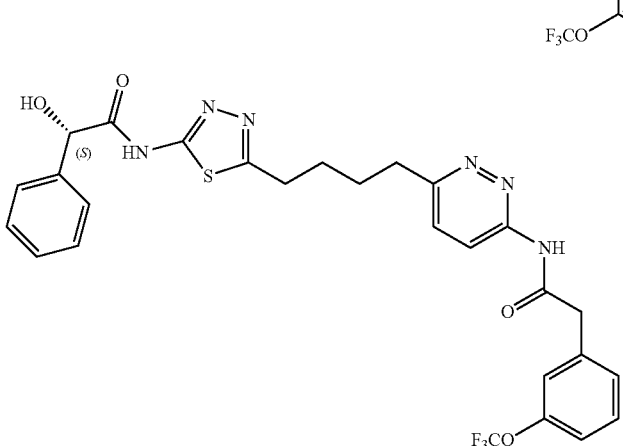 |
| 704 | 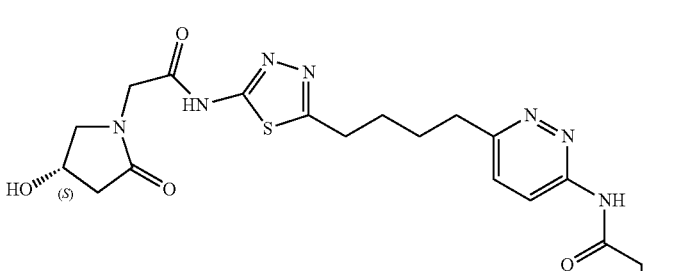 |

TABLE 1-continued
Selected Compounds of Formula I
| Compound ID | Structure |
|---|---|
| 705 | 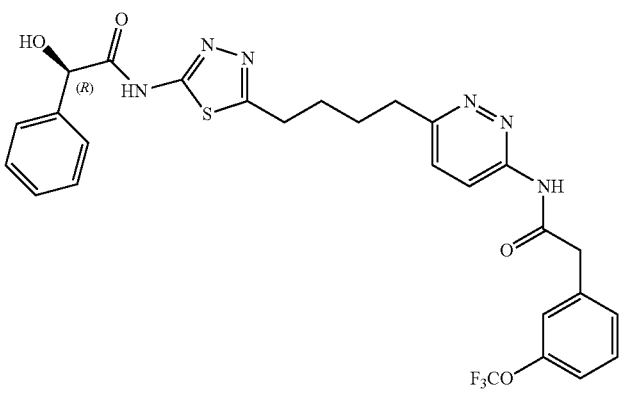 |
| 706 | 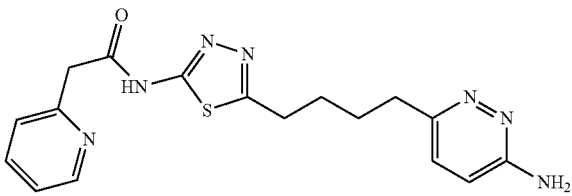 |
| 707 | 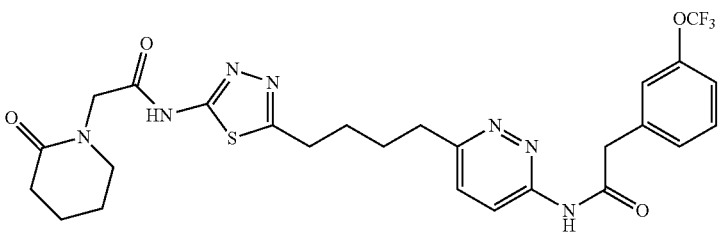 [SMILES: O=C(Cc1cccc(OC(F)(F)F)c1)Nc1ccc(CCCCc2nnc(NC(=O)CN3CCCCC3=O)s2)nn1] |
| 708 | 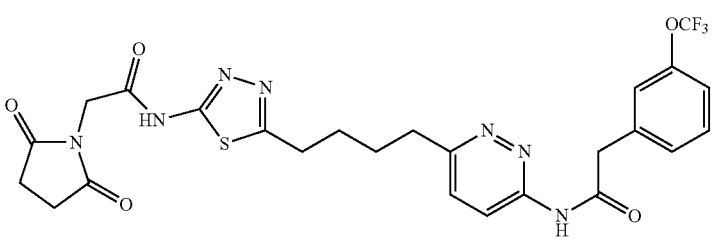 [SMILES: O=C(Cc1cccc(OC(F)(F)F)c1)Nc1ccc(CCCCc2nnc(NC(=O)CN3C(=O)CCC3=O)s2)nn1] |
| 709 | 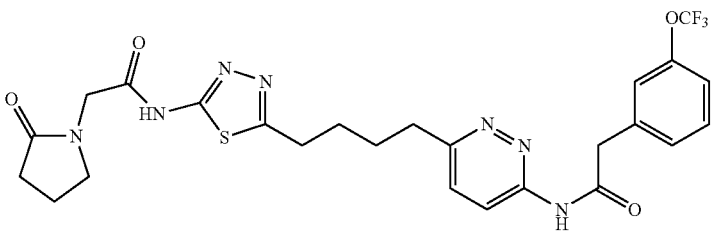 [SMILES: O=C(Cc1cccc(OC(F)(F)F)c1)Nc1ccc(CCCCc2nnc(NC(=O)CN3CCCC3=O)s2)nn1] |

In certain embodiments of the methods of treating lung cancer described herein, the glutaminase inhibitor is a compound having the structure of Formula (IV):

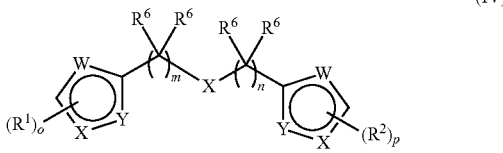

wherein:
X is a bond, —S—, —S(O)—, —SO$_2$—, —CH=CH—, or —C(O)—;
each W, Y and Z is independently —S—, —CH=, —O—, —N=, or —NH—, provided that (1) at least one of W, Y and Z is not —CH= and (2) when one of W is —S— and the Y in the same ring is N, then the Z in the same ring is not —CH=;
each R$^1$ and R$^2$ is independently C$_{1-6}$ alkylene-R$^4$, —N(R$^3$)—R$^4$, —N(R$^3$)—C(O)—R$^4$, —C(O)—N(R$^3$)—R$^4$, —N(R$^3$)—C(O)—O—R$^4$, —N(R$^3$)—C(O)—N(R$^3$)—R$^4$—, O—C(O)—N(R$^3$)—R$^4$, —N(R$^3$)—C(O)—C$_{1-6}$alkylene-C(O)—R$^4$, —N(R$^3$)—C(O)—C$_{1-6}$alkylene-N(R$^3$)—C(O)—R$^4$ or —N(R$^{3a}$)—C(O)—CH$_2$—N(R$^3$)—C(O)—R$^4$;
each R$^3$ is independently hydrogen, C$_{1-6}$ alkyl or aryl;
each R$^4$ is independently C$_{1-6}$ alkyl, C$_{1-6}$ alkenyl, aryl, heteroaryl, aralkyl, heteroaralkyl, heterocyclylalkyl, heterocyclyl, cycloalkyl or cycloalkylalkyl, each of which is substituted with 0-3 occurrences of R$^5$, or two adjacent R$^5$ moieties, taken together with the atoms to which they are attached form a heterocyclyl, heteroaryl, cycloalkyl or aryl;
each R$^5$ is independently oxo (=O), C$_{1-6}$ alkyl, C$_{1-6}$ haloalkyl, C$_{1-6}$ alkoxy, cyano, halo, —OH, —SH, —OCF$_3$, —SO$_2$—C$_{1-6}$ alkyl, —NO$_2$, —N(R$^7$)—C(O)—C$_{1-6}$ alkyl, —N(R$^6$)$_2$, —O—C(O)—C$_{1-6}$ alkyl, C$_{3-7}$ cycloalkyl, (C$_{3-7}$cycloalkyl)alkyl, aryl, aryloxy, —C(O)-aryl, heteroaryl, aralkyl, heteroaralkyl, heterocyclylalkyl or heterocyclyl, wherein each aryl, heteroaryl or heterocyclyl is further substituted with 0-3 occurrences of R$^7$;
each R$^6$ is independently hydrogen, fluoro, OH or C$_{1-6}$ alkyl;
each R$^7$ is independently hydrogen, C$_{1-6}$ alkyl, —OH, —SH, cyano, halo, —CF$_3$, —OCF$_3$, —SO$_2$—C$_{1-6}$ alkyl, —NO$_2$, —N(R$^7$)—C(O)—C$_{1-6}$ alkyl, —N(R$^6$)$_2$ or C$_{1-6}$ alkoxy;
m is 1, 2 or 3;
n is 1, 2 or 3; provided that when X is bond, the sum of m and n is from 3 to 6 and when X is —S—, —S(O)—, —SO$_2$—, —CH=CH—, or —C(O)—, the sum of m and n is from 2 to 4;
o is 1, 2 or 3; and
p is 1, 2 or 3;
with the proviso that: (1) when X is —S—, m and n are both 2, each R$^6$ is H, then (i) R$^1$ and R$^2$ are not both —NHC(O)—R$^4$, wherein R$^4$ is C$_{1-6}$ alkyl, monocyclic aryl, monocyclic heteroaryl, monocyclic aralkyl, monocyclic heteroaralkyl and each member of R$^4$ is substituted with 0-3 occurrences of R$^5$; and (ii) R$^1$ and R$^2$ are not both —NHC(O)O-methyl, —NHC(O)O-ethyl, —NHC(±)-6-pyrimidine-2,4(1H,3H)-dionyl, or —NHC(O)NH-phenyl wherein said phenyl of the —NHC(O)NH-phenyl moiety is optionally substituted with 1 or 2 groups selected from methyl, nitro, and halo;

(2) when X is —S—, m and n are both 1, each R$^6$ is H, then (i) R$^1$ and R$^2$ are not both —NH-phenyl or —NH-4-methoxy-phenyl;
(3) when X is a bond, the sum of m and n is 3, each R$^6$ is H, then R$^1$ and R$^2$ are not both —NHC(O)-phenyl;
(4) when X is a bond, m and n are both 2, each R$^6$ is H, then R$^1$ and R$^2$ are not both —NHC(O)-furanyl, —NHC(O)-phenyl, —NHC(O)-o-methoxy-phenyl, —NHC(O)—C$_{1-6}$ alkyl, —NH-benzyl, or —NH-phenyl wherein said phenyl of the —NH-phenyl moiety is substituted with 0-3 occurrences of R$^5$;
(5) when X is a bond, the sum of m and n is 5, each R$^6$ is H, then R$^1$ and R$^2$ are not both —NHC(O)—C$_{1-6}$ alkyl, —NHC(O)-cyclohexyl, or —NH-phenyl wherein said phenyl of the —NH-phenyl moiety is optionally substituted with methyl; and
(6) when X is a bond, m and n are both 3, each R$^6$ is H, then R$^1$ and R$^2$ are not both NH-phenyl.

In certain embodiments, W is —S—, each Y is —N=, and each Z is —N=.
In certain embodiments, W is —CH=, each Z is —O—, and each Y is —N=.
In certain embodiments, o is 1 and p is 1.
In certain embodiments, R$^1$ and R$^2$ are each —N(R$^3$)—C(O)—O—R$^4$.
In certain embodiments, the compound having the structure of Formula (IV) has the structure of Formula (IVa):

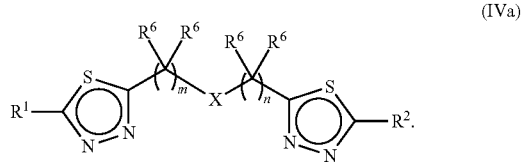

In certain embodiments, R$^1$ and R$^2$ are the same.
In certain embodiments, the compound having the structure of Formula (IV) is a compound having the structure of Formula (IVb):

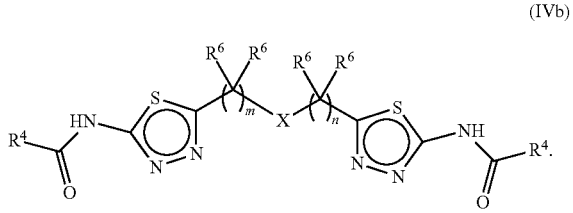

In certain embodiments of the methods of treating lung cancer described herein, the glutamines inhibitor is a compound having the structure of Formula (V):

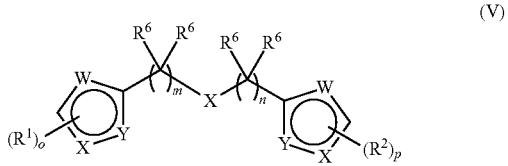

wherein:

X is $C_3$-$C_7$ cycloalkylene;

each W, Y and Z is independently —S—, —CH═, —O—, —N═, or —NH—, provided that at least one of W, Y and Z is not —CH═;

each $R^1$ and $R^2$ is independently —$NH_2$, —$N(R^3)$—C(O)—$R^4$, —C(O)—$N(R^3)$—$R^4$, —$N(R^3)$—C(O)—O—$R^4$, —$N(R^3)$—C(O)—$N(R^3)$—$R^4$ or —$N(R^3)$—C(O)—$SR^4$;

each $R^3$ is independently hydrogen, $C_{1-6}$ alkyl or aryl;

each $R^4$ is independently $C_{1-6}$ alkyl, aryl, heteroaryl, aralkyl, heteroaralkyl, cycloalkyl, cycloalkylalkyl, heterocyclylalkyl, or heterocyclyl, each of which is substituted with 0-3 occurrences of $R^5$;

each $R^5$ is independently $C_{1-6}$ alkyl, $C_{1-6}$ alkoxy, —O—$C_{1-6}$ alkylene$C_{1-6}$alkoxy, $C_{1-6}$thioalkoxy, $C_{1-6}$ haloalkyl, $C_{3-7}$ cycloalkyl, $C_{3-7}$ cycloalkylalkyl, aryl, heteroaryl, aralkyl, heteroaralkyl, heterocyclylalkyl, heterocyclyl, cyano, halo, oxo, —OH, —$OCF_3$, —$OCHF_2$, —$SO_2$—$C_{1-6}$ alkyl, —$NO_2$, —$N(R^7)$—C(O)—$C_{1-6}$ alkyl, —C(O)N $(R^7)_2$, —$N(R^7)S(O)_{1-2}$—$C_{1-6}$ alkyl, —$S(O)_2N(R^7)_2$, —$N(R^7)_2$, —$C_{1-6}$alkylene-$N(R^7)_2$, wherein said alkyl, $C_{1-6}$ alkoxy, —O—$C_{1-6}$ alkylene$C_{1-6}$alkoxy, $C_{1-6}$ thioalkoxy, $C_{1-6}$ haloalkyl, $C_{3-7}$ cycloalkyl, $C_{3-7}$ cycloalkylalkyl, aryl, heteroaryl, aralkyl, heteroaralkyl, heterocyclylalkyl, heterocyclyl, —$SO_2$—$C_{1-6}$alkyl, —$NO_2$, —$N(R^7)$—C(O)—$C_{1-6}$ alkyl, —$C(O)N(R^7)_2$, —$N(R^7)S$ $(O)_{1-2}$—$C_{1-6}$alkyl, —$S(O)_2N(R^7)_2$, —$N(R^7)_2$, or —$C_{1-6}$ alkylene-$N(R^7)_2$ is optionally substituted with 0-3 occurrences of $R^8$; or two adjacent $R^5$ moieties, taken together with the atoms to which they are attached form a cycloalkyl or heterocyclyl;

each $R^6$ is independently hydrogen, fluoro, $C_{1-6}$ alkyl, —OH, —$NH_2$, —$NH(CH_3)$, —$N(CH_3)_2$, or $C_{1-6}$ alkoxy;

each $R^7$ is independently hydrogen or $C_{1-6}$ alkyl;

each $R^8$ is independently halo, $C_{1-6}$ alkyl, $C_{1-6}$ haloalkyl, —OH, —$N(R^7)_2$, or $C_{1-6}$ alkoxy, —O—$C_{1-6}$alkylene$C_{1-6}$ alkoxy, CN, $NO_2$, —$N(R^7)$—C(O)—$C_{1-6}$ alkyl, —C(O) $N(R^7)_2$, —$N(R^7)S(O)_{1-2}C_{1-6}$ alkyl, or —$S(O)_2N(R^7)_2$;

m is 0, 1, or 2;

n is 0, 1, or 2;

o is 1, 2 or 3; and p is 1, 2 or 3; provided that (1) when X is unsubstituted cyclopropyl, $R^1$ and $R^2$ are not both NH-phenyl; and (2) X is other than substituted cyclobutyl or substituted cyclopentyl.

In certain embodiments, W is —S—, each Y is —N═, and each Z is —N═.

In certain embodiments, o is 1 and p is 1.

In certain embodiments, m is 0 and n is 0. Alternatively, m and n can each be 1.

In certain embodiments, $R^1$ and $R^2$ are different. Alternatively, $R^1$ and $R^2$ can be the same.

In certain embodiments, $R^1$ and $R^2$ are each —$N(R^3)$—C(O)—O—$R^4$, wherein each $R^3$ is hydrogen and each $R^4$ is aralkyl or heteroaralkyl, each of which is substituted with 0-3 occurrences of $R^5$.

In certain embodiments, the compound having the structure of Formula (V) is a compound having the structure of Formula (Va):

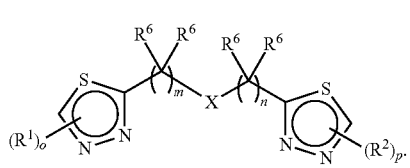

In certain embodiments, the compound having the structure of Formula (V) is a compound having the structure of Formula (Vb):

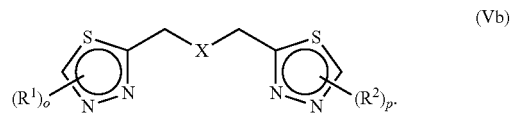

In certain embodiments, the compound having the structure of Formula (V) has the structure of formula (Vc):

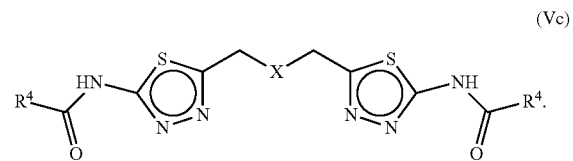

In certain embodiments, the compound of formula (V) is a compound of formula (VI):

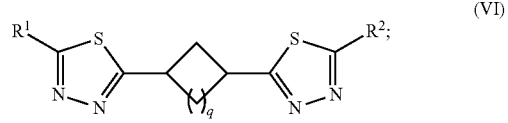

wherein q is 0, 1, 2, 3, or 4.

In certain embodiments, the compound of formula (V) has the structure of formula (VIa):

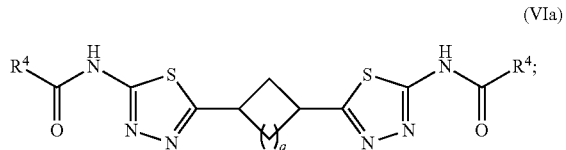

wherein q is 0, 1, 2, 3, or 4.

In certain embodiments, the compound of formula (V) has the structure of formula (VIb):

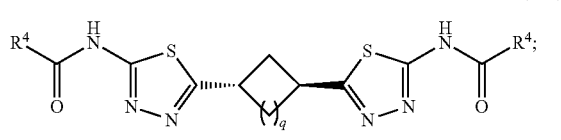

wherein q is 0, 1, 2, 3, or 4.

In certain embodiments, the compound of formula (V) has the structure of formula (VIc):

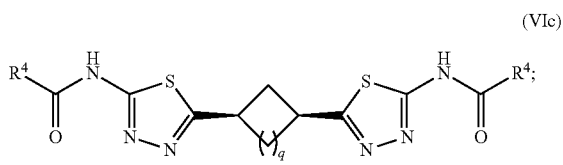

(VIc)

wherein q is 0, 1, 2, 3, or 4.

Compounds of formulas IV to VI are shown in Appendix A. In certain embodiments, the compound is selected from any one of the compounds disclosed in Appendix A.

In certain embodiments, compounds of the invention may be prodrugs of the compounds of any of formulae I-VI, e.g., wherein a hydroxyl in the parent compound is presented as an ester or a carbonate, or carboxylic acid present in the parent compound is presented as an ester. In certain such embodiments, the prodrug is metabolized to the active parent compound in vivo (e.g., the ester is hydrolyzed to the corresponding hydroxyl, or carboxylic acid).

In certain embodiments, compounds of the invention may be racemic. In certain embodiments, compounds of the invention may be enriched in one enantiomer. For example, a compound of the invention may have greater than 30% ee, 40% ee, 50% ee, 60% ee, 70% ee, 80% ee, 90% ee, or even 95% or greater ee. In certain embodiments, compounds of the invention may have more than one stereocenter. In certain such embodiments, compounds of the invention may be enriched in one or more diastereomer. For example, a compound of the invention may have greater than 30% de, 40% de, 50% de, 60% de, 70% de, 80% de, 90% de, or even 95% or greater de.

In certain embodiments, the present invention relates to methods of treating or preventing lung cancer with a compound of any one of formulae I-III, or a pharmaceutically acceptable salt thereof. In certain embodiments, the present invention relates to methods of treating or preventing lung cancer with a compound of any of formulae IV-VI (e.g., a compound of any of formulae (IV), (IVa), (IVb), (V), (Va), (Vb), (Vc), (VI), (VIa), (VIb), or (VIc)), or a pharmaceutically acceptable salt thereof. In certain embodiments, the therapeutic preparation may be enriched to provide predominantly one enantiomer of a compound (e.g., of formulae I, II, or III, or of formulae IV-VI). An enantiomerically enriched mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, the therapeutic preparation may be enriched to provide predominantly one diastereomer of a compound (e.g., of formulae I-III, or of formulae IV-VI). A diastereomerically enriched mixture may comprise, for example, at least 60 mol percent of one diastereomer, or more preferably at least 75, 90, 95, or even 99 mol percent.

In certain embodiments, the present invention provides a pharmaceutical preparation suitable for use in a human patient in the treatment of lung cancer, comprising an effective amount of any of the compounds shown above (e.g., a compound of any of formulae I-III, or any of formulae IV-VI), and one or more pharmaceutically acceptable excipients. In certain embodiments, the pharmaceutical preparations may be for use in treating or preventing a condition or disease as described herein. In certain embodiments, the pharmaceutical preparations have a low enough pyrogen activity to be suitable for use in a human patient.

Compounds of any of the above structures may be used in the manufacture of medicaments for the treatment of any diseases or conditions disclosed herein.

In certain embodiments of the invention relating to methods of identifying a lung cancer patient that may benefit from treatment with a glutaminase inhibitor, the glutaminase inhibitor for administration to the patient can be any of the compounds described herein, e.g., a compound of any one of formulae I-III, or any of formulae IV-VI.

II. Uses of Enzyme Inhibitors

Glutamine plays an important role as a carrier of nitrogen, carbon, and energy. It is used for hepatic urea synthesis, for renal ammoniagenesis, for gluconeogenesis, and as respiratory fuel for many cells. The conversion of glutamine into glutamate is initiated by the mitochondrial enzyme, glutaminase ("GLS"). There are two major forms of the enzyme, K-type and L-type, which are distinguished by their Km values for glutamine and response to glutamate, wherein the Km value, or Michaelis constant, is the concentration of substrate required to reach half the maximal velocity. The L-type, also known as "liver-type" or GLS2, has a high Km for glutamine and is glutamate resistant. The K-type, also known as "kidney-type" or GLS1 or "KGA", has a low Km for glutamine and is inhibited by glutamate. An alternative splice form of GLS1, referred to as glutaminase C or "GAC", has recently been identified and has similar activity characteristics of GLS1. In certain embodiments, the compounds may selectively inhibit GLS1, GLS2 and GAC. In certain preferred embodiments, the compounds selectively inhibit GLS1 and GAC.

In addition to serving as the basic building blocks of protein synthesis, amino acids have been shown to contribute to many processes critical for growing and dividing cells, and this is particularly true for cancer cells. Nearly all definitions of cancer include reference to dysregulated proliferation. Numerous studies on glutamine metabolism in cancer indicate that many tumors are avid glutamine consumers. Certain embodiments of the invention relate to the use of the compounds described herein for the treatment of lung cancer.

While many cancer cells depend on exogenous glutamine for survival, the degree of glutamine dependence among tumor cell subtypes may make a population of cells more susceptible to the reduction of glutamine.

In some instances, oncogenic mutations promote glutamine metabolism. In certain embodiments, the presence of such a mutation can indicate the susceptibility of a particular cancer type to treatment with a glutaminase inhibitor. For example, certain non-small cell lung cancers can be characterized by a mutation in the gene encoding KRAS or the gene encoding EGFR, and in certain embodiments, these cancers are particularly sensitive to treatment with a glutaminase inhibitor.

Therefore, in certain embodiments, the invention relates to methods for treating lung cancer in a patient, the method comprising: a) determining whether the lung cancer is characteritized by a KRAS mutation or EGFR mutation; and b) if the lung cancer is characterized by a KRAS mutation or EGFR mutation, then administering to the patient an effective amount of a glutaminase inhibitor.

In certain other embodiments, the invention relates to methods of identifying a lung cancer patient that may benefit from treatment with a glutaminase inhibitor, comprising determining whether a lung cancer cell of the patient has a KRAS mutation or EGFR mutation, wherein a KRAS mutation or EGFR mutation in the lung cancer cells of the patient indicates that the patient may benefit from treatment with a glutaminase inhibitor.

In some embodiments, the KRAS mutation or EGFR mutation results in a different amino acid sequence of the KRAS or EGFR (e.g., relative to a wild-type (predominant) form). In other embodiments, the KRAS mutation or EGFR mutation results in a different level of expression or activity of the KRAS or EGFR (e.g., relative to a wild-type cell of a similar type). A KRAS mutation can include, for example, amino acid substitutions in KRAS at, for example, the 12-, 13-, 19-, 59- or 61-position. Exemplary KRAS mutations include G12S, G12C, L19F, G13V, and G13D. An EGFR mutation can include, for example, a mutation (e.g., a deletion) in the gene (e.g., in the kinase domain). Exemplary mutations in the gene include EGFR exon 19 deletion. An EGFR mutation can also include an amino acid substitution in in EGFR. Exemplary EGFR mutations include L858R and T790M.

The mutation can be detected either directly, e.g., by genomic analysis or genetic probing, or indirectly, e.g., by measuring relative levels of gene products to detect abnormal expression levels. Enzyme expression levels can be determined in multiple manners, and quantitation is relative, based on a specific standard for each assay. The results can be used to provide a genetic profile, where the levels of certain genes, mRNAs or resulting expression products form a signature pattern that can used to characterize cell types.

Methods for detecting the presence of a mutation in a gene of interest are known in the art. Suitable methods for determining whether or not a particular mutation in a gene exists include, e.g., Southern blot (see, e.g., Sambrook et al. (supra)), real-time PCR analysis (see, e.g., Oliver et al. (2000) *J Mol Diagnostics* 2(4):202-208), nucleic acid array analysis, allele-specific PCR (e.g., quantitative allele-specific PCR), pyrosequencing, DNA sequencing (e.g., Sanger chemistry sequencing), or through the use of molecular beacons (e.g., Tyagi et al. (1998) *Nat Biotechnol* 16:49-53; Abravaya et al. (2003) *Clin Chem Lab Med* 41:468-474; and Mullah et al. (1999) *Nucleos Nucleot* 18:1311-1312, the disclosures of each of which are incorporated herein by reference in their entirety).

To determine a genotype using Southern blot analysis, first, genomic DNA is isolated from a biological sample from a subject (e.g., a human patient), e.g., using a detergent (e.g., NP40 and/or sodium dodecyl sulfate), and proteinase K digestion, followed by sodium chloride extraction, and ethanol wash of the extracted DNA. Regions of DNA containing the mutation of interest can be amplified using PCR. The amplicons can be subjected to gel-electrophoresis to separate the nucleic acids by size, and then transferred to a solid support such as a nitrocellulose membrane. To detect the presence of a gene mutation in the biological sample, the solid support containing the amplicons can be contacted with a detectably-labeled, complementary oligonucleotide probe that specifically hybridizes to a nucleic acid containing a mutation under appropriate stringency conditions. The binding of the probe to an amplicon indicates the presence of the corresponding nucleic acid containing the mutation in the biological sample.

In another example, a particular genotype can also be detected using nucleic acid arrays. For example, genomic DNA isolated from a biological sample can be amplified using PCR as described above. The amplicons can be detectably-labeled during the PCR amplification process (e.g., using one or more detectably labeled deoxynucleotides (dNTPs)) or subsequent to the amplification process using a variety of chemical or enzymatic techniques such as nick-translation. Following amplification and labeling, the detectably-labeled-amplicons are then contacted to a plurality of polynucleotide probe sets, each set containing one or more of a polynucleotide (e.g., an oligonucleotide) probe specific for (and capable of binding to) a corresponding amplicon, and where the plurality contains many probe sets each corresponding to a different amplicon. Generally, the probe sets are bound to a solid support and the position of each probe set is predetermined on the solid support. The binding of a detectably-labeled amplicon to a corresponding probe of a probe set indicates the presence of the gene mutation so amplified in the biological sample. Suitable conditions and methods for detecting gene mutations using nucleic acid arrays are further described in, e.g., Lamy et al. (2006) *Nucleic Acids Research* 34(14): e100; European Patent Application Publication No. 1234058; U.S. Patent Application Publication Nos. 20060008823 and 20030059813; and U.S. Pat. No. 6,410,231; the disclosures of each of which are incorporated herein by reference in their entirety.

Any of the methods of detecting a gene mutation can, optionally, be performed in formats that allow for rapid preparation, processing, and analysis of multiple samples.

RAS proteins are small GTPases that cycle between inactive guanosine diphosphate (GDP)-bound and active guanosine triphosphate (GTP)-bound forms. RAS proteins are central mediators downstream of growth factor receptor signaling and therefore are critical for cell proliferation, survival, and differentiation. Three different human RAS genes have been identified: KRAS (homologous to the oncogene from the Kirsten rat sarcoma virus), HRAS (homologous to the oncogene from the Harvey rat sarcoma virus), and NRAS (first isolated from a human neuroblastoma). Although the different RAS genes are highly homologous, they appear to be functionally distinct.

RAS has been implicated in the pathogenesis of several cancers. In fact, approximately 15-25% of patients with lung adenocarcinoma have tumor-associated KRAS mutations. The most common mutations substitute an amino acid at positions 12, 13, 59 or 61. The result is a sustained proliferation signal (i.e., constitutive activation) within the cell. These activating mutations within the RAS gene result in constitutive activation of the RAS GTPase, even in the absence of growth factor signaling. Another type of mutation giving rise to increased RAS activity is an amplification of the gene encoding RAS (chromosome 12p12), resulting in increased levels of RAS expression. Therefore, in certain embodiments, the mutation in KRAS or in EGFR is an activating mutation. Notably, KRAS mutations are particularly common in colon cancer, lung cancer, and pancreatic cancer. See Riely, et al. ("KRAS Mutations in NSCLC" Proceedings of the American Thoracic Society, 2009, Vol. 6, 201-205) for a review of KRAS mutations in non-small cell lung cancer.

Cells expressing oncogenic KRAS exhibit increased utilization of glutamine. Accordingly, in certain embodiments, cancers exhibiting a KRAS mutation are particularly sensitive to treatment with a glutaminase inhibitor. In certain embodiments, the cancer cells have a mutated gene encoding KRAS. In certain embodiments, the mutation results in an expression level of KRAS that is different from normal lung cells. In certain embodiments, the mutation results in a level of constitutive activity of KRAS that is different from normal lung cells. In certain embodiments, the mutation results in overexpression or increased constitutive activity of KRAS, as compared to normal lung cells. In certain embodiments, the mutation includes a change to the sequence of KRAS.

EGFR (Epidermal growth factor receptor) is the cell-surface receptor for members of the epidermal growth factor (EGF) family of extracellular protein ligands. Mutations associated with EGFR overexpression have been associated with certain cancers, including lung cancers. Approximately 10% of non-small cell lung cancer patients in the United States, and approximately 35% of nscic patients in East Asia have tumors associated with an EGFR mutation. Typically the EGFR mutation occurs in a region of the gene that encodes a portion of the EGFR kinase domain. Usually, such mutations result in gene amplification, increased kinase activity of EGFR, and hyperactivation of downstream pro-survival signaling pathways. See A. Kuykendall, et al. ("Advanced EGFR Mutation-Positive Non-Small Cell Lung Cancer: Case Report, Literature Review, and Treatment Recommendations" Cancer Control, 2014, V. 21, No. 1, 67-73) for a review about nscic and EGFR mutations.

In certain embodiments of the methods of the invention, the cancer cells have a mutated gene encoding EGFR. In certain embodiments, the mutation results in an expression level of EGFR that is different from normal lung cells. In certain embodiments, the mutation results in a level of constitutive activity of EGFR that is different from normal lung cells. In certain embodiments, the mutation results in overexpression or increased constitutive activity of EGFR, as compared to normal lung cells. In certain embodiments, the mutation includes a change to the sequence of EGFR.

In certain embodiments of the methods of the invention, the mutation is an amplification of the gene encoding KRAS or EGFR.

In certain embodiments of the methods of the invention, the mutation is a deletion of the gene encoding KRAS or EGFR.

In certain embodiments of the methods of the invention, the mutation is an insertion in the gene encoding KRAS or EGFR.

In certain embodiments, the mutation is a point mutation resulting in a change of at least one amino acid residue in the amino acid sequence of KRAS or EGFR.

In certain embodiments, the cancer is associated with tissue of the bladder, bone marrow, breast, colon, kidney, liver, lung, ovary, pancreas, prostate, skin or thyroid. In certain preferred embodiments, the cancer is associated with tissue of the lung. In certain such embodiments, the lung cancer is non-small cell lung carcinoma (nscic).

In certain embodiments, the nscic is lung adenocarcinoma.

In certain embodiments, the method of treating lung cancer further comprises conjointly administering radiation therapy.

In some embodiments, the method of treating lung cancer further comprises conjointly administering one or more additional chemotherapeutic agents. Chemotherapeutic agents that may be conjointly administered with compounds of the invention include: ABT-263, aminoglutethimide, amsacrine, anastrozole, asparaginase, AZD5363, *Bacillus* Calmette-Guérin vaccine (bcg), bicalutamide, bleomycin, bortezomib, buserelin, busulfan, campothecin, capecitabine, carboplatin, carfilzomib, carmustine, chlorambucil, chloroquine, cisplatin, cladribine, clodronate, cobimetinib, colchicine, cyclophosphamide, cyproterone, cytarabine, dacarbazine, dactinomycin, daunorubicin, demethoxyviridin, dexamethasone, dichloroacetate, dienestrol, diethylstilbestrol, docetaxel, doxorubicin, epirubicin, estradiol, estramustine, etoposide, everolimus, exemestane, filgrastim, fludarabine, fludrocortisone, fluorouracil and 5-fluorouracil, fluoxymesterone, flutamide, gemcitabine, genistein, goserelin, hydroxyurea, idarubicin, ifosfamide, imatinib, interferon, irinotecan, lenalidomide, letrozole, leucovorin, leuprolide, levamisole, lomustine, lonidamine, mechlorethamine, medroxyprogesterone, megestrol, melphalan, mercaptopurine, mesna, metformin, methotrexate, miltefosine, mitomycin, mitotane, mitoxantrone, MK2206, nilutamide, nocodazole, octreotide, oxaliplatin, olaparib, paclitaxel, pamidronate, pentostatin, pazopanib, perifosine, PF-04691502, plicamycin, pomalidomide, porfimer, procarbazine, raltitrexed, rituximab, romidepsin, rucaparib, selumetinib, sorafenib, streptozocin, sunitinib, suramin, talazoparib, tamoxifen, temozolomide, temsirolimus, teniposide, testosterone, thalidomide, thioguanine, thiotepa, titanocene dichloride, topotecan, trametinib, trastuzumab, tretinoin, veliparib, vinblastine, vincristine, vindesine, vinorelbine, and vorinostat (SAHA). For example, chemotherapeutic agents that may be conjointly administered with compounds of the invention include: aminoglutethimide, amsacrine, anastrozole, asparaginase, bcg, bicalutamide, bleomycin, bortezomib, buserelin, busulfan, campothecin, capecitabine, carboplatin, carfilzomib, carmustine, chlorambucil, chloroquine, cisplatin, cladribine, clodronate, colchicine, cyclophosphamide, cyproterone, cytarabine, dacarbazine, dactinomycin, daunorubicin, demethoxyviridin, dichloroacetate, dienestrol, diethylstilbestrol, docetaxel, doxorubicin, epirubicin, estradiol, estramustine, etoposide, everolimus, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, lenalidomide, letrozole, leucovorin, leuprolide, levamisole, lomustine, lonidamine, mechlorethamine, medroxyprogesterone, megestrol, melphalan, mercaptopurine, mesna, metformin, methotrexate, mitomycin, mitotane, mitoxantrone, nilutamide, nocodazole, octreotide, oxaliplatin, paclitaxel, pamidronate, pentostatin, perifosine, plicamycin, pomalidomide, porfimer, procarbazine, raltitrexed, rituximab, sorafenib, streptozocin, sunitinib, suramin, tamoxifen, temozolomide, temsirolimus, teniposide, testosterone, thalidomide, thioguanine, thiotepa, titanocene dichloride, topotecan, trastuzumab, tretinoin, vinblastine, vincristine, vindesine, and vinorelbine. In other embodiments, chemotherapeutic agents that may be conjointly administered with compounds of the invention include: ABT-263, dexamethasone, 5-fluorouracil, PF-04691502, romidepsin, and vorinostat (SAHA). In certain embodiments of the methods of the invention described herein, the chemotherapeutic agent conjointly administered with compounds of the invention is a taxane chemotherapeutic agent, such as paclitaxel or docetaxel. In certain embodiments of the methods of the invention described herein, the chemotherapeutic agent conjointly administered with compounds of the invention is doxorubicin. In certain embodiments of the methods of the invention described herein, a compound of the invention is administered conjointly with a taxane chemotherapeutic agent (e.g., paclitaxel) and doxorubicin.

In certain embodiments, the methods include conjoint administration with a chemotherapeutic agent selected from afatinib dimaleate, bevacizumab, carboplatin, ceritinib, cisplatin, crizotinib, docetaxel, doxorubicin hydrochloride; erlotinib hydrochloride, etoposide, gefitinib, gemcitabine hydrochloride, mechlorethamine hydrochloride, methotrexate, paclitaxel, pemetrexed disodium, ramucirumab, topotecan hydrochloride, vinorelbine tartrate.

In certain exemplary embodiments, the methods include conjoint administration of compound CB-839 (i.e., a compound of formula (III)) with selumetinib. In certain such embodiments, the combination of CB-839 and selumetinib provides improved therapeutic efficacy in treating a cancer as compared to the therapeutic efficacy of each compound individually.

Many combination therapies have been developed for the treatment of cancer. In certain embodiments, compounds of the invention may be conjointly administered with a combination therapy. Examples of combination therapies with which compounds of the invention may be conjointly administered are included in Table 2.

TABLE 2

Exemplary combinatorial therapies for the treatment of cancer.

| Name | Therapeutic agents |
|---|---|
| ABV | Doxorubicin, Bleomycin, Vinblastine |
| ABVD | Doxorubicin, Bleomycin, Vinblastine, Dacarbazine |
| AC (Breast) | Doxorubicin, Cyclophosphamide |
| AC (Sarcoma) | Doxorubicin, Cisplatin |
| AC (Neuroblastoma) | Cyclophosphamide, Doxorubicin |
| ACE | Cyclophosphamide, Doxorubicin, Etoposide |
| ACe | Cyclophosphamide, Doxorubicin |
| AD | Doxorubicin, Dacarbazine |
| AP | Doxorubicin, Cisplatin |
| ARAC-DNR | Cytarabine, Daunorubicin |
| B-CAVe | Bleomycin, Lomustine, Doxorubicin, Vinblastine |
| BCVPP | Carmustine, Cyclophosphamide, Vinblastine, Procarbazine, Prednisone |
| BEACOPP | Bleomycin, Etoposide, Doxorubicin, Cyclophosphamide, Vincristine, Procarbazine, Prednisone, Filgrastim |
| BEP | Bleomycin, Etoposide, Cisplatin |
| BIP | Bleomycin, Cisplatin, Ifosfamide, Mesna |
| BOMP | Bleomycin, Vincristine, Cisplatin, Mitomycin |
| CA | Cytarabine, Asparaginase |
| CABO | Cisplatin, Methotrexate, Bleomycin, Vincristine |
| CAF | Cyclophosphamide, Doxorubicin, Fluorouracil |
| CAL-G | Cyclophosphamide, Daunorubicin, Vincristine, Prednisone, Asparaginase |
| CAMP | Cyclophosphamide, Doxorubicin, Methotrexate, Procarbazine |
| CAP | Cyclophosphamide, Doxorubicin, Cisplatin |
| CaT | Carboplatin, Paclitaxel |
| CAV | Cyclophosphamide, Doxorubicin, Vincristine |
| CAVE ADD | CAV and Etoposide |
| CA-VP16 | Cyclophosphamide, Doxorubicin, Etoposide |
| CC | Cyclophosphamide, Carboplatin |
| CDDP/VP-16 | Cisplatin, Etoposide |
| CEF | Cyclophosphamide, Epirubicin, Fluorouracil |
| CEPP(B) | Cyclophosphamide, Etoposide, Prednisone, with or without/Bleomycin |
| CEV | Cyclophosphamide, Etoposide, Vincristine |
| CF | Cisplatin, Fluorouracil or Carboplatin Fluorouracil |
| CHAP | Cyclophosphamide or Cyclophosphamide, Altretamine, Doxorubicin, Cisplatin |
| ChlVPP | Chlorambucil, Vinblastine, Procarbazine, Prednisone |
| CHOP | Cyclophosphamide, Doxorubicin, Vincristine, Prednisone |
| CHOP-BLEO | Add Bleomycin to CHOP |
| CISCA | Cyclophosphamide, Doxorubicin, Cisplatin |
| CLD-BOMP | Bleomycin, Cisplatin, Vincristine, Mitomycin |
| CMF | Methotrexate, Fluorouracil, Cyclophosphamide |
| CMFP | Cyclophosphamide, Methotrexate, Fluorouracil, Prednisone |
| CMFVP | Cyclophosphamide, Methotrexate, Fluorouracil, Vincristine, Prednisone |
| CMV | Cisplatin, Methotrexate, Vinblastine |
| CNF | Cyclophosphamide, Mitoxantrone, Fluorouracil |
| CNOP | Cyclophosphamide, Mitoxantrone, Vincristine, Prednisone |
| COB | Cisplatin, Vincristine, Bleomycin |
| CODE | Cisplatin, Vincristine, Doxorubicin, Etoposide |
| COMLA | Cyclophosphamide, Vincristine, Methotrexate, Leucovorin, Cytarabine |
| COMP | Cyclophosphamide, Vincristine, Methotrexate, Prednisone |
| Cooper Regimen | Cyclophosphamide, Methotrexate, Fluorouracil, Vincristine, Prednisone |
| COP | Cyclophosphamide, Vincristine, Prednisone |
| COPE | Cyclophosphamide, Vincristine, Cisplatin, Etoposide |
| COPP | Cyclophosphamide, Vincristine, Procarbazine, Prednisone |
| CP(Chronic lymphocytic leukemia) | Chlorambucil, Prednisone |

TABLE 2-continued

Exemplary combinatorial therapies for the treatment of cancer.

| Name | Therapeutic agents |
|---|---|
| CP (Ovarian Cancer) | Cyclophosphamide, Cisplatin |
| CT | Cisplatin, Paclitaxel |
| CVD | Cisplatin, Vinblastine, Dacarbazine |
| CVI | Carboplatin, Etoposide, Ifosfamide, Mesna |
| CVP | Cyclophosphamide, Vincristine, Prednisome |
| CVPP | Lomustine, Procarbazine, Prednisone |
| CYVADIC | Cyclophosphamide, Vincristine, Doxorubicin, Dacarbazine |
| DA | Daunorubicin, Cytarabine |
| DAT | Daunorubicin, Cytarabine, Thioguanine |
| DAV | Daunorubicin, Cytarabine, Etoposide |
| DCT | Daunorubicin, Cytarabine, Thioguanine |
| DHAP | Cisplatin, Cytarabine, Dexamethasone |
| DI | Doxorubicin, Ifosfamide |
| DTIC/Tamoxifen | Dacarbazine, Tamoxifen |
| DVP | Daunorubicin, Vincristine, Prednisone |
| EAP | Etoposide, Doxorubicin, Cisplatin |
| EC | Etoposide, Carboplatin |
| EFP | Etoposie, Fluorouracil, Cisplatin |
| ELF | Etoposide, Leucovorin, Fluorouracil |
| EMA 86 | Mitoxantrone, Etoposide, Cytarabine |
| EP | Etoposide, Cisplatin |
| EVA | Etoposide, Vinblastine |
| FAC | Fluorouracil, Doxorubicin, Cyclophosphamide |
| FAM | Fluorouracil, Doxorubicin, Mitomycin |
| FAMTX | Methotrexate, Leucovorin, Doxorubicin |
| FAP | Fluorouracil, Doxorubicin, Cisplatin |
| F-CL | Fluorouracil, Leucovorin |
| FEC | Fluorouracil, Cyclophosphamide, Epirubicin |
| FED | Fluorouracil, Etoposide, Cisplatin |
| FL | Flutamide, Leuprolide |
| FZ | Flutamide, Goserelin acetate implant |
| HDMTX | Methotrexate, Leucovorin |
| Hexa-CAF | Altretamine, Cyclophosphamide, Methotrexate, Fluorouracil |
| ICE-T | Ifosfamide, Carboplatin, Etoposide, Paclitaxel, Mesna |
| IDMTX/6-MP | Methotrexate, Mercaptopurine, Leucovorin |
| IE | Ifosfamide, Etoposie, Mesna |
| IfoVP | Ifosfamide, Etoposide, Mesna |
| IPA | Ifosfamide, Cisplatin, Doxorubicin |
| M-2 | Vincristine, Carmustine, Cyclophosphamide, Prednisone, Melphalan |
| MAC-III | Methotrexate, Leucovorin, Dactinomycin, Cyclophosphamide |
| MACC | Methotrexate, Doxorubicin, Cyclophosphamide, Lomustine |
| MACOP-B | Methotrexate, Leucovorin, Doxorubicin, Cyclophosphamide, Vincristine, Bleomycin, Prednisone |
| MAID | Mesna, Doxorubicin, Ifosfamide, Dacarbazine |
| m-BACOD | Bleomycin, Doxorubicin, Cyclophosphamide, Vincristine, Dexamethasone, Methotrexate, Leucovorin |
| MBC | Methotrexate, Bleomycin, Cisplatin |
| MC | Mitoxantrone, Cytarabine |
| MF | Methotrexate, Fluorouracil, Leucovorin |
| MICE | Ifosfamide, Carboplatin, Etoposide, Mesna |
| MINE | Mesna, Ifosfamide, Mitoxantrone, Etoposide |
| mini-BEAM | Carmustine, Etoposide, Cytarabine, Melphalan |
| MOBP | Bleomycin, Vincristine, Cisplatin, Mitomycin |
| MOP | Mechlorethamine, Vincristine, Procarbazine |
| MOPP | Mechlorethamine, Vincristine, Procarbazine, Prednisone |
| MOPP/ABV | Mechlorethamine, Vincristine, Procarbazine, Prednisone, Doxorubicin, Bleomycin, Vinblastine |
| MP (multiple myeloma) | Melphalan, Prednisone |
| MP (prostate cancer) | Mitoxantrone, Prednisone |
| MTX/6-MO | Methotrexate, Mercaptopurine |
| MTX/6-MP/VP | Methotrexate, Mercaptopurine, Vincristine, Prednisone |
| MTX-CDDPAdr | Methotrexate, Leucovorin, Cisplatin, Doxorubicin |
| MV (breast cancer) | Mitomycin, Vinblastine |
| MV (acute myelocytic leukemia) | Mitoxantrone, Etoposide |
| M-VAC Methotrexate | Vinblastine, Doxorubicin, Cisplatin |
| MVP Mitomycin | Vinblastine, Cisplatin |
| MVPP | Mechlorethamine, Vinblastine, Procarbazine, Prednisone |
| NFL | Mitoxantrone, Fluorouracil, Leucovorin |
| NOVP | Mitoxantrone, Vinblastine, Vincristine |

TABLE 2-continued

Exemplary combinatorial therapies for the treatment of cancer.

| Name | Therapeutic agents |
|---|---|
| OPA | Vincristine, Prednisone, Doxorubicin |
| OPPA | Add Procarbazine to OPA. |
| PAC | Cisplatin, Doxorubicin |
| PAC-I | Cisplatin, Doxorubicin, Cyclophosphamide |
| PA-CI | Cisplatin, Doxorubicin |
| PC | Paclitaxel, Carboplatin or Paclitaxel, Cisplatin |
| PCV | Lomustine, Procarbazine, Vincristine |
| PE | Paclitaxel, Estramustine |
| PFL | Cisplatin, Fluorouracil, Leucovorin |
| POC | Prednisone, Vincristine, Lomustine |
| ProMACE | Prednisone, Methotrexate, Leucovorin, Doxorubicin, Cyclophosphamide, Etoposide |
| ProMACE/cytaBOM | Prednisone, Doxorubicin, Cyclophosphamide, Etoposide, Cytarabine, Bleomycin, Vincristine, Methotrexate, Leucovorin, Cotrimoxazole |
| PRoMACE/MOPP | Prednisone, Doxorubicin, Cyclophosphamide, Etoposide, Mechlorethamine, Vincristine, Procarbazine, Methotrexate, Leucovorin |
| Pt/VM | Cisplatin, Teniposide |
| PVA | Prednisone, Vincristine, Asparaginase |
| PVB | Cisplatin, Vinblastine, Bleomycin |
| PVDA | Prednisone, Vincristine, Daunorubicin, Asparaginase |
| SMF | Streptozocin, Mitomycin, Fluorouracil |
| TAD | Mechlorethamine, Doxorubicin, Vinblastine, Vincristine, Bleomycin, Etoposide, Prednisone |
| TCF | Paclitaxel, Cisplatin, Fluorouracil |
| TIP | Paclitaxel, Ifosfamide, Mesna, Cisplatin |
| TTT | Methotrexate, Cytarabine, Hydrocortisone |
| Topo/CTX | Cyclophosphamide, Topotecan, Mesna |
| VAB-6 | Cyclophosphamide, Dactinomycin, Vinblastine, Cisplatin, Bleomycin |
| VAC | Vincristine, Dactinomycin, Cyclophosphamide |
| VACAdr | Vincristine, Cyclophosphamide, Doxorubicin, Dactinomycin, Vincristine |
| VAD | Vincristine, Doxorubicin, Dexamethasone |
| VATH | Vinblastine, Doxorubicin, Thiotepa, Flouxymesterone |
| VBAP | Vincristine, Carmustine, Doxorubicin, Prednisone |
| VBCMP | Vincristine, Carmustine, Melphalan, Cyclophosphamide, Prednisone |
| VC | Vinorelbine, Cisplatin |
| VCAP | Vincristine, Cyclophosphamide, Doxorubicin, Prednisone |
| VD | Vinorelbine, Doxorubicin |
| VelP | Vinblastine, Cisplatin, Ifosfamide, Mesna |
| VIP | Etoposide, Cisplatin, Ifosfamide, Mesna |
| VM | Mitomycin, Vinblastine |
| VMCP | Vincristine, Melphalan, Cyclophosphamide, Prednisone |
| VP | Etoposide, Cisplatin |
| V-TAD | Etoposide, Thioguanine, Daunorubicin, Cytarabine |
| 5 + 2 | Cytarabine, Daunorubicin, Mitoxantrone |
| 7 + 3 | Cytarabine with/, Daunorubicin or Idarubicin or Mitoxantrone |
| "8 in 1" | Methylprednisolone, Vincristine, Lomustine, Procarbazine, Hydroxyurea, Cisplatin, Cytarabine, Dacarbazine |

In certain embodiments, the compounds of the invention may be conjointly administered with an immunomodulatory agent. Examples of immunomodulatory agents with which the compounds of the invention may be administered in a combination therapy include granulocyte colony-stimulating factor (G-CSF), interferons, imiquimod, IL-2, IL-7, IL-12, various chemokines, synthetic cytosine phosphate-guanosine (CpG) oligodeoxynucleotides, glucans, and synthetic small molecules such as apremilast, CC-122, CC-11006, CC-10015, lenalidomide, pomalidomide, and thalidomide. In certain embodiments, the immunomodulatory agent is a thalidomide analog, such as those disclosed in WO 1999/46258, WO 2008/033567, WO 2010/093434, WO 2010/093605, WO 2011/100380, and WO 2012/097116.

In certain embodiments, the compounds of the invention may be conjointly administered with an anticancer agent selected from an enzyme inhibitor (such as a kinase inhibitor), a mitotic inhibitor, a DNA-modifying agent, and a cytidine analog. Examples of anticancer agents with which the compounds of the invention may be administered in a combination therapy include microtubule assembly inhibitors, AKT inhibitors, mTOR inhibitors, MEK inhibitors, RTK inhibitors, ATM inhibitors, ATR inhibitors, PI3K inhibitors, EGFR inhibitors, B-Raf inhibitors, C-kit inhibitors, DNA cross-linking agents, DNA intercalating agents, and cytidine analogs. In certain embodiments, the anticancer agent vincristine, carboplatin, cisplatin, gemcitabine, MK2206, everolimus, trametinib, sunitinib, sorafenib, BEZ235, paclitaxel, docetaxel, erlotinib, selumetinib, sirolimus, trametinib, temsirolimus, pazopanib, or GSK1120212.

In certain embodiments, the compounds of the invention are coadministered with one or more of lenalidomide, pomalidomide, and dexamethasone in the treatment of lung cancer.

In certain embodiments, conjoint administration of glutaminase inhibitors with one or more additional therapeutic agent(s) (e.g., one or more additional chemotherapeutic agent(s)) provides improved efficacy relative to each individual administration of the glutaminase inhibitor (e.g., a compound of any of Formulae I-III or IV-VI) or the one or more additional therapeutic agent(s). In certain such embodiments, the conjoint administration provides an additive effect, wherein an additive effect refers to the sum of each of the effects of individual administration of the glutaminase inhibitor and the one or more additional therapeutic agent(s). In certain embodiments, coadministration produces a synergistic effect.

In certain embodiments, the glutaminase inhibitor and the one or more additional chemotherapeutic agents are administered simultaneously. In alternative embodiments, the one or more additional chemotherapeutic agents are administered within about 5 minutes to within about 168 hours prior to or after administration of the glutaminase inhibitor.

The proliferation of cancer cells requires lipid synthesis. Normally, acetyl-coA used for lipid synthesis is formed from a mitochondrial pool of pyruvate that is derived from glycolysis. Yet under hypoxic conditions, such as those normally found in a tumor environment, the conversion of pyruvate to acetyl-coA within the mitochondria is downregulated. Recent studies from Metallo et al. (2011) and Mullen et al. (2011) revealed that under such hypoxic conditions, cells instead largely switch to using a pathway involving the reductive carboxylation of alpha-ketoglutarate to make acetyl-coA for lipid synthesis. The first step in this pathway involves converting glutamine to glutamate via glutaminase enzymes. Subsequently, glutamate is converting to alpha-ketoglutarate, and the resulting alpha-ketoglutarate is converted to isocitrate in a reductive carboxylation step mediated by the isocitrate dehydrogenase enzymes. A switch to this reductive carboxylation pathway also occurs in some renal carcinoma cell lines that contain either impaired mitochondria or an impaired signal for induction of the enzyme responsible for converting glycolytic pyruvate to acetyl-coA (Mullen et al 2011). A similar switch occurs in cells exposed to mitochondrial respiratory chain inhibitors such as metformin, rotenone, and antimycin (Mullen at al. 2011). Therefore, in some embodiments of this invention, we propose using combinations of mitochondrial respiratory chain inhibitors and glutaminase inhibitors to simultaneously increase cancer cells' dependence on glutaminase-dependent pathways for lipid synthesis while inhibiting those very pathways.

The increased dependence on glycolysis in tumor cells is likely because the hypoxic tumor environment impairs mitochondrial respiration. Furthermore, depletion of glucose induces apoptosis in cells transformed with the MYC oncogene. These findings suggest that inhibiting glycolysis would have a therapeutic value in preventing cancer cell proliferation. There are currently many documented glycolytic inhibitors (Pelicano et al. 2006). However, as pointed out by Zhao et al. (2012), "available glycolytic inhibitors are generally not very potent, and high doses are required, which may cause high levels of systemic toxicity." Since cancer cells typically use both glucose and glutamine at higher levels than normal cells, impairing utilization of each of those metabolites will likely have a synergistic effect. Therefore, in some embodiments of this invention, we propose using combinations of glycolytic pathway inhibitors and glutaminase inhibitors. Such glycolytic inhibitors include 2-deoxyglucose, lonidamine, 3-bromopyruvate, imatinib, oxythiamine, rapamycin, and their pharmacological equivalents. Glycolysis can be inhibited indirectly by depleting NAD+via DNA damage induced by DNA alkylating agents through a pathway activated by poly(ADP-ribose) polymerase (Zong et al. 2004). Therefore, in some embodiments of this invention, we propose using a combination of DNA alkylating agents and glutaminase inhibitors. Cancer cells use the pentose phosphate pathway along with the glycolytic pathway to create metabolic intermediates derived from glucose. Therefore, in some embodiments of this invention, we propose using a combination of pentose phosphate inhibitors such as 6-aminonicotinamide along with glutaminase inhibitors.

In certain embodiments, a compound of the invention may be conjointly administered with non-chemical methods of cancer treatment. In certain embodiments, a compound of the invention may be conjointly administered with radiation therapy. In certain embodiments, a compound of the invention may be conjointly administered with surgery, with thermoablation, with focused ultrasound therapy, with cryotherapy, or with any combination of these.

In certain embodiments, different compounds of the invention may be conjointly administered with one or more other compounds of the invention. Moreover, such combinations may be conjointly administered with other therapeutic agents, such as other agents suitable for the treatment of cancer, immunological or neurological diseases, such as the agents identified above.

In certain embodiments, a mutation can be characterized according to the expression level of the protein (e.g., EGFR or KRAS) or the amino acid sequence of the protein that it encodes. For example, protein amounts can be measured using antibodies. Antibodies suitable for use in the methods disclosed herein are commercially available, or can be prepared routinely. Methods for preparing and using antibodies in assays for proteins of interest are conventional, and are described in, for example, Green et al., Production of Polyclonal Antisera, in Immunochemical Protocols (Manson, ed.), (Humana Press 1992); Coligan et al., in Current Protocols in Immunology, Sec. 2.4.1 (1992); Kohler & Milstein (1975), Nature 256, 495; Coligan et al., sections 2.5.1-2.6.7; and Harlow et al., Antibodies: A Laboratory Manual, page 726 (Cold Spring Harbor Laboratory Pub. 1988).

Any of a variety of antibodies can be used in methods of the invention. Such antibodies include, for example, polyclonal, monoclonal (mAbs), recombinant, humanized or partially humanized, single chain, Fab, and fragments thereof. The antibodies can be of any isotype, e.g., IgM, various IgG isotypes such as IgG1, IgG2a, etc., and they can be from any animal species that produces antibodies, including goat, rabbit, mouse, chicken or the like. The term "an antibody specific for" a protein means that the antibody recognizes a defined sequence of amino acids, or epitope, in the protein, and binds selectively to the protein and not generally to proteins unintended for binding to the antibody. The parameters required to achieve specific binding can be determined routinely, using conventional methods in the art.

In some embodiments of the invention, antibodies specific for EGFR or KRAS are immobilized on a surface (e.g., are reactive elements on an array, such as a microarray, or are on another surface, such as used for surface plasmon resonance (SPR)-based technology, such as Biacore), and proteins in the sample are detected by virtue of their ability to bind specifically to the antibodies. Alternatively, proteins in the sample can be immobilized on a surface, and detected by virtue of their ability to bind specifically to the antibodies. Methods of preparing the surfaces and performing the analyses, including conditions effective for specific binding, are conventional and well-known in the art.

Among the many types of suitable immunoassays are immunohistochemical staining, ELISA, Western blot (immunoblot), immunoprecipitation, radioimmunoassay (MA), fluorescence-activated cell sorting (FACS), etc. Assays used in methods of the invention can be based on colorimetric readouts, fluorescent readouts, mass spectroscopy, visual inspection, etc.

As mentioned above, expression levels of EGFR or KRAS can be measured by measuring mRNA amounts. The amount of an mRNA encoding a EGFR or KRAS can be measured using any suitable method. Examples of such methods include, for example, reverse transcriptase-polymerase chain reaction (RT-PCR), including real time PCR, microarray analysis, nanostring, Northern blot analysis, differential hybridization, and ribonuclease protection assay. Such methods are well-known in the art and are described in, for example, Sambrook et al., Molecular Cloning: A Laboratory Manual, current edition, Cold Spring Harbor Laboratory, Cold Spring Harbor, N.Y., and Ausubel et al., Current Protocols in Molecular Biology, John Wiley & sons, New York, N.Y.

In some embodiments of the invention, a histological sample is obtained from a subject (e.g., from a tumor biopsy), using any method known in the art, and include, but are not limited to, tissue section, needle biopsy, and the like. Frequently the sample will be a "clinical sample", which is a sample derived from a patient, including sections of tissues such as frozen sections or paraffin sections taken for histological purposes. The sample can also be derived from supernatants (of cells) or the cells themselves from cell cultures, cells from tissue culture and other media. Protein or mRNA is then obtained from the sample, and used to quantitate the amounts of KRAS or EGFR and/or to identify mutations relative to the wild-type (predominant) sequence.

III. Kits

In certain embodiments, the present invention provides a kit comprising: a) one or more single dosage forms of a glutaminase inhibitor described herein; b) one or more single dosage forms of a chemotherapeutic agent as mentioned above; and c) instructions for the administration of the compound of the invention and the chemotherapeutic agent for the treatment of lung cancer.

The present invention provides a kit comprising:
a) a pharmaceutical formulation (e.g., one or more single dosage forms) comprising a compound of the invention; and
b) instructions for the administration of the pharmaceutical formulation, e.g., for treating or preventing lung cancer.

In certain embodiments, the kit further comprises instructions for the administration of the pharmaceutical formulation comprising a compound of the invention conjointly with a chemotherapeutic agent as mentioned above. In certain embodiments, the kit further comprises a second pharmaceutical formulation (e.g., as one or more single dosage forms) comprising a chemotherapeutic agent as mentioned above.

The disclosure also provides kits for detecting whether a subject having a cancer is likely to be responsive to glutaminase inhibitors. The kit may include one or more agents for detecting the amount of expression of a protein of the invention [e.g., the amount of the protein, and/or the amount of a nucleic acid (e.g., an mRNA) encoding the protein]. The agents in the kit can encompass, for example, antibodies specific for the proteins, or probes specific for the mRNA that can be used to hybridize to the RNA (or to a cDNA generated from it) or to perform RT-PCR. The kit may also include additional agents suitable for detecting, measuring and/or quantitating the amount of protein or nucleic acid. Among other uses, kits of the invention can be used in experimental applications. A skilled worker will recognize components of kits suitable for carrying out a method of the invention.

Optionally, a kit of the invention may comprise instructions for performing the method. Optional elements of a kit of the invention include suitable buffers, containers, or packaging materials. The reagents of the kit may be in containers in which the reagents are stable, e.g., in lyophilized form or stabilized liquids. The reagents may also be in single use form, e.g., for the performance of an assay for a single subject.

Definitions

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O) NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Exemplary substituted alkyls are described below. Cycloalkyls can be further substituted with alkyls, alkenyls, alkoxys, alkylthios, aminoalkyls, carbonyl-substituted alkyls, —CF$_3$, —CN, and the like.

The term "C$_{x-y}$" when used in conjunction with a chemical moiety, such as, acyl, acyloxy, alkyl, alkenyl, alkynyl, or alkoxy is meant to include groups that contain from x to y carbons in the chain. For example, the term "C$_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. C$_0$ alkyl indicates a hydrogen where the group is in a terminal position, a bond if internal. The terms "C$_{2-y}$alkenyl" and "C$_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

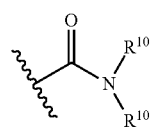

wherein each R$^{10}$ independently represent a hydrogen or hydrocarbyl group, or two R$^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

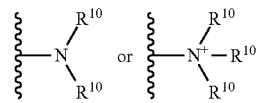

wherein each R$^{10}$ independently represents a hydrogen or a hydrocarbyl group, or two R$^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

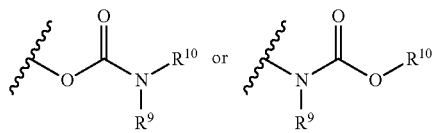

wherein R$^9$ and R$^{10}$ independently represent hydrogen or a hydrocarbyl group, such as an alkyl group, or R$^9$ and R$^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0] octane, 4,5,6,7-tetrahydro-1H-indene and bicyclo[4.1.0] hept-3-ene. "Carbocycles" may be susbstituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —OCO$_2$—R$^{10}$, wherein R$^{10}$ represents a hydrocarbyl group.

The term "carboxy", as used herein, refers to a group represented by the formula —CO$_2$H.

The term "ester", as used herein, refers to a group —C(O)OR$^{10}$ wherein R$^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

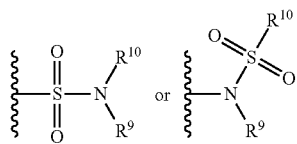

wherein $R^9$ and $R^{10}$ independently represents hydrogen or hydrocarbyl, such as alkyl, or $R^9$ and $R^{10}$ taken together with the intervening atom(s) complete a heterocycle having from 4 to 8 atoms in the ring structure.

The term "sulfoxide" is art-recognized and refers to the group —S(O)—$R^{10}$, wherein $R^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—$R^{10}$, wherein $R^{10}$ represents a hydrocarbyl.

The term "thioalkyl", as used herein, refers to an alkyl group substituted with a thiol group.

The term "thioester", as used herein, refers to a group —C(O)S$R^{10}$ or —SC(O)$R^{10}$ wherein $R^{10}$ represents a hydrocarbyl.

The term "thioether", as used herein, is equivalent to an ether, wherein the oxygen is replaced with a sulfur.

The term "urea" is art-recognized and may be represented by the general formula

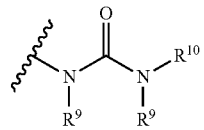

wherein $R^9$ and $R^{10}$ independently represent hydrogen or a hydrocarbyl, such as alkyl, or either occurrence of $R^9$ taken together with $R^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxylprotecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The term "healthcare providers" refers to individuals or organizations that provide healthcare services to a person, community, etc. Examples of "healthcare providers" include doctors, hospitals, continuing care retirement communities, skilled nursing facilities, subacute care facilities, clinics, multi specialty clinics, freestanding ambulatory centers, home health agencies, and HMO's.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "prodrug" is intended to encompass compounds which, under physiologic conditions, are converted into the therapeutically active agents of the present invention (e.g., a compound of formula I). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds of formula I in a formulation represented above can be replaced with the corresponding suitable prodrug, e.g., wherein a hydroxyl in the parent compound is presented as an ester or a carbonate or carboxylic acid present in the parent compound is presented as an ester.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatable with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

In certain embodiments, conjoint administration of compounds of the invention with one or more additional therapeutic agent(s) (e.g., one or more additional chemotherapeutic agent(s)) provides improved efficacy relative to each individual administration of the compound of the invention (e.g., compound of formula I or Ia) or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

EXAMPLES

The synthesis of exemplary compounds of the invention is described in U.S. Pat. No. 8,604,016, which is incorporated herein by reference. Also described in U.S. Pat. No. 8,604,016 are protocols for various assays including recombinant enzyme assays and assays surveying cell proliferation, solubility, and Caco-2 permeability using the compounds of the invention.

IC50 is a quantitative measure indicating how much compound is needed to inhibit a given biological activity by half.

Various in vitro and in vivo studies examining the efficacy of the exemplary glutaminase inhibitors against various cancer types are presented in U.S. Application Publication No. 2015/0004134, which is incorporated herein by reference.

Example 1

Lung Adenocarcinoma Xenograft Efficacy Study

Female scid/beige mice (n=20) age 6-8 weeks were implanted subcutaneously with $1\times10^7$ H2122 lung adenocarcinoma cells per mouse suspended in PBS. Mice were randomized into the following two groups of n=10 mice/group: 1) Vehicle control (25% Hydroxypropyl-β-cyclodextrin) and 2) Compound 670 dosed orally at 200 mg/kg (formulated at 20 mg/mL in 25% HP-β-CD). For both groups, dosing was initiated 24 hours post-implant and continued orally BID for 23 days. Tumors were measured with calipers three times per week and tumor volume calculated using the formula tumor volume $(mm^3)=(a\times b^2/2)$ where 'b' is the smallest diameter and 'a' is the largest perpendicular diameter. **P-value<0.01 (Two-sided T-test). Results are shown in FIG. 1.

Example 2

Activating Mutations in KRAS or EGFR Predict Sensitivity of Compound 670 in NSCLC As shown in FIG. 2, non-small cell lung cancer cell lines exhibiting a KRAS mutation were typically more sensitive to treatment with compound 670 (CB-839) than wild-type nscic cell lines, with higher occurrences of arrested growth and/or cell death.

Sensitivity to compound 670 (CB-839) is correlated to the presence of KRAS and EGFR mutations for a number of non-small cell lung carcinomas, as shown in Table 3.

TABLE 3

EGFR/KRAS mutations and sensitivity to glutaminase inhibitors

| cell line | Sensitivity to CB-839 average | SEM | n | KRAS | KRAS AMP | EGFR |
|---|---|---|---|---|---|---|
| A549 (CALA) | −68.565 | 0.206 | 2 | KRAS G12S | no amp | wt |
| H2023 (CALA) | −47 | 11.533 | 3 | wt | no amp | wt |
| H1568 (CALA) | −38 | 8.073 | 4 | wt | no amp | wt |
| H358 (CALA) | −34 | 13.22 | 4 | KRAS G12C | no amp | wt |
| H2030 (CALA) | −30 | 4.58 | 3 | KRAS G12C | no amp | wt |
| H2122 (CALA) | −28.637 | 14.635 | 5 | KRAS G12C | no amp | wt |
| H2347 (CALA) | −14 | 4.16 | 3 | KRAS L19F | no amp | wt |
| H23 (CALA) | −13 | 8.052 | 4 | KRAS G12C | AMP | wt |
| H1703 (CALA) | −10 | 3.764 | 4 | wt | AMP | wt |
| HCC827 (CALA) | −9 | 11.93 | 3 | wt | no amp | EGFR exon 19 deletion |
| H441 (CALA) | −2.67 | 0.67 | 3 | KRAS G13V | AMP | wt |
| H661 (CALA) | 1.33 | 7.86 | 3 | wt | AMP | wt |
| H1437 (CALA) | 8.33 | 1.86 | 3 | wt | no amp | wt |
| H647 (CALA) | 18.267 | 6.871 | 3 | KRAS G13D | no amp | wt |
| H1650 (CALA) | 19 | 0 | 1 | wt | no amp | EGFR exon 19 deletion |
| H1975 (CALA) | 22.225 | 16.481 | 4 | wt | no amp | EGFR L858R/T790M |
| H226 (CALA) | 38.75 | 14.659 | 4 | wt | no amp | wt |
| H2073 (CALA) | 57.67 | 20.22 | 3 | wt | no amp | wt |
| H1563 (CALA) | 61.5 | 12.26 | 4 | wt | no amp | wt |
| H1299 (CALA) | 68.67 | 4.91 | 3 | wt | no amp | wt |
| H2085 (CALA) | 80.667 | 23.877 | 3 | wt | no amp | no data |
| H838 (CALA) | 82 | 5.29 | 3 | wt | AMP | wt |
| H1693 (CALA) | 82.67 | 9.53 | 3 | wt | no amp | wt |
| ChaGo-K1 (CALA) | 86 | 6 | 3 | wt | no amp | wt |

The genetic mutation in each of the cell lines listed in Table 3 was determined through CCLE (Cancer Cell Line Encyclopedia), except for H2085, which was determined via the University of Texas Southwestern database.

Example 3

Co-Administration of Glutaminase Inhibitor and Anti-Cancer Agent

Cells were treated with a dose titration of either CB-839, an anti-cancer agent or a mixture thereof for 72 hours in growth media. At the end of the incubation, cell viability was measured using Cell Titer Glo as per manufacturer's protocol (Promega, Madison, Wis.). Cell proliferation for all compound treatments are represented as bar graphs, where luminescent output, Relative Light Units (RLU), correlates with viable cell number. Combination indices were calculated using the Calcusyn program (biosoft.com) and reported for individual mixtures of CB-839 and each agent. Results for combination therapy are shown in FIG. 3.

Example 4

Xenograft Study with CB-839, Selumetinib, and Combination CB-839 and Selumetinib Female scid/beige mice (age 7-9 weeks) were implanted subcutaneously with $1 \times 10^7$ H2122 lung cancer cells mixed 1:1 with matrigel. Tumors were measured with calipers three times per week and tumor volume calculated using the formula tumor volume $(mm^3) = (a \times b^2/2)$ where 'b' is the smallest diameter and 'a' is the largest perpendicular diameter. When tumor volume had increased in three consecutive measurements (mean tumor volume ~450 $mm^3$) mice were randomized into the following four treatment groups of n=10 mice per group: 1) Vehicle control (25% Hydroxypropyl-β-cyclodextrin) dosed orally BID; 2) CB-839 (Compound 670) at 200 mg/kg (formulated at 20 mg/mL in 25% HP-β-CD) dosed orally BID; 3) selumetinib at 1 mg/kg (formulated in 0.5% CMC/0.1% PS80) dosed orally QD; and 4) CB-839 at 200 mg/kg orally BID and selumetinib at 1 mg/kg dosed orally once daily. **P-value<0.01 (Two-sided T-test). Results are shown in FIG. 3.

Incorporation By Reference

All publications and patents mentioned herein are hereby incorporated by reference in their entirety as if each individual publication or patent was specifically and individually indicated to be incorporated by reference. In case of conflict, the present application, including any definitions herein, will control. The compounds, synthetic methods, and experimental protocols and results of U.S. Pat. No. 8,604,016, filed Nov. 19, 2012 and issued Dec. 10, 2013, are hereby incorporated by reference.

Equivalents

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A method for therapeutically treating lung cancer in a patient, the method comprising:
   a) determining whether the lung cancer is characterized by a KRAS mutation or EGFR mutation; and
   b) if the lung cancer is characterized by a KRAS mutation or EGFR mutation, then administering to the patient an effective amount of a compound of Formula III:

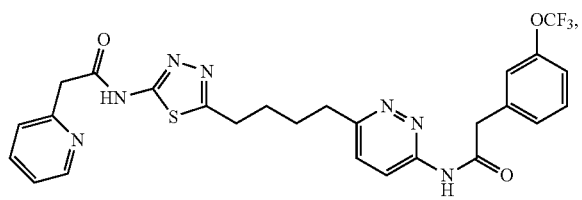 [SMILES: O=C(Cc1cccc(OC(F)(F)F)c1)Nc1ccc(CCCCc2nnc(NC(=O)Cc3ccccn3)s2)nn1]

or a pharmaceutically acceptable salt thereof.

2. The method of claim 1, wherein the mutation results in an expression level of KRAS or EGFR that is different from normal lung cells, or in a level of constitutive activity of KRAS or EGFR that is different from normal lung cells.

3. The method of claim 1, wherein the mutation results in overexpression or increased constitutive activity of KRAS or EGFR.

4. The method of claim 3, wherein the mutation is an amplification of the gene encoding KRAS or EGFR.

5. The method of claim 3, wherein the mutation is a deletion in the gene encoding KRAS or EGFR.

6. The method of claim 3, wherein the mutation is an insertion in the gene encoding KRAS or EGFR.

7. The method of claim 3, wherein the mutation is a point mutation resulting in a change of at least one amino acid residue in the amino acid sequence of KRAS or EGFR protein.

8. The method of claim 1, wherein the lung cancer is non-small cell lung carcinoma (NSCLC).

9. The method of claim 1, further comprising conjointly administering radiation therapy.

10. The method of claim 1, further comprising conjointly administering one or more additional chemotherapeutic agents.

11. The method of claim 10, wherein the one or more additional chemotherapeutic agents are selected from afatinib dimaleate, bevacizumab, carboplatin, ceritinib, cisplatin, crizotinib, docetaxel, doxorubicin hydrochloride; erlotinib hydrochloride, etoposide, gefitinib, gemcitabine hydrochloride, mechlorethamine hydrochloride, methotrexate, paclitaxel, pemetrexed disodium, ramucirumab, topotecan hydrochloride, vinorelbine tartrate.

12. The method of claim 10, wherein the one or more additional chemotherapeutic agents is selumetinib.

* * * * *